US010533005B2

(12) United States Patent
Glick et al.

(10) Patent No.: US 10,533,005 B2
(45) Date of Patent: Jan. 14, 2020

(54) NLRP3 MODULATORS

(71) Applicant: Innate Tumor Immunity, Inc., Princeton, NJ (US)

(72) Inventors: Gary Glick, Ann Arbor, MI (US); Shomir Ghosh, Brookline, MA (US); William R. Roush, Jupiter, FL (US); Edward James Olhava, Newton, MA (US); Daniel O'Malley, New Hope, PA (US)

(73) Assignee: Innate Tumor Immunity, Inc., Princeton, NJ (US)

( * ) Notice: Subject to any disclaimer, the term of this patent is extended or adjusted under 35 U.S.C. 154(b) by 0 days.

(21) Appl. No.: 15/898,258

(22) Filed: Feb. 16, 2018

(65) Prior Publication Data

US 2019/0055236 A1     Feb. 21, 2019

Related U.S. Application Data

(60) Provisional application No. 62/460,677, filed on Feb. 17, 2017, provisional application No. 62/490,881, filed on Apr. 27, 2017, provisional application No. 62/573,991, filed on Oct. 18, 2017.

(51) Int. Cl.
| | |
|---|---|
| *C07D 471/04* | (2006.01) |
| *A61P 35/00* | (2006.01) |
| *A61P 37/00* | (2006.01) |
| *A61K 31/4745* | (2006.01) |
| *A61K 31/5377* | (2006.01) |
| *A61K 45/06* | (2006.01) |

(52) U.S. Cl.
CPC ........ *C07D 471/04* (2013.01); *A61K 31/4745* (2013.01); *A61K 31/5377* (2013.01); *A61K 45/06* (2013.01); *A61P 35/00* (2018.01); *A61P 37/00* (2018.01)

(58) Field of Classification Search
None
See application file for complete search history.

(56) References Cited

U.S. PATENT DOCUMENTS

| | | | |
|---|---|---|---|
| 5,389,640 | A | 2/1995 | Gerster et al. |
| 6,348,462 | B1 | 2/2002 | Gerster et al. |
| 7,091,214 | B2 | 8/2006 | Hays et al. |
| 7,598,382 | B2 | 10/2009 | Hays et al. |
| 7,858,637 | B2 | 12/2010 | Averett |
| 8,017,779 | B2 | 9/2011 | Merrill et al. |
| 8,728,486 | B2 | 5/2014 | David et al. |
| 9,295,732 | B2 | 3/2016 | Lioux et al. |
| 2007/0259881 | A1 | 11/2007 | Dellaria, Jr. et al. |
| 2009/0069314 | A1 | 3/2009 | Kshiragar et al. |
| 2017/0217960 | A1 | 8/2017 | Ferguson |

FOREIGN PATENT DOCUMENTS

| | | |
|---|---|---|
| EP | 0 145 340 | 6/1985 |
| EP | 2 674 170 A1 | 12/2013 |
| JP | 11-80156 | 4/1997 |
| WO | WO1993/05042 A1 | 3/1993 |
| WO | WO2002/24225 A1 | 3/2002 |
| WO | WO2004/058759 A1 | 7/2004 |
| WO | WO2005/018555 A2 | 3/2005 |
| WO | WO2005/020999 A1 | 3/2005 |
| WO | WO2005/025583 A2 | 3/2005 |
| WO | WO2005/051317 A2 | 6/2005 |
| WO | WO2005/076783 A2 | 8/2005 |
| WO | WO2005/123079 A2 | 12/2005 |
| WO | WO2005/123080 A2 | 12/2005 |
| WO | WO2006/009832 A1 | 1/2006 |
| WO | WO2006/031878 A2 | 3/2006 |
| WO | WO2006/065280 A2 | 6/2006 |
| WO | WO2006/073940 A2 | 7/2006 |
| WO | WO2006/091394 A2 | 8/2006 |
| WO | WO2006/091567 A2 | 8/2006 |
| WO | WO2006/098852 A2 | 9/2006 |
| WO | WO2007/079086 A1 | 7/2007 |
| WO | WO2010/088924 A1 | 8/2010 |
| WO | WO2013/033345 A1 | 3/2013 |
| WO | WO2015/095780 A1 | 6/2015 |
| WO | WO2016/004875 A1 | 1/2016 |
| WO | WO2016/034085 A1 | 3/2016 |
| WO | WO2016/055812 A1 | 4/2016 |
| WO | WO2017/040670 A1 | 3/2017 |
| WO | WO2017/184735 A1 | 10/2017 |
| WO | WO2017/184746 A1 | 10/2017 |

OTHER PUBLICATIONS

Baldwin, Alex G. et al., "Inhibiting the Inflammasome: A Chemical Perspective", Journal of Medicinal Chemistry, vol. 59, pp. 1691-1710 (2016).
Bauernfeind, F. et al., "Of inflammasomes and pathogens—sensing of microbes by the inflammasome", EMBO Molecular Medicine, vol. 5, pp. 814-826 (2013).
Chaput, Catherine et al., "NOD-like receptors in lung diseases" Frontiers in Immunology, vol. 4, Article 393 pp. 1-12 (2013).
Chen, Lih-Chyang et al., "Tumour inflammasome-derived IL-1β recruits neutrophils and improves local recurrence-free survival in EBV-induced nasopharyngeal carcinoma", EMBO Molecular Medicine, vol. 4, pp. 1276-1293 (2012).
Fuertes, Mercedes B. et al., "Type I interferon response and innate immune sensing of cancer", Trends in Immunology, vol. 34(2), pp. 67-73 (2013).

(Continued)

*Primary Examiner* — Jared Barsky
(74) *Attorney, Agent, or Firm* — Jing G. Sun

(57) ABSTRACT

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) in a subject (e.g., a human). This disclosure also features compositions as well as other methods of using and making the same.

41 Claims, No Drawings

(56) References Cited

OTHER PUBLICATIONS

Gerster, John F. et al., "Synthesis and Structure—Activity-Relationships of 1H-Imidazo[4,5-c]quinolones That Induce Interferon Production", J. Med Chemistry, vol. 48, pp. 3481-3491 (2005).
Hirota, Jeremy A. et al., "The airway epithelium nucleotide-binding domain and leucine-rich repeat protein 3 inflammasome is activated by urban particulate matter", J. Allergy Clinical Immunology, vol. 129, pp. 1116-1125 (2012).
Lin, Chu et al., "Inflammasomes in Inflammation-Induced Cancer", Frontiers in Immunology, vol. 8, Article 271, pp. 1-22 (2017).
Ma, Zhifeng et al., "Augmentation of Immune Checkpoint Cancer Immunotherapy with IL18" Clinical Cancer Research, vol. 22(12), pp. 2969-2980 (2016).
Ting, Jenny P.Y. et al., "The NLR Gene Family: A Standard Nomenclature", Immunity, vol. 28, pp. 285-287 (2008).
Tse, Brian Wan-Chi et al., "IL-18 Inhibits Growth of Murine Orthotopic Prostate Carcinomas via Both Adaptive and Innate Immune Mechanisms", PLOS One, vol. 6(9), pp. 1-12 (2011).
CAS Registry No. 1027225-83-7 entered Jun. 11, 2008.
U.S. Appl. No. 16/094,000, filed Oct. 16, 2018, Glick, et al.
U.S. Appl. No. 16/093,990, filed Oct. 16, 2018, Glick, et al.
ISR of corresponding International application No. PCT/US2018/018484.

NLRP3 MODULATORS

CROSS-REFERENCE TO RELATED APPLICATIONS

This application claims the priority benefit of U.S. Provisional Application No. 62/460,677, filed Feb. 17, 2017, U.S. Provisional Application No. 62/490,881, filed Apr. 27, 2017, and U.S. Provisional Application No. 62/573,991, filed Oct. 18, 2017; the contents of which are herein incorporated by reference in their entirety.

TECHNICAL FIELD

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity that contributes to the pathology and/or symptoms and/or progression and/or treatment refractory state of the condition, disease or disorder (e.g., cancers with low T-cell infiltration) in a subject (e.g., a human). This disclosure also features compositions as well as other methods of using and making the same.

BACKGROUND

Nucleotide-binding oligomerization domain-like receptors ("NLRs") include a family of intracellular receptors that detect pathogen-associated molecular patterns ("PAMPs") and endogenous molecules (see, e.g., Ting, J. P. Y. et al., "The NLR gene family: a standard nomenclature," *Immunity*, 28(3):285-287, (2008)).

NLRPs represent a subfamily of NLRs that include a Pyrin domain and are constituted by proteins such as NLRP1, NLRP3, NLRP4, NLRP6, NLRP7, and NLRP12. NLRPs are believed to be involved with the formation of multiprotein complexes termed inflammasomes (see, e.g., Chaput, C. et al., "NOD-like receptors in lung diseases," *Frontiers in Immunology*, 4: article 393, (2013)). These complexes typically include one or two NLR proteins, the adapter molecule apoptosis associated speck-like containing a CARD domain (ASC) and pro-caspase-1 F (see, e.g., Bauernfeind, F and Hornung, V. "Of inflammasomes and pathogens-sensing of microbes by the inflammasome," *EMBO Molecular Medicine*, 5(6):814-826, (2013)).

One such inflammasome is formed by the NLRP3 scaffold, the ASC adaptor and pro-caspase-1 (see, e.g., Hirota, J. A., et al., "The airway epithelium nucleotide-binding domain and leucine-rich repeat protein 3 inflammasome is activated by urban particulate matter," *Journal of Allergy and Clinical Immunology*, 129(4): 1116.e6-1125.e6, (2012)), and its expression is believed to be induced by inflammatory cytokines and TLR agonists in myeloid cells and human bronchial epithelial cells (Id.). The NLRP3 inflammasome is believed to mediate the caspase-1-dependent conversion of pro-IL-1β and pro-IL-18 to IL-1β and IL-18. Further, IL-1β and IL-18 have potential in the treatment of various types of cancer (see, e.g., Chen, L-C. et al., *EMBO Mol Med.*, 4(12):1276-1293 (2012) and Tse, B. W-C. et al., *PLoS One*, 6(9):e24241 (2011)). IL-18 has been shown to override resistance to checkpoint inhibitors in colon cancer animal tumor models (see e.g., Ma, Z. et al., *Clin. Cancer Res*. Jan. 11. (2016) DOI: 10.1158/1078-0432.CCR-15-1655).

SUMMARY

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity contributes to the pathology and/or symptoms and/or progression and/or treatment refractory state of the condition, disease or disorder (e.g., cancers with low T-cell infiltration) in a subject (e.g., a human). This disclosure also features compositions as well as other methods of using and making the same.

An "agonist" of NLRP3 includes compounds that, at the protein level, directly bind or modify NLRP3 such that an activity of NLRP3 is increased, e.g., by activation, stabilization, altered distribution, or otherwise.

Certain compounds described herein that agonize NLRP3 to a lesser extent than a NLRP3 full agonist can function in assays as antagonists as well as agonists. These compounds antagonize activation of NLRP3 by a NLRP3 full agonist because they prevent the full effect of NLRP3 interaction. However, the compounds also, on their own, activate some NLRP3 activity, typically less than a corresponding amount of the NLRP3 full agonist. Such compounds may be referred to as "partial agonists of NLRP3".

In some embodiments, the compounds described herein are agonists (e.g. full agonists) of NLRP3. In other embodiments, the compounds described herein are partial agonists of NLRP3.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

In one aspect, compounds of Formula I, or a pharmaceutically acceptable salt thereof, are featured:

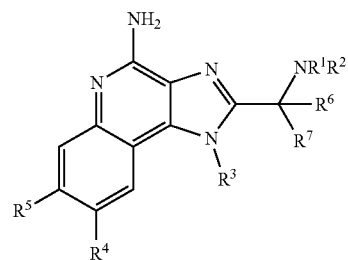

in which $R^1$, $R^2$, $R^3$, $R^4$, $R^5$, $R^6$, and $R^7$ can be as defined anywhere herein.

In one aspect, methods for modulating (e.g., agonizing, partially agonizing, antagonizing) NLRP3 activity are featured that include contacting NLRP3 with a chemical entity described herein (e.g., a compound described generically or specifically herein or a pharmaceutically acceptable salt thereof or compositions containing the same). In preferred embodiments, methods for modulating NLRP3 activity are agonizing and partially agonizing. In certain embodiments, methods for modulating NLRP3 activity are agonizing. In certain embodiments, methods for modulating NLRP3 activity are partially agonizing. Methods include in vitro methods, e.g., contacting a sample that includes one or more cells comprising NLRP3 (e.g., THP-1 cells) with the chemical entity. Methods can also include in vivo methods; e.g., administering the chemical entity to a subject (e.g., a human) having a disease in which an increase in NLRP3 signaling may correct a deficiency in innate immune activity that contributes to the pathology and/or symptoms and/or progression of the disease (e.g., cancer; e.g., a refractory cancer).

In some embodiments, compounds of the invention are useful for treating a condition, disease or disorder in which a decrease in NLRP3 activity (e.g., a condition, disease or disorder associated with repressed or impaired NLRP3 signaling) contributes to the pathology and/or symptoms and/or progression of the condition, disease or disorder (e.g., cancer) in a subject (e.g., a human).

A cancer is said to be refractory when it does not respond to (or is resistant to) cancer treatment. Refractory cancer is also known as resistant cancer.

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same). In some embodiments, the cancer may be a refractory cancer In a further aspect, methods of treatment of a disease in which an increase in NLRP3 signaling may correct a deficiency in innate immune activity that contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering to a subject having a disease in which an increase in NLRP3 signaling may correct a deficiency in innate immune activity that contributes to the pathology and/or symptoms and/or progression of the disease an effective amount of a chemical entity described herein (e.g., a compound described generically or specifically herein or a pharmaceutically acceptable salt thereof or compositions containing the same).

In a further aspect, methods of treatment that include administering to a subject a chemical entity described herein (e.g., a compound described generically or specifically herein or a pharmaceutically acceptable salt thereof or compositions containing the same), wherein the chemical entity is administered in an amount effective to treat a disease in which an increase in NLRP3 signaling may correct a deficiency in innate immune activity that contributes to the pathology and/or symptoms and/or progression of the disease, thereby treating the disease.

Embodiments can include one or more of the following features.

The chemical entity can be administered in combination with one or more additional cancer therapies (e.g., surgery, radiotherapy, chemotherapy, toxin therapy, immunotherapy, cryotherapy or gene therapy, or a combination thereof; e.g., cancer therapies that include administering one or more (e.g., two, three, four, five, six, or more) additional anti-cancer agents. Non-limiting examples of additional anti-cancer agents (chemotherapeutic agents) are selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a $vinca$ alkaloid and/or a taxane; e.g., Vincristine, Vinblastine, Vinorelbine and/or Vindesine Taxol, Pacllitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine-TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12.

The subject can have cancer; e.g., the subject has undergone and/or is undergoing and/or will undergo one or more cancer therapies.

Non-limiting examples of cancer include acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In other embodiments, the mammal has been identified as having a cancer or an infectious disease. Representative infectious diseases include, without limitation, *Acinobacter* infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, *Burkholderi* infection, Buruli ulcer, *Calicivirus* infection, camptobacteriosis, candidiasis, cat-scratch disease, cellulitis, Chagas disease, chancroid, chickenpox, chikungunya, chlamydia, *Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, *Desmodesmus* infection, deintamoebiasis, diphtheria, diphyllobothriasis, dracunculiasis, ebola hemorrhagic fever, echinococcosis, ehrlichiosis, enterobiasis, *Enterococcus* infection, *Enterovirus* infection, epidemic typhus, erythema infection, exanthema subitum, fasciolopsiasis, fasciolosis, fatal familial insomnia, filariasis, food poisoning by *Clostridium myonecrosis*, free-living amebic infection, *Fusobacterium* infection, gas gangrene, geotrichosis, Gerstmann-Sträussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human ewingii ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, *Kingella kingae* infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, staphylococcal infection, strongyloidiasis, subacute sclerosing panencephalitis, syphilis, taeniasis, tetanus, tinea barabe, tinea capitis, tinea corporis, tinea cruris, tinea manum, tinea nigra, tinea pedis, tinea unguium, tinea *versicolor*, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

The chemical entity can be administered intratumorally.

The chemical entity can be administered systemically (including but not limited to orally, subcutaneously, intramuscular, intravenously).

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP3 molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 22nd Edition, Pharmaceutical Press, London, U K (2012); *Handbook of Pharmaceutical Excipients, 6th ed.*; Rowe et al., Eds.; The Pharmaceutical Press and the American Pharmaceutical Association: (2009); *Handbook of Pharmaceutical Additives, 3rd ed.*; Ash and Ash Eds.; Gower Publishing Company: (2007); *Pharmaceutical Preformulation and Formulation, 2nd ed.*; Gibson Ed.; CRC Press LLC: Boca Raton, Fla., (2009).

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt is not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "alkylene" refers to a branched or unbranched divalent alkyl (e.g., —CH$_2$—).

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkylene" as used herein refers to divalent cycloalkyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Examples of heteroaryl groups also include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. The term "heterocycloalkylene" refers to divalent heterocyclyl.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The details of one or more embodiments of the invention are set forth in the accompanying drawings and the description below. Other features and advantages of the invention will be apparent from the description and drawings, and from the claims.

DETAILED DESCRIPTION

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) in a subject (e.g., a human). This disclosure also features compositions as well as other methods of using and making the same.

Formula I Compounds

In one aspect, compounds of Formula I, or a pharmaceutically acceptable salt thereof are featured:

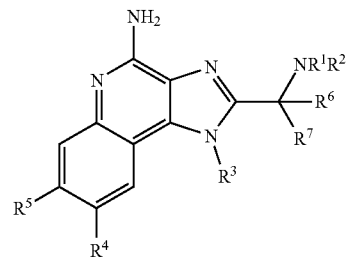

(I)

wherein $R^1$ and $R^2$, are defined according to (1) or (2) below:

(1):

$R^1$ is independently selected from the group consisting of: H, unsubstituted $C_{1-6}$ alkyl, CHO, C(=O)$R^a$, —C(=O)O$R^a$, —S(O)$_{1-2}$($R^b$), —S(O)$_{1-2}$N$R^c R^d$, and —C(=O)N$R^c R^d$;

$R^2$ is independently selected from the group consisting of: H and unsubstituted $C_{1-6}$ alkyl;

OR (2):

$R^1$ and $R^2$, together with the nitrogen atom to which each is attached forms a saturated or unsaturated ring including from 3-10 ring atoms, wherein the ring includes:

(a) from 1-9 ring carbon atoms, each of which is optionally substituted with from 1-2 independently selected $R^f$, and (b) from 0-3 ring heteroatoms (in addition to the nitrogen atom attached to $R^1$ and $R^2$), each of which is independently selected from the group consisting of N, N($R^e$), O, and S; and provided that at least one of the 3-10 ring atoms is —C(O)—;

$R^3$ is:

(i) H;

(ii) unsubstituted $C_{1-2}$ alkyl;

(iii) X—$R^8$, wherein X is an unbranched $C_{1-6}$ alkylene, and $R^8$ is —OH, $C_{1-4}$ alkoxy, —$C_{1-4}$ haloalkoxy, CO$_2R^a$, —CON$R^c R^d$, cyano, or —N$R^c R^d$;

(iv) ($C_{1-3}$ alkylene)-($C_6$-$C_{10}$ aryl), wherein the aryl is optionally substituted with from 1-3 substituents independently selected from of: $C_{1-6}$ alkyl, $C_{1-4}$ haloalkyl, $C_{1-4}$ alkoxy, and $C_{1-4}$ haloalkoxy; or (v) ($C_{1-3}$ alkylene)heteroaryl including from 5-6 ring atoms, wherein from 1-4 ring atoms are each independently selected from the group consisting of N, N($R^e$), O, and S, and wherein the heteroaryl is optionally substituted with from 1-3 substituents independently selected from the group consisting of: $C_{1-6}$ alkyl, $C_{1-4}$ haloalkyl, $C_{1-4}$ alkoxy, and $C_{1-4}$ haloalkoxy;

$R^4$ and $R^5$ are each independently selected from the group consisting of:

(i) hydrogen;

(ii) halo;

(iii) cyano;

(iv) —C(=O)OH;

(iv) —C(=O)O$R^a$;

(v) —C(=O)N$R^c R^d$;

(vi) —($C_{0-3}$ alkylene)-$C_{3-10}$ cycloalkyl, wherein the cycloalkyl is optionally substituted with from 1-4 independently selected $R^f$;

(vii) —($C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$;

(viii) —($C_{0-3}$ alkylene)-($C_6$-$C_{10}$ aryl) optionally substituted with from 1-4 $R^g$;

(ix) —($C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$;

(x) —Y—$C_6$-$C_{10}$ aryl optionally substituted with from 1-4 $R^g$, wherein Y is O, N($R^e$), or S;

(xi) —Y-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$, wherein Y is O, N($R^e$), or S;

(xii) —$NR^{c}R^{d'}$;

(xiii) $C_{1-6}$ alkyl optionally substituted with from 1-2 independently selected $R^h$;

(xiv) $C_{1-4}$ haloalkyl;

(xv) $C_{1-6}$ alkoxy;

(xvi) $C_{1-4}$ haloalkoxy;

(xvii) —$S(O)_{1-2}(R^b)$;

(xviii) —$S(O)_{1-2}NR^{c}R^d$;

(xviv) —($C_{0-3}$ alkylene)-heterocycloalkenyl including from 3-10 ring atoms, wherein from 1-3 ring atoms are each independently selected from the group consisting of N($R^e$), O, and S, wherein the heterocyclyl is optionally substituted with from 1-4 independently selected $R^f$;

each of $R^6$ and $R^7$ is independently selected from the group consisting of: H and unsubstituted $C_{1-2}$ alkyl; or $R^6$ and $R^7$ together with the carbon atom to which each is attached, forms a $C_3$-$C_5$ cycloalkyl, optionally substituted with from 1-4 independently selected $R^f$;

provided that when $R^1$ and $R^2$, are defined according to (1), then each of $R^6$ and $R^7$ is H;

provided that when $R^1$ and $R^2$, are defined according to (2), then each of $R^6$ and $R^7$ is independently selected from the group consisting of: H and unsubstituted $C_{1-2}$ alkyl; or $R^6$ and $R^7$ together with the carbon atom to which each is attached, forms a $C_3$-$C_5$ cycloalkyl, optionally substituted with from 1-4 independently selected $R^f$;

$R^a$ is:

(i) $C_{1-6}$ alkyl optionally substituted with from 1-2 independently selected $R^h$;

(ii) —($C_{0-3}$ alkylene)-$C_{3-10}$ cycloalkyl, wherein the cycloalkyl is optionally substituted with from 1-4 independently selected $R^f$;

(iii) —($C_{1-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$;

(iv) —($C_{0-3}$ alkylene)-phenyl optionally substituted with from 1-5 independently selected $R^g$; or (v) —($C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 independently selected $R^g$;

$R^b$ is: $C_{1-6}$ alkyl, $C_{1-4}$ haloalkyl, $C_{1-4}$ alkoxy, $C_{1-4}$ haloalkoxy, phenyl optionally substituted with from 1-3 $R^g$, or heteroaryl including from 5-6 ring atoms, wherein from 1-4 ring atoms are each independently selected from the group consisting of N, N($R^e$), O, and S, wherein the heteroaryl is optionally substituted with from 1-3 $R^g$;

each occurrence of $R^c$ and $R^d$ is independently selected from the group consisting of: H and $C_{1-4}$ alkyl; or $R^c$ and $R^d$ together with the nitrogen atom to which each is attached forms a ring including from 3-8 ring atoms, wherein the ring includes: (a) from 1-7 ring carbon atoms, each of which is optionally substituted with from 1-2 independently selected $R^f$; and (b) from 0-3 ring heteroatoms (in addition to the nitrogen atom attached to $R^c$ and $R^d$), which are each independently selected from the group consisting of N($R^e$), O, and S;

each occurrence of $R^{c'}$ and $R^{d'}$ is independently selected from the group consisting of: H, $R^a$, —$C(=O)R^a$, —$C(=O)OR^a$, —$S(O)_{1-2}(R^b)$, and —$C(=O)NR^{c}R^d$; or $R^{c'}$ and $R^{d'}$ together with the nitrogen atom to which each is attached forms a ring including from 3-8 ring atoms, wherein the ring includes: (a) from 1-7 ring carbon atoms, each of which is optionally substituted with from 1-2 independently selected $R^f$; and (b) from 0-3 ring heteroatoms (in addition to the nitrogen atom attached to $R^{c'}$ and $R^{d'}$), which are each independently selected from the group consisting of N($R^e$), O, and S;

each occurrence of $R^e$ is independently selected from the group consisting of: H; $C_{1-4}$ alkyl; $C_{3-6}$ cycloalkyl; phenyl; —$C(=O)(C_{1-4}$ alkyl); —$C(=O)O(C_{1-4}$ alkyl); and —$S(O)_{1-2}$ ($C_{1-4}$ alkyl); wherein each $C_{1-4}$ alkyl is optionally substituted with from 1-2 independently selected $R^h$; each $C_{3-6}$ cycloalkyl is optionally substituted with from 1-2 independently selected $R^f$; and each phenyl is optionally substituted with from 1-2 independently selected $R^g$;

each occurrence of $R^f$ is independently selected from the group consisting of: $C_{1-6}$ alkyl optionally substituted with from 1-2 independently selected $R^h$; $C_{1-4}$ haloalkyl; —OH; oxo; —F; —Cl; —N(R')(R''); —N(R')(C(=O)$C_{1-4}$ alkyl); $C_{1-4}$ alkoxy; $C_{1-4}$ haloalkoxy; —$C(=O)(C_{1-4}$ alkyl); —$C(=O)O(C_{1-4}$ alkyl); —C(=O)OH; —C(=O)N(R')(R''); —$S(O)_{1-2}(C_{1-4}$ alkyl); cyano; heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and phenyl optionally substituted with from 1-4 $R^g$; and wherein each occurrence of R' and R" is independently selected from the group consisting of: H and $C_{1-4}$ alkyl;

each occurrence of $R^g$ is independently selected from the group consisting of:

(i) halo;

(ii) cyano;

(iii) $C_{1-6}$ alkyl optionally substituted with from 1-2 independently selected $R^h$;

(iv) $C_{2-6}$ alkenyl;

(v) $C_{2-6}$ alkynyl;

(vi) $C_{1-4}$ haloalkyl;

(vii) $C_{1-4}$ alkoxy;

(viii) $C_{1-4}$ haloalkoxy;

(ix) —($C_{0-3}$ alkylene)-$C_{3-6}$ cycloalkyl optionally substituted with from 1-4 independently selected $C_{1-4}$ alkyl;

(x) —($C_{0-3}$ alkylene)-heterocyclyl including from 3-6 ring atoms, wherein from 1-3 ring atoms are each independently selected from the group consisting of nitrogen, oxygen and sulfur, wherein the heterocyclyl is optionally substituted with from 1-4 independently selected $C_{1-4}$ alkyl;

(xi) —$S(O)_{1-2}(C_{1-6}$ alkyl);

(xii) —$NO_2$;

(xiii) —OH;

(xiv) —N(R')(R'');

(xv) —N(R')(C(=O)$C_{1-3}$ alkyl);

(xvi) —C(=O)($C_{1-4}$ alkyl);

(xvii) —C(=O)O(C$_{1-4}$ alkyl);
(xviii) —C(=O)OH; and
(xix) —C(=O)N(R')(R");

wherein each occurrence of R' and R" is independently selected from the group consisting of: H and C$_{1-4}$ alkyl; and each occurrence of R$^h$ is independently selected from the group consisting of: —OH, —OBn, —F, —N(R')(R"), —N(R')(C(=O)C$_{1-4}$ alkyl), —N(R')(C(=O)OC$_{1-4}$ alkyl), C$_{1-4}$ alkoxy, C$_{1-4}$ haloalkoxy, —C(=O)O(C$_{1-4}$ alkyl), —C(=O)OH, —C(=O)N(R')(R"), —S(O)$_{1-2}$(C$_{1-4}$ alkyl), and cyano; wherein each occurrence of R' and R" is independently selected from the group consisting of: H and C$_{1-4}$ alkyl.

In some embodiments, one or more (e.g., all) of the provisions apply:

with the proviso that when R$^8$ is NR$^{c'}$R$^{d'}$, then R$^1$ is not —S(O)$_{1-2}$(R$^b$);

with the proviso that when R$^8$ is NR$^{c'}$R$^{d'}$ and R$^1$ and R$^2$, together with the nitrogen atom to which each is attached, forms heterocyclyl including from 3-10 ring atoms, then none of the ring atoms of the heterocyclyl formed from R$^1$ and R$^2$ are S;

with the proviso that when R$^8$ is NR$^{c'}$R$^{d'}$ and R$^1$ and R$^2$, together with the nitrogen atom to which each is attached, forms heterocyclyl, then the heterocyclyl formed from R$^1$ and R$^2$ does not include 5 ring atoms;

with the proviso that when R$^8$ is NR$^{c'}$R$^{d'}$, then R$^1$ and R$^2$, together with the nitrogen atom to which each is attached does not form

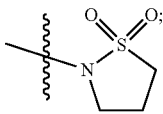 [SMILES: *N1CCCS1(=O)=O]

with the proviso that when R$^8$ is NR$^{c'}$R$^{d'}$, then R$^1$ is not —C(=O)NR$^c$R$^d$;

with the proviso that when R$^8$ is NR$^{c'}$R$^{d'}$, R$^1$ is —C(=O)NR$^c$R$^d$, and one of R$^c$ and R$^d$ is H; then the other of R$^c$ and R$^d$ is not selected from H or C$_{1-4}$ alkyl;

with the proviso that when R$^8$ is NR$^{c'}$R$^{d'}$, R$^1$ is —C(=O)NR$^c$R$^d$, and one of R$^c$ and R$^d$ is H; then the other of R$^c$ and R$^d$ is not selected from H, Me, or Et;

with the proviso that the compound of Formula I is not selected from:

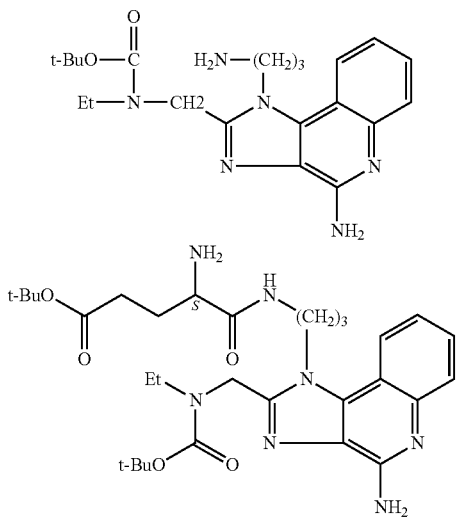

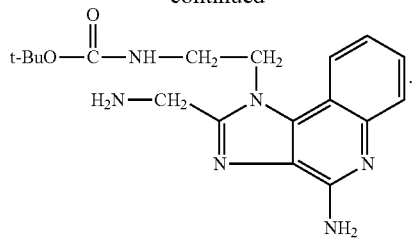

In one aspect, compounds of Formula I, or a pharmaceutically acceptable salt thereof are featured:

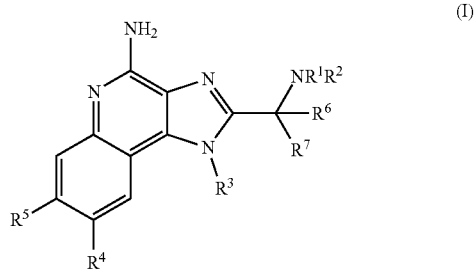

wherein R$^1$ and R$^2$, are defined according to (1) or (2) below:

(1):

R$^1$ is independently selected from the group consisting of: H, unsubstituted C$_{1-6}$ alkyl, C(=O)R$^a$, —C(=O)OR$^a$, —S(O)$_{1-2}$(R$^b$), —S(O)$_{1-2}$NR$^c$R$^d$, and —C(=O)NR$^c$R$^d$;

R$^2$ is independently selected from the group consisting of: H and unsubstituted C$_{1-6}$ alkyl;

OR (2):

R$^1$ and R$^2$, together with the nitrogen atom to which each is attached forms a saturated or unsaturated ring including from 3-10 ring atoms, wherein the ring includes:

(a) from 1-9 ring carbon atoms, each of which is optionally substituted with from 1-2 independently selected R$^f$, and (b) from 0-3 ring heteroatoms (in addition to the nitrogen atom attached to R$^1$ and R$^2$), each of which is independently selected from the group consisting of N, N(R$^e$), O, and S; and provided that at least one of the 3-10 ring atoms is —C(O)—;

R$^3$ is:

(i) H;

(ii) unsubstituted C$_{1-2}$ alkyl;

(iii) X—R$^8$, wherein X is an unbranched C$_{1-6}$ alkylene, and R$^8$ is —OH, C$_{1-4}$ alkoxy, —C$_{1-4}$ haloalkoxy, CO$_2$R$^a$, —CONR$^c$R$^d$, cyano, or —NR$^{c'}$R$^{d'}$;

(iv) (C$_{1-3}$ alkylene)-(C$_6$-C$_{10}$ aryl), wherein the aryl is optionally substituted with from 1-3 substituents independently selected from the group consisting of: C$_{1-6}$ alkyl, C$_{1-4}$ haloalkyl, C$_{1-4}$ alkoxy, and C$_{1-4}$ haloalkoxy; or (v) (C$_{1-3}$ alkylene)heteroaryl including from 5-6 ring atoms, wherein from 1-4 ring atoms are each independently selected from the group consisting of N, N(R$^e$), O, and S, and wherein the heteroaryl is optionally substituted with from 1-3 substituents independently selected from the group consisting of: C$_{1-6}$ alkyl, C$_{1-4}$ haloalkyl, C$_{1-4}$ alkoxy, and C$_{1-4}$ haloalkoxy;

$R^4$ and $R^5$ are each independently selected from the group consisting of:
  (i) hydrogen;
  (ii) halo;
  (iii) cyano;
  (iv) —C(=O)OH;
  (iv) —C(=O)OR$^a$;
  (v) —C(=O)NR$^c$R$^d$;
  (vi) —(C$_{0-3}$ alkylene)-C$_{3-10}$ cycloalkyl, wherein the cycloalkyl is optionally substituted with from 1-4 independently selected R$^f$;
  (vii) —(C$_{0-3}$ alkylene)-heterocyclyl including from 3-10 ring atoms, wherein from 1-3 ring atoms are each independently selected from the group consisting of N(R$^e$), O, and S, wherein the heterocyclyl is optionally substituted with from 1-4 independently selected R$^f$;
  (viii) —(C$_{0-3}$ alkylene)-(C$_6$-C$_{10}$ aryl) optionally substituted with from 1-4 R$^g$;
  (ix) —(C$_{0-3}$ alkylene)-heteroaryl including from 5-10 ring atoms, wherein from 1-4 ring atoms are each independently selected from the group consisting of N, N(R$^e$), O, and S, wherein the heteroaryl is optionally substituted with from 1-3 R$^g$;
  (x) —Y— C$_6$-C$_{10}$ aryl optionally substituted with from 1-4 R$^g$, wherein Y is O, N(R$^e$), or S;
  (xi) —Y-heteroaryl including from 5-10 ring atoms, wherein from 1-4 ring atoms are each independently selected from the group consisting of N, N(R$^e$), O, and S, wherein the heteroaryl is optionally substituted with from 1-3 R$^g$, wherein Y is O, N(R$^e$), or S;
  (xii) —NR$^c$'R$^d$';
  (xiii) C$_{1-6}$ alkyl optionally substituted with from 1-2 independently selected R$^h$;
  (xiv) C$_{1-4}$ haloalkyl;
  (xv) C$_{1-6}$ alkoxy;
  (xvi) C$_{1-4}$ haloalkoxy;
  (xvii) —S(O)$_{1-2}$(R$^b$);
  (xviii) —S(O)$_{1-2}$NR$^c$R$^d$;
  (xviv) —(C$_{0-3}$ alkylene)-heterocycloalkenyl including from 3-10 ring atoms, wherein from 1-3 ring atoms are each independently selected from the group consisting of N(R$^e$), O, and S, wherein the heterocyclyl is optionally substituted with from 1-4 independently selected R$^f$;

each of $R^6$ and $R^7$ is independently selected from the group consisting of: H and unsubstituted C$_{1-2}$ alkyl; or $R^6$ and $R^7$ together with the carbon atom to which each is attached, forms a C$_3$-C$_5$ cycloalkyl, optionally substituted with from 1-4 independently selected R$^f$;

provided that when $R^1$ and $R^2$, are defined according to (1), then each of $R^6$ and $R^7$ is H;

provided that when $R^1$ and $R^2$, are defined according to (2), then each of $R^6$ and $R^7$ is independently selected from the group consisting of: H and unsubstituted C$_{1-2}$ alkyl; or $R^6$ and $R^7$ together with the carbon atom to which each is attached, forms a C$_3$-C$_5$ cycloalkyl, optionally substituted with from 1-4 independently selected R$^f$;

$R^a$ is:
  (i) C$_{1-6}$ alkyl optionally substituted with from 1-2 independently selected R$^h$;
  (ii) —(C$_{0-3}$ alkylene)-C$_{3-10}$ cycloalkyl, wherein the cycloalkyl is optionally substituted with from 1-4 independently selected R$^f$;
  (iii) —(C$_{1-3}$ alkylene)-heterocyclyl including from 3-10 ring atoms, wherein from 1-3 ring atoms are each independently selected from the group consisting of N(R$^e$), O, and S, wherein the heterocyclyl is optionally substituted with from 1-4 independently selected R$^f$;
  (iv) —(C$_{0-3}$ alkylene)-phenyl optionally substituted with from 1-5 independently selected R$^g$; or
  (v) —(C$_{0-3}$ alkylene)-heteroaryl including from 5-10 ring atoms, wherein from 1-4 ring atoms are each independently selected from the group consisting of N, N(R$^e$), O, and S, wherein the heteroaryl is optionally substituted with from 1-3 independently selected R$^g$;

$R^b$ is: C$_{1-6}$ alkyl, C$_{1-4}$ haloalkyl, C$_{1-4}$ alkoxy, C$_{1-4}$ haloalkoxy, phenyl optionally substituted with from 1-3 R$^g$, or heteroaryl including from 5-6 ring atoms, wherein from 1-4 ring atoms are each independently selected from the group consisting of N, N(R$^e$), O, and S, wherein the heteroaryl is optionally substituted with from 1-3 R$^g$;

each occurrence of R$^c$ and R$^d$ is independently selected from the group consisting of: H and C$_{1-4}$ alkyl; or R$^c$ and R$^d$ together with the nitrogen atom to which each is attached forms a ring including from 3-8 ring atoms, wherein the ring includes: (a) from 1-7 ring carbon atoms, each of which is optionally substituted with from 1-2 independently selected R$^f$; and (b) from 0-3 ring heteroatoms (in addition to the nitrogen atom attached to R$^c$ and R$^d$), which are each independently selected from the group consisting of N(R$^e$), O, and S;

each occurrence of R$^{c'}$ and R$^{d'}$ is independently selected from the group consisting of: H, R$^a$, —C(=O)R$^a$, —C(=O)OR$^a$, —S(O)$_{1-2}$(R$^b$), and —C(=O)NR$^c$R$^d$; or R$^{c'}$ and R$^{d'}$ together with the nitrogen atom to which each is attached forms a ring including from 3-8 ring atoms, wherein the ring includes: (a) from 1-7 ring carbon atoms, each of which is optionally substituted with from 1-2 independently selected R$^f$; and (b) from 0-3 ring heteroatoms (in addition to the nitrogen atom attached to R$^{c'}$ and R$^{d'}$), which are each independently selected from the group consisting of N(R$^e$), O, and S;

each occurrence of R$^e$ is independently selected from the group consisting of: H; C$_{1-4}$ alkyl; C$_{3-6}$ cycloalkyl; phenyl; —C(=O)(C$_{1-4}$ alkyl); —C(=O)O(C$_{1-4}$ alkyl); and —S(O)$_{1-2}$(C$_{1-4}$ alkyl); wherein each C$_{1-4}$ alkyl is optionally substituted with from 1-2 independently selected R$^h$; each C$_{3-6}$ cycloalkyl is optionally substituted with from 1-2 independently selected R$^f$; and each phenyl is optionally substituted with from 1-2 independently selected R$^g$;

each occurrence of R$^f$ is independently selected from the group consisting of: C$_{1-6}$ alkyl optionally substituted with from 1-2 independently selected R$^h$; C$_{1-4}$ haloalkyl; —OH; oxo; —F; —Cl; —N(R')(R''); —N(R')(C(=O)C$_{1-4}$ alkyl); C$_{1-4}$ alkoxy; C$_{1-4}$ haloalkoxy; —C(=O)(C$_{1-4}$ alkyl); —C(=O)O(C$_{1-4}$ alkyl); —C(=O)OH; —C(=O)N(R')(R''); —S(O)$_{1-2}$(C$_{1-4}$ alkyl); cyano; heteroaryl including from 5-10 ring atoms, wherein from 1-4 ring atoms are each independently selected from the group consisting of N, N(R$^e$), O, and S, wherein the heteroaryl is optionally substituted with from 1-3 R$^g$; and phenyl optionally substituted with from 1-4 R$^g$; and wherein each occurrence of R' and R'' is independently selected from the group consisting of: H and C$_{1-4}$ alkyl;

each occurrence of R$^g$ is independently selected from the group consisting of:
  (i) halo;
  (ii) cyano;
  (iii) C$_{1-6}$ alkyl optionally substituted with from 1-2 independently selected R$^h$;
  (iv) C$_{2-6}$ alkenyl;
  (v) C$_{2-6}$ alkynyl;
  (vi) C$_{1-4}$ haloalkyl;

(vii) C$_{1-4}$ alkoxy;

(viii) C$_{1-4}$ haloalkoxy;

(ix) —(C$_{0-3}$ alkylene)-C$_{3-6}$ cycloalkyl optionally substituted with from 1-4 independently selected C$_{1-4}$ alkyl;

(x) —(C$_{0-3}$ alkylene)-heterocyclyl including from 3-6 ring atoms, wherein from 1-3 ring atoms are each independently selected from the group consisting of nitrogen, oxygen and sulfur, wherein the heterocyclyl is optionally substituted with from 1-4 independently selected C$_{1-4}$ alkyl;

(xi) —S(O)$_{1-2}$(C$_{1-6}$ alkyl);

(xii) —NO$_2$;

(xiii) —OH;

(xiv) —N(R')(R");

(xv) —N(R')(C(=O)C$_{1-3}$ alkyl);

(xvi) —C(=O)(C$_{1-4}$ alkyl);

(xvii) —C(=O)O(C$_{1-4}$ alkyl);

(xviii) —C(=O)OH; and (xix) —C(=O)N(R')(R");

wherein each occurrence of R' and R" is independently selected from the group consisting of: H and C$_{1-4}$ alkyl; and each occurrence of R$^h$ is independently selected from the group consisting of: —OH, —F, —N(R')(R"), —N(R')(C(=O)C$_{1-4}$ alkyl), —N(R')(C(=O)OC$_{1-4}$ alkyl), C$_{1-4}$ alkoxy, C$_{1-4}$ haloalkoxy, —C(=O)O(C$_{1-4}$ alkyl), —C(=O)OH, —C(=O)N(R')(R"), —S(O)$_{1-2}$(C$_{1-4}$ alkyl), and cyano; wherein each occurrence of R' and R" is independently selected from the group consisting of: H and C$_{1-4}$ alkyl.

In some embodiments, one or more (e.g., all) of the provisions apply:

with the proviso that when R$^8$ is NR$^{c'}$R$^{d'}$, then R$^1$ is not —S(O)$_{1-2}$(R$^b$);

with the proviso that when R$^8$ is NR$^{c'}$R$^{d'}$ and R$^1$ and R$^2$, together with the nitrogen atom to which each is attached, forms heterocyclyl including from 3-10 ring atoms, then none of the ring atoms of the heterocyclyl formed from R$^1$ and R$^2$ are S;

with the proviso that when R$^8$ is NR$^{c'}$R$^{d'}$ and R$^1$ and R$^2$, together with the nitrogen atom to which each is attached, forms heterocyclyl, then the heterocyclyl formed from R$^1$ and R$^2$ does not include 5 ring atoms;

with the proviso that when R$^8$ is NR$^{c'}$R$^{d'}$, then R$^1$ and R$^2$, together with the nitrogen atom to which each is attached does not form

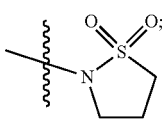 [SMILES: *N1CCCS1(=O)=O]

with the proviso that when R$^8$ is NR$^{c'}$R$^{d'}$, then R$^1$ is not —C(=O)NR$^c$R$^d$;

with the proviso that when R$^8$ is NR$^{c'}$R$^{d'}$, R$^1$ is —C(=O)NR$^c$R$^d$, and one of R$^c$ and R$^d$ is H; then the other of R$^c$ and R$^d$ is not selected from H or C$_{1-4}$ alkyl;

with the proviso that when R$^8$ is NR$^{c'}$R$^{d'}$, R$^1$ is —C(=O)NR$^c$R$^d$, and one of R$^c$ and R$^d$ is H; then the other of R$^c$ and R$^d$ is not selected from H, Me, or Et;

with the proviso that the compound of Formula I is not selected from:

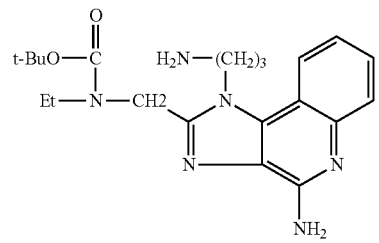

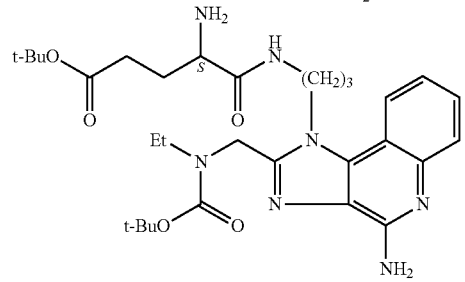

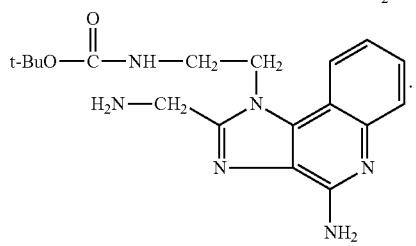

In some embodiments, R$^3$ is H.

In some embodiments, R$^3$ is unsubstituted C$_{1-2}$ alkyl (e.g., CH$_3$).

In some embodiments, one of R$^4$ and R$^5$ is other than hydrogen.

In some embodiments, R$^1$ and R$^2$ are defined according to (1).

In some embodiments, R$^1$ and R$^2$ are defined according to (2).

In some embodiments, R$^4$ and R$^5$ further include C$_5$-C$_7$ cycloalkenyl and/or azido.

In some embodiments, it is provided that R$^3$ is hydrogen and/or one of R$^4$ and R$^5$ is other than hydrogen.

In some embodiments, each of R$^6$ and R$^7$ is H.

In some embodiments, R$^8$ is —OH, C$_{1-4}$ alkoxy, —C$_{1-4}$ haloalkoxy, CO$_2$R$^a$, —CONR$^c$R$^d$, and cyano.

Variables R$^1$, R$^2$, R$^6$, and R$^7$

In some embodiments, R$^1$, R$^2$, R$^6$, and R$^7$ are defined according to (1) below:

(1):

R$^1$ is independently selected from the group consisting of: H, unsubstituted C$_{1-6}$ alkyl, C(=O)R$^a$, —C(=O)OR$^a$, —S(O)$_{1-2}$(R$^b$), —S(O)$_{1-2}$NR$^c$R$^d$; and —C(=O)NR$^c$R$^d$;

R$^2$ is independently selected from the group consisting of: H and unsubstituted C$_{1-6}$ alkyl.

In these embodiments, each of R$^6$ and R$^7$ is H.

Variable R$^1$

In some embodiments, R$^1$ is independently selected from the group consisting of: —C(=O)R$^a$, —C(=O)OR$^a$, —S(O)$_{1-2}$(R$^b$), and —C(=O)NR$^c$R$^d$.

In certain embodiments, R$^1$ is —C(=O)R$^a$.

In certain embodiments, R$^a$ is C$_{1-6}$ alkyl optionally substituted with from 1-2 independently selected R$^h$. In certain embodiments, R$^a$ is unsubstituted C$_{1-6}$ alkyl. For example, R$^a$ can be selected from the group consisting of CH$_3$, CH$_2$CH$_3$, and unsubstituted, unbranched C$_{3-6}$ alkyl (e.g., $CH_3$ or $CH_2CH_3$). As another example, $R^a$ can be unsubstituted, branched $C_{3-6}$ alkyl (e.g., iso-propyl).

In other embodiments, $R^a$ is —($C_{0-3}$ alkylene)-$C_{3-10}$ cycloalkyl, wherein the cycloalkyl is optionally substituted with from 1-4 independently selected $R^f$. For example, $R^a$ can be $C_{3-10}$ (e.g., $C_{3-8}$ or $C_{3-6}$) cycloalkyl, wherein the cycloalkyl is optionally substituted with from 1-4 independently selected $R^f$; e.g., $R^a$ can be unsubstituted $C_{3-10}$ (e.g., $C_{3-8}$ or $C_{3-6}$ or $C_{3-5}$ or $C_{3-4}$) cycloalkyl. In each of the foregoing embodiments, the cycloalkyl is cyclopropyl.

In other embodiments, $R^a$ is —($C_{0-3}$ alkylene)-heteroaryl including from 3-10 ring atoms, wherein from 1-3 ring atoms are each independently selected from the group consisting of N, N($R^e$), O, and S, wherein the heteroaryl is optionally substituted with from 1-3 independently selected $R^g$. For example, $R^a$ can be heteroaryl including from 5-10 ring atoms, wherein from 1-3 ring atoms are each independently selected from the group consisting of N, N($R^e$), O, and S, wherein the heteroaryl is optionally substituted with from 1-3 independently selected $R^g$.

In other embodiments, $R^a$ is heteroaryl including from 3-10 ring atoms, wherein from 1-3 ring atoms are each independently selected from the group consisting of N, N($R^e$), O, and S, wherein the heteroaryl is optionally substituted with from 1-3 independently selected $R^g$.

In certain embodiments, $R^1$ is —$S(O)_{1-2}(R^b)$. In certain of these embodiments, $R^b$ is $C_{1-6}$ alkyl (e.g., $CH_3$).

In certain embodiments, $R^1$ is —$C(\!=\!O)NR^cR^d$. In certain of these embodiments, each of $R^c$ and $R^d$ is independently selected from the group consisting of: H and $C_{1-4}$ alkyl.

In some embodiments, $R^1$ is unsubstituted $C_{1-6}$ alkyl. For example, $R^1$ can be selected from the group consisting of $CH_3$, $CH_2CH_3$, and unsubstituted, unbranched $C_{3-6}$ alkyl (e.g., $R^1$ can be $CH_3$ or $CH_2CH_3$).

In some embodiments, $R^1$ is H.

Variable $R^2$

In some embodiments, $R^2$ is unsubstituted $C_{1-6}$ alkyl. For example, $R^2$ can be selected from the group consisting of $CH_3$, $CH_2CH_3$, and unsubstituted, unbranched $C_{3-6}$ alkyl (e.g., $R^2$ can be $CH_3$ or $CH_2CH_3$).

In some embodiments, $R^2$ is H.

Non-Limiting Combinations

In some embodiments, $R^1$ is independently selected from the group consisting of: —$C(\!=\!O)R^a$, —$C(\!=\!O)OR^a$, —$S(O)_{1-2}(R^b)$, and —$C(\!=\!O)NR^cR^d$ (as defined anywhere herein); and $R^2$ is unsubstituted $C_{1-6}$ alkyl (as defined anywhere herein).

In some embodiments, $R^1$ is independently selected from the group consisting of: —$C(\!=\!O)R^a$, —$C(\!=\!O)OR^a$, —$S(O)_{1-2}(R^b)$, and —$C(\!=\!O)NR^cR^d$ (as defined anywhere herein); and $R^2$ is H.

In some embodiments, $R^1$ is unsubstituted $C_{1-6}$ alkyl (as defined anywhere herein); and $R^2$ is unsubstituted $C_{1-6}$ alkyl (as defined anywhere herein).

In some embodiments, $R^1$ is unsubstituted $C_{1-6}$ alkyl (as defined anywhere herein); and $R^2$ is H.

In some embodiments, $R^1$ is H; and $R^2$ is H.

In some embodiments, $R^1$, $R^2$, $R^6$, and $R^7$ are defined according to (2) below:

(2):

$R^1$ and $R^2$, together with the nitrogen atom to which each is attached forms a saturated or unsaturated (e.g., 1 double bond or 2 double bonds) ring including from 3-10 ring atoms, wherein the ring includes:

(a) from 1-9 ring carbon atoms, each of which is optionally substituted with from 1-2 independently selected $R^f$, and (b) from 0-3 ring heteroatoms (in addition to the nitrogen atom attached to $R^1$ and $R^2$), each of which is independently selected from the group consisting of N, N($R^e$), O, and S; and provided that at least one of the 3-10 ring atoms is —C(O)—.

In some embodiments:

$R^1$ and $R^2$, together with the nitrogen atom to which each is attached forms a saturated ring including from 3-10 ring atoms, wherein the ring includes:

(a) from 1-9 ring carbon atoms, each of which is optionally substituted with from 1-2 independently selected $R^f$, and (b) from 0-3 ring heteroatoms (in addition to the nitrogen atom attached to $R^1$ and $R^2$), each of which is independently selected from the group consisting of N, N($R^e$), O, and S; and provided that at least one of the 3-10 ring atoms is —C(O)—.

In some embodiments:

$R^1$ and $R^2$, together with the nitrogen atom to which each is attached forms a saturated or unsaturated (e.g., saturated) ring including from 4-7 (e.g., 5-6) ring atoms, wherein the ring includes:

(a) from 1-6 (e.g., 1-5) ring carbon atoms, each of which is optionally substituted with from 1-2 independently selected $R^f$, and (b) from 0-2 ring heteroatoms, each of which is independently selected from the group consisting of N, N($R^e$), O, and S; and provided that one ring atom is —C(O)—.

In some embodiments, —$C(R^6)(R^7)$—$NR^1R^2$ in formula (I) has the following formula:

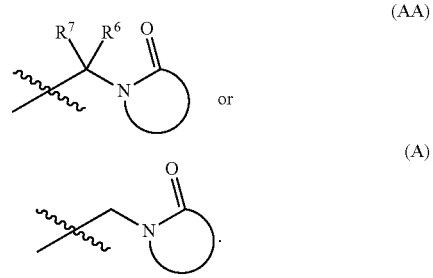

In certain embodiments, —$C(R^6)(R^7)$—$NR^1R^2$ in formula (I) has the following formula:

In some embodiments, each of $R^6$ and $R^7$ is independently selected from the group consisting of: H and unsubstituted $C_{1-2}$ alkyl; or $R^6$ and $R^7$ together with the carbon atom to which each is attached, forms a $C_3$-$C_5$ cycloalkyl, optionally substituted with from 1-4 independently selected $R^f$.

In certain embodiments, each of $R^6$ and $R^7$ is H.

In certain embodiments, —$C(R^6)(R^7)$—$NR^1R^2$ in formula (I) has the following formula:

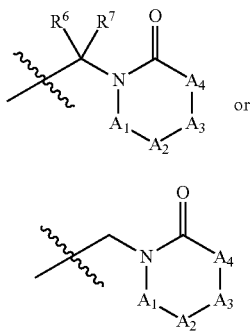

(BB)

wherein:
A₁ is a bond, C(O), CH₂, CHR$^f$, or C(R$^f$)₂;
A₂ is C(O), CH₂, CHR$^f$, or C(R$^f$)₂;
A₃ is C(O), CH₂, CHR$^f$, or C(R$^f$)₂; O, or N(R$^e$);
A₄ is CH₂, CHR$^f$, or C(R$^f$)₂; O, or N(R$^e$); provided that both A₃ and A₃ cannot both be N(R$^e$), O or a combination thereof.

In certain embodiments, —C(R⁶)(R⁷)—NR¹R² in formula (I) has the following formula:

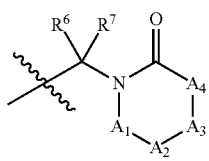

(BB)

wherein:
A₁ is a bond, C(O), CH₂, CHR$^f$, or C(R$^f$)₂;
A₂ is C(O), CH₂, CHR$^f$, or C(R$^f$)₂;
A₃ is C(O), CH₂, CHR$^f$, or C(R$^f$)₂; or N(R$^e$);
A₄ is CH₂, CHR$^f$, or C(R$^f$)₂; or N(R$^e$); provided that both A₃ and A₃ cannot both be N(R$^e$).

In some embodiments, each of R⁶ and R⁷ is independently selected from the group consisting of: H and unsubstituted C$_{1-2}$ alkyl; or R⁶ and R⁷ together with the carbon atom to which each is attached, forms a C₃-C₅ cycloalkyl, optionally substituted with from 1-4 independently selected R$^f$.

In certain embodiments, each of R⁶ and R⁷ is H.

In some embodiments, A₁ can be a bond (i.e., forming a 5-membered ring).

In certain of these embodiments, each of A₂ and A₄ can be independently selected from CH₂, CHR$^f$, and C(R$^f$)₂. For example, each of A₂ and A₄ can be CH₂. In certain of these embodiments, A₃ is CH₂ or CHR$^f$.

In other of these embodiments, one of A₂ and A₄ (e.g., A₂) can be C(O), and the other of A₂ and A₄ (e.g., A₄) can be independently selected from CH₂, CHR$^f$, and C(R$^f$)₂. For example, A₂ can be C(O), and A₄ can be CH₂. In certain of these embodiments, A₃ is CH₂ or CHR$^f$.

In still other of these embodiments, A₄ can be O or N(R$^e$); and each of A₂ and A₃ can be independently selected from CH₂, CHR$^f$, and C(R$^f$)₂ (e.g., one of A₂ and A₃ is CH₂, and the other is CHR$^f$ or C(R$^f$)₂.

In some embodiments, A₁ is C(O), CH₂, CHR$^f$, or C(R$^f$)₂ (i.e., forming a 6-membered ring). In certain of these embodiments, A₂ and A₄ are independently selected from CH₂, CHR$^f$, and C(R$^f$)₂.

In certain of these embodiments, A₃ is CH₂ or CHR$^f$; or A₃ is O, or N(R$^e$).

In certain of the foregoing embodiments, R¹ is, —OH, C$_{1-4}$ alkoxy, C$_{1-4}$ haloalkoxy, -heteroaryl including from 5-10 ring atoms, wherein from 1-3 ring atoms are each independently selected from the group consisting of N, N(R$^e$), O, and S, wherein the heteroaryl is optionally substituted with from 1-3 R$^g$; and phenyl optionally substituted with from 1-4 R$^g$.

In some embodiments of (2), each of R⁶ and R⁷ is H.

Variable R³

In some embodiments, R³ is H.

In some embodiments, R³ is unsubstituted C$_{1-2}$ alkyl (e.g., CH₃).

In some embodiments, R³ is X—R⁸, wherein X is an unbranched C$_{1-6}$ alkylene, and R⁸ is —OH, C$_{1-4}$ alkoxy, —C$_{1-4}$ haloalkoxy, CO₂R$^a$; —CONR$^c$R$^d$, cyano, or —NR$^c$R$^{d'}$. In certain embodiments, R⁸ is —OH, C$_{1-4}$ alkoxy, —C$_{1-4}$ haloalkoxy, CO₂R$^a$; —CONR$^c$R$^d$, and cyano.

In some embodiments, R³ is —(C$_{1-3}$ alkylene)-(C₆-C$_{10}$ aryl), wherein the aryl is optionally substituted with from 1-3 substituents independently selected from the group consisting of: C$_{1-6}$ alkyl, C$_{1-4}$ haloalkyl, C$_{1-4}$ alkoxy, and C$_{1-4}$ haloalkoxy.

In some embodiments, R³ is —(C$_{1-3}$ alkylene)heteroaryl including from 5-6 ring atoms, wherein from 1-3 ring atoms are each independently selected from the group consisting of N, N(R$^e$), O, and S, and wherein the heteroaryl is optionally substituted with from 1-3 substituents independently selected from the group consisting of: C$_{1-6}$ alkyl, C$_{1-4}$ haloalkyl, C$_{1-4}$ alkoxy, and C$_{1-4}$ haloalkoxy.

Variables R⁴ and R⁵

In some embodiments, each of R⁴ and R⁵ is hydrogen.

In some embodiments, one of R⁴ and R⁵ is hydrogen (e.g., R⁴), and the other is a substituent other than hydrogen (e.g., R⁵).

In some embodiments, R⁴ and R⁵ are each independently selected from the group consisting of:
(i) hydrogen;
(ii) halo;
(iii) cyano;
(vi) —(C$_{0-3}$ alkylene)-C$_{3-10}$ cycloalkyl, wherein the cycloalkyl is optionally substituted with from 1-4 independently selected R$^f$;
(vii) —(C$_{0-3}$ alkylene)-heterocyclyl including from 3-10 ring atoms, wherein from 1-3 ring atoms are each independently selected from the group consisting of N(R$^e$), O, and S, wherein the heterocyclyl is optionally substituted with from 1-4 independently selected R$^f$;
(viii) —(C$_{0-3}$ alkylene)-C$_{6-10}$ aryl optionally substituted with from 1-4 R$^g$;
(ix) —(C$_{0-3}$ alkylene)-heteroaryl including from 5-10 ring atoms, wherein from 1-3 ring atoms are each independently selected from the group consisting of N, N(R$^e$), O, and S, wherein the heteroaryl is optionally substituted with from 1-3 R$^g$; and
(xiv) C$_{1-4}$ haloalkyl.

In some embodiments, one of R⁴ and R⁵ (e.g., R⁵) is:
(ii) halo;
(iii) cyano;
(vi) —(C$_{0-3}$ alkylene)-C$_{3-10}$ cycloalkyl, wherein the cycloalkyl is optionally substituted with from 1-4 independently selected R$^f$;
(vii) —(C$_{0-3}$ alkylene)-heterocyclyl including from 3-10 ring atoms, wherein from 1-3 ring atoms are each independently selected from the group consisting of N(R$^e$), O, and S, wherein the heterocyclyl is optionally substituted with from 1-4 independently selected $R^f$;

(viii) —$(C_{0-3}$ alkylene)-$C_{6-10}$ aryl optionally substituted with from 1-4 $R^g$;

(ix) —$(C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and (xiv) $C_{1-4}$ haloalkyl;

and the other (e.g., $R^4$) is H.

In some embodiments, one of $R^4$ and $R^5$ (e.g., $R^5$) is —$(C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and the other (e.g., $R^4$) is H.

In certain embodiments, one of $R^4$ and $R^5$ (e.g., $R^5$) is heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and the other (e.g., $R^4$) is H.

Representative heteroaryl groups include, without limitation, thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, In certain embodiments, one of $R^4$ and $R^5$ (e.g., $R^5$) is heteroaryl including from 5-6 ring atoms, wherein from 1-4 ring atoms are each independently selected from the group consisting of N, N($R^e$), O, and S, wherein the heteroaryl is optionally substituted with from 1-2 $R^g$; and the other (e.g., $R^4$) is H.

In certain embodiments, one of $R^4$ and $R^5$ (e.g., $R^5$) is heteroaryl including from 5-6 ring atoms, wherein from 1-4 ring atoms are each independently selected from the group consisting of N and N($R^e$), wherein the heteroaryl is optionally substituted with from 1-2 $R^g$; and the other (e.g., $R^4$) is H.

In certain embodiments, one of $R^4$ and $R^5$ (e.g., $R^5$) is pyrrolyl (C-linked pyrolyl or N-linked pyrolyl), imidazolyl, pyrazolyl, triazolyl, tetrazolyl, pyridyl, pyrimidinyl, or pyrazinyl, wherein each is optionally substituted with from 1-2 $R^g$; and the other (e.g., $R^{4)}$ is H.

In certain embodiments, one of $R^4$ and $R^5$ (e.g., $R^5$) is pyrrolyl (C-linked pyrolyl or N-linked pyrolyl), imidazolyl, pyrazolyl, triazolyl, or tetrazolyl, wherein each is optionally substituted with from 1-2 $R^g$; and the other (e.g., $R^4$) is H.

In certain embodiments, one of $R^4$ and $R^5$ (e.g., $R^5$) is N-linked-pyrazolyl, N-linked pyrrolyl, N-linked imidazolyl, N-linked triazolyl, or N-linked tetrazolyl, optionally substituted with from 1-2 $R^g$; and the other (e.g., $R^4$) is H.

In certain embodiments, one of $R^4$ and $R^5$ (e.g., $R^5$) is C-linked-pyrazolyl, C-linked pyrrolyl, C-linked imidazolyl, C-linked triazolyl, or C-linked tetrazolyl, optionally substituted with from 1-2 $R^g$; and the other (e.g., $R^4$) is H.

In certain embodiments, one of $R^4$ and $R^5$ (e.g., $R^5$) is pyrazolyl, optionally substituted with from 1-2 $R^g$; and the other (e.g., $R^4$) is H.

In certain embodiments, one of $R^4$ and $R^5$ (e.g., $R^5$) is C-linked pyrazolyl, optionally substituted with from 1-2 $R^g$; and the other (e.g., $R^4$) is H.

In certain embodiments, one of $R^4$ and $R^5$ (e.g., $R^5$) is N-linked pyrazolyl, optionally substituted with from 1-2 $R^g$; and the other (e.g., $R^4$) is H.

In some embodiments, one of $R^4$ and $R^5$ (e.g., $R^5$) is —$(C_{0-3}$ alkylene)-$C_{6-10}$ aryl, wherein the aryl is optionally substituted with from 1-3 $R^g$; and the other (e.g., $R^4$) is H.

In certain embodiments, one of $R^4$ and $R^5$ (e.g., $R^5$) is $C_{6-10}$ aryl (e.g., phenyl), optionally substituted with from 1-3 $R^g$; and the other (e.g., $R^4$) is H.

In some embodiments, one of $R^4$ and $R^5$ (e.g., $R^5$) is —$(C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$; and the other (e.g., $R^4$) is H.

In some embodiments, one of $R^4$ and $R^5$ (e.g., $R^5$) is heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$ (e.g., oxo), and the other (e.g., $R^4$) is H.

Non-Limiting Combinations

[1] In some embodiments:

$R^1$ is independently selected from the group consisting of: —C(=O)$R^a$, —C(=O)O$R^a$, —S(O)$_{1-2}$($R^b$), and —C(=O)N$R^cR^d$;

$R^2$ is selected from the group consisting of H, $CH_3$, $CH_2CH_3$, and unsubstituted, unbranched $C_{3-6}$ alkyl;

$R^3$ is:

(i) H; or (ii) unsubstituted $C_{1-2}$ alkyl; and one of $R^4$ and $R^5$ (e.g., $R^5$) is:

(ii) halo;

(iii) cyano;

(vi) —$(C_{0-3}$ alkylene)-$C_{3-10}$ cycloalkyl, wherein the cycloalkyl is optionally substituted with from 1-4 independently selected $R^f$;

(vii) —$(C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$;

(viii) —$(C_{0-3}$ alkylene)-phenyl optionally substituted with from 1-4 $R^g$;

(ix) —$(C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and (xiv) $C_{1-4}$ haloalkyl; and the other (e.g., $R^4$) is H.

[2] In some embodiments:

$R^1$ is independently selected from the group consisting of: H, $CH_3$, $CH_2CH_3$, and unsubstituted, unbranched $C_{3-6}$ alkyl;

$R^2$ is selected from the group consisting of H, $CH_3$, $CH_2CH_3$, and unsubstituted, unbranched $C_{3-6}$ alkyl;

$R^3$ is:

(i) H; or (ii) unsubstituted $C_{1-2}$ alkyl; and one of $R^4$ and $R^5$ (e.g., $R^4$) is:

(ii) halo;

(iii) cyano;

(vi) —(C$_{0-3}$ alkylene)-C$_{3-10}$ cycloalkyl, wherein the cycloalkyl is optionally substituted with from 1-4 independently selected R$^f$;

(vii) —(C$_{0-3}$ alkylene)-heterocyclyl including from 3-10 ring atoms, wherein from 1-3 ring atoms are each independently selected from the group consisting of N(R$^e$), O, and S, wherein the heterocyclyl is optionally substituted with from 1-4 independently selected R$^f$;

(viii) —(C$_{0-3}$ alkylene)-phenyl optionally substituted with from 1-4 R$^g$;

(ix) —(C$_{0-3}$ alkylene)-heteroaryl including from 5-10 ring atoms, wherein from 1-4 ring atoms are each independently selected from the group consisting of N, N(R$^e$), O, and S, wherein the heteroaryl is optionally substituted with from 1-3 R$^g$; and (xiv) C$_{1-4}$ haloalkyl;

and the other (e.g., R$^4$) is H.

[3] In some embodiments:

R$^1$ and R$^2$, together with the nitrogen atom to which each is attached forms a saturated or unsaturated ring including from 3-10 ring atoms, wherein the ring includes:

(a) from 1-9 ring carbon atoms, each of which is optionally substituted with from 1-2 independently selected R$^f$, and (b) from 0-3 ring heteroatoms (in addition to the nitrogen atom attached to R$^1$ and R$^2$), each of which is independently selected from the group consisting of N, N(R$^e$), O, and S; and provided that one ring atom is —C(O)—;

R$^3$ is:

(i) H; or (ii) unsubstituted C$_{1-2}$ alkyl; and one of R$^4$ and R$^5$ (e.g., R$^5$) is:

(ii) halo;

(iii) cyano;

(vi) —(C$_{0-3}$ alkylene)-C$_{3-10}$ cycloalkyl, wherein the cycloalkyl is optionally substituted with from 1-4 independently selected R$^f$;

(vii) —(C$_{0-3}$ alkylene)-heterocyclyl including from 3-10 ring atoms, wherein from 1-3 ring atoms are each independently selected from the group consisting of N(R$^e$), O, and S, wherein the heterocyclyl is optionally substituted with from 1-4 independently selected R$^f$;

(viii) —(C$_{0-3}$ alkylene)-phenyl optionally substituted with from 1-4 R$^g$;

(ix) —(C$_{0-3}$ alkylene)-heteroaryl including from 5-10 ring atoms, wherein from 1-4 ring atoms are each independently selected from the group consisting of N, N(R$^e$), O, and S, wherein the heteroaryl is optionally substituted with from 1-3 R$^g$; and (xiv) C$_{1-4}$ haloalkyl;

and the other (e.g., R$^4$) is H.

Embodiments of combinations [1]-[3] can include any one or more of the features delineated in the Detailed Descriptions and/or claims.

In some embodiments, R$^1$ is independently selected from the group consisting of: —C(=O)R$^a$, —C(=O)OR$^a$, —S(O)$_{1-2}$(R$^b$), and —C(=O)NR$^c$R$^d$ (as defined anywhere herein); and R$^2$ is unsubstituted C$_{1-6}$ alkyl (as defined anywhere herein; e.g., CH$_3$, CH$_2$CH$_3$, and unsubstituted, unbranched C$_{3-6}$ alkyl; e.g., CH$_3$, CH$_2$CH$_3$); or R$^1$ is independently selected from the group consisting of: —C(=O)R$^a$, —C(=O)OR$^a$, —S(O)$_{1-2}$(R$^b$), and —C(=O)NR$^c$R$^d$ (as defined anywhere herein); and R$^2$ is H; or R$^1$ is unsubstituted C$_{1-6}$ alkyl (as defined anywhere herein); and R$^2$ is unsubstituted C$_{1-6}$ alkyl ((as defined anywhere herein; e.g., CH$_3$, CH$_2$CH$_3$, and unsubstituted, unbranched C$_{3-6}$ alkyl; e.g., CH$_3$, CH$_2$CH$_3$)); and R$^2$ is H; or R$^1$ is unsubstituted C$_{1-6}$ alkyl ((as defined anywhere herein; e.g., CH$_3$, CH$_2$CH$_3$, and unsubstituted, unbranched C$_{3-6}$ alkyl; e.g., CH$_3$, CH$_2$CH$_3$)); and R$^2$ is H; or R$^1$ is H; and R$^2$ is H.

In some embodiments, R$^1$ is —C(=O)R$^a$ (e.g., R$^a$ is C$_{1-6}$ alkyl optionally substituted with from 1-2 independently selected R$^h$ e.g., R$^a$ is unsubstituted C$_{1-6}$ alkyl; e.g., R$^a$ is selected from the group consisting of CH$_3$, CH$_2$CH$_3$, and unsubstituted, unbranched C$_{3-6}$ alkyl; e.g., R$^a$ is CH$_3$ or CH$_2$CH$_3$).

In some embodiments, —C(R$^6$)(R$^7$)—NR$^1$R$^2$ in formula (I) has formula (A) or (B) as defined anywhere herein.

In some embodiments, wherein R$^3$ is H; or R$^3$ is unsubstituted C$_{1-2}$ alkyl (e.g., CH$_3$).

In some embodiments, the compound is selected from the compounds delineated in Table 1.

In another aspect, the invention provides a compound of Formula (II):

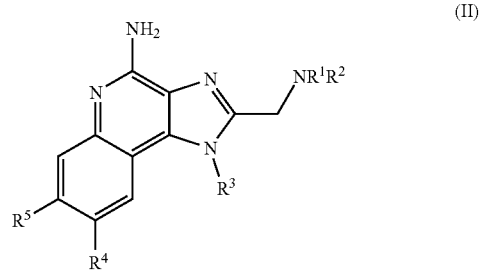

or a pharmaceutically acceptable salt thereof, wherein:

R$^1$ is independently unsubstituted C$_{1-6}$ alkyl, C(=O)R$^a$, —C(=O)OR$^a$, —S(O)$_{1-2}$(R$^b$), —S(O)$_{1-2}$NR$^c$R$^d$, or —C(=O)NR$^c$R$^d$;

R$^2$ is independently H or unsubstituted C$_{1-6}$ alkyl;

R$^3$ is:

(i) H;

(ii) unsubstituted C$_{1-2}$ alkyl;

(iii) X—R$^8$, wherein X is an unbranched C$_{1-6}$ alkylene, and R$^8$ is —OH, C$_{1-4}$ alkoxy, —C$_{1-4}$ haloalkoxy, CO$_2$R$^a$, or —CONR$^c$R$^d$;

(iv) (C$_{1-3}$ alkylene)-(C$_6$-C$_{10}$ aryl), wherein the aryl is optionally substituted with from 1-3 substituents independently selected from C$_{1-6}$ alkyl, C$_{1-4}$ haloalkyl, C$_{1-4}$ alkoxy, and C$_{1-4}$ haloalkoxy; or (v) (C$_{1-3}$ alkylene)heteroaryl including from 5 to 6 ring atoms, wherein from 1 to 4 ring atoms are each independently selected from N, N(R$^e$), O, and S, and wherein the heteroaryl is optionally substituted with from 1 to 3 substituents independently selected from C$_{1-6}$ alkyl, C$_{1-4}$ haloalkyl, C$_{1-4}$ alkoxy, and C$_{1-4}$ haloalkoxy;

R$^4$ and R$^5$ are each independently selected from:

(i) H;

(ii) halo;

(iii) —(C$_{0-3}$ alkylene)-C$_{3-10}$ cycloalkyl, wherein the cycloalkyl is optionally substituted with from 1 to 4 independently selected R$^f$;

(iv) —(C$_{0-3}$ alkylene)-heterocyclyl including from 3 to 10 ring atoms, wherein from 1 to 3 ring atoms are each independently selected from: N(R$^e$), O, and S, wherein the heterocyclyl is optionally substituted with from 1 to 4 R$^f$;

(v) —(C$_{0-3}$ alkylene)-(C$_6$-C$_{10}$ aryl) optionally substituted with from 1 to 4 R$^g$;

(vi) —(C$_{0-3}$ alkylene)-heteroaryl including from 5 to 10 ring atoms, wherein from 1 to 4 ring atoms are each independently selected from: N, NHO, and S, wherein the heteroaryl is optionally substituted with from 1 to 3 $R^g$;

(vii) $C_{1-6}$ alkyl optionally substituted with from 1-2 independently selected $R^h$; and (viii) —$(C_{0-3}$ alkylene)-$C_{4-10}$ cycloalkenyl, wherein the cycloalkenyl is optionally substituted with from 1 to 2 $R^f$;

$R^a$ is:

(i) $C_{1-6}$ alkyl optionally substituted with from 1 to 2 $R^h$;

(ii) —$(C_{0-3}$ alkylene)-$C_{3-10}$ cycloalkyl, wherein the cycloalkyl is optionally substituted with from 1 to 2 $R^f$;

(iii) —$(C_{1-3}$ alkylene)-heterocyclyl including from 3 to 10 ring atoms, wherein from 1 to 3 ring atoms are each independently selected from $N(R^e)$, O, and S, wherein the heterocyclyl is optionally substituted with from 1 to 4 independently selected $R^f$;

(iv) —$(C_{0-3}$ alkylene)-phenyl optionally substituted with from 1 to 4 independently selected $R^g$; or (v) —$(C_{0-3}$ alkylene)-heteroaryl including from 5 to 10 ring atoms, wherein from 1 to 4 ring atoms are each independently selected from N, $N(R^e)$, O, and S, wherein the heteroaryl is optionally substituted with from 1 to 3 independently selected $R^g$;

$R^b$ is $C_{1-6}$ alkyl;

each occurrence of $R^c$ and $R^d$ is independently H or $C_{1-4}$ alkyl;

each occurrence of $R^e$ is independently H or $C_{1-4}$ alkyl;

each occurrence of $R^f$ is independently $C_{1-6}$ alkyl, $C_{1-4}$ haloalkyl, —OH, F, Cl, $C_{1-4}$ alkoxy, $C_{1-4}$ haloalkoxy, cyano, or phenyl optionally substituted with from 1 to 4 $R^g$;

each occurrence of $R^g$ is independently halo, cyano, $C_{1-6}$ alkyl, $C_{1-4}$ haloalkyl, $C_{1-4}$ alkoxy, or $C_{1-4}$ haloalkoxy; and each occurrence of $R^h$ is independently —OH, F, $C_{1-4}$ alkoxy, $C_{1-4}$ haloalkoxy, or cyano.

In another aspect, the invention provides a compound of Formula (II) or a pharmaceutically acceptable salt thereof, wherein:

$R^3$ is H, unsubstituted $C_{1-2}$ alkyl, or X—$R^8$, wherein X is an unbranched $C_{2-6}$ alkylene, and $R^8$ is $CO_2R^a$, or —$CONR^cR^d$;

$R^4$ is independently H or halo;

$R^5$ is independently selected from:

(i) H;

(ii) halo;

(iii) —$(C_{0-3}$ alkylene)-$C_{3-10}$ cycloalkyl, wherein the cycloalkyl is optionally substituted with from 1 to 4 independently selected $R^f$;

(iv) —$(C_{0-3}$ alkylene)-heterocyclyl including from 3 to 10 ring atoms, wherein from 1 to 3 ring atoms are each independently selected from: $N(R^e)$, O, and S, wherein the heterocyclyl is optionally substituted with from 1 to 4 $R^f$;

(v) —$(C_{0-3}$ alkylene)-($C_6$-$C_{10}$ aryl) optionally substituted with from 1 to 4 $R^g$;

(v) —$(C_{0-3}$ alkylene)-heteroaryl including from 5 to 10 ring atoms, wherein from 1 to 4 ring atoms are each independently selected from: N, NH, O, and S, wherein the heteroaryl is optionally substituted with from 1 to 3 $R^g$;

(vi) $C_{1-6}$ alkyl optionally substituted with from 1-2 independently selected $R^h$; and (vii) —$(C_{0-3}$ alkylene)-$C_{4-10}$ cycloalkenyl, wherein the cycloalkenyl is optionally substituted with from 1 to 2 $R^f$.

In another aspect, the invention provides a compound of Formula (II) or a pharmaceutically acceptable salt thereof, wherein:

$R^1$ is independently unsubstituted $C_{1-6}$ alkyl, $C(=O)R^a$, —$C(=O)OR^a$, —$S(O)_2(R^b)$, or —$C(=O)NR^cR^d$;

$R^2$ is independently H or unsubstituted $C_{1-3}$ alkyl;

$R^3$ is H, unsubstituted $C_{1-2}$ alkyl, or X—$R^8$, wherein X is an unbranched $C_{2-4}$ alkylene, and $R^8$ is $CO_2R^a$, or —$CONR^cR^d$;

$R^5$ is independently selected from:

(i) $C_{3-6}$ cycloalkyl optionally substituted with 1 to 2 independently selected $R^f$.

(ii) phenyl optionally substituted with from 1 to 3 $R^g$;

(iii) heteroaryl including from 5 to 6 ring atoms, wherein from 1 to 3 ring atoms are each independently selected from: N, NH, O, and S, wherein the heteroaryl is optionally substituted with from 1 to 3 $R^g$;

(iv) $C_{1-6}$ alkyl optionally substituted with from 1 to 2 independently selected $R^h$; and (v) $C_{5-6}$ cycloalkenyl optionally substituted with from 1 to 2 $R^f$;

$R^a$ is H, $C_{1-4}$ alkyl optionally substituted with OH, $C_{3-6}$ cycloalkyl, phenyl, or heteroaryl including from 5 to 6 ring atoms, wherein from 1 to 4 ring atoms are each independently selected from N, $N(R^e)$, O, and S; and $R^b$ is $C_{1-4}$ alkyl.

In another aspect, the invention provides a compound of Formula (II) or a pharmaceutically acceptable salt thereof, wherein:

$R^1$ is independently $C_{1-6}$ alkyl, $C(=O)R^a$, —$C(=O)OR^a$, —$S(O)_2(CH_3)$, or —$C(=O)N(CH_3)_2$;

$R^2$ is independently H, $CH_3$ or $CH_2CH_3$;

$R^3$ is H, $CH_3$, or —$(CH_2)_3C(=O)OCH_3$;

$R^5$ is independently $CH_3$, cyclopentyl, cyclopentenyl, phenyl, pyrazol-1-yl, or pyrazol-3-yl; and $R^a$ is H, $CH_3$, $CH_2CH_3$, $CH(CH_3)_2$, $C(CH_3)_3$, cyclopropyl, or thiazolyl.

In another aspect, the invention provides a compound of Formula (II) or a pharmaceutically acceptable salt thereof, wherein:

$R^1$ is independently $C_{1-6}$ alkyl, $C(=O)R^a$, —$C(=O)OR^a$, —$S(O)_2(CH_3)$, or —$C(=O)N(CH_3)_2$;

$R^2$ is independently H, $CH_3$ or $CH_2CH_3$;

$R^3$ is H or $CH_3$;

$R^5$ is independently $CH_3$, cyclopentyl, cyclopentenyl, phenyl, pyrazol-1-yl, or pyrazol-3-yl; and $R^a$ is $CH_3$, $CH_2CH_3$, $CH(CH_3)_2$, $C(CH_3)_3$, or cyclopropyl.

In another aspect, the invention provides a compound of Formula (II) or a pharmaceutically acceptable salt thereof, wherein:

$R^1$ is independently $CH_3$, $CH_2CH_3$, $CH(CH_3)_2$, $C(CH_3)_3$, or $C(=O)R^a$;

$R^2$ is independently H, $CH_3$ or $CH_2CH_3$;

$R^3$ is H;

$R^5$ is independently cyclopentyl, cyclopentenyl, phenyl, pyrazol-1-yl, or pyrazol-3-yl; and $R^a$ is $CH_3$, $CH_2CH_3$, $CH(CH_3)_2$, $C(CH_3)_3$, or cyclopropyl.

In another aspect, the invention provides a compound of Formula (II) or a pharmaceutically acceptable salt thereof, wherein:

$R^1$ is independently $CH_3$, $CH_2CH_3$, $CH(CH_3)_2$, or $C(CH_3)_3$;

$R^2$ is independently H, $CH_3$ or $CH_2CH_3$;

$R^3$ is independently H, $CH_3$ or $CH_2CH_3$;

$R^4$ is H; and $R^5$ is independently pyrazol-1-yl, pyrazol-3-yl or pyrazol-5-yl.

In another aspect, the invention provides a compound of Formula (II) or a pharmaceutically acceptable salt thereof, wherein:

$R^1$ is $C(=O)R^a$;

$R^2$ is independently H, $CH_3$ or $CH_2CH_3$;

$R^3$ is independently H, $CH_3$, $CH_2CH_3$ or $CH_2CH_2OH$;

R⁴ is H;
R⁵ is independently cyclopentyl, cyclopentenyl, thienyl, pyrazol-1-yl, pyrazol-3-yl, pyrazol-5-yl or (phenyl substituted with 0-1 C$_{1-4}$ alkyl); and
R$^a$ is CH$_3$, CH$_2$CH$_3$, CH(CH$_3$)$_2$, C(CH$_3$)$_3$, —(CH)$_2$CH (CH$_3$)$_2$, cyclopropyl, 1-methyl-1H-pyrrol-2-yl, or (phenyl substituted with C$_{1-4}$ alkoxy or Cl).

In some aspects, R¹ is unsubstituted C$_{1-6}$ alkyl, C(=O)R$^a$, —C(=O)OR$^a$, —S(O)$_{1-2}$(R$^b$), —S(O)$_{1-2}$NR$^c$R$^d$ or —C(=O)NR$^c$R$^d$. In other aspects, R¹ is unsubstituted C$_{1-6}$ alkyl, C(=O)R$^a$, —C(=O)OR$^a$, —S(O)$_2$(R$^b$), and —C(=O)NR$^c$R$^d$. In other aspects, R¹ is C$_{1-6}$ alkyl, C(=O) R$^a$, —C(=O)OR$^a$, —S(O)$_2$(CH$_3$), and —C(=O)N(CH$_3$)$_2$. In other aspects, R¹ is unsubstituted C$_{1-6}$ alkyl. In other aspects, R¹ is CH$_3$ or CH$_2$CH$_3$. In other aspects, R¹ is CH$_3$. In other aspects, R¹ is CH$_2$CH$_3$. In other aspects, R¹ is C(=O)R$^a$. In other aspects, R¹ is C(=O)CH$_3$. In other aspects, R¹ is C(=O)CH(CH$_3$)$_2$. In other aspects, R¹ is C(=O)CH$_2$(CH$_3$)$_2$. In other aspects, R¹ is C(=O)(cyclopropyl). In other aspects, R¹ is —C(=O)OR$^a$. In other aspects, R¹ is —C(=O)OC(CH$_3$)$_3$. In other aspects, R¹ is —S(O)$_{1-2}$(R$^b$). In other aspects, R¹ is —S(O)$_2$(R$^b$). In other aspects, R¹ is —S(O)$_2$(CH$_3$). In other aspects, R¹ is —S(O)$_{1-2}$NR$^c$R$^d$. In other aspects, R¹ is —C(=O)NR$^c$R$^d$. In other aspects, R¹ is —C(=O)N(CH$_3$)$_2$.

In some aspects, R² is H or unsubstituted C$_{1-6}$ alkyl. In other aspects, R² is H or unsubstituted C$_{1-3}$ alkyl. In other aspects, R² is H, CH$_3$ or CH$_2$CH$_3$. In other aspects, R² is H. In other aspects, R² is CH$_3$ or CH$_2$CH$_3$. In other aspects, R² is CH$_3$. In other aspects, R² is CH$_2$CH$_3$.

In some aspects, R³ is H, unsubstituted C$_{1-2}$ alkyl, or X—R⁸, wherein X is an unbranched C$_{2-6}$ alkylene, and R⁸ is CO$_2$R$^a$, or —CONR$^c$R$^d$. In other aspects, R³ is H, unsubstituted C$_{1-2}$ alkyl, or X—R⁸, wherein X is an unbranched C$_{2-4}$ alkylene, and R⁸ is CO$_2$R$^a$, or —CONR$^c$R$^d$. In other aspects, R³ is H, CH$_3$, or —(CH$_2$)$_3$C(=O)OCH$_3$. In other aspects, R³ is H or unsubstituted C$_{1-2}$ alkyl. In other aspects, In other aspects, R³ is H or CH$_3$. In other aspects, R³ is H. In other aspects, R³ is CH$_3$.

In some aspects, R⁴ is H or halo. In other aspects, R⁴ is H.

In some aspects, R⁵ is independently selected from: (i) —(C$_{0-3}$ alkylene)-C$_{3-10}$ cycloalkyl, wherein the cycloalkyl is optionally substituted with from 1 to 4 independently selected R$^f$; (ii) —(C$_{0-3}$ alkylene)-heterocyclyl including from 3 to 10 ring atoms, wherein from 1 to 3 ring atoms are each independently selected from: N(R$^e$), O, and S, wherein the heterocyclyl is optionally substituted with from 1 to 4 R$^f$; (iii) —(C$_{0-3}$ alkylene)-(C$_6$-C$_{10}$ aryl) optionally substituted with from 1 to 4 R$^g$; (iv) —(C$_{0-3}$ alkylene)-heteroaryl including from 5 to 10 ring atoms, wherein from 1 to 4 ring atoms are each independently selected from: N, NH, O, and S, wherein the heteroaryl is optionally substituted with from 1 to 3 R$^g$; (v) C$_{1-6}$ alkyl optionally substituted with from 1-2 independently selected R$^h$; and (iv) —(C$_{0-3}$ alkylene)-C$_{3-10}$ cycloalkenyl, wherein the cycloalkenyl is optionally substituted with from 1 to 2 R$^f$.

In other aspects, R⁵ is independently selected from: (i) C$_{3-6}$ cycloalkyl optionally substituted with from 1 to 2 independently selected R$^f$; (ii) phenyl optionally substituted with from 1 to 3 R$^g$; (iii) heteroaryl including from 5 to 6 ring atoms, wherein from 1 to 3 ring atoms are each independently selected from: N, NH, O, and S, wherein the heteroaryl is optionally substituted with from 1 to 3 R$^g$; (iv) C$_{1-6}$ alkyl optionally substituted with from 1 to 2 independently selected R$^h$; and (v) C$_{5-6}$ cycloalkenyl optionally substituted with from 1 to 2 R$^f$.

In other aspects, R⁵ is independently CH$_3$, cyclopentyl, cyclopentenyl, phenyl, pyrazol-1-yl, or pyrazol-3-yl. In other aspects, R⁵ is CH$_3$. In other aspects, R⁵ is cyclopentyl or cyclopentenyl. In other aspects, R⁵ is cyclopentyl. In other aspects, R⁵ is cyclopentenyl. In other aspects, R⁵ is phenyl. In other aspects, R⁵ is pyrazolyl. In other aspects, R⁵ is pyrazol-1-yl, or pyrazol-3-yl. In other aspects, R⁵ is pyrazol-1-yl. In other aspects, R⁵ is pyrazol-3-yl.

In some aspects, (i) C$_{1-6}$ alkyl optionally substituted with from 1 to 2 R$^h$; (ii) —(C$_{0-3}$ alkylene)-C$_{3-10}$ cycloalkyl, wherein the cycloalkyl is optionally substituted with from 1 to 2 R$^f$; (iii) —(C$_{0-3}$ alkylene)-phenyl optionally substituted with from 1 to 4 independently selected R$^g$; or (v) —(C$_{0-3}$ alkylene)-heteroaryl including from 5 to 10 ring atoms, wherein from 1 to 4 ring atoms are each independently selected from N, N(R$^e$), O, and S, wherein the heteroaryl is optionally substituted with from 1 to 3 independently selected R$^g$. In other aspects, R$^a$ is (i) C$_{1-6}$ alkyl optionally substituted with from 1 to 2 R$^h$; (ii) —(C$_{0-3}$ alkylene)-C$_{3-10}$ cycloalkyl, wherein the cycloalkyl is optionally substituted with from 1 to 2 R$^f$. In other aspects, R$^a$ is H, C$_{1-4}$ alkyl optionally substituted with OH, C$_{3-6}$ cycloalkyl, phenyl, or heteroaryl including from 5 to 6 ring atoms, wherein from 1 to 4 ring atoms are each independently selected from N, N(R$^e$), O, and S. In other aspects, R$^a$ is C$_{1-6}$ alkyl optionally substituted with from 1 to 2 R$^h$. In other aspects, R$^a$ is C$_{1-6}$ alkyl. In other aspects, R$^a$ is —(C$_{0-3}$ alkylene)-C$_{3-10}$ cycloalkyl, wherein the cycloalkyl is optionally substituted with from 1 to 2 R$^f$. In other aspects, R$^a$ is —C$_{3-10}$ cycloalkyl optionally substituted with from 1 to 2 R$^f$. In other aspects, R$^a$ is —C$_{3-6}$ cycloalkyl. In other aspects, R$^a$ is C$_{1-4}$ alkyl or C$_{3-6}$ cycloalkyl. In other aspects, R$^a$ is CH$_3$, CH$_2$CH$_3$, CH$_2$(CH$_3$)$_2$, or cyclopropyl. In other aspects, R$^a$ is CH$_3$, CH$_2$CH$_3$, or CH$_2$(CH$_3$)$_2$. In other aspects, R$^a$ is cyclopropyl.

In another aspect, the compound of the invention is selected from:

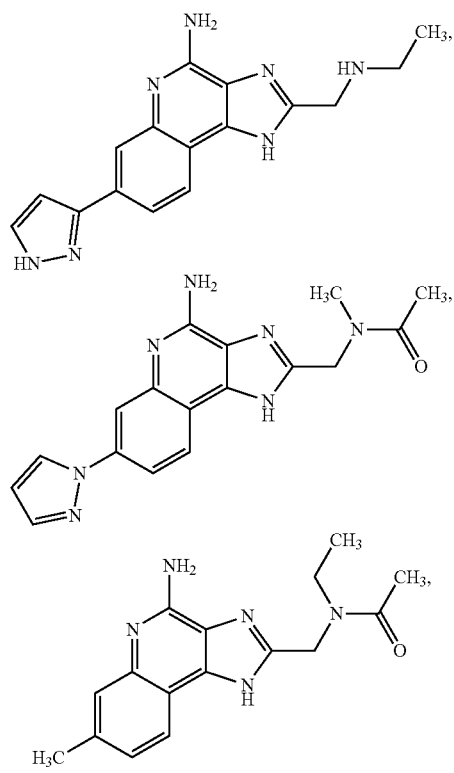

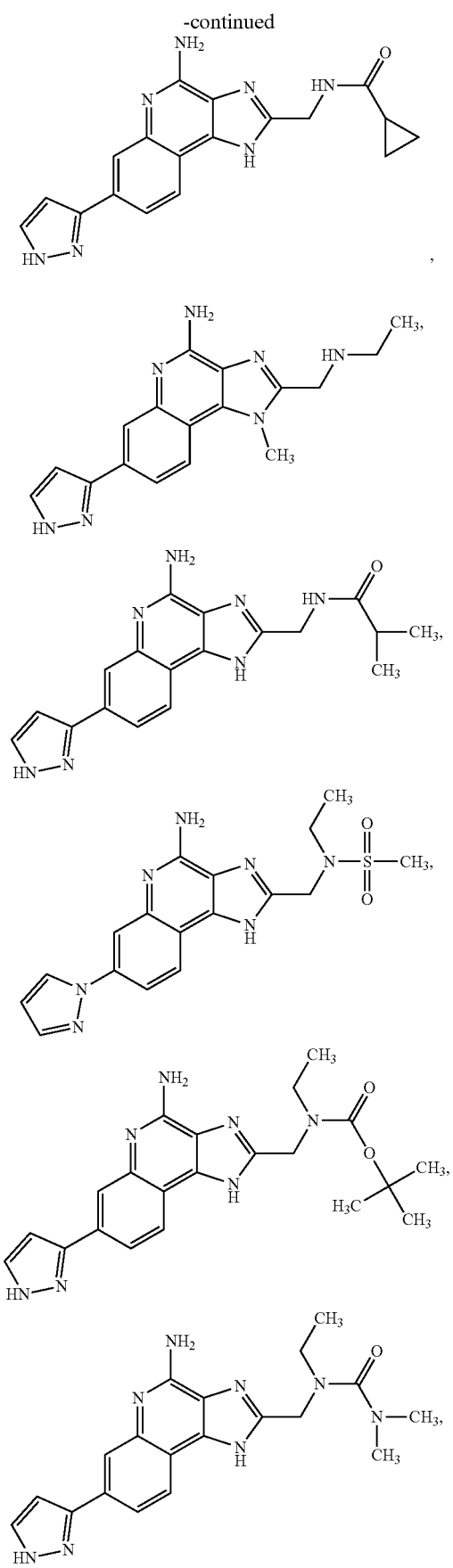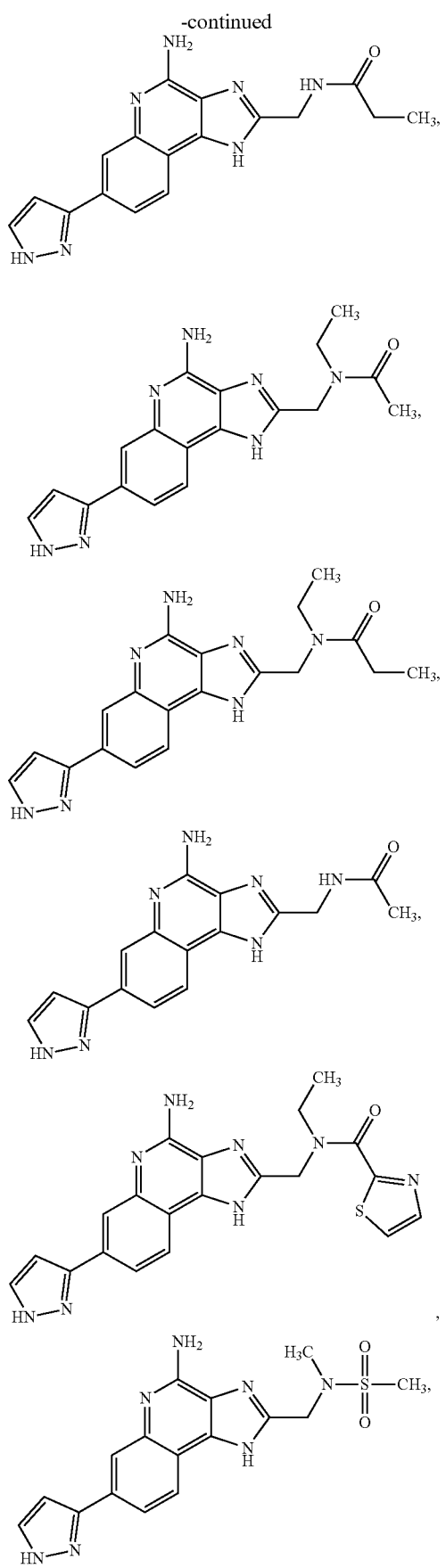

33
-continued
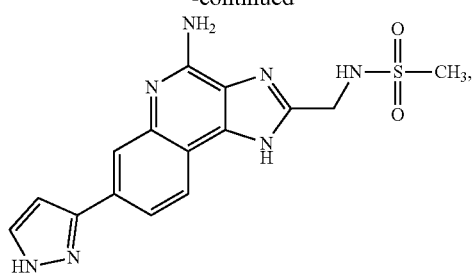
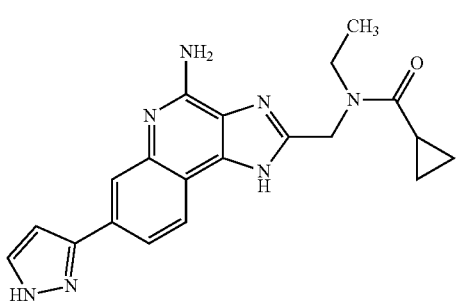
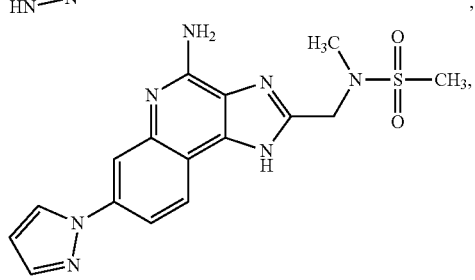
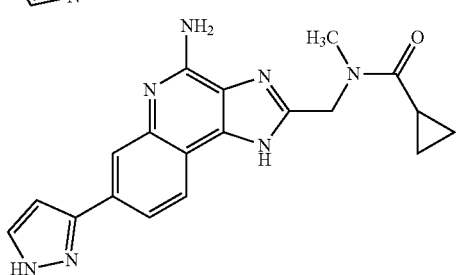
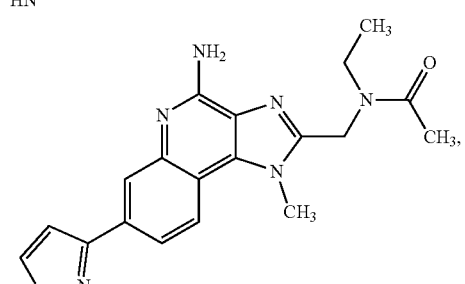
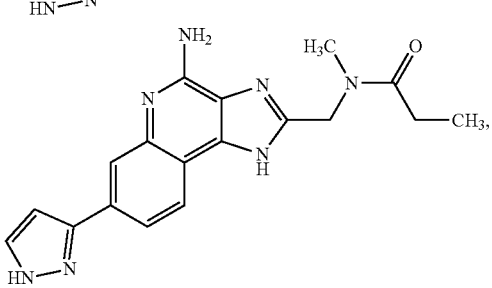
34
-continued
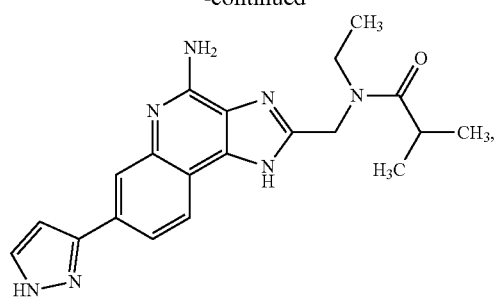
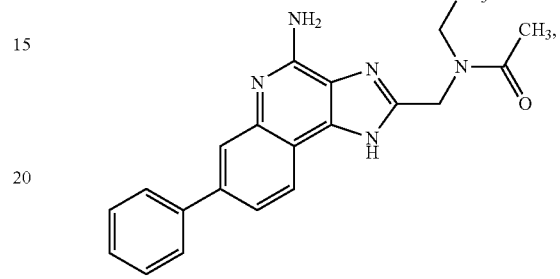
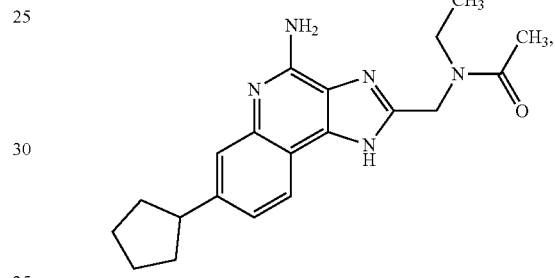
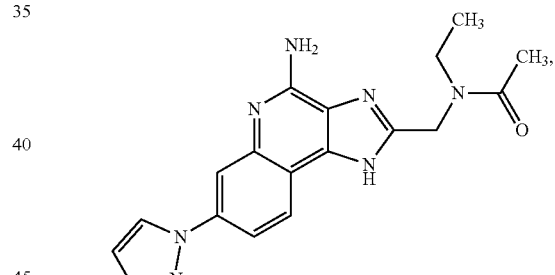
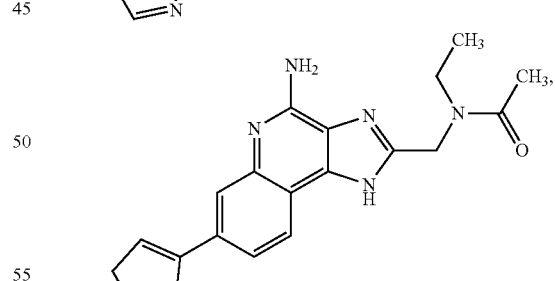
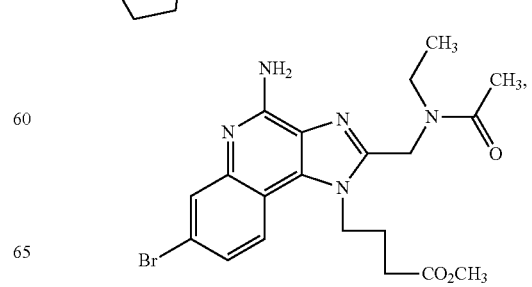

-continued or a pharmaceutically acceptable salt thereof.

In another aspect, the compound of the invention is selected from:

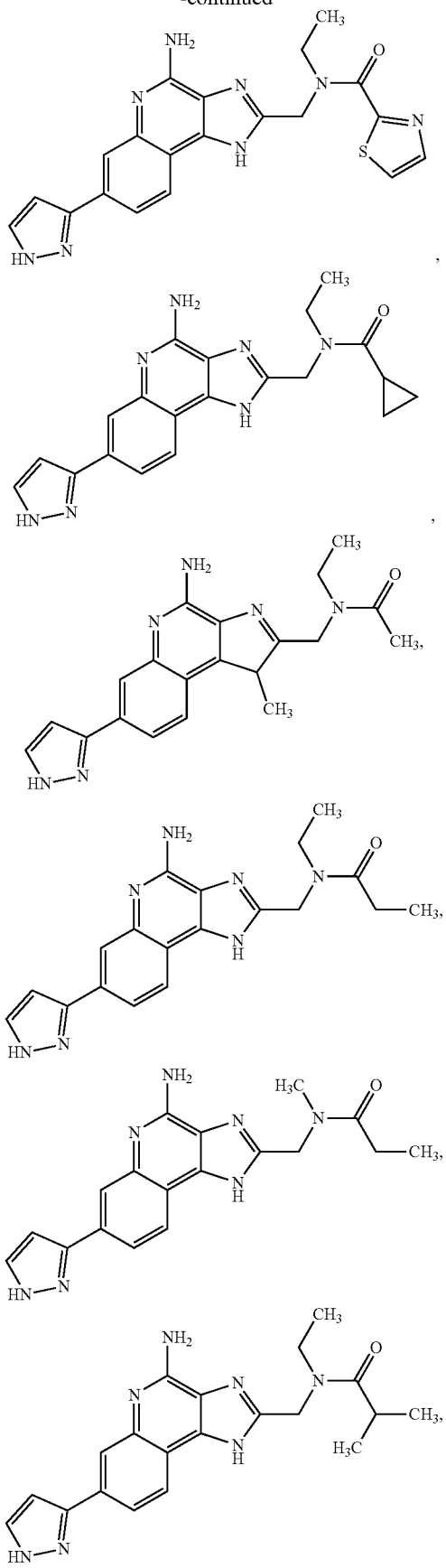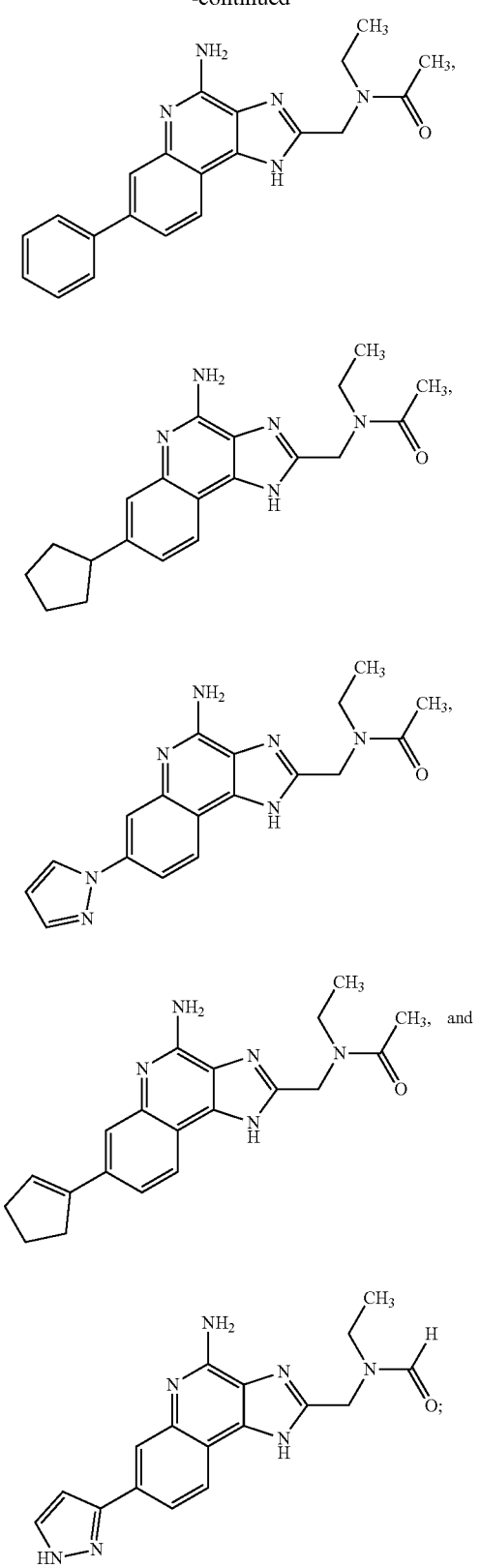
or a pharmaceutically acceptable salt thereof.
In another aspect, the compound of the invention is selected from:

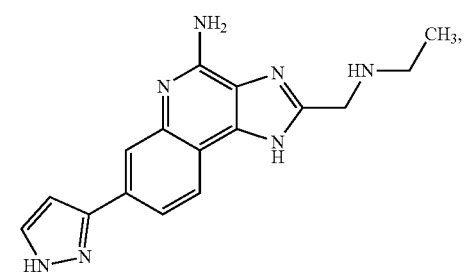
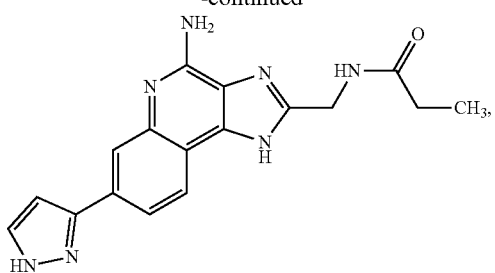
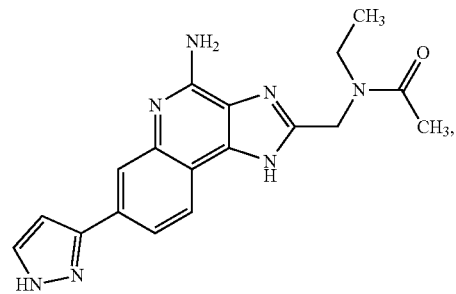
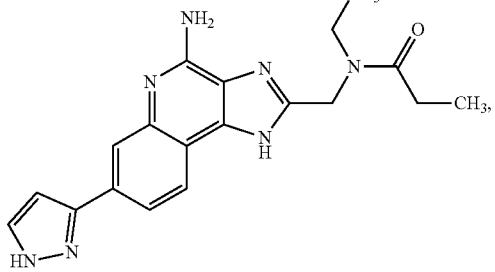
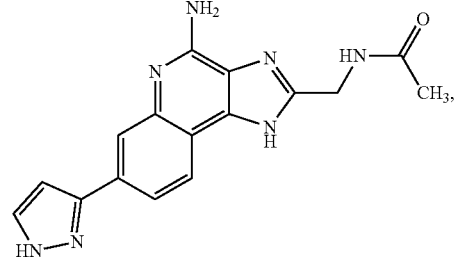
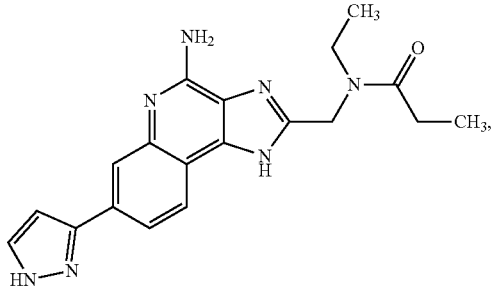
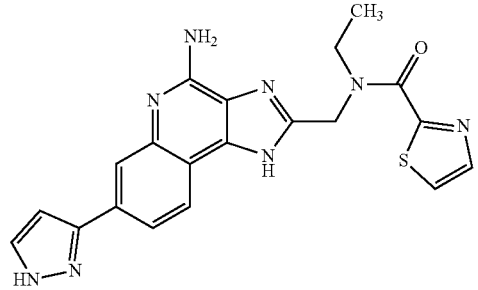

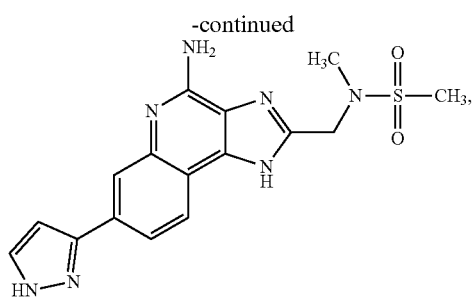
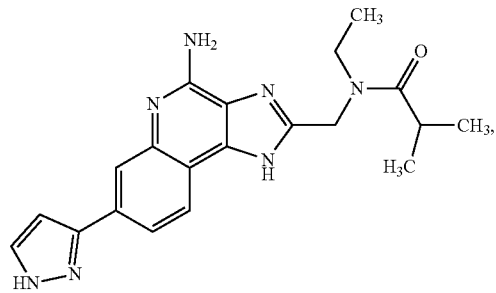
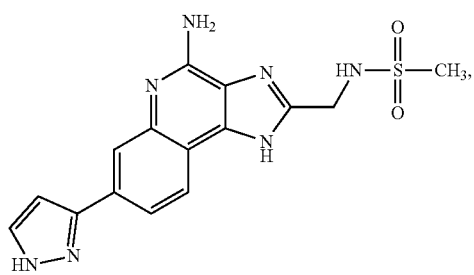
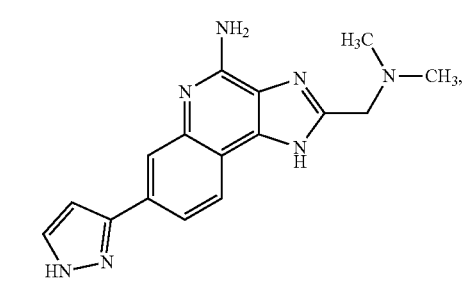
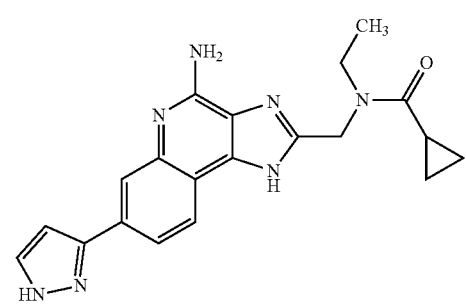
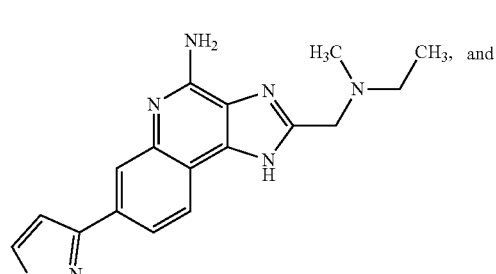
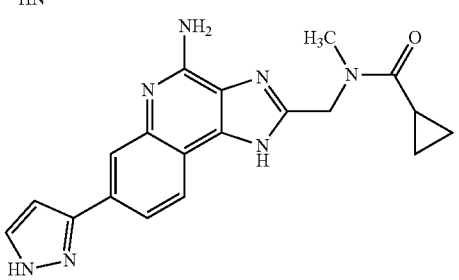
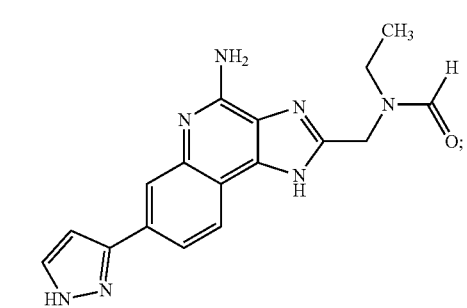
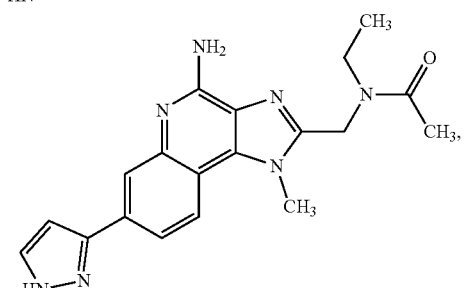
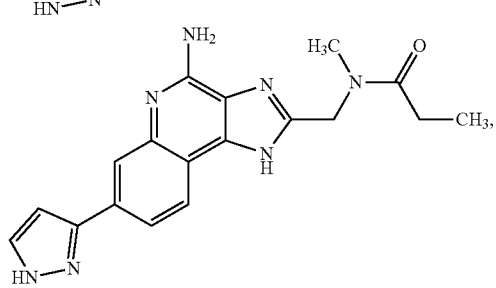
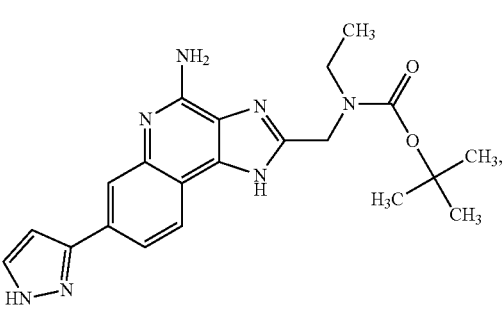
or a pharmaceutically acceptable salt thereof.
In another aspect, the compound of the invention is selected from:

-continued
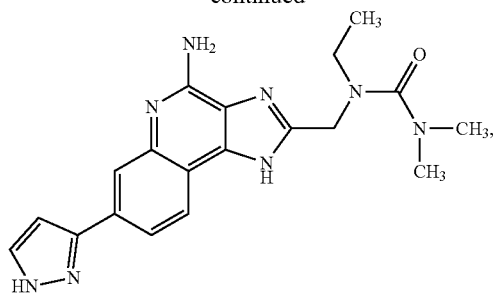
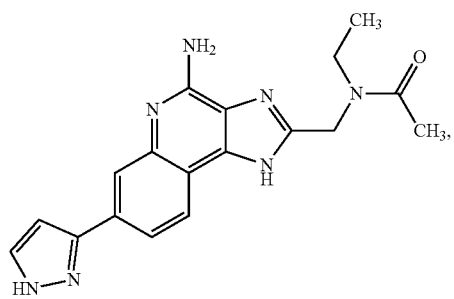 [SMILES: CCN(Cc1nc2c(N)nc3cc(-c4cc[nH]n4)ccc3c2[nH]1)C(C)=O]
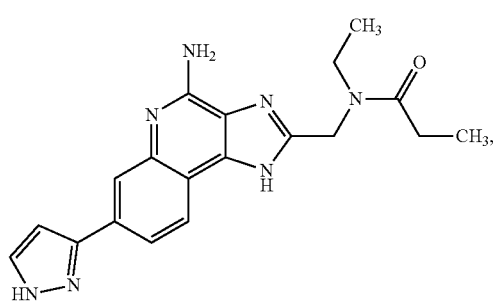
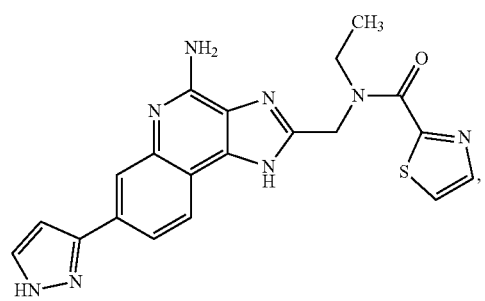
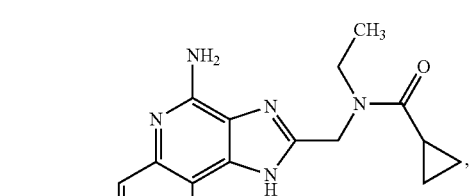
-continued
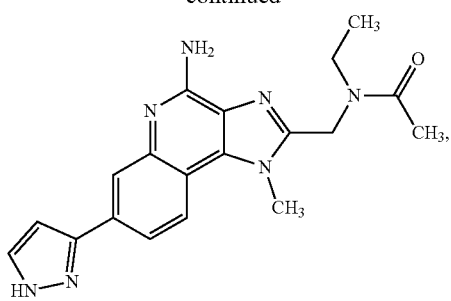
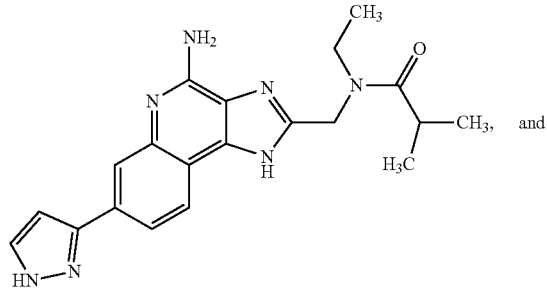 and
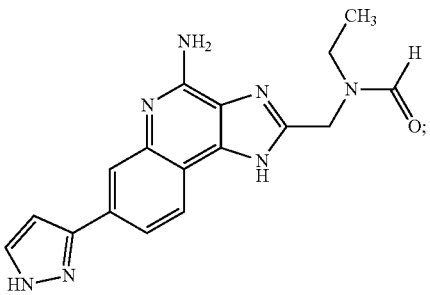
or a pharmaceutically acceptable salt thereof.
In another aspect, the compound of the invention is selected from:
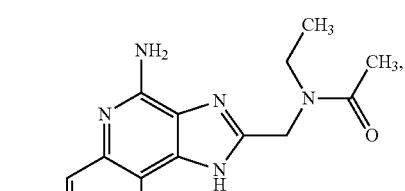
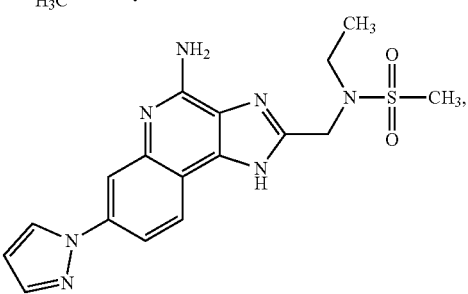

45
-continued
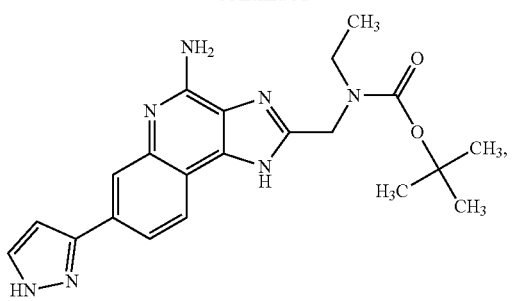
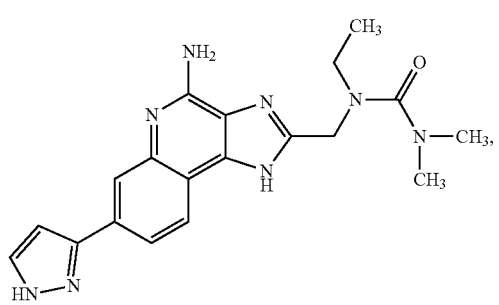
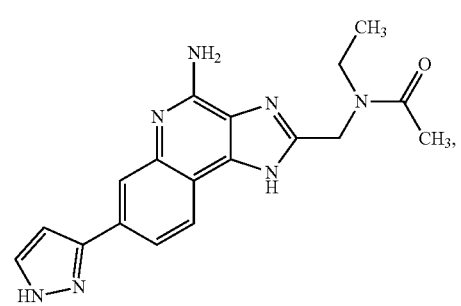
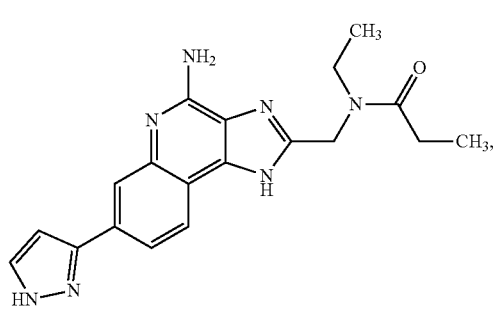
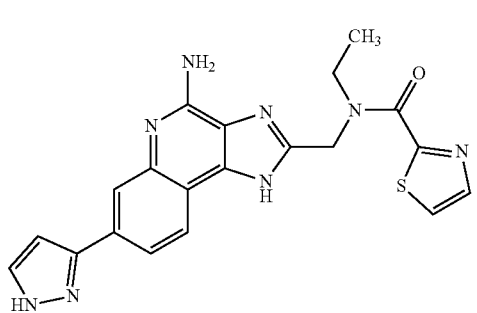
,
46
-continued
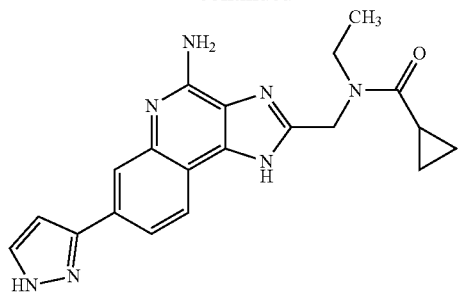
,
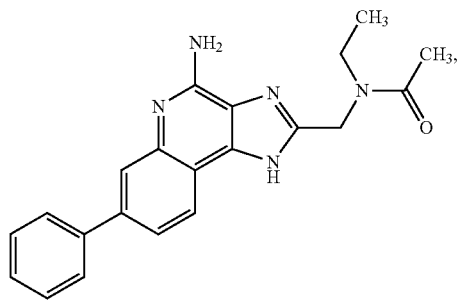
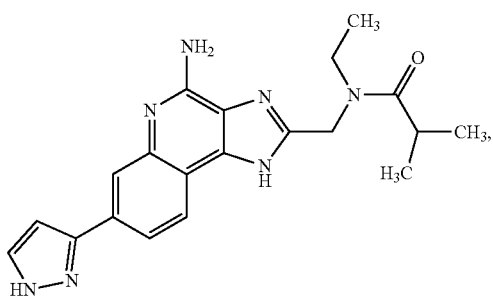
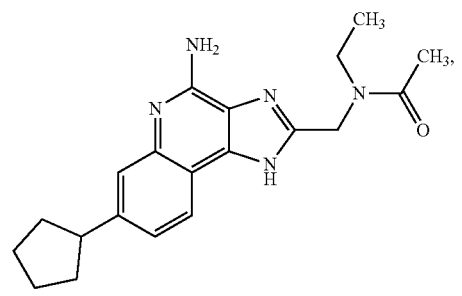
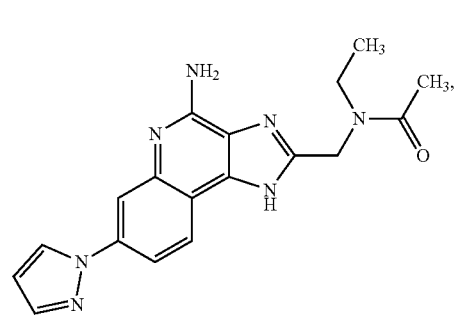

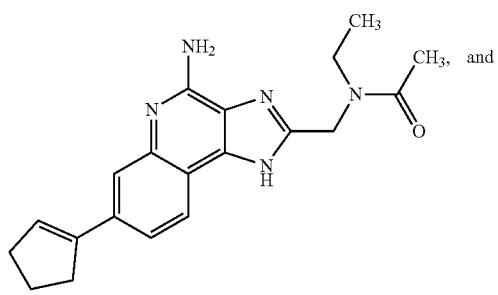
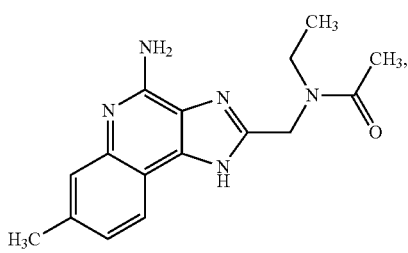
or a pharmaceutically acceptable salt thereof.
In another aspect, the compound of the invention is selected from:
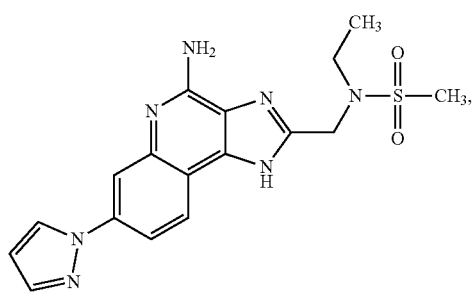
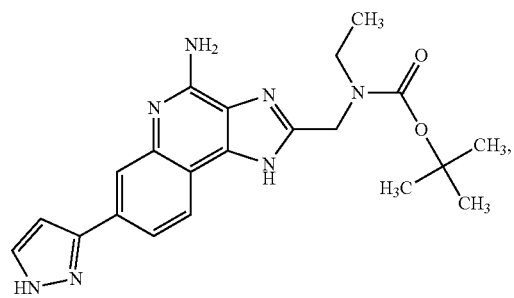
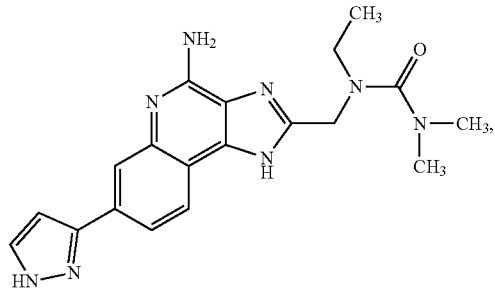
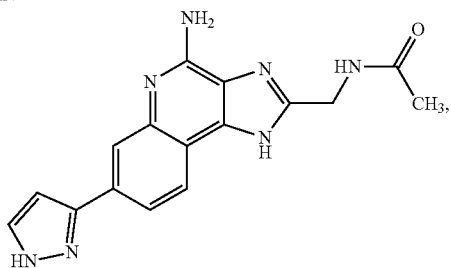
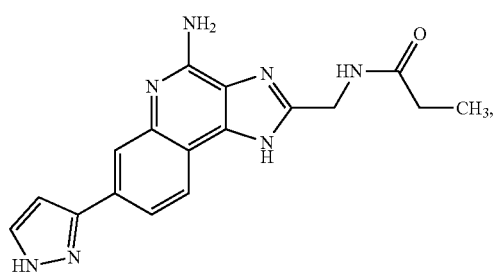
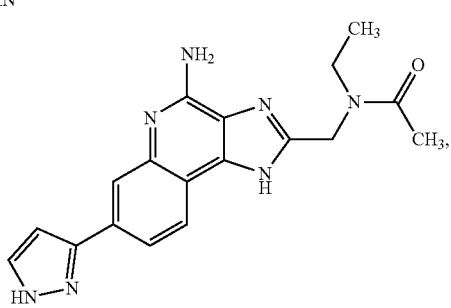
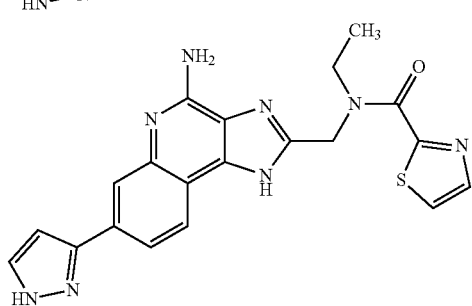
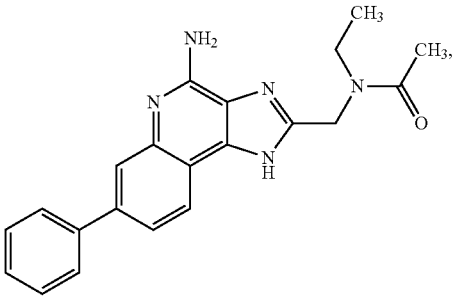

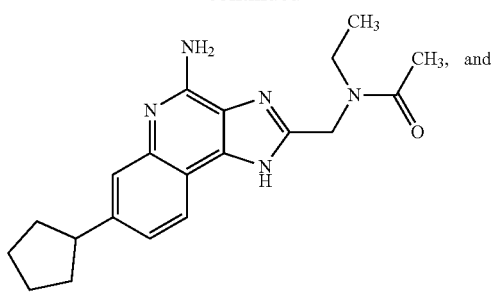
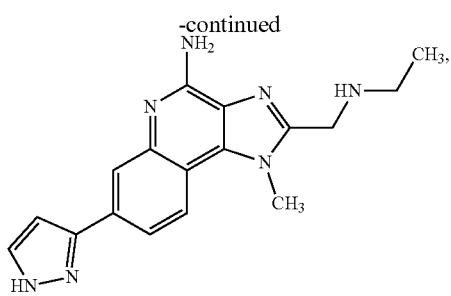
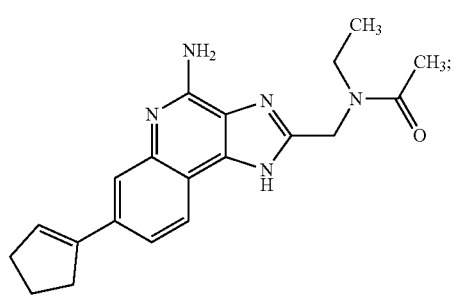
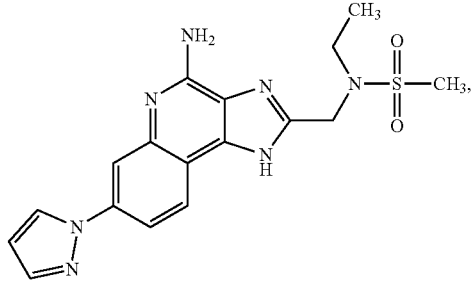
or a pharmaceutically acceptable salt thereof.
In another aspect, the compound of the invention is selected from:
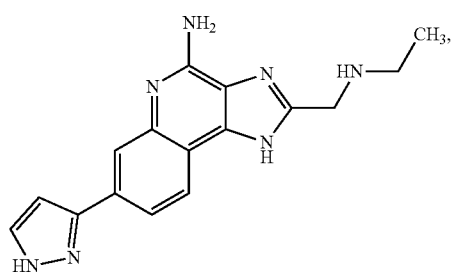
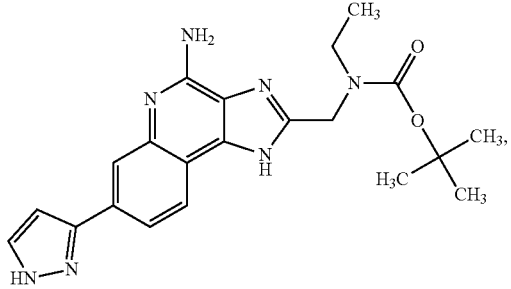
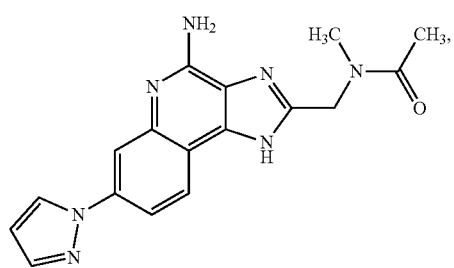
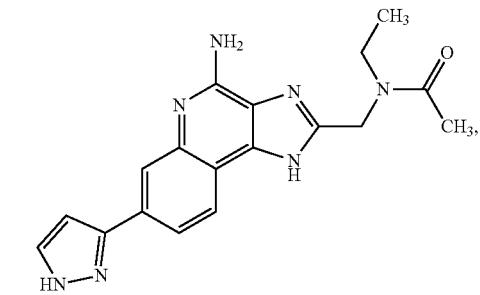
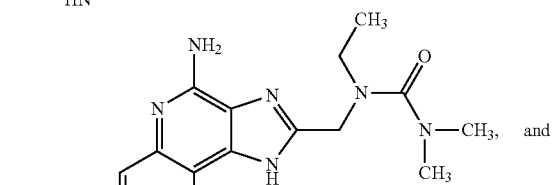
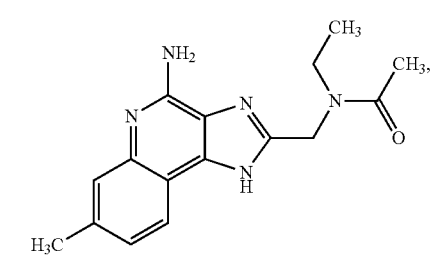
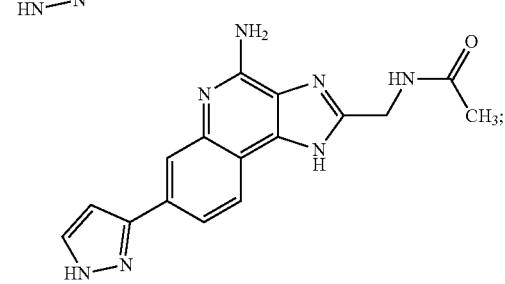
or a pharmaceutically acceptable salt thereof.

In another aspect, the compound of the invention is selected from:
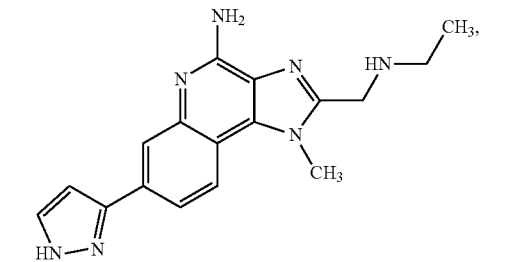
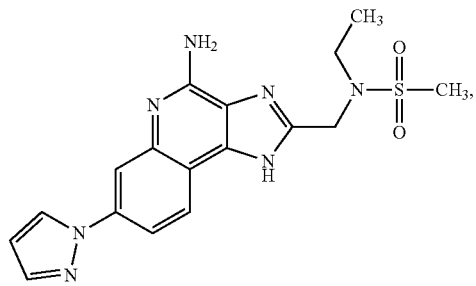
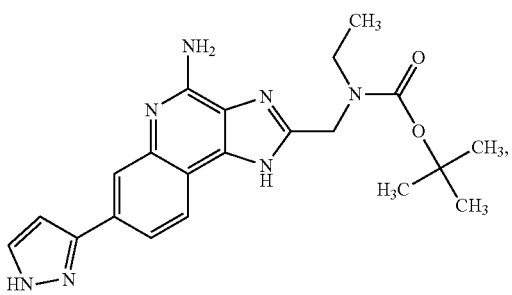
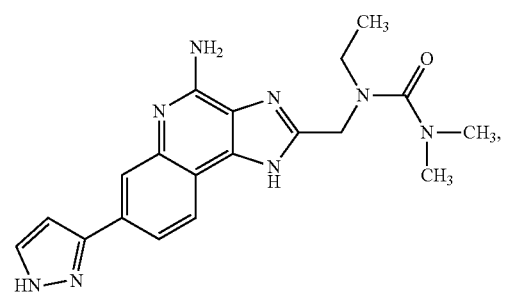
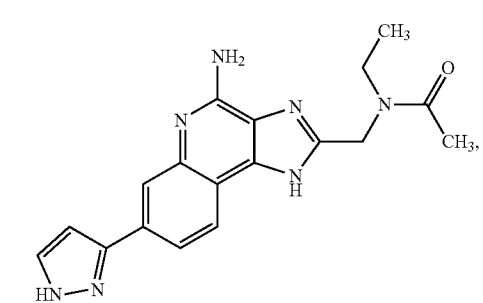
-continued
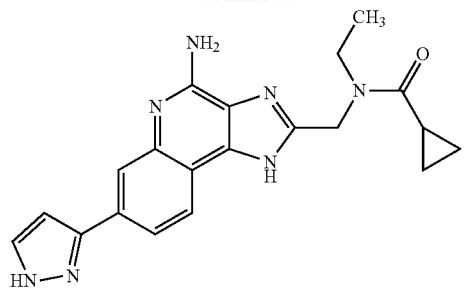
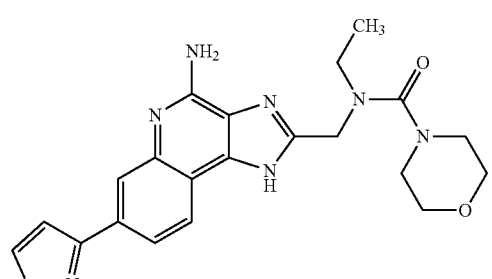
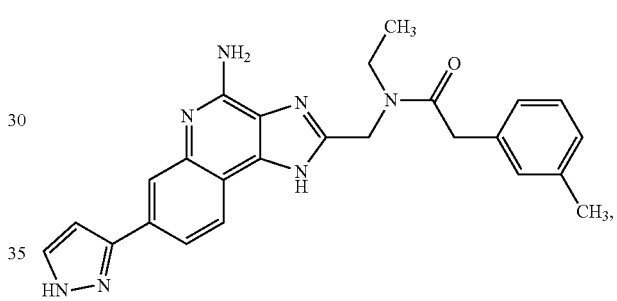
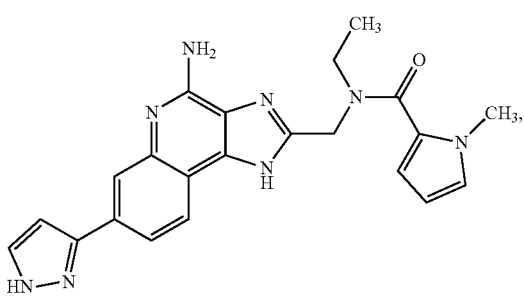
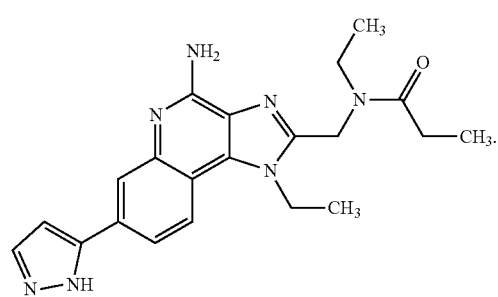
or a pharmaceutically acceptable salt thereof.
In another aspect, the compound of the invention is selected from:

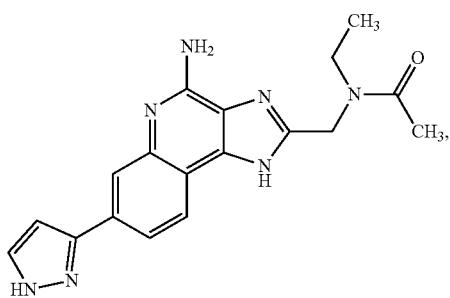
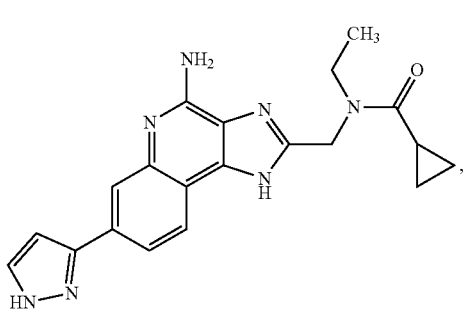 [SMILES: CCN(Cc1nc2c(N)nc3cc(-c4cc[nH]n4)ccc3c2[nH]1)C(=O)C1CC1]
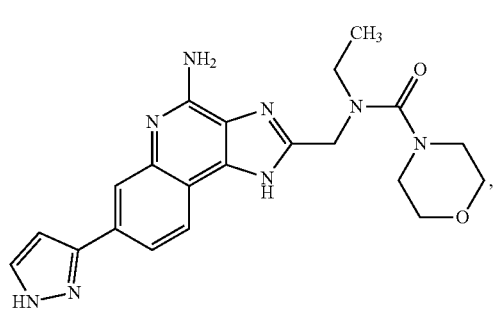 [SMILES: CCN(Cc1nc2c(N)nc3cc(-c4cc[nH]n4)ccc3c2[nH]1)C(=O)N1CCOCC1]
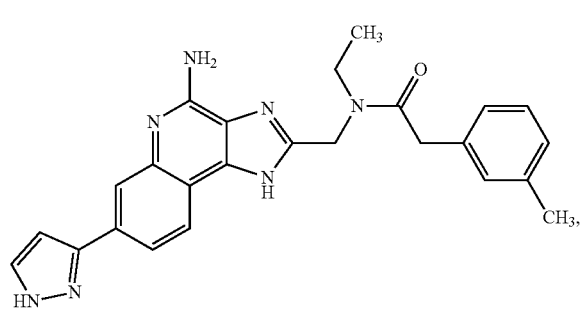 [SMILES: CCN(Cc1nc2c(N)nc3cc(-c4cc[nH]n4)ccc3c2[nH]1)C(=O)Cc1cccc(C)c1]
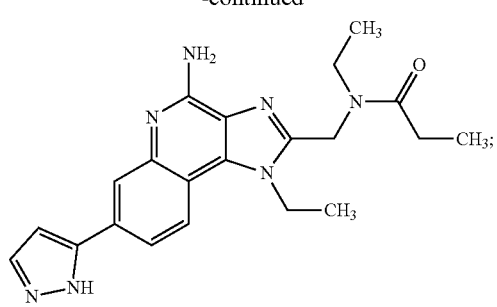
or a pharmaceutically acceptable salt thereof.
In another aspect, the compound of the invention is
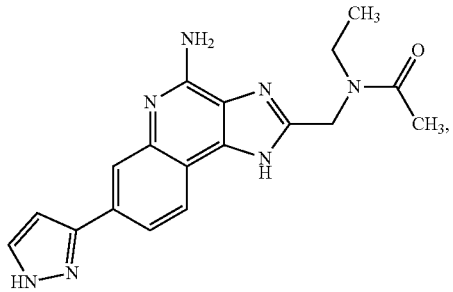
or a pharmaceutically acceptable salt thereof.
In another aspect, the compound of the invention is
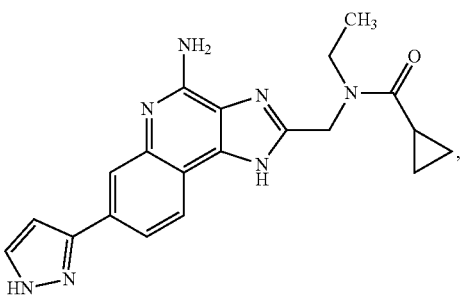
or a pharmaceutically acceptable salt thereof.
In another aspect, the compound of the invention is
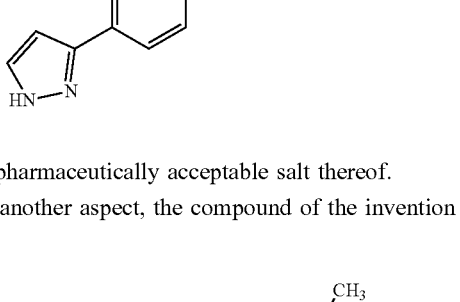, and
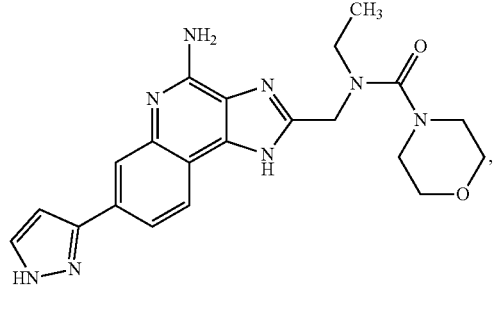
or a pharmaceutically acceptable salt thereof.

In another aspect, the compound of the invention is

[Chemical structure: 4-amino-imidazoquinoline with pyrazole substituent, bearing CH2-N(ethyl)-C(O)-CH2-(3-methylphenyl) side chain]

or a pharmaceutically acceptable salt thereof.

In another aspect, the compound of the invention is

[Chemical structure: 4-amino-imidazoquinoline with pyrazole substituent, bearing CH2-N(ethyl)-C(O)-(N-methylpyrrole) side chain]

or a pharmaceutically acceptable salt thereof.

In another aspect, the compound of the invention is

[Chemical structure: 4-amino-imidazoquinoline (N1-methyl) with pyrazole substituent, bearing CH2-N(ethyl)-C(O)-CH2CH3 side chain]

or a pharmaceutically acceptable salt thereof.

In another aspect, the invention provides a compound of Formula (I) or a pharmaceutically acceptable salt thereof, wherein:

$R^1$ and $R^2$, together with the nitrogen atom to which each is attached forms a saturated or unsaturated ring including from 5 to 6 ring atoms, wherein the ring includes:

(a) from 3 to 5 ring carbon atoms, each of which is optionally substituted with from 1 to 2 independently selected $R^f$; and (b) from 0 to 1 ring heteroatom (in addition to the nitrogen atom attached to $R^1$ and $R^2$), which is independently selected from: N, N($R^e$), O, and S; and provided that one of the 5 to 6 ring atoms is —C(O)—;

$R^3$ is:
(i) H;
(ii) unsubstituted $C_{1-2}$ alkyl;
(iii) X—$R^8$, wherein X is an unbranched $C_{1-6}$ alkylene, and $R^8$ is —OH, $C_{1-4}$ alkoxy, —$C_{1-4}$ haloalkoxy, $CO_2R^a$, —CONR$^c$R$^d$, cyano, or —NR$^c$R$^{d'}$;

(iv) ($C_{1-3}$ alkylene)-($C_6$-$C_{10}$ aryl), wherein the aryl is optionally substituted with from 1-3 substituents independently selected from $C_{1-6}$ alkyl, $C_{1-4}$ haloalkyl, $C_{1-4}$ alkoxy, and $C_{1-4}$ haloalkoxy; or (v) ($C_{1-3}$ alkylene)heteroaryl including from 5-6 ring atoms, wherein from 1-4 ring atoms are each independently selected from N, N($R^e$), O, and S, and wherein the heteroaryl is optionally substituted with from 1-3 substituents independently selected from $C_{1-6}$ alkyl, $C_{1-4}$ haloalkyl, $C_{1-4}$ alkoxy, and $C_{1-4}$ haloalkoxy;

$R^4$ and $R^5$ are each independently selected from:
(i) H;
(ii) halo;
(iv) —($C_{0-3}$ alkylene)-$C_{3-10}$ cycloalkyl, wherein the cycloalkyl is optionally substituted with from 1 to 4 independently selected $R^f$;
(v) —($C_{0-3}$ alkylene)-heterocyclyl including from 3 to 10 ring atoms, wherein from 1 to 3 ring atoms are each independently selected from: N($R^e$), O, and S, wherein the heterocyclyl is optionally substituted with from 1 to 4 $R^f$;
(vi) —($C_{0-3}$ alkylene)-($C_6$-$C_{10}$ aryl) optionally substituted with from 1 to 4 $R^g$;
(vii) —($C_{0-3}$ alkylene)-heteroaryl including from 5 to 10 ring atoms, wherein from 1 to 4 ring atoms are each independently selected from: N, NH, O, and S, wherein the heteroaryl is optionally substituted with from 1 to 3 $R^g$;
(viii) $C_{1-6}$ alkyl optionally substituted with from 1-2 independently selected $R^h$; and
(ix) —($C_{0-3}$ alkylene)-$C_{4-10}$ cycloalkenyl, wherein the cycloalkenyl is optionally substituted with from 1 to 2 $R^f$;

each of $R^6$ and $R^7$ is independently H or unsubstituted $C_{1-2}$ alkyl;

$R^a$ is:
(i) $C_{1-6}$ alkyl optionally substituted with from 1 to 2 $R^h$; or
(ii) —($C_{0-3}$ alkylene)-$C_{3-10}$ cycloalkyl, wherein the cycloalkyl is optionally substituted with from 1 to 2 $R^f$;

$R^b$ is $C_{1-6}$ alkyl;

each occurrence of $R^c$ and $R^d$ is independently H or $C_{1-4}$ alkyl;

each occurrence of $R^e$ is independently H or $C_{1-4}$ alkyl;

each occurrence of $R^f$ is independently $C_{1-6}$ alkyl, $C_{1-4}$ haloalkyl, —OH, F, Cl, $C_{1-4}$ alkoxy, $C_{1-4}$ haloalkoxy, cyano, or phenyl optionally substituted with from 1 to 4 $R^g$;

each occurrence of $R^g$ is independently halo, cyano, $C_{1-6}$ alkyl, $C_{1-4}$ haloalkyl, $C_{1-4}$ alkoxy, or $C_{1-4}$ haloalkoxy; and each occurrence of $R^h$ is independently —OH, F, $C_{1-4}$ alkoxy, $C_{1-4}$ haloalkoxy, or cyano.

In another aspect, the invention provides a compound of Formula (I) or a pharmaceutically acceptable salt thereof, wherein:

$R^1$ and $R^2$, together with the nitrogen atom to which each is attached forms a saturated or unsaturated ring including from 5 to 6 ring atoms, wherein the ring includes:

(a) from 3 to 5 ring carbon atoms, each of which is optionally substituted with from 1 to 2 independently selected $R^f$, and (b) from 0 to 1 ring heteroatom (in addition to the nitrogen atom attached to $R^1$ and $R^2$), which is independently selected from: N, N($R^e$), O, and S; and provided that one of the ring atoms is —C(O)—;

$R^3$ is: H, unsubstituted $C_{1-2}$ alkyl, X—$R^8$, wherein X is an unbranched $C_{1-6}$ alkylene, and $R^8$ is $CO_2R^a$, or —CONR$^c$R$^d$;

R⁴ is independently H or halo;
R⁵ is independently selected from:
(i) H;
(ii) halo;
(iii) $C_{3-8}$ cycloalkyl optionally substituted with from 1 to 2 independently selected $R^f$;
(iv) phenyl optionally substituted with from 1 to 3 $R^g$; and
(v) heteroaryl including from 5 to 9 ring atoms, wherein from 1 to 3 ring atoms are each independently selected from: N, N($R^e$), O, and S, wherein the heteroaryl is optionally substituted with from 1 to 3 $R^g$;
(vi) $C_{1-6}$ alkyl optionally substituted with from 1 to 2 independently selected $R^h$; and
(vii) $C_{5-6}$ cycloalkenyl optionally substituted with from 1 to 2 $R^f$.

In another aspect, the invention provides a compound of Formula (I) or a pharmaceutically acceptable salt thereof, wherein:
$R^1$ and $R^2$, together with the nitrogen atom to which each is attached forms a saturated or unsaturated ring including from 5 to 6 ring atoms, wherein the ring includes:
(a) from 3 to 5 ring carbon atoms, each of which is optionally substituted with from 1 to 2 independently selected $R^f$, and
(b) from 0 to 1 ring heteroatom (in addition to the nitrogen atom attached to $R^1$ and $R^2$), which is independently selected from: N, N($R^e$), and O; and
provided that one of the ring atoms is —C(O)—;
$R^3$ is H, $C_{1-2}$ alkyl, or X—$R^8$, wherein X is an unbranched $C_{2-6}$ alkylene, and $R^8$ is $CO_2(C_{1-4}$ alkyl);
$R^4$ is H;
$R^5$ is independently selected from:
(i) halo;
(ii) $C_{3-7}$ cycloalkyl optionally substituted with from 1 to 2 independently selected $R^f$;
(iii) phenyl optionally substituted with from 1 to 3 $R^g$;
(iv) heteroaryl including from 5 to 6 ring atoms, wherein from 1 to 3 ring atoms are each independently selected from: N, NH, O, and S, wherein the heteroaryl is optionally substituted with from 1 to 3 $R^g$;
each occurrence of $R^f$ is independently $C_{1-6}$ alkyl, $C_{1-4}$ haloalkyl, —OH, F, Cl, $C_{1-4}$ alkoxy, $C_{1-4}$ haloalkoxy, cyano, or phenyl.

In another aspect, the invention provides a compound of Formula (I) or a pharmaceutically acceptable salt thereof, wherein:
$R^1$ and $R^2$, together with the nitrogen atom to which each is attached forms $R^3$ is H, unsubstituted $C_{1-2}$ alkyl, or X—$R^8$, wherein X is an unbranched $C_{2-4}$ alkylene, and $R^8$ is $CO_2(C_{1-4}$ alkyl);

$R^4$ is H;
$R^5$ is independently Br, $C_{6-7}$ cycloalkyl, (phenyl optionally substituted with one to two substituents selected from halo, $C_{1-2}$ alkyl, $C_{1-2}$ alkoxy, and CN) or (a heteroaryl selected from pyrazolyl, theinyl and pyridyl, wherein each of the heteroaryl is optionally substituted with one to two substituents selected from halo, $C_{1-2}$ alkyl, $C_{1-2}$ alkoxy, and CN);
$R^6$ is H or unsubstituted $C_{1-2}$ alkyl; and
$R^7$ is H.

In another aspect, the invention provides a compound of Formula (I) or a pharmaceutically acceptable salt thereof, wherein:
$R^1$ and $R^2$, together with the nitrogen atom to which each is attached forms $R^3$ is H;
$R^4$ is H;
$R^5$ is independently Br, cyclohexyl, pyrazol-1-yl, pyrazol-3-yl, thien-2-yl, thien-3-yl, (phenyl optionally substituted with one substituent selected from F, Cl, $CH_3$, $OCH_3$, and CN), or (pyrid-3-yl optionally substituted with one substituent selected from F and Cl);
$R^6$ is H or $CH_3$; and
$R^7$ is H.

In another aspect, the invention provides a compound of Formula (I) or a pharmaceutically acceptable salt thereof, wherein:
$R^1$ and $R^2$, together with the nitrogen atom to which each is attached forms $R^3$ is independently H, $CH_3$, $CH_2CH_3$ or $CH_2CH_2OH$;
$R^4$ is H;
$R^5$ is independently cyclohexyl, pyrazol-1-yl, pyrazol-3-yl, thien-2-yl, thien-3-yl, (phenyl optionally substituted with one substituent selected from F, Cl, $CH_3$, $OCH_3$, and CN), or (pyrid-3-yl optionally substituted with one substituent selected from F and Cl);
$R^6$ is H; and
$R^7$ is H.

In another aspect, the compound of the invention is selected from:

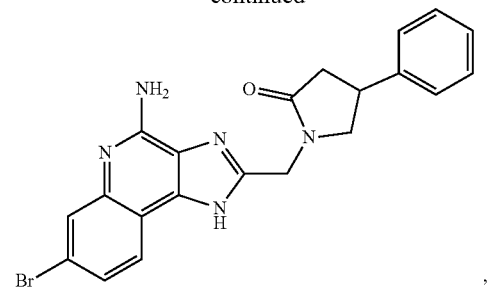
,
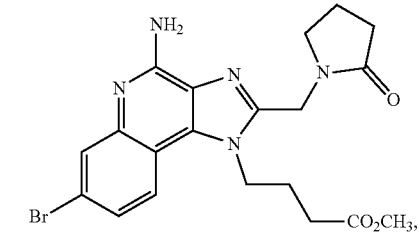
,
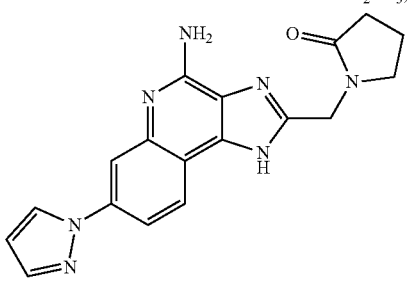
,
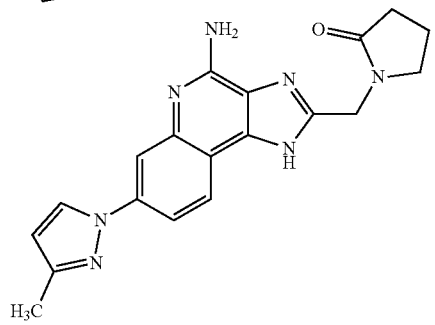
,
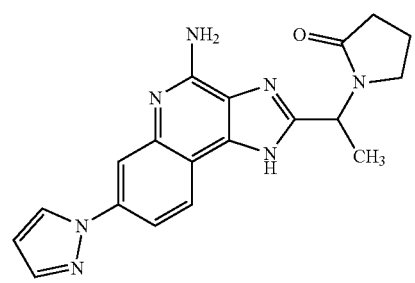
,
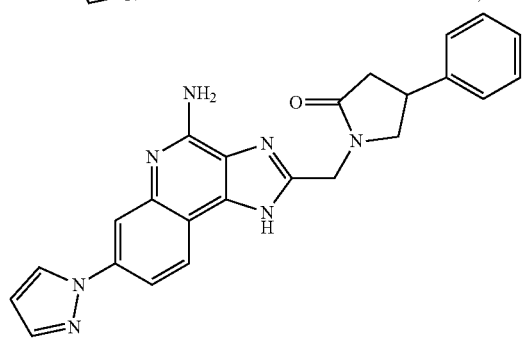
,
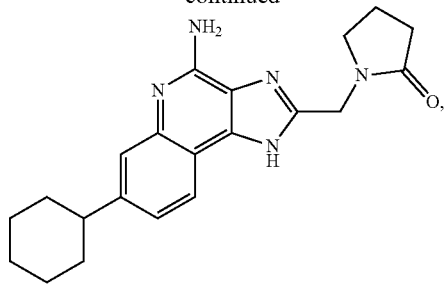
,
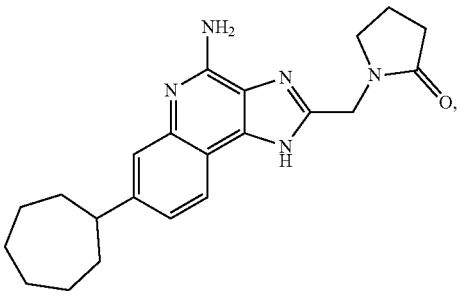
,
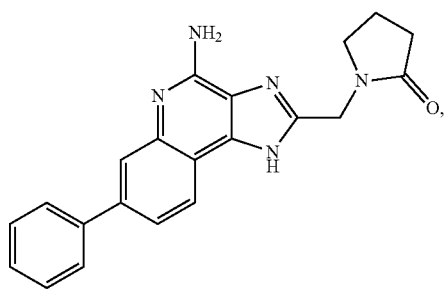
,
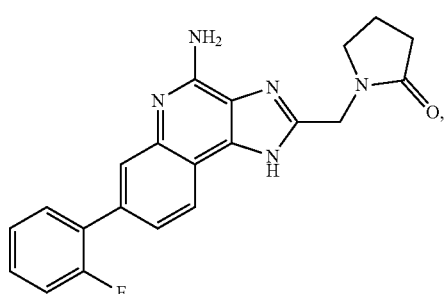
,
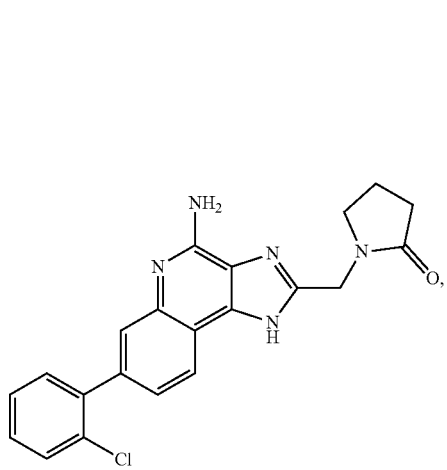
,

61
-continued
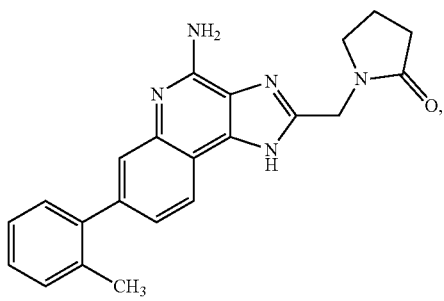
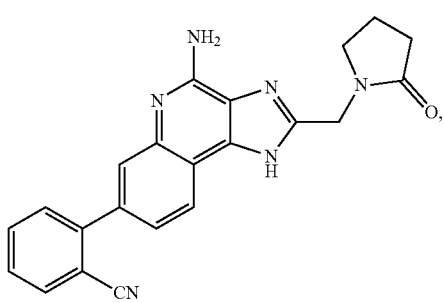
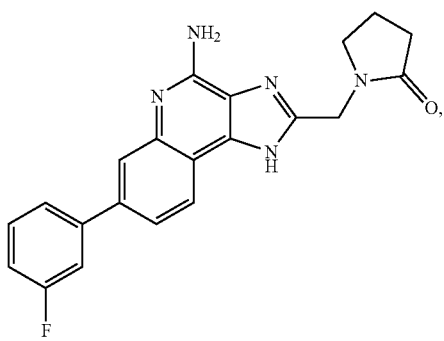
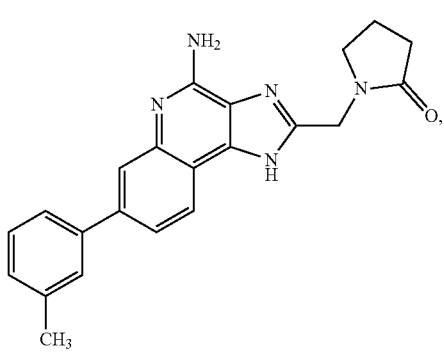
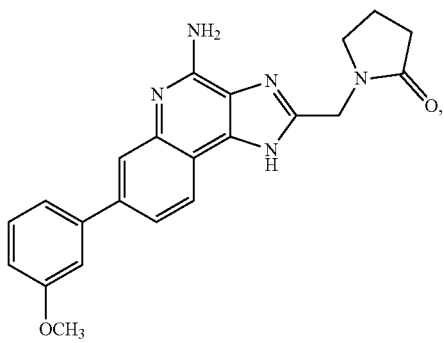
62
-continued
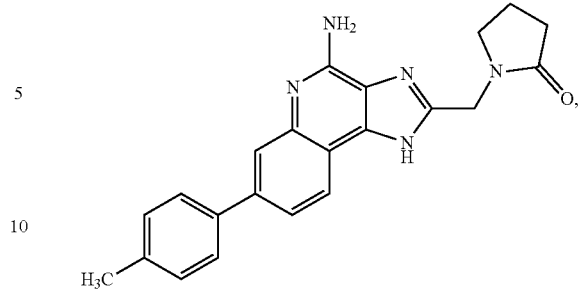
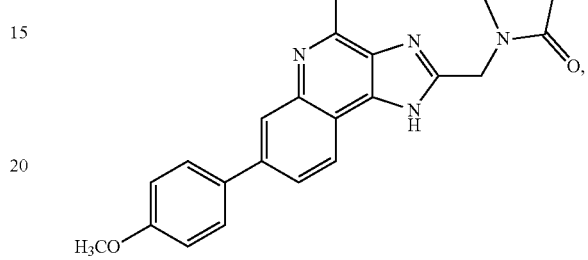
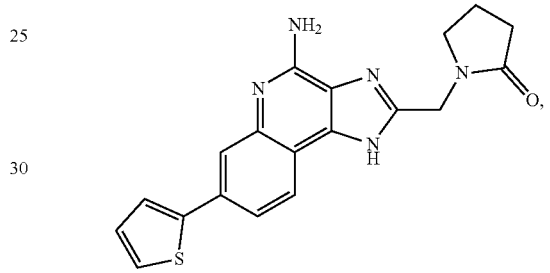
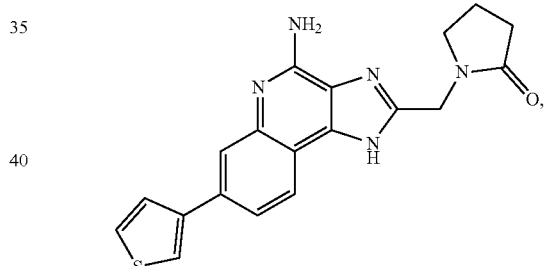
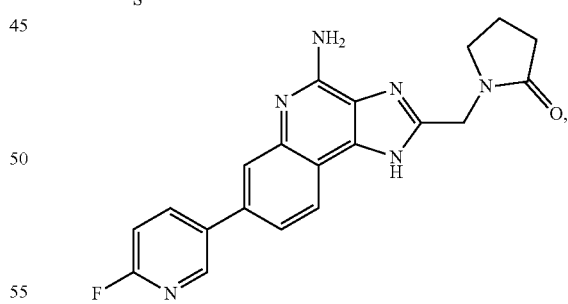
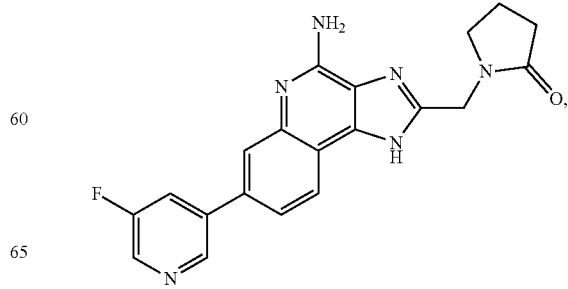

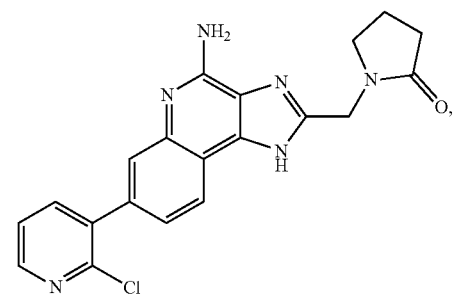
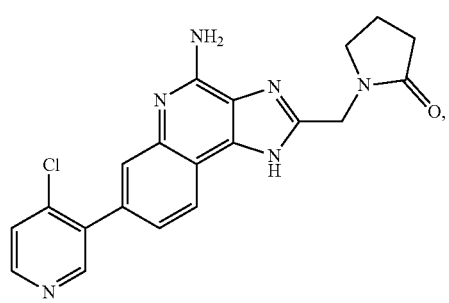
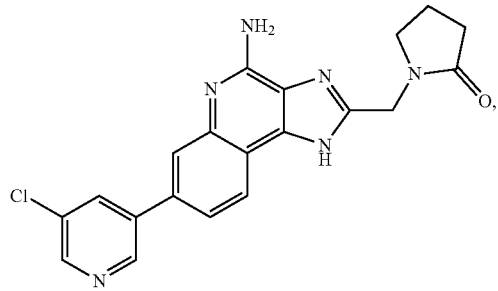
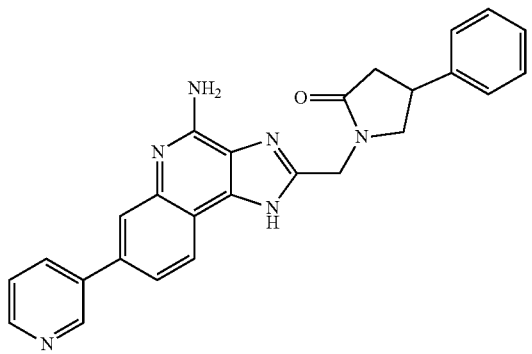
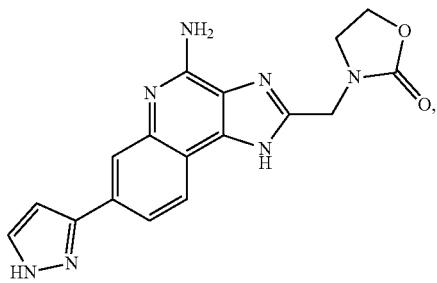
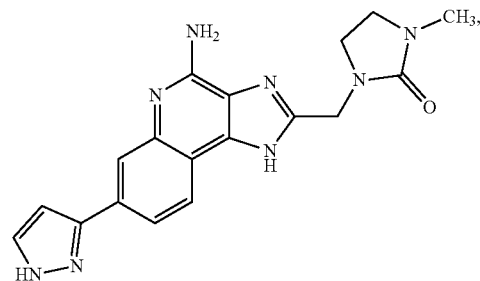
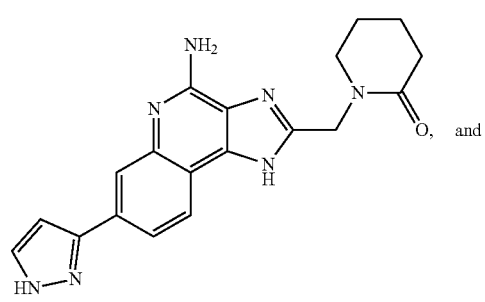
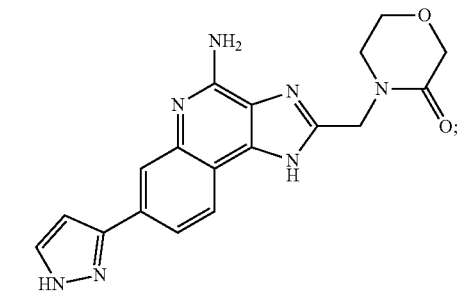
or a pharmaceutically acceptable salt thereof.
In another aspect, the compound of the invention is selected from:
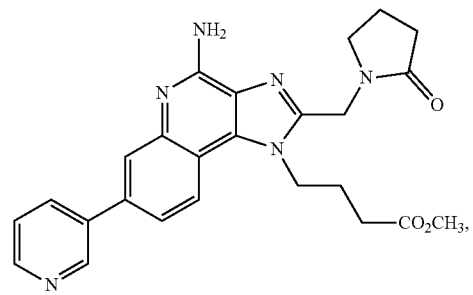
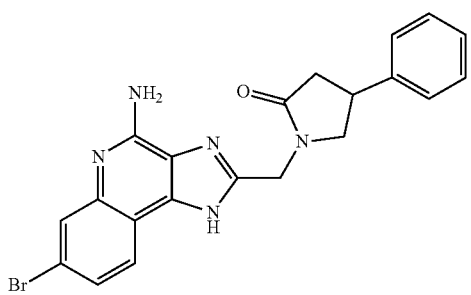

65
-continued
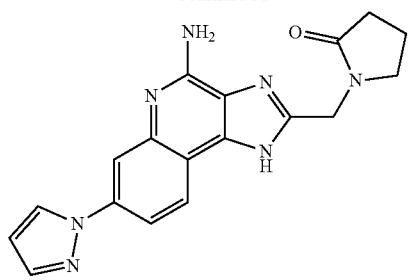
,
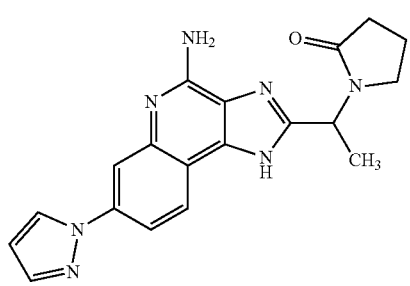
,
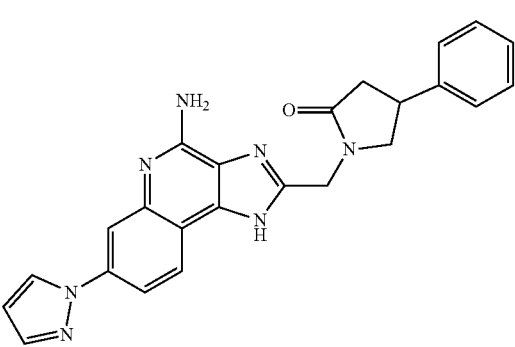
,
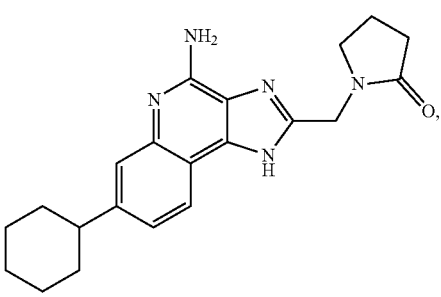
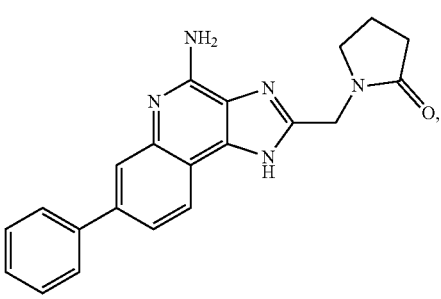
66
-continued
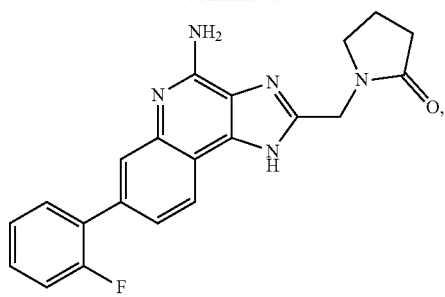
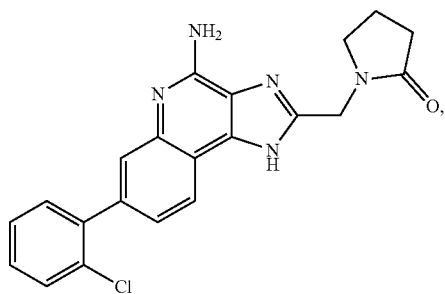
,
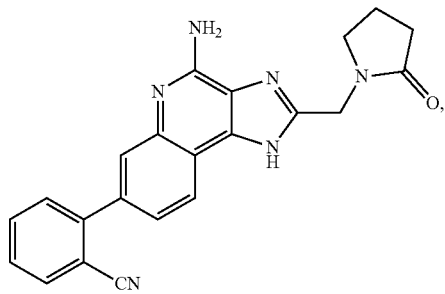
,
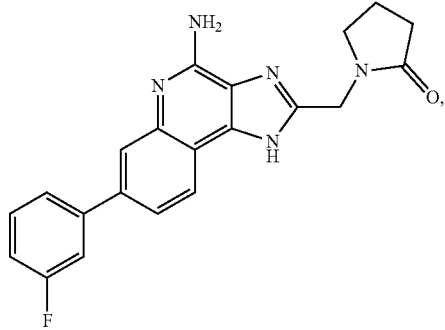
,
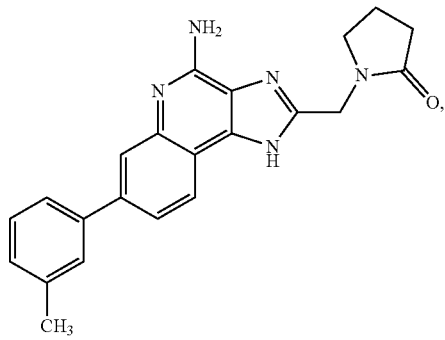

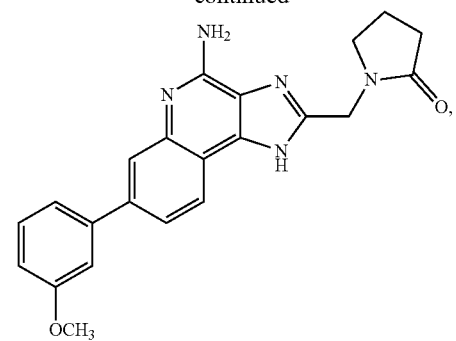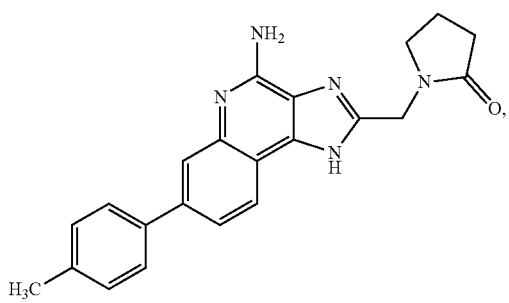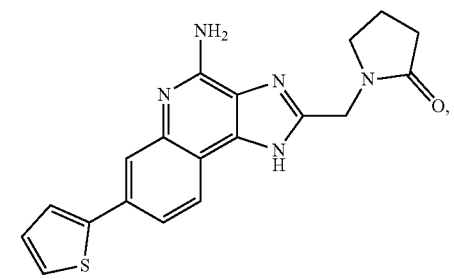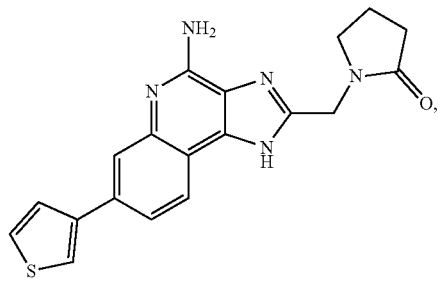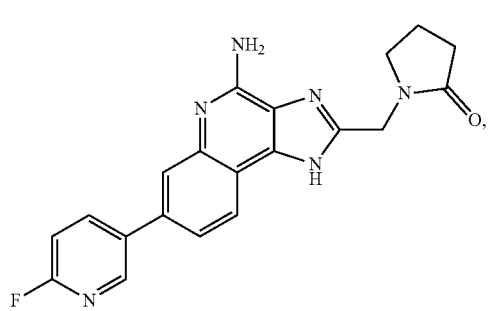
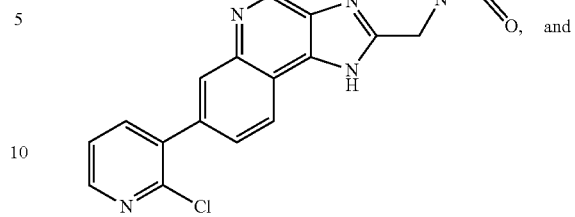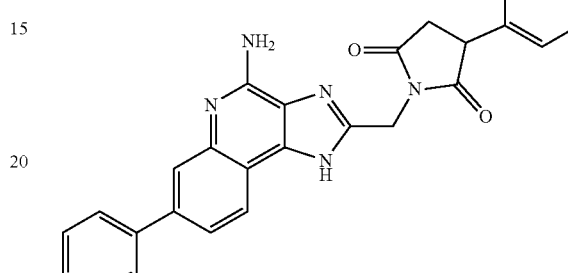
or a pharmaceutically acceptable salt thereof.
In another aspect, the compound of the invention is selected from:
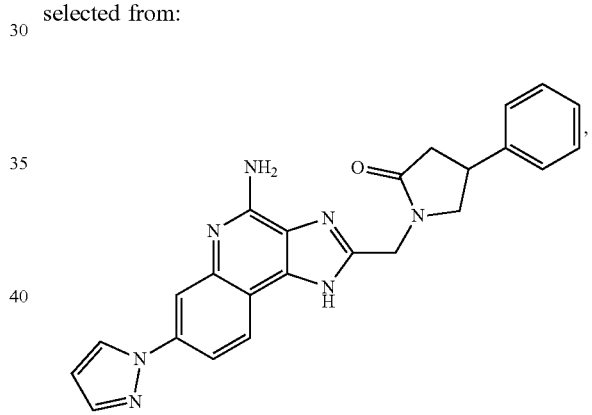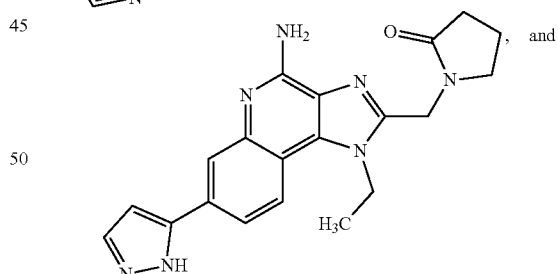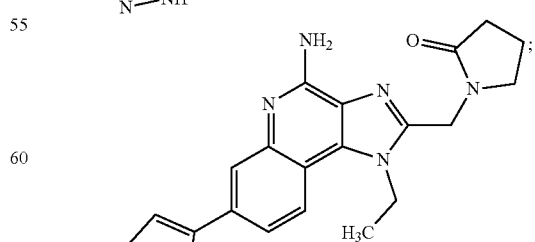
or a pharmaceutically acceptable salt thereof.

In another aspect, the compound of the invention is selected from:

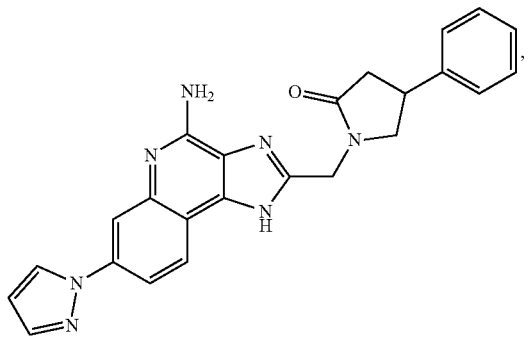 [SMILES: Nc1nc2cc(-n3cccn3)ccc2c2[nH]c(CN3CC(c4ccccc4)CC3=O)nc12]

or a pharmaceutically acceptable salt thereof.

In another aspect, the compound of the invention is

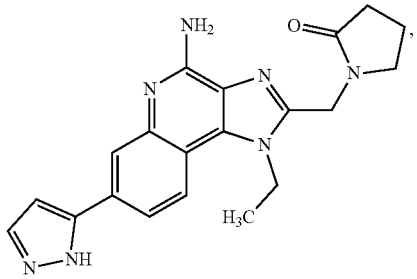 [SMILES: CCn1c(CN2CCCC2=O)nc2c(N)nc3cc(-c4ccn[nH]4)ccc3c21]

or a pharmaceutically acceptable salt thereof.

In another aspect, the compound of the invention is

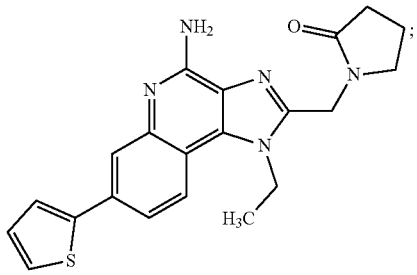 [SMILES: CCn1c(CN2CCCC2=O)nc2c(N)nc3cc(-c4cccs4)ccc3c21]

or a pharmaceutically acceptable salt thereof.

In some aspects, $R^1$ and $R^2$, together with the nitrogen atom to which each is attached forms a saturated or unsaturated ring including from 5 to 6 ring atoms, wherein the ring includes: (a) from 3 to 5 ring carbon atoms, each of which is optionally substituted with from 1 to 2 independently selected $R^f$, and (b) from 0 to 1 ring heteroatom (in addition to the nitrogen atom attached to $R^1$ and $R^2$), which is independently selected from: N, N($R^e$), O, and S; and provided that one of the ring atoms is —C(O)—. In other aspects, $R^1$ and $R^2$, together with the nitrogen atom to which each is attached forms a saturated or unsaturated ring including from 5 to 6 ring atoms, wherein the ring includes: (a) from 3 to 5 ring carbon atoms, each of which is optionally substituted with from 1 to 2 independently selected $R^f$, and (b) from 0 to 1 ring heteroatom (in addition to the nitrogen atom attached to $R^1$ and $R^2$), which is independently selected from: N, N($R^e$), O, and S; and provided that one of the ring atoms is —C(O)—. In other aspects, $R^1$ and $R^2$, together with the nitrogen atom to which each is attached forms a saturated or unsaturated ring including from 5 to 6 ring atoms, wherein the ring includes: (a) from 3 to 5 ring carbon atoms, each of which is optionally substituted with from 1 to 2 independently selected $R^f$, and (b) from 0 to 1 ring heteroatom (in addition to the nitrogen atom attached to $R^1$ and $R^2$), which is independently selected from: N, N($R^e$), and O; and provided that one of the ring atoms is —C(O)—. In other aspects, $R^1$ and $R^2$, together with the nitrogen atom to which each is attached forms

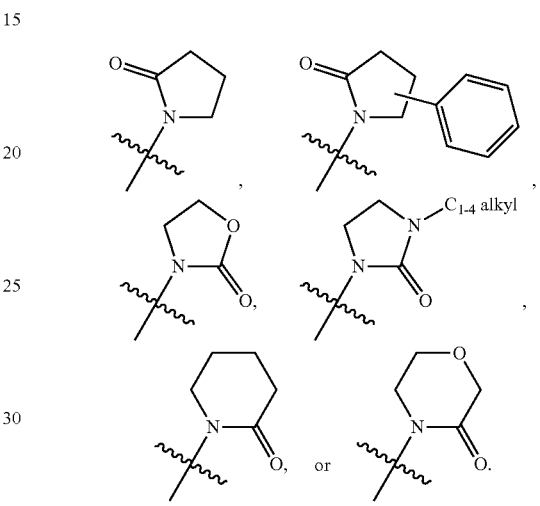

In other aspects, $R^1$ and $R^2$, together with the nitrogen atom to which each is attached forms

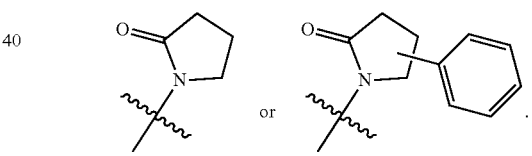

In another aspect, the invention provides a compound selected from the exemplified examples or a pharmaceutically acceptable salt thereof.

In another aspect, the invention provides a compound selected from any subset list of compounds or a single compound from the exemplified examples within the scope of any of the above aspects.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s).

Such compounds are clearly contemplated within the scope of this disclosure, though such resonance forms or tautomers are not explicitly represented herein.

In some embodiments, the compound of Formula I is a compound selected from compounds in Table 1 below. The biological assays used to test the compounds are discussed in the examples section. Key to activity ranges: A=≤1 µM; B=>1 µM, ≤20 µM; C=>20 µM, ≤100 µM; D=>100 µM.

TABLE 1

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 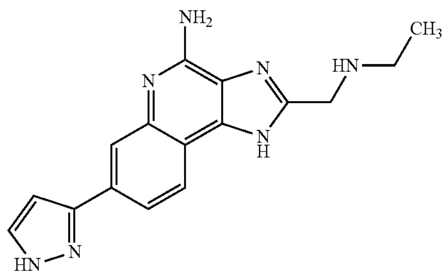 [SMILES: CCNCc1nc2c(N)nc3cc(-c4cc[nH]n4)ccc3c2[nH]1] | 101 | 0.27 | D | D | 308.3 |
| 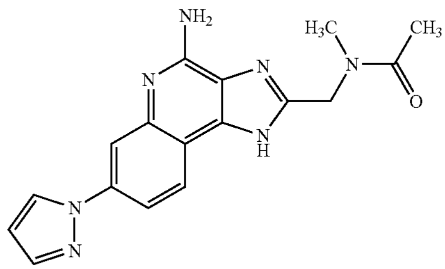 [SMILES: CC(=O)N(C)Cc1nc2c(N)nc3cc(-n4cccn4)ccc3c2[nH]1] | 102 | 1.60 | D | D | 336.3 |
| 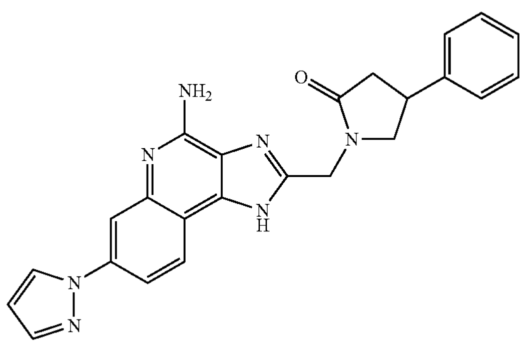 [SMILES: Nc1nc2cc(-n3cccn3)ccc2c2[nH]c(CN3CC(c4ccccc4)CC3=O)nc12] | 103 | 0.52 | D | D | 424.3 |
| 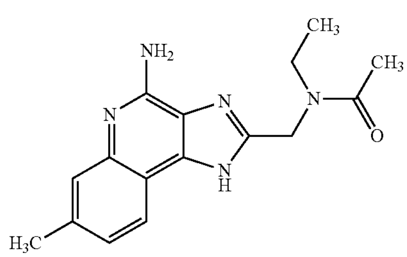 [SMILES: CCN(Cc1nc2c(N)nc3cc(C)ccc3c2[nH]1)C(C)=O] | 104 | 0.60 | D | D | 298.1 |
| 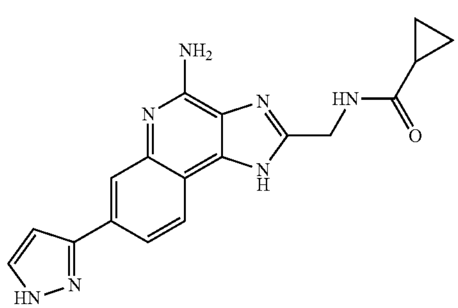 [SMILES: Nc1nc2cc(-c3cc[nH]n3)ccc2c2[nH]c(CNC(=O)C3CC3)nc12] | 105 | 0.69 | | | 348.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| (structure) | 106 | 0.70 | D | D | 322.1 |
| (structure) | 107 | 0.64 | | | 350.3 |
| (structure) | 108 | 0.87 | D | D | 386.3 |
| (structure) | 109 | 0.88 | D | D | 408.3 |
| (structure) | 110 | 0.90 | D | D | 379.3 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
| --- | --- | --- | --- | --- | --- |
| (structure) | 111 | 0.72 | D | D | 336.3 |
| (structure) | 112 | 1.28 | D | D | 350.1 |
| (structure) | 113 | 0.56 | | | 322.3 |
| (structure) | 114 | 1.04 | D | D | 419.4 |
| (structure) | 115 | 0.90 | D | D | 372.1 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 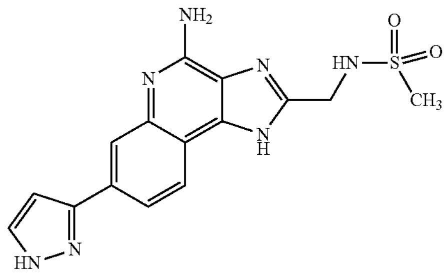 [SMILES: CS(=O)(=O)NCc1nc2c(N)nc3cc(-c4cc[nH]n4)ccc3c2[nH]1] | 116 | 1.16 | | | 358.0 |
| 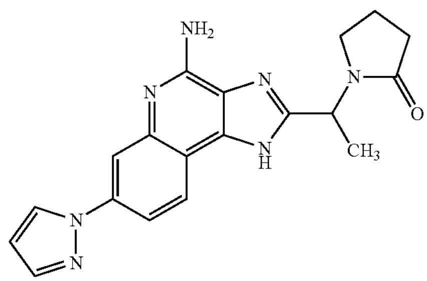 [SMILES: CC(c1nc2c(N)nc3cc(-n4cccn4)ccc3c2[nH]1)N1CCCC1=O] | 117 | 1.26 | C | D | 362.4 |
| 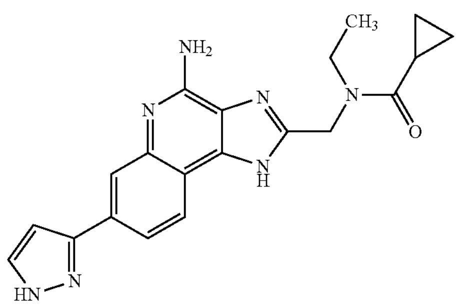 [SMILES: CCN(Cc1nc2c(N)nc3cc(-c4cc[nH]n4)ccc3c2[nH]1)C(=O)C1CC1] | 118 | 1.36 | D | D | 376.2 |
| 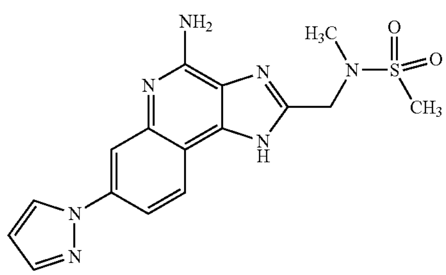 [SMILES: CN(Cc1nc2c(N)nc3cc(-n4cccn4)ccc3c2[nH]1)S(C)(=O)=O] | 119 | 1.38 | D | D | 372.1 |
| 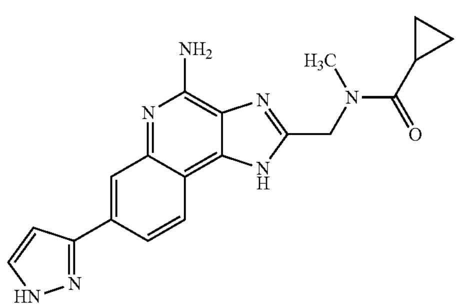 [SMILES: CN(Cc1nc2c(N)nc3cc(-c4cc[nH]n4)ccc3c2[nH]1)C(=O)C1CC1] | 120 | 1.69 | D | D | 362.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| (structure) | 121 | 1.82 | D | D | 364.2 |
| (structure) | 122 | 1.40 | D | D | 350.2 |
| (structure) | 123 | 1.9 | D | D | 376.2 |
| (structure) | 124 | 2.4 | D | D | 386.2 |
| (structure) | 125 | 2.1 | D | D | 364.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 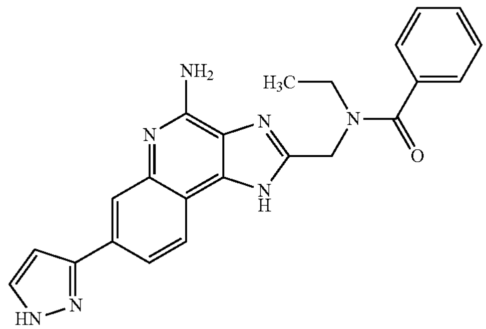 [SMILES: CCN(Cc1nc2c(N)nc3cc(-c4cc[nH]n4)ccc3c2[nH]1)C(=O)c1ccccc1] | 126 | 2.1 | | | 412.4 |
| 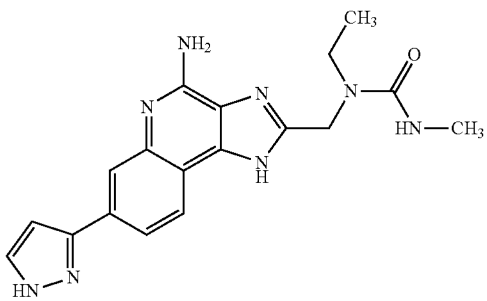 [SMILES: CCN(Cc1nc2c(N)nc3cc(-c4cc[nH]n4)ccc3c2[nH]1)C(=O)NC] | 128 | 2.9 | D | D | 365.2 |
| 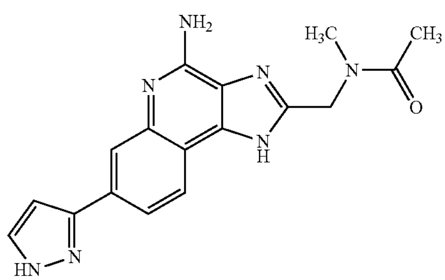 [SMILES: CC(=O)N(C)Cc1nc2c(N)nc3cc(-c4cc[nH]n4)ccc3c2[nH]1] | 129 | 3.6 | D | D | 336.2 |
| 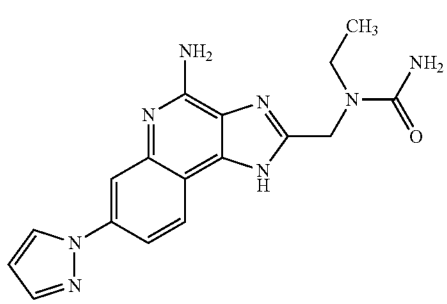 [SMILES: CCN(Cc1nc2c(N)nc3cc(-n4cccn4)ccc3c2[nH]1)C(N)=O] | 130 | 3.3 | D | D | 351.2 |
| 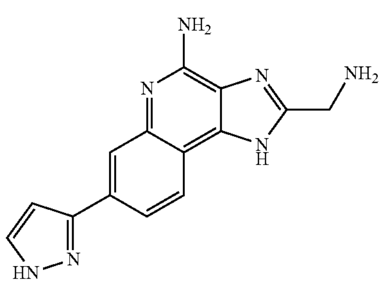 [SMILES: NCc1nc2c(N)nc3cc(-c4cc[nH]n4)ccc3c2[nH]1] | 131 | 3.5 | D | D | 280.3 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 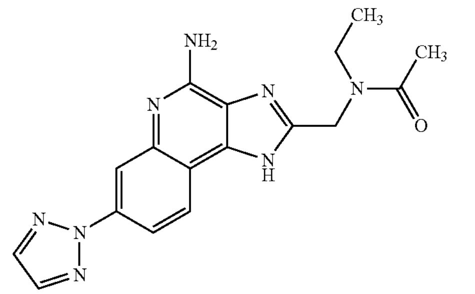 [SMILES: CCN(Cc1nc2c(N)nc3cc(-n4nccn4)ccc3c2[nH]1)C(C)=O] | 132 | 3.5 | D | D | 350.9 |
| 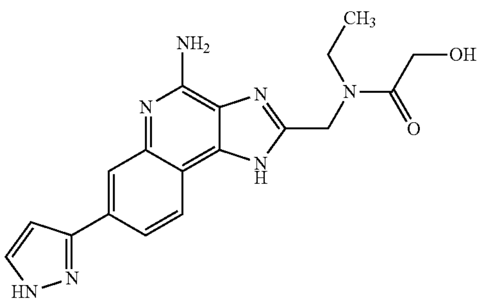 [SMILES: CCN(Cc1nc2c(N)nc3cc(-c4cc[nH]n4)ccc3c2[nH]1)C(=O)CO] | 133 | 3.5 | | | 366.3 |
| 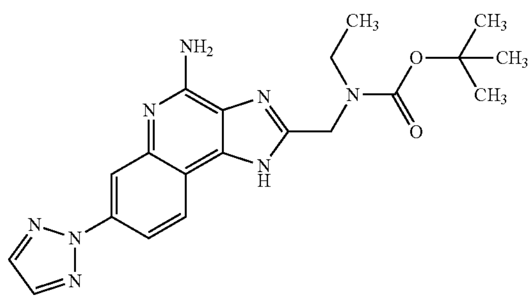 [SMILES: CCN(Cc1nc2c(N)nc3cc(-n4nccn4)ccc3c2[nH]1)C(=O)OC(C)(C)C] | 135 | 4.6 | | | 409.2 |
| 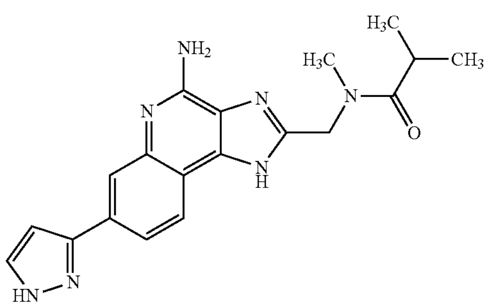 [SMILES: CC(C)C(=O)N(C)Cc1nc2c(N)nc3cc(-c4cc[nH]n4)ccc3c2[nH]1] | 136 | 4.8 | D | D | 362.2 |
| 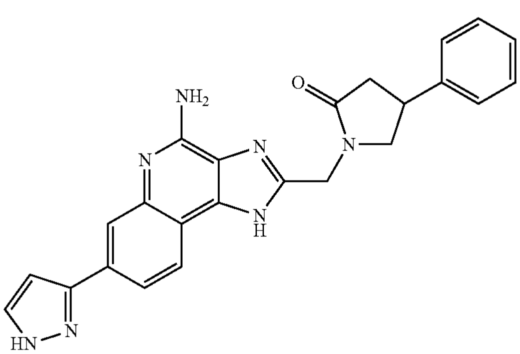 [SMILES: Nc1nc2cc(-c3cc[nH]n3)ccc2c2[nH]c(CN3CC(c4ccccc4)CC3=O)nc12] | 137 | 5.4 | | | 424.4 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 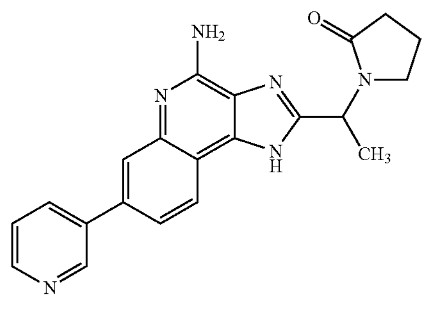 [SMILES: CC(c1nc2c(N)nc3cc(-c4cccnc4)ccc3c2[nH]1)N1CCCC1=O] | 138 | 6.7 | C | D | 373.2 |
| 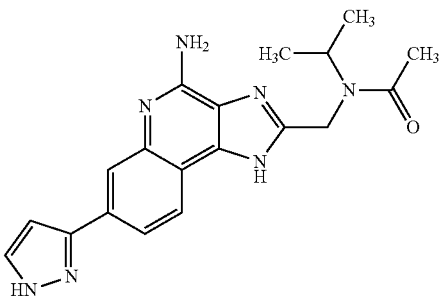 [SMILES: CC(=O)N(Cc1nc2c(N)nc3cc(-c4cc[nH]n4)ccc3c2[nH]1)C(C)C] | 140 | 7.3 | D | D | 364.2 |
| 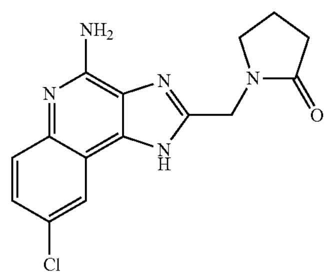 [SMILES: Nc1nc2ccc(Cl)cc2c2[nH]c(CN3CCCC3=O)nc12] | 141 | 9.0 | D | D | 316.1 |
| 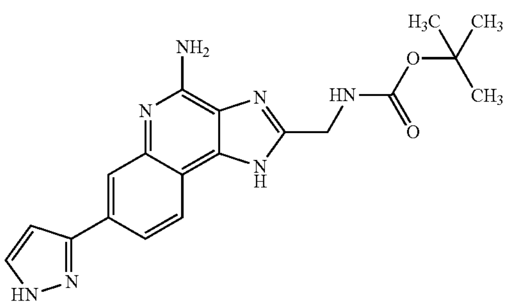 [SMILES: CC(C)(C)OC(=O)NCc1nc2c(N)nc3cc(-c4cc[nH]n4)ccc3c2[nH]1] | 142 | 9.1 | D | D | 380.2 |
| 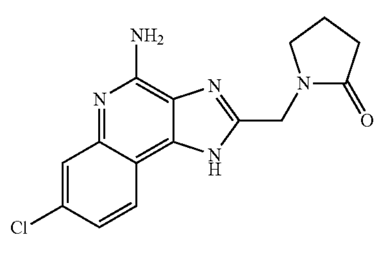 [SMILES: Nc1nc2cc(Cl)ccc2c2[nH]c(CN3CCCC3=O)nc12] | 143 | 9.4 | C | D | 316.1 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 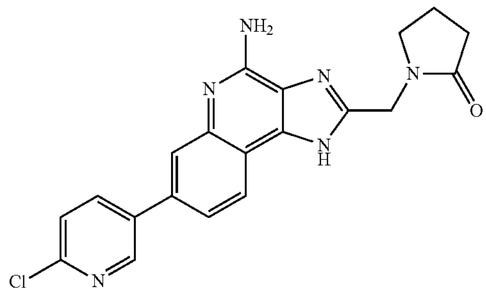 [SMILES: Nc1nc2cc(-c3ccc(Cl)nc3)ccc2c2[nH]c(CN3CCCC3=O)nc12] | 153 | 12.0 | C | D | 393.4 |
| 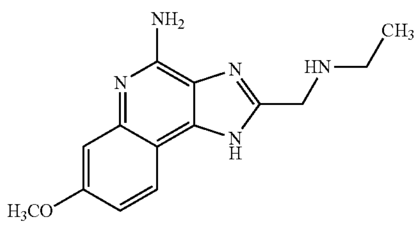 [SMILES: CCNCc1nc2c(N)nc3cc(OC)ccc3c2[nH]1] | 154 | 16.1 | D | C | 272.0 |
| 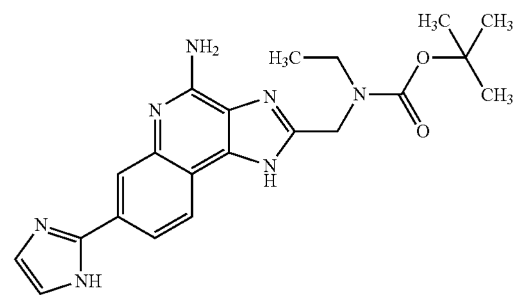 [SMILES: CCN(Cc1nc2c(N)nc3cc(-c4ncc[nH]4)ccc3c2[nH]1)C(=O)OC(C)(C)C] | 155 | 17.4 | D | D | 408.2 |
| 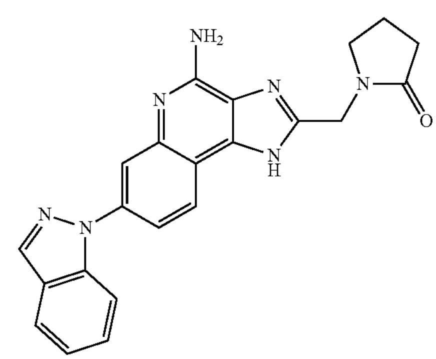 [SMILES: Nc1nc2cc(-n3ncc4ccccc43)ccc2c2[nH]c(CN3CCCC3=O)nc12] | 157 | 23.4 | C | C | 398.2 |
| 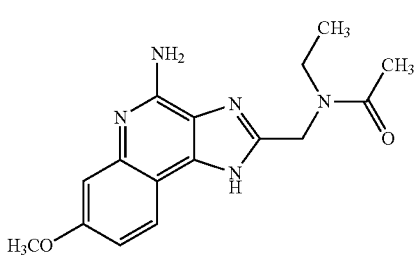 [SMILES: CCN(Cc1nc2c(N)nc3cc(OC)ccc3c2[nH]1)C(C)=O] | 158 | 24.5 | D | D | 314.3 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 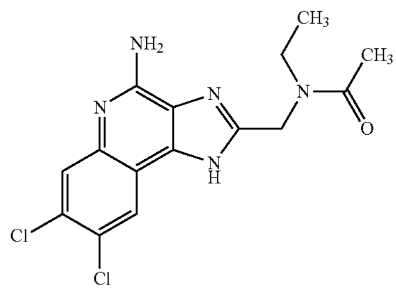 [SMILES: CCN(Cc1nc2c(N)nc3cc(Cl)c(Cl)cc3c2[nH]1)C(C)=O] | 159 | 25.9 | D | D | 352.0 |
| 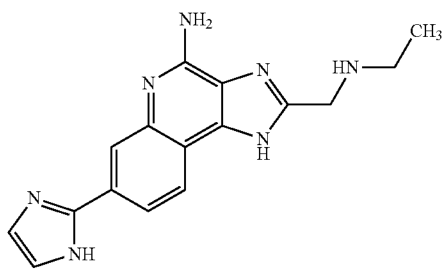 [SMILES: CCNCc1nc2c(N)nc3cc(-c4ncc[nH]4)ccc3c2[nH]1] | 162 | 42.0 | D | D | 308.3 |
| 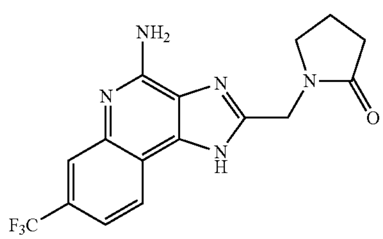 [SMILES: Nc1nc2cc(C(F)(F)F)ccc2c2[nH]c(CN3CCCC3=O)nc12] | 163 | 48.4 | C | D | 350.2 |
| 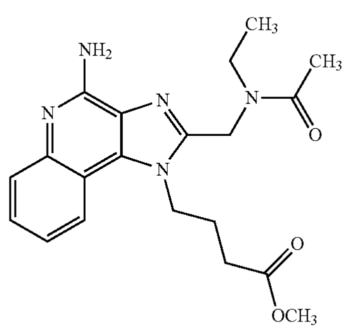 [SMILES: CCN(Cc1nc2c(N)nc3ccccc3c2n1CCCC(=O)OC)C(C)=O] | 164 | 4.6 | D | D | 384.2 |
| 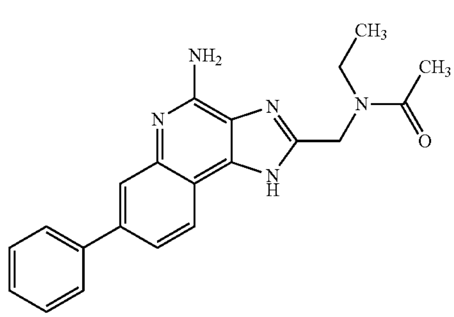 [SMILES: CCN(Cc1nc2c(N)nc3cc(-c4ccccc4)ccc3c2[nH]1)C(C)=O] | 165 | 0.19 | D | D | 360.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 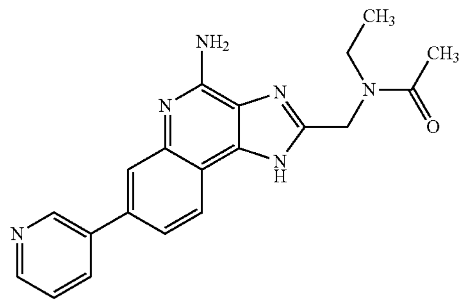 [SMILES: CCN(Cc1nc2c(N)nc3cc(-c4cccnc4)ccc3c2[nH]1)C(C)=O] | 166 | 3.4 | D | D | 361.2 |
| 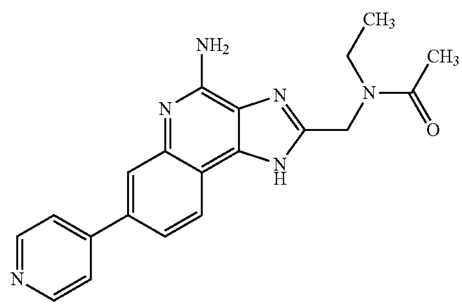 [SMILES: CCN(Cc1nc2c(N)nc3cc(-c4ccncc4)ccc3c2[nH]1)C(C)=O] | 167 | 58 | D | D | 361.2 |
| 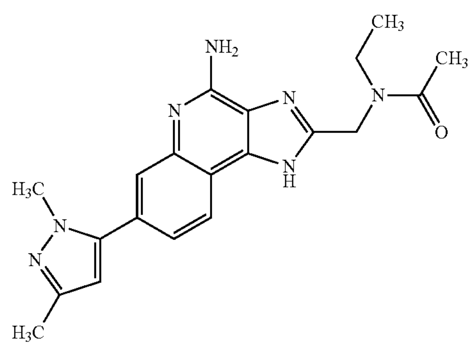 [SMILES: CCN(Cc1nc2c(N)nc3cc(-c4cc(C)nn4C)ccc3c2[nH]1)C(C)=O] | 168 | 101 | D | D | 378.2 |
| 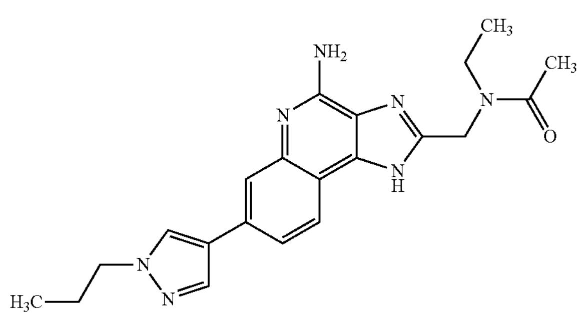 [SMILES: CCCn1cc(-c2ccc3c(c2)nc(N)c2nc(CN(CC)C(C)=O)[nH]c23)cn1] | 169 | 92 | D | D | 392.2 |
| 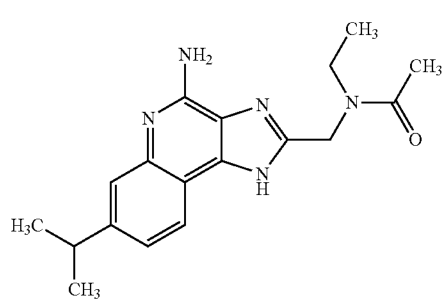 [SMILES: CCN(Cc1nc2c(N)nc3cc(C(C)C)ccc3c2[nH]1)C(C)=O] | 170 | 7.9 | C | D | 326.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 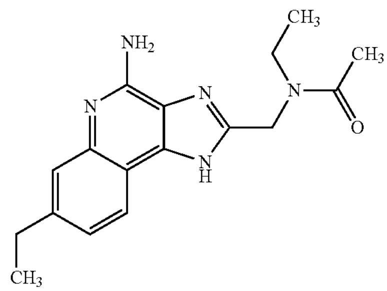 [SMILES: CCc1ccc2c(c1)nc(N)c1nc(CN(CC)C(C)=O)[nH]c12] | 171 | 3.2 | B | D | 312.2 |
| 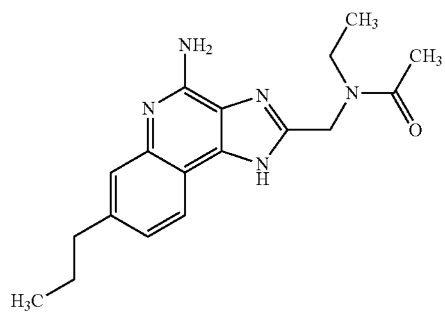 [SMILES: CCCc1ccc2c(c1)nc(N)c1nc(CN(CC)C(C)=O)[nH]c12] | 172 | 2.1 | B | D | 326.2 |
| 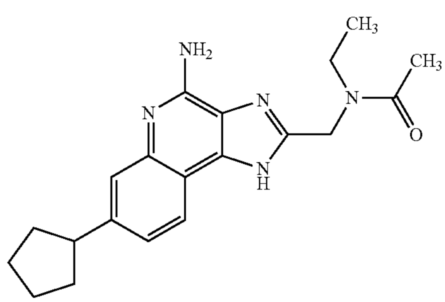 [SMILES: CCN(Cc1nc2c(N)nc3cc(C4CCCC4)ccc3c2[nH]1)C(C)=O] | 173 | 0.84 | D | D | 352.2 |
| 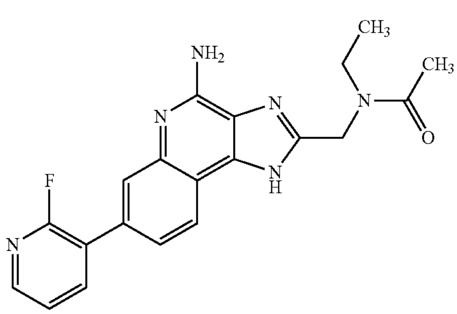 [SMILES: CCN(Cc1nc2c(N)nc3cc(-c4cccnc4F)ccc3c2[nH]1)C(C)=O] | 175 | 2.6 | D | D | 379.2 |
| 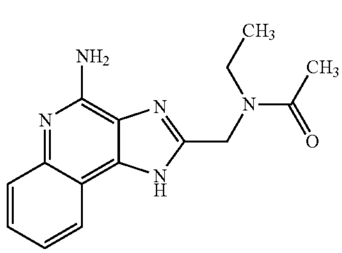 [SMILES: CCN(Cc1nc2c(N)nc3ccccc3c2[nH]1)C(C)=O] | 176 | 25.7 | D | D | 284.1 |

TABLE 1-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 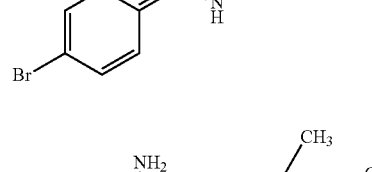 | 177 | 7.4 | D | D | 362.1 |
| 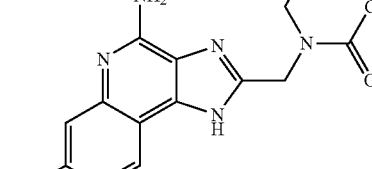 | 179 | 12.5 | D | D | 318.1 |
| 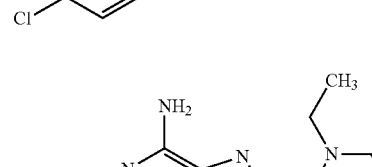 | 180 | 1.5 | D | D | 350.2 |
| 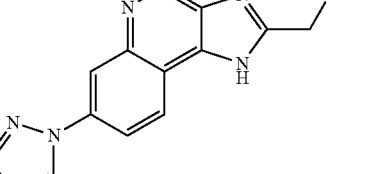 | 182 | 5.9 | D | D | 376.1 |
| 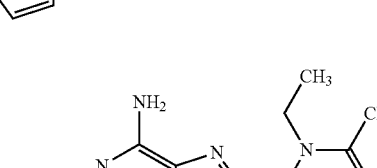 | 183 | 0.52 | D | D | 350.3 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 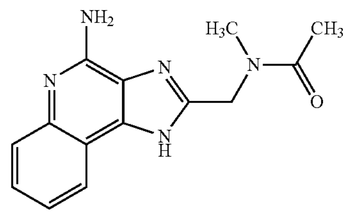 [SMILES: CC(=O)N(C)Cc1nc2c(N)nc3ccccc3c2[nH]1] | 187 | 64 | B | C | 270.2 |
| 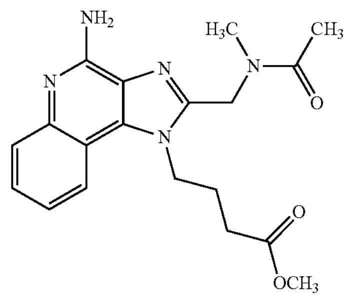 [SMILES: COC(=O)CCCn1c(CN(C)C(C)=O)nc2c(N)nc3ccccc3c21] | 188 | 5.7 | D | D | 370.2 |
| 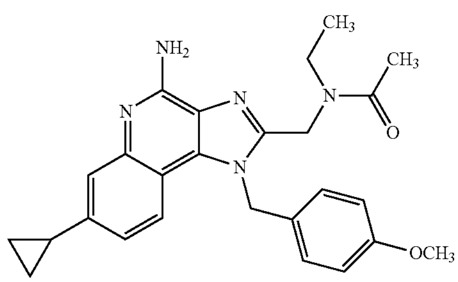 [SMILES: CCN(Cc1nc2c(N)nc3cc(C4CC4)ccc3c2n1Cc1ccc(OC)cc1)C(C)=O] | 190 | 10.3 | D | D | 444.4 |
| 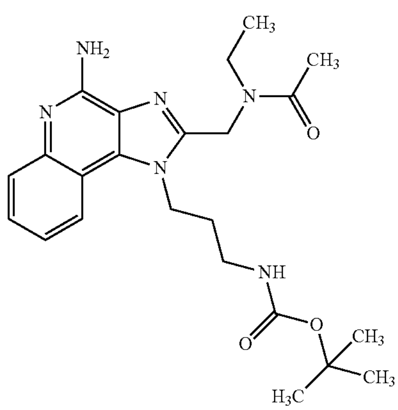 [SMILES: CCN(Cc1nc2c(N)nc3ccccc3c2n1CCCNC(=O)OC(C)(C)C)C(C)=O] | 191 | 65 | D | D | 441.2 |
| 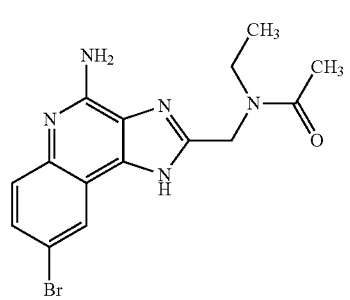 [SMILES: CCN(Cc1nc2c(N)nc3ccc(Br)cc3c2[nH]1)C(C)=O] | 194 | 7.9 | D | D | 362.1 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 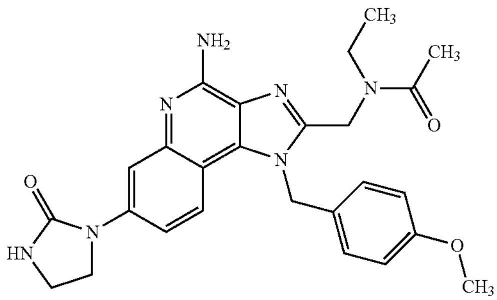 [SMILES: CCN(Cc1nc2c(N)nc3cc(N4CCNC4=O)ccc3c2n1Cc1ccc(OC)cc1)C(C)=O] | 196 | 32.7 | D | D | 488.2 |
| 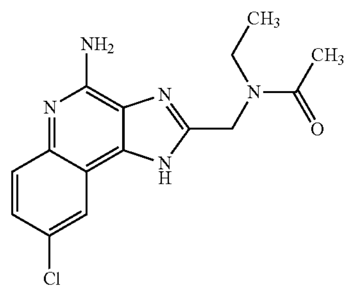 [SMILES: CCN(Cc1nc2c(N)nc3ccc(Cl)cc3c2[nH]1)C(C)=O] | 197 | 13.7 | D | D | 318.0 |
| 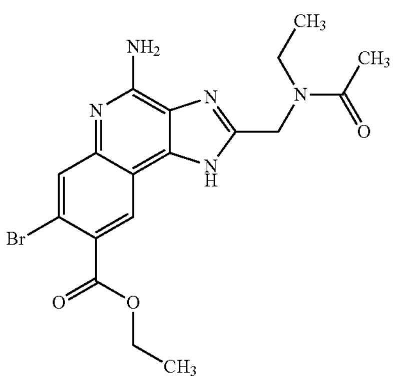 [SMILES: CCOC(=O)c1cc2c(cc1Br)nc(N)c1nc(CN(CC)C(C)=O)[nH]c12] | 198 | 24.2 | D | D | 434.2 |
| 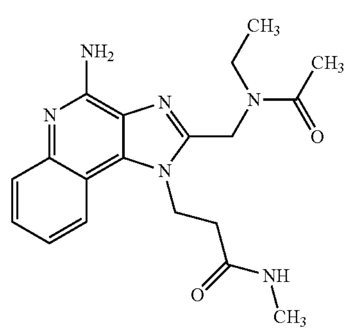 [SMILES: CCN(Cc1nc2c(N)nc3ccccc3c2n1CCC(=O)NC)C(C)=O] | 199 | | D | D | 369.3 |

TABLE 1-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 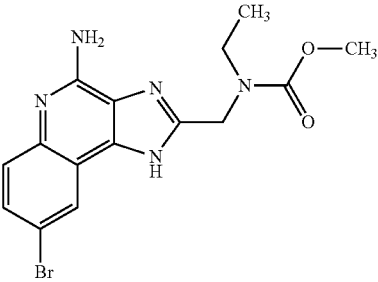 [SMILES: CCN(Cc1nc2c(N)nc3ccc(Br)cc3c2[nH]1)C(=O)OC] | 200 | 11.9 | D | D | 378.0 |
| 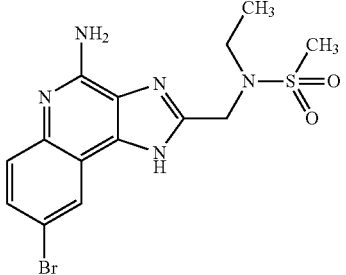 [SMILES: CCN(Cc1nc2c(N)nc3ccc(Br)cc3c2[nH]1)S(C)(=O)=O] | 201 | 20.8 | D | D | 398.2 |
| 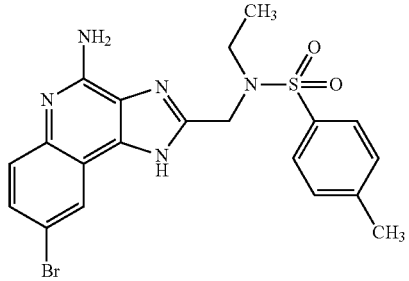 [SMILES: CCN(Cc1nc2c(N)nc3ccc(Br)cc3c2[nH]1)S(=O)(=O)c1ccc(C)cc1] | 202 | 35.9 | D | D | 474.1 |
| 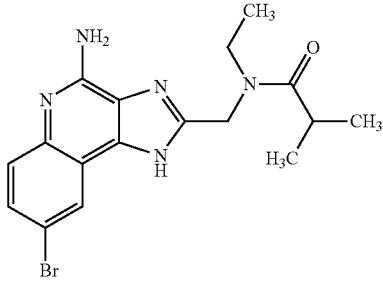 [SMILES: CCN(Cc1nc2c(N)nc3ccc(Br)cc3c2[nH]1)C(=O)C(C)C] | 203 | 10.8 | D | D | 390.4 |
| 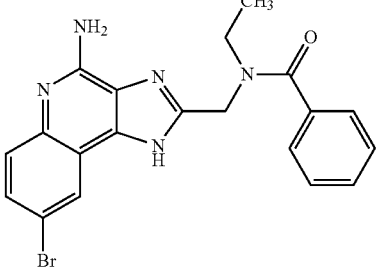 | 204 | 6.7 | D | D | 424.0 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 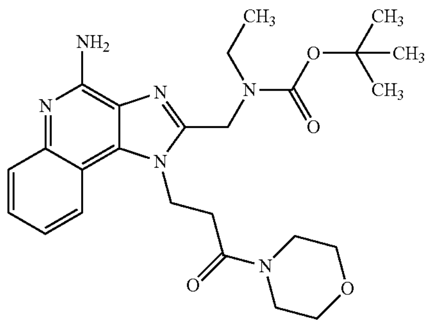 [SMILES: CCN(Cc1nc2c(N)nc3ccccc3c2n1CCC(=O)N1CCOCC1)C(=O)OC(C)(C)C] | 205 | 36 | D | D | 483.4 |
| 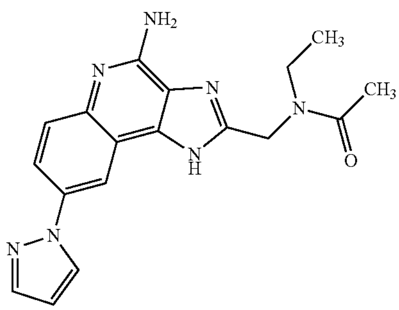 [SMILES: CCN(Cc1nc2c(N)nc3ccc(-n4cccn4)cc3c2[nH]1)C(C)=O] | 207 | 73 | D | D | 350.1 |
| 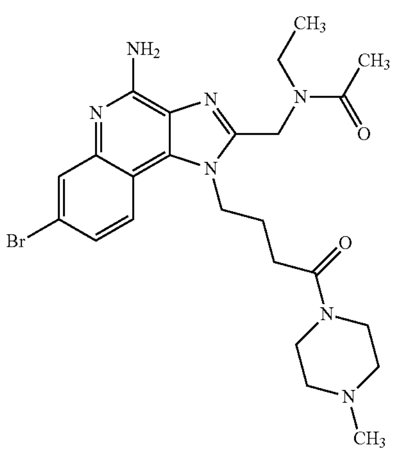 | 209 | 22 | D | D | 530.2 |
| 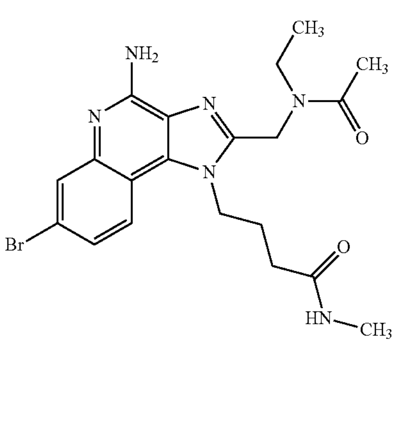 | 210 | 61 | D | D | 463.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 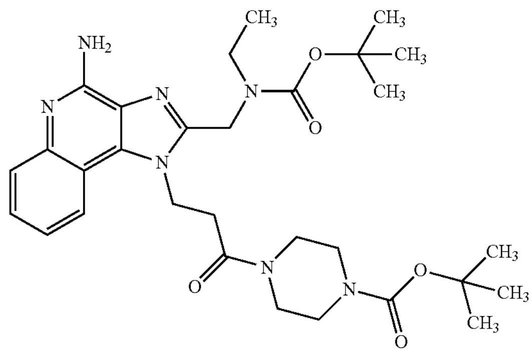 [SMILES: CCN(Cc1nc2c(N)nc3ccccc3c2n1CCC(=O)N1CCN(C(=O)OC(C)(C)C)CC1)C(=O)OC(C)(C)C] | 211 | 40 | D | D | 582.4 |
| 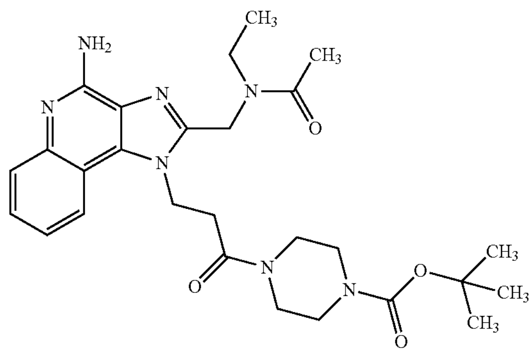 [SMILES: CCN(Cc1nc2c(N)nc3ccccc3c2n1CCC(=O)N1CCN(C(=O)OC(C)(C)C)CC1)C(C)=O] | 212 | 85 | D | D | 524.4 |
| 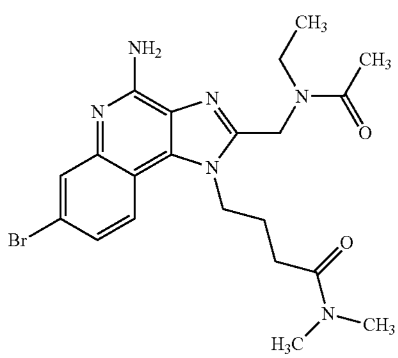 [SMILES: CCN(Cc1nc2c(N)nc3cc(Br)ccc3c2n1CCCC(=O)N(C)C)C(C)=O] | 213 | 17.6 | D | D | 477.2 |
| 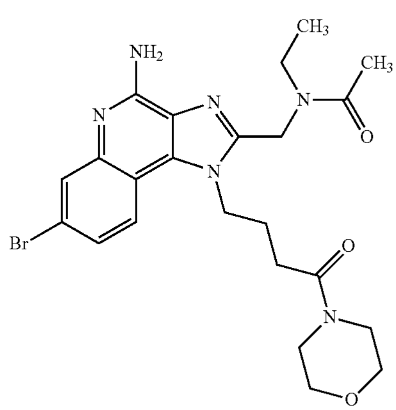 | 214 | 51.5 | D | D | 517.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 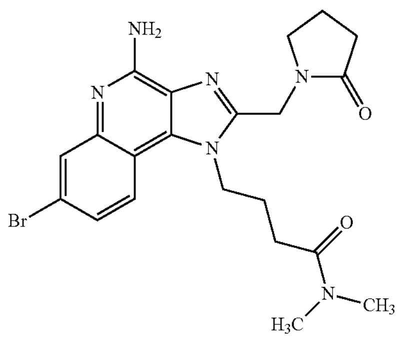 | 215 | 18.2 | D | D | 473.1 |
| 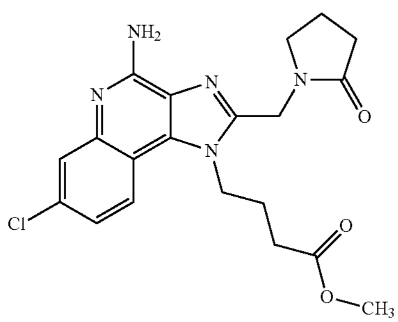 [SMILES: COC(=O)CCCn1c(CN2CCCC2=O)nc2c(N)nc3cc(Cl)ccc3c21] | 216 | 6.6 | D | D | 416.2 |
| 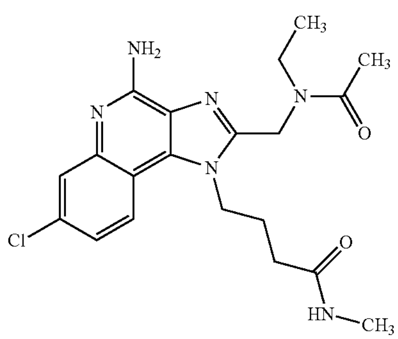 [SMILES: CCN(Cc1nc2c(N)nc3cc(Cl)ccc3c2n1CCCC(=O)NC)C(C)=O] | 217 | 96 | D | D | 417.2 |
| 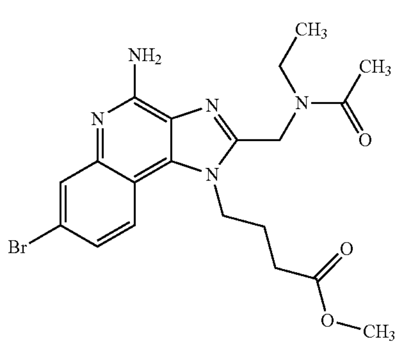 [SMILES: CCN(Cc1nc2c(N)nc3cc(Cl)ccc3c2n1CCCC(=O)OC)C(C)=O] | 218 | 1.2 | D | D | 464.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 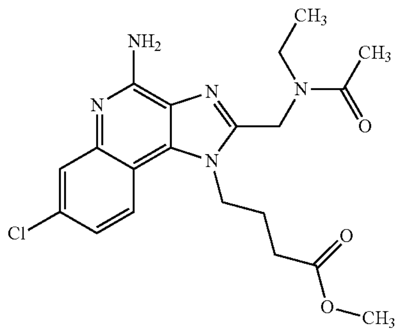 | 219 | 2.0 | D | D | 418.2 |
| 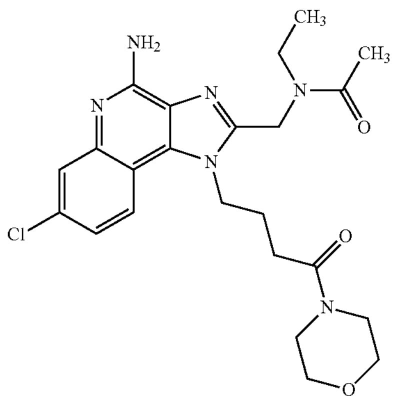 [SMILES: CCN(Cc1nc2c(N)nc3cc(Cl)ccc3c2n1CCCC(=O)N1CCOCC1)C(C)=O] | 220 | 51 | D | D | 473.2 |
| 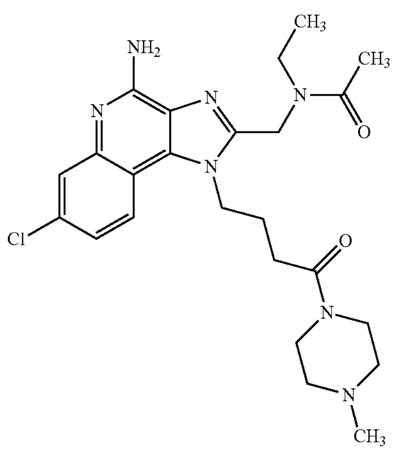 [SMILES: CCN(Cc1nc2c(N)nc3cc(Cl)ccc3c2n1CCCC(=O)N1CCN(C)CC1)C(C)=O] | 221 | 85 | D | D | 486.4 |
| 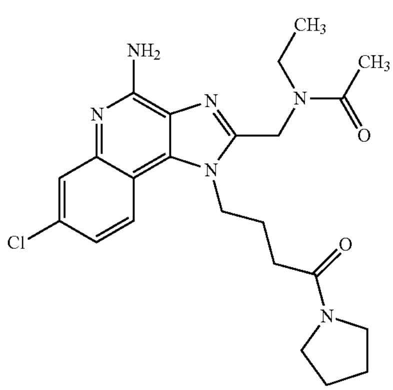 [SMILES: CCN(Cc1nc2c(N)nc3cc(Cl)ccc3c2n1CCCC(=O)N1CCCC1)C(C)=O] | 222 | 42 | D | D | 457.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 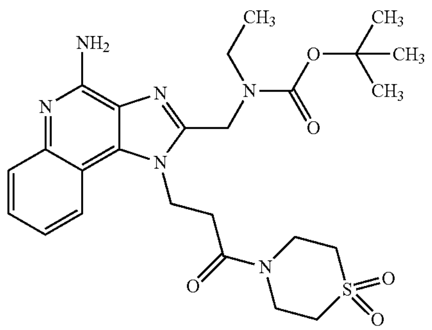 [SMILES: CCN(Cc1nc2c(N)nc3ccccc3c2n1CCC(=O)N1CCS(=O)(=O)CC1)C(=O)OC(C)(C)C] | 223 | 77 | C | D | 531.3 |
| 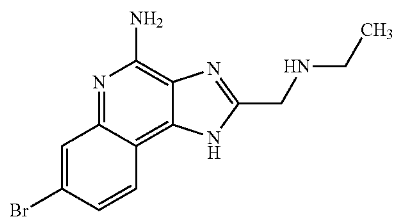 [SMILES: CCNCc1nc2c(N)nc3cc(Br)ccc3c2[nH]1] | 225 | 10.9 | D | B | 321.9 |
| 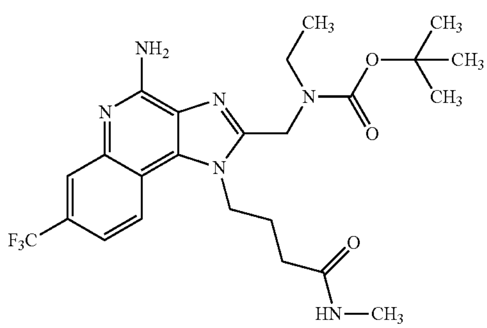 [SMILES: CCN(Cc1nc2c(N)nc3cc(C(F)(F)F)ccc3c2n1CCCC(=O)NC)C(=O)OC(C)(C)C] | 226 | 85 | D | D | 509.4 |
| 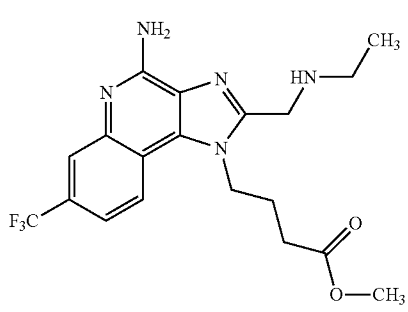 [SMILES: CCNCc1nc2c(N)nc3cc(C(F)(F)F)ccc3c2n1CCCC(=O)OC] | 227 | 22.7 | C | D | 410.3 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 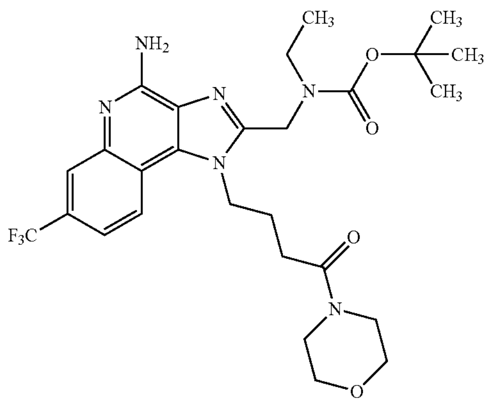 [SMILES: CCN(Cc1nc2c(N)nc3cc(C(F)(F)F)ccc3c2n1CCCC(=O)N1CCOCC1)C(=O)OC(C)(C)C] | 228 | 93 | D | D | 565.3 |
| 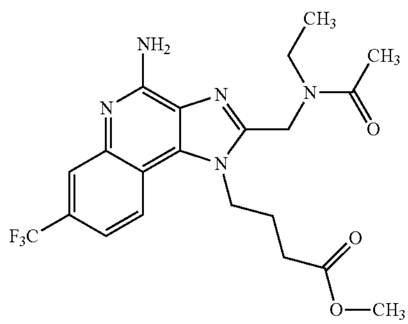 [SMILES: CCN(Cc1nc2c(N)nc3cc(C(F)(F)F)ccc3c2n1CCCC(=O)OC)C(C)=O] | 229 | 12.3 | D | D | 452.2 |
| 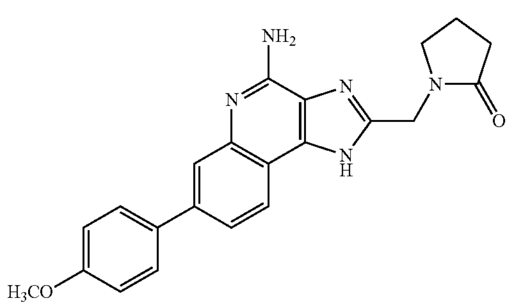 [SMILES: COc1ccc(-c2ccc3c(c2)nc(N)c2nc(CN4CCCC4=O)[nH]c23)cc1] | 230 | 4.5 | D | D | 388.2 |
| 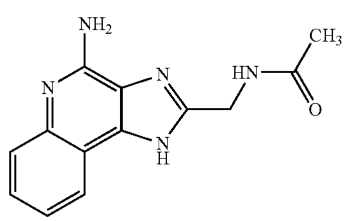 [SMILES: CC(=O)NCc1nc2c(N)nc3ccccc3c2[nH]1] | 233 | 120 | B | D | 256.1 |
| 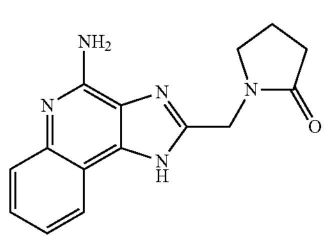 [SMILES: Nc1nc2ccccc2c2[nH]c(CN3CCCC3=O)nc12] | 278 | 10.8 | C | D | 282.1 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 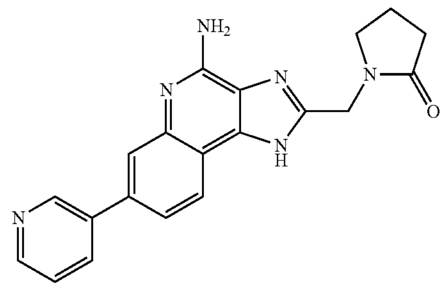 [SMILES: Nc1nc2cc(-c3cccnc3)ccc2c2[nH]c(CN3CCCC3=O)nc12] | 279 | 7.5 | D | D | 359.1 |
| 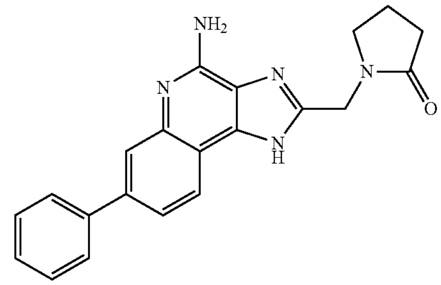 [SMILES: Nc1nc2cc(-c3ccccc3)ccc2c2[nH]c(CN3CCCC3=O)nc12] | 280 | 0.22 | D | D | 358.2 |
| 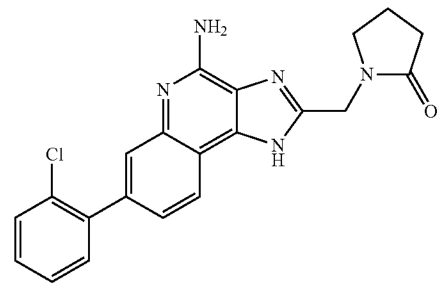 [SMILES: Nc1nc2cc(-c3ccccc3Cl)ccc2c2[nH]c(CN3CCCC3=O)nc12] | 281 | 1.4 | D | D | 392.1 |
| 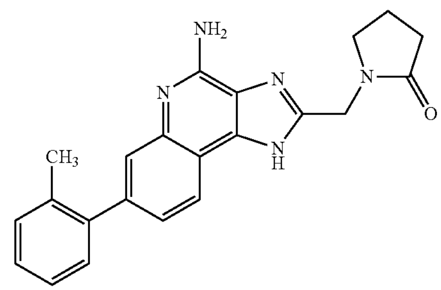 [SMILES: Cc1ccccc1-c1ccc2c(c1)nc(N)c1nc(CN3CCCC3=O)[nH]c12] | 282 | 4.8 | D | D | 372.2 |
| 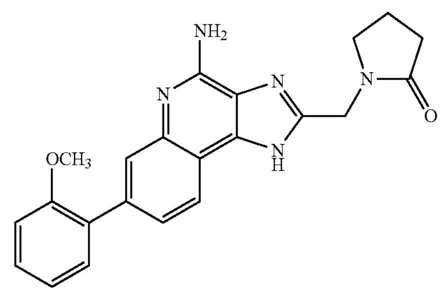 [SMILES: COc1ccccc1-c1ccc2c(c1)nc(N)c1nc(CN3CCCC3=O)[nH]c12] | 283 | 6.5 | D | D | 388.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| (2-fluorophenyl substituted imidazoquinoline-pyrrolidinone) | 284 | 0.86 | D | D | 376.1 |
| (3-chlorophenyl substituted imidazoquinoline-pyrrolidinone) | 285 | 5.7 | D | D | 392.1 |
| (3-methylphenyl substituted imidazoquinoline-pyrrolidinone) | 286 | 0.61 | D | D | 372.2 |
| (3-methoxyphenyl substituted imidazoquinoline-pyrrolidinone) | 287 | 1.08 | D | D | 388.2 |
| (3-cyanophenyl substituted imidazoquinoline-pyrrolidinone) | 288 | 10.1 | D | D | 383.1 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 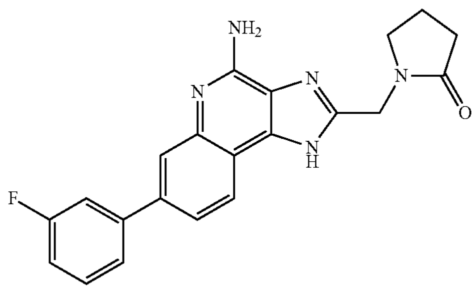 [SMILES: Nc1nc2cc(-c3cccc(F)c3)ccc2c2[nH]c(CN3CCCC3=O)nc12] | 289 | 1.58 | D | D | 376.1 |
| 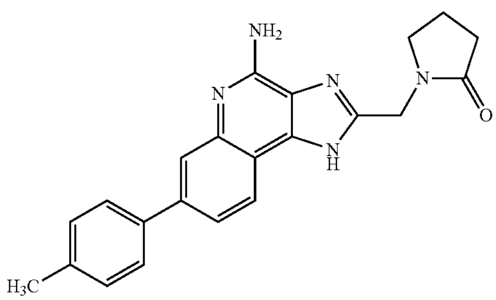 [SMILES: Cc1ccc(-c2ccc3c(c2)nc(N)c2nc(CN4CCCC4=O)[nH]c23)cc1] | 291 | 0.11 | D | D | 372.2 |
| 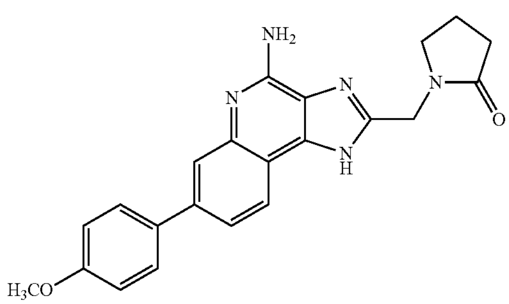 [SMILES: COc1ccc(-c2ccc3c(c2)nc(N)c2nc(CN4CCCC4=O)[nH]c23)cc1] | 292 | 4.48 | D | D | 388.2 |
| 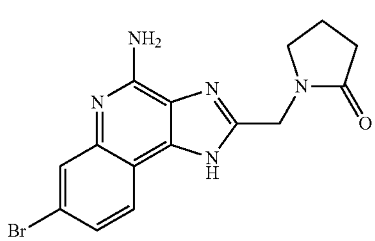 | 294 | 4.6 | C | D | 360.0 |
| 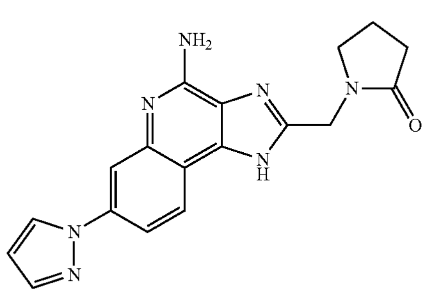 [SMILES: Nc1nc2cc(-n3cccn3)ccc2c2[nH]c(CN3CCCC3=O)nc12] | 295 | 1.20 | D | D | 348.1 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 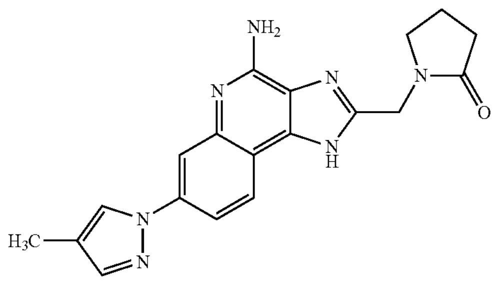 [SMILES: Cc1cnn(-c2ccc3c(c2)nc(N)c2nc(CN4CCCC4=O)[nH]c23)c1] | 296 | 5.1 | D | D | 362.2 |
| 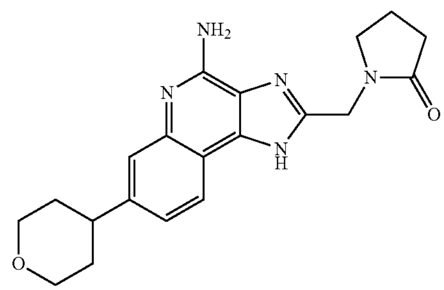 [SMILES: Nc1nc2cc(C3CCOCC3)ccc2c2[nH]c(CN3CCCC3=O)nc12] | 298 | 21 | B | D | 366.2 |
| 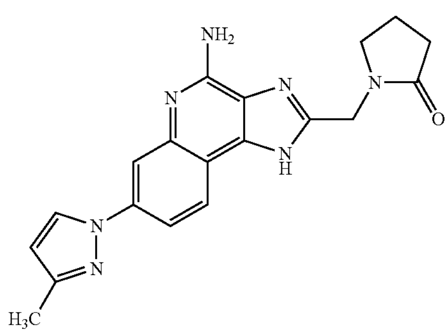 [SMILES: Cc1ccn(-c2ccc3c(c2)nc(N)c2nc(CN4CCCC4=O)[nH]c23)n1] | 301 | 2.93 | D | D | 362.2 |
| 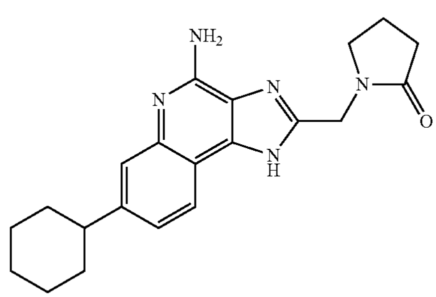 [SMILES: Nc1nc2cc(C3CCCCC3)ccc2c2[nH]c(CN3CCCC3=O)nc12] | 302 | 0.93 | D | D | 364.2 |
| 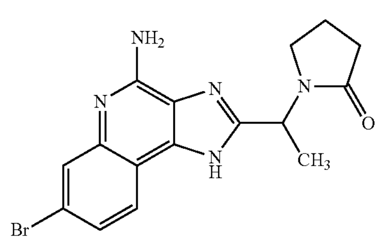 | 303 | 11.1 | C | C | 373.8 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 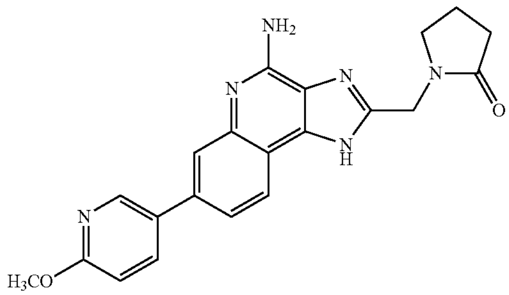 [SMILES: COc1ccc(-c2ccc3c(c2)nc(N)c2nc(CN4CCCC4=O)[nH]c23)cn1] | 304 | 36.4 | | | 389.2 |
| 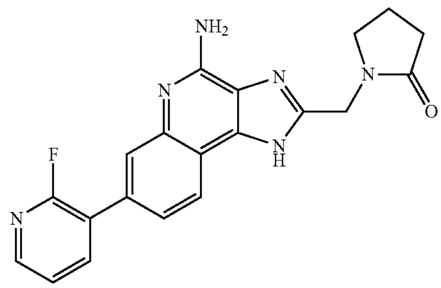 [SMILES: Nc1nc2cc(-c3cccnc3F)ccc2c2[nH]c(CN3CCCC3=O)nc12] | 307 | 12.3 | | | 377.1 |
| 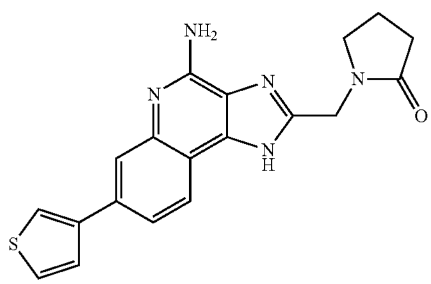 [SMILES: Nc1nc2cc(-c3ccsc3)ccc2c2[nH]c(CN3CCCC3=O)nc12] | 308 | 1.06 | | | 364.1 |
| 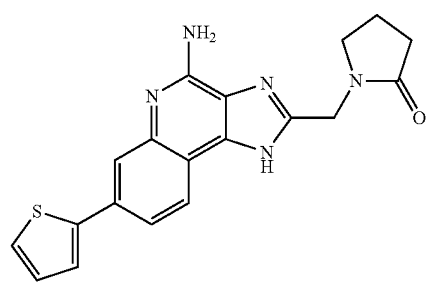 [SMILES: Nc1nc2cc(-c3cccs3)ccc2c2[nH]c(CN3CCCC3=O)nc12] | 309 | 0.24 | D | D | 364.1 |
| 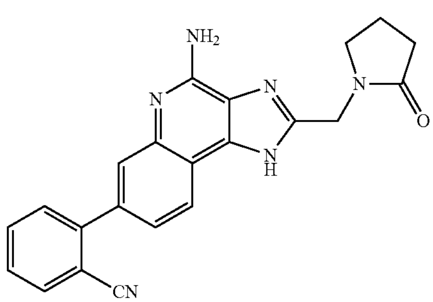 [SMILES: N#Cc1ccccc1-c1ccc2c(c1)nc(N)c1nc(CN3CCCC3=O)[nH]c12] | 315 | 1.18 | D | D | 383.2 |

TABLE 1-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 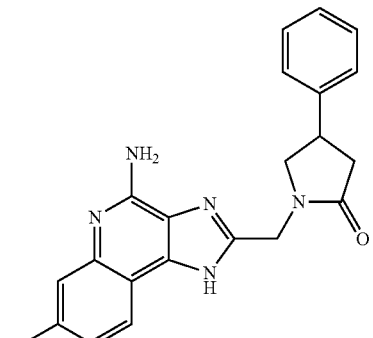 | 316 | 1.10 | D | D | 436.1 |
| 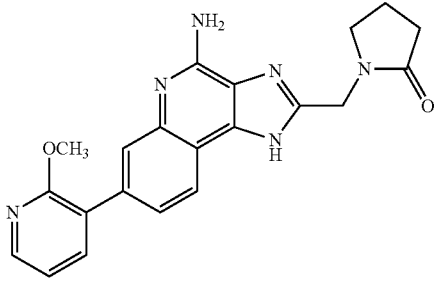 [SMILES: COc1ncccc1-c1ccc2c(c1)nc(N)c1nc(CN3CCCC3=O)[nH]c12] | 319 | 6.2 | D | D | 389.2 |
| 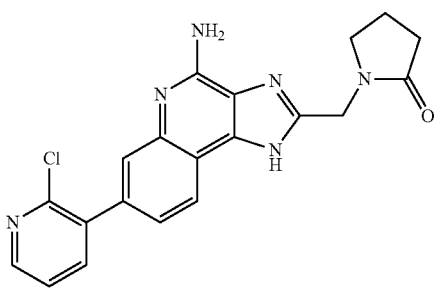 [SMILES: Nc1nc2cc(-c3cccnc3Cl)ccc2c2[nH]c(CN3CCCC3=O)nc12] | 320 | 1.5 | D | D | 393.1 |
| 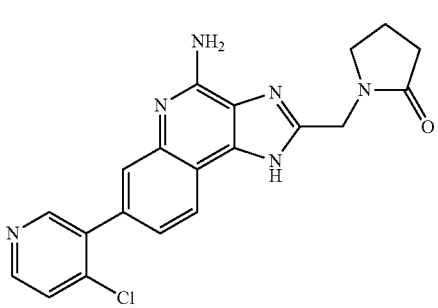 [SMILES: Nc1nc2cc(-c3cnccc3Cl)ccc2c2[nH]c(CN3CCCC3=O)nc12] | 321 | 4.5 | C | D | 393.1 |
| 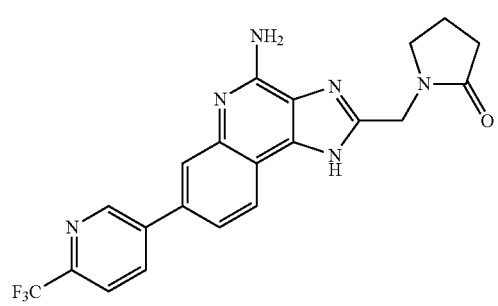 | 324 | 6.7 | D | D | 427.1 |

TABLE 1-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 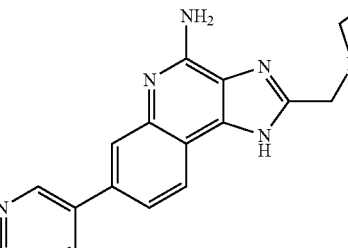 | 326 | 2.7 | D | D | 384.1 |
| 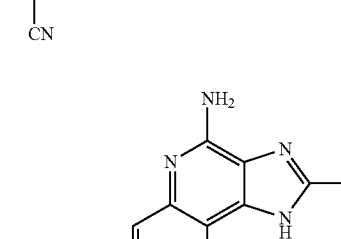 | 327 | 13 | D | D | 384.1 |
| 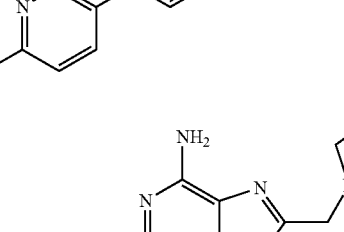 | 328 | 4.1 | D | D | 393.1 |
| 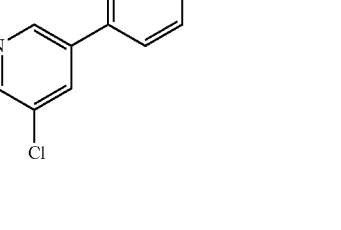 | 330 | 1.6 | D | D | 377.1 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 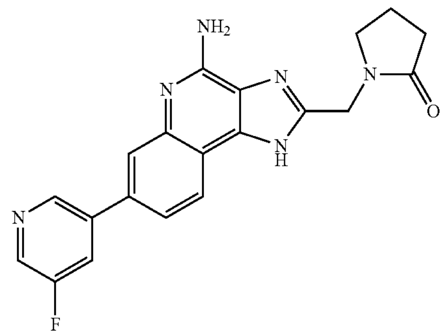 [SMILES: Nc1nc2cc(-c3cncc(F)c3)ccc2c2[nH]c(CN3CCCC3=O)nc12] | 331 | 3.2 | D | D | 377.1 |
| 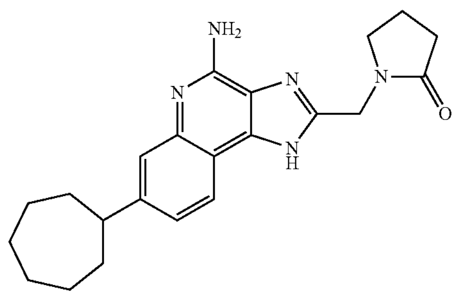 [SMILES: Nc1nc2cc(C3CCCCCC3)ccc2c2[nH]c(CN3CCCC3=O)nc12] | 332 | 3.3 | D | D | 378.2 |
| 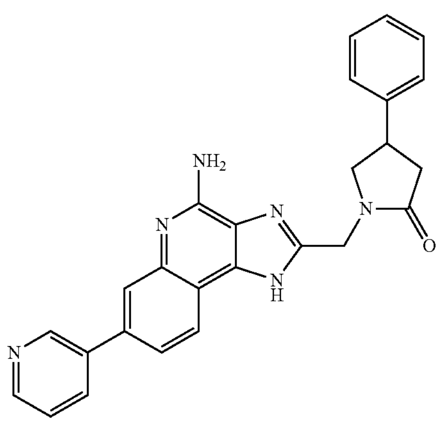 [SMILES: Nc1nc2cc(-c3cccnc3)ccc2c2[nH]c(CN3CC(c4ccccc4)CC3=O)nc12] | 333 | 1.9 | D | D | 435.2 |
| 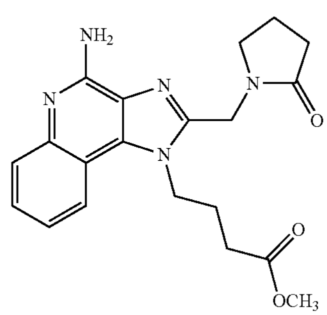 [SMILES: COC(=O)CCCn1c(CN2CCCC2=O)nc2c(N)nc3ccccc3c21] | 335 | 6.5 | D | D | 382.2 |

TABLE 1-continued
| Structure | Compound | hNLRP3 Agonist EC50 (μM) | TLR7 EC50 (μM) | TLR8 EC50 (μM) | LCMS [M + H]+ |
|---|---|---|---|---|---|
| 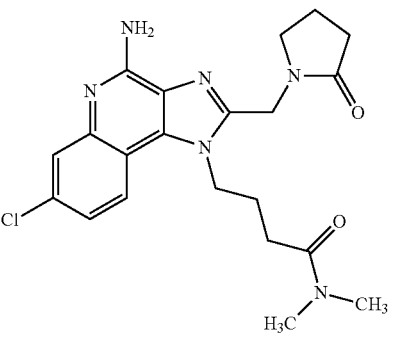 [SMILES: CN(C)C(=O)CCCn1c(CN2CCCC2=O)nc2c(N)nc3cc(Cl)ccc3c21] | 337 | 80 | D | D | 429.2 |
| 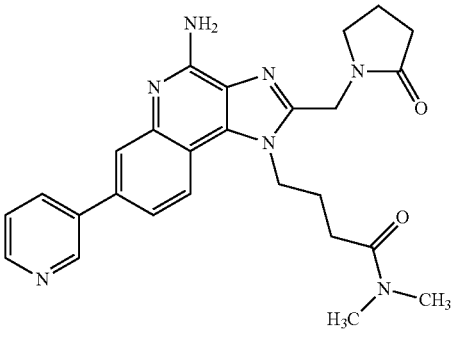 [SMILES: CN(C)C(=O)CCCn1c(CN2CCCC2=O)nc2c(N)nc3cc(-c4cccnc4)ccc3c21] | 340 | 50 | D | D | 472.4 |
| 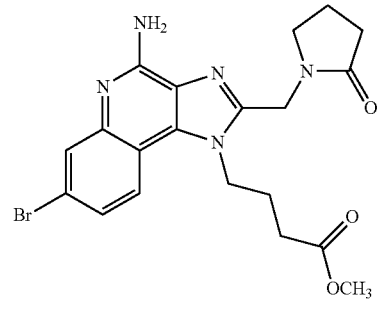 [SMILES: COC(=O)CCCn1c(CN2CCCC2=O)nc2c(N)nc3cc(Br)ccc3c21] | 341 | 2.1 | D | D | 462.2 |
| 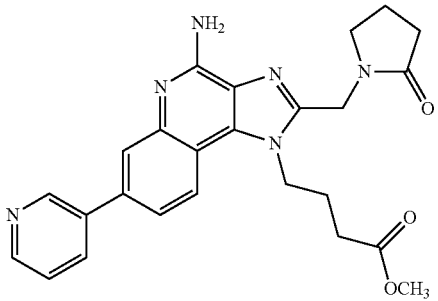 [SMILES: COC(=O)CCCn1c(CN2CCCC2=O)nc2c(N)nc3cc(-c4cccnc4)ccc3c21] | 342 | 3.3 | D | D | 459.3 |

TABLE 1-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 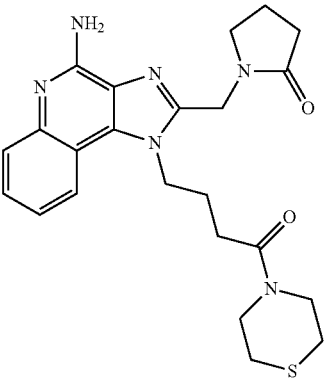 [SMILES: Nc1nc2ccccc2c2c1nc(CN1CCCC1=O)n2CCCC(=O)N1CCSCC1] | 345 | 64 | | | 453.2 |
| 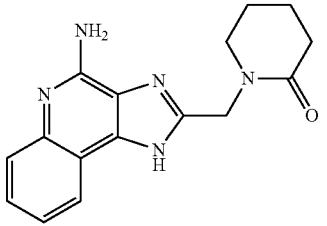 [SMILES: Nc1nc2ccccc2c2[nH]c(CN3CCCCC3=O)nc12] | 346 | 17.3 | D | D | 296.1 |
| 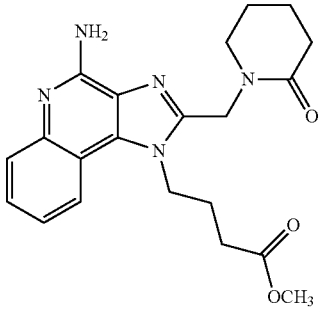 [SMILES: COC(=O)CCCn1c(CN2CCCCC2=O)nc2c(N)nc3ccccc3c21] | 347 | 41 | D | D | 396.2 |
| 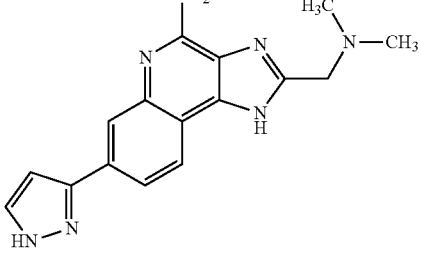 | 348 | 0.89 | D | D | 308.0 |
| 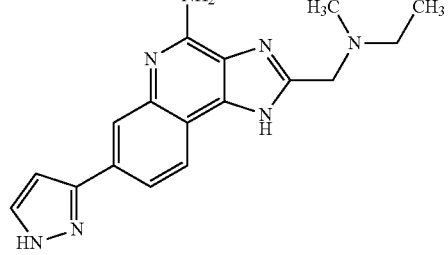 | 349 | 0.60 | D | D | 322.1 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
| --- | --- | --- | --- | --- | --- |
| 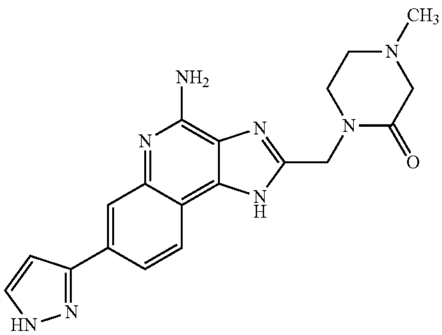 [SMILES: CN1CCN(Cc2nc3c(N)nc4cc(-c5cc[nH]n5)ccc4c3[nH]2)C(=O)C1] | 350 | 10 | | | 377.2 |
| 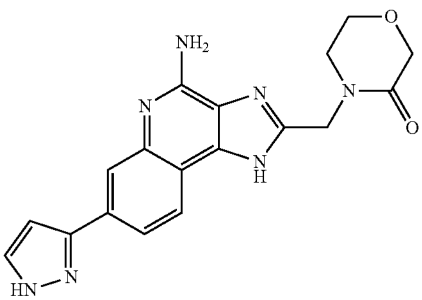 [SMILES: Nc1nc2cc(-c3cc[nH]n3)ccc2c2[nH]c(CN3CCOCC3=O)nc12] | 351 | 2.17 | | | 364.2 |
| 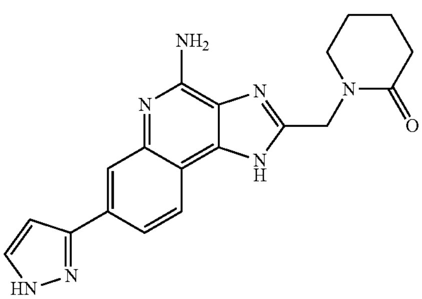 [SMILES: Nc1nc2cc(-c3cc[nH]n3)ccc2c2[nH]c(CN3CCCCC3=O)nc12] | 352 | 2.23 | | | 362.1 |
| (R)-enantiomer | 357 | 0.64 | D | D | 424.4 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| (S)-enantiomer | 358 | 0.63 | D | D | 424.4 |
| 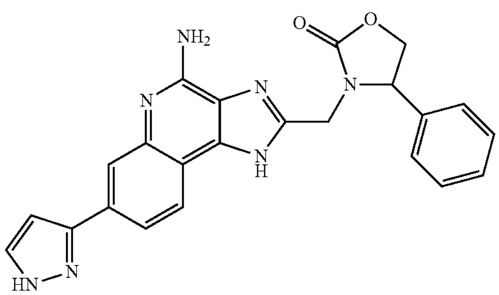 [SMILES: Nc1nc2cc(-c3cc[nH]n3)ccc2c2[nH]c(CN3C(=O)OCC3c3ccccc3)nc12] | 363 | 5.8 | D | D | 426.4 |
| 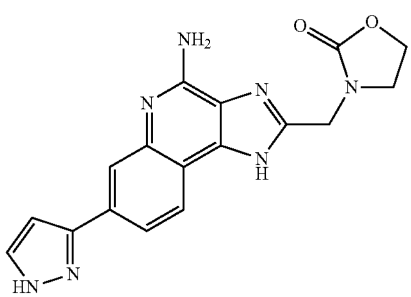 [SMILES: Nc1nc2cc(-c3cc[nH]n3)ccc2c2[nH]c(CN3CCOC3=O)nc12] | 365 | 5.0 | D | D | 350.2 |
| 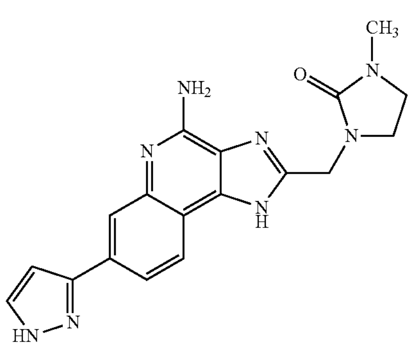 [SMILES: CN1CCN(Cc2nc3c(N)nc4cc(-c5cc[nH]n5)ccc4c3[nH]2)C1=O] | 368 | 3.9 | D | D | 363.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| (structure) | 370 | 4.8 | D | D | 352.3 |
| (structure) | 372 | 8.3 | D | D | 351.3 |
| (structure) | 375 | 2.4 | D | D | 365.2 |
| (structure) | 376 | 3.6 | D | D | 398.3 |
| (structure) | 377 | 4.3 | D | D | 405.3 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| (structure) | 379 | 2.0 | D | D | 336.3 |
| (structure) | 383 | 3.6 | D | D | 393.4 |
| (structure) | 393 | 7.11 | D | D | 422.2 |
| (structure) | 397 | 1.05 | D | D | 424.4 |
| (structure) | 398 | 1.22 | D | D | 308.3 |

TABLE 1-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 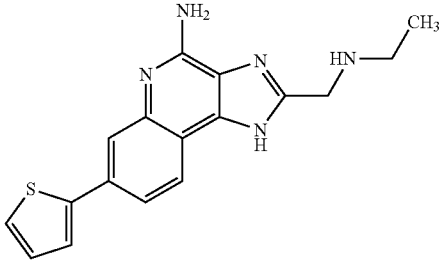 [SMILES: CCNCc1nc2c(N)nc3cc(-c4cccs4)ccc3c2[nH]1] | 399 | 1.06 | D | D | 324.2 |
| 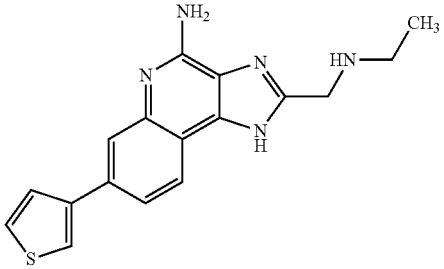 [SMILES: CCNCc1nc2c(N)nc3cc(-c4ccsc4)ccc3c2[nH]1] | 400 | 1.79 | D | D | 324.2 |
| 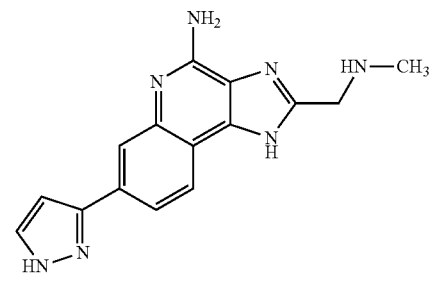 [SMILES: CNCc1nc2c(N)nc3cc(-c4cc[nH]n4)ccc3c2[nH]1] | 401 | 1.23 | D | D | 294.3 |
| 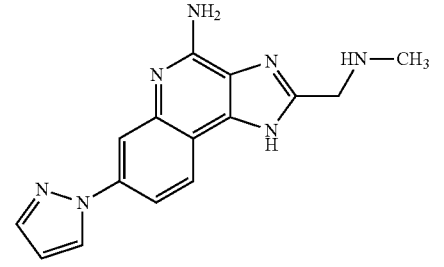 [SMILES: CNCc1nc2c(N)nc3cc(-n4cccn4)ccc3c2[nH]1] | 402 | 1.31 | D | D | 294.3 |
| 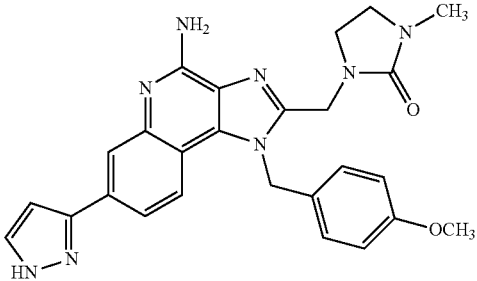 [SMILES: COc1ccc(Cn2c(CN3CCN(C)C3=O)nc3c(N)nc4cc(-c5cc[nH]n5)ccc4c32)cc1] | 403 | 3.66 | D | D | 483.3 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
| --- | --- | --- | --- | --- | --- |
| 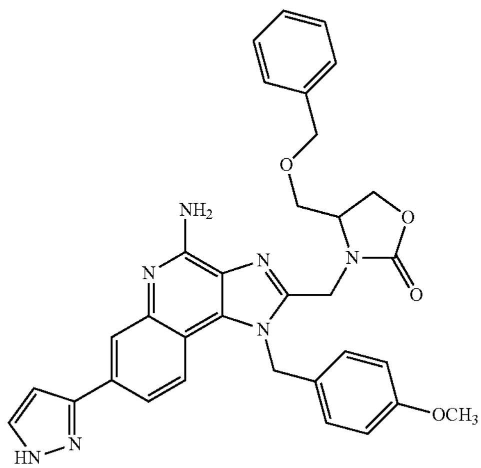 [SMILES: COc1ccc(Cn2c(CN3C(=O)OCC3COCc3ccccc3)nc3c(N)nc4cc(-c5cc[nH]n5)ccc4c32)cc1] | 404 | 2.50 | D | D | 590.3 |
| 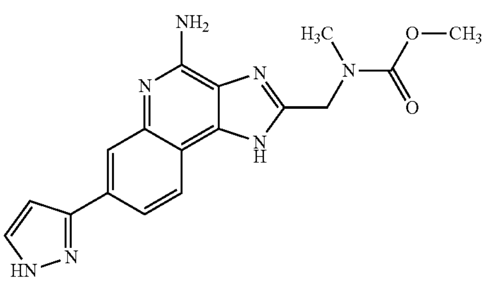 | 405 | 2.19 | D | D | 352.3 |
| 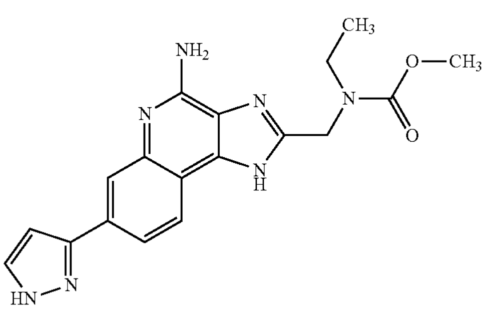 [SMILES: CCN(Cc1nc2c(N)nc3cc(-c4cc[nH]n4)ccc3c2[nH]1)C(=O)OC] | 406 | 1.37 | D | D | 366.1 |
| (R)-enantiomer | 407 | 6.55 | D | D | 424.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| (S)-enantiomer | 408 | 5.23 | D | D | 424.2 |
| 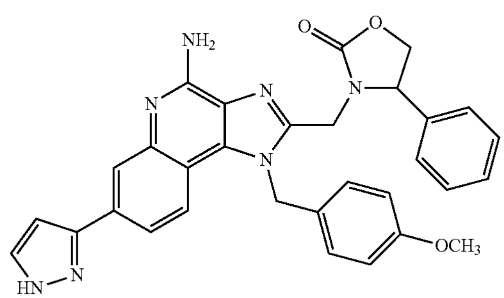 [SMILES: COc1ccc(Cn2c(CN3C(=O)OCC3c3ccccc3)nc3c(N)nc4cc(-c5cc[nH]n5)ccc4c32)cc1] | 409 | 2.36 | D | D | 546.5 |
| 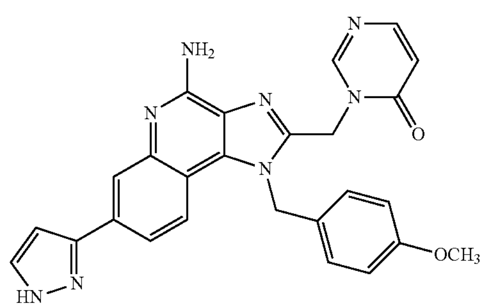 [SMILES: COc1ccc(Cn2c(Cn3cnccc3=O)nc3c(N)nc4cc(-c5cc[nH]n5)ccc4c32)cc1] | 414 | 3.83 | D | D | 479.4 |
| 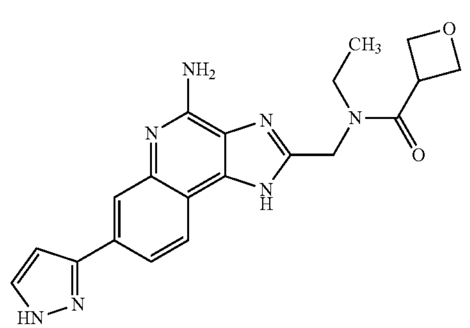 [SMILES: CCN(Cc1nc2c(N)nc3cc(-c4cc[nH]n4)ccc3c2[nH]1)C(=O)C1COC1] | 417 | 7.4 | D | D | 392.4 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 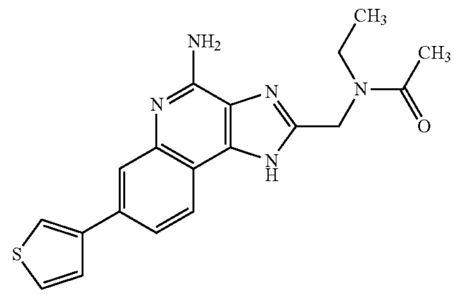 [SMILES: CCN(Cc1nc2c(N)nc3cc(-c4ccsc4)ccc3c2[nH]1)C(C)=O] | 419 | 0.91 | D | D | 366.3 |
| 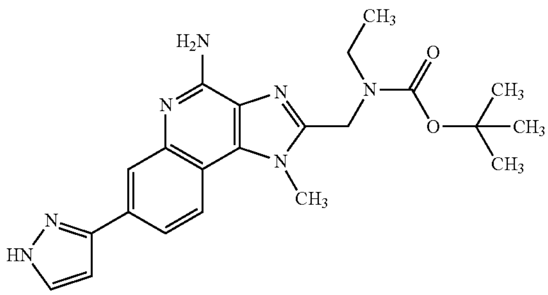 [SMILES: CCN(Cc1nc2c(N)nc3cc(-c4cc[nH]n4)ccc3c2n1C)C(=O)OC(C)(C)C] | 420 | 0.19 | D | D | 422.4 |
| 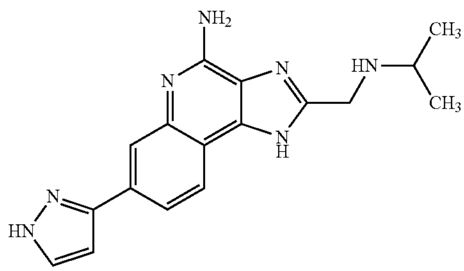 [SMILES: CC(C)NCc1nc2c(N)nc3cc(-c4cc[nH]n4)ccc3c2[nH]1] | 421 | 0.24 | | | 322.0 |
| 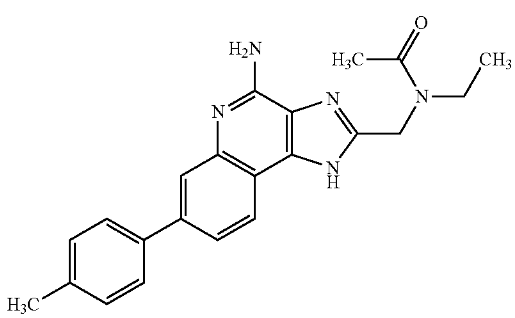 [SMILES: CCN(Cc1nc2c(N)nc3cc(-c4ccc(C)cc4)ccc3c2[nH]1)C(C)=O] | 422 | 0.28 | >10 | >10 | 374.1 |
| 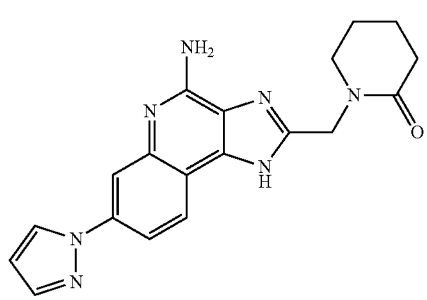 [SMILES: Nc1nc2cc(-n3cccn3)ccc2c2[nH]c(CN3CCCCC3=O)nc12] | 423 | 0.62 | D | D | |

TABLE 1-continued
| Structure | Compound | hNLRP3 Agonist EC$_{50}$ (µM) | TLR7 EC$_{50}$ (µM) | TLR8 EC$_{50}$ (µM) | LCMS [M + H]+ |
|---|---|---|---|---|---|
| 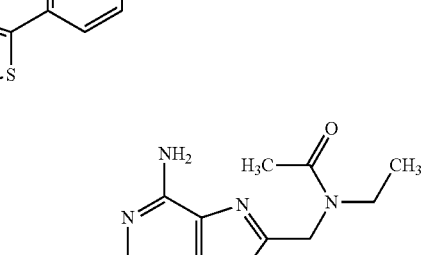 | 424 | 0.79 | D | | 424.2 |
| 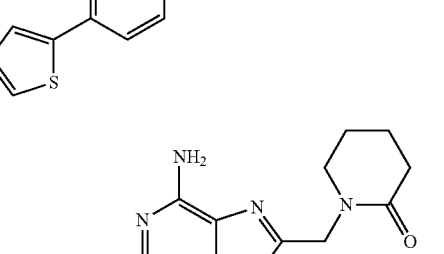 | 425 | 0.44 | D | | 366.2 |
| 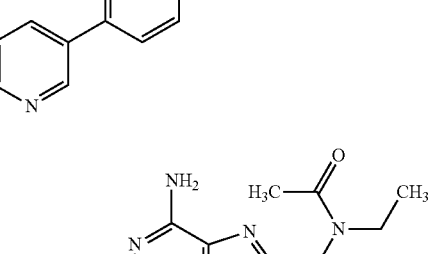 | 426 | 4.3 | D | | |
| 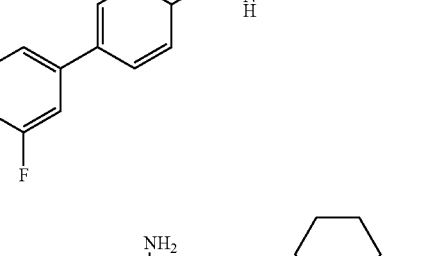 | 427 | 5.0 | D | D | 379.0 |
| 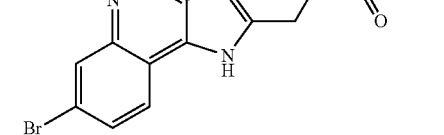 | 428 | 5.1 | D | | |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 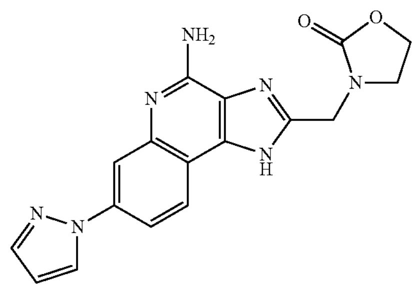 [SMILES: Nc1nc2cc(-n3cccn3)ccc2c2[nH]c(CN3CCOC3=O)nc12] | 429 | 5.8 | D | | 350.2 |
| 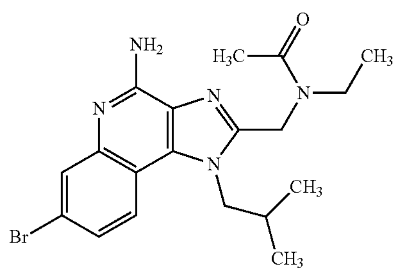 [SMILES: CCN(Cc1nc2c(N)nc3cc(Br)ccc3c2n1CC(C)C)C(C)=O] | 430 | 7.45 | D | >10 | 418.1 |
| 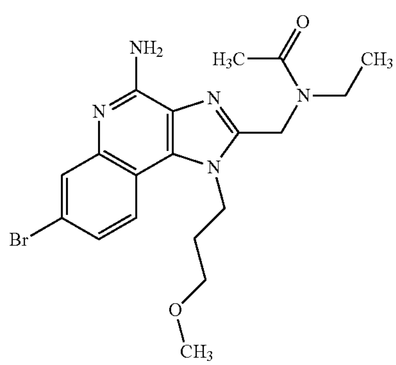 [SMILES: CCN(Cc1nc2c(N)nc3cc(Br)ccc3c2n1CCCOC)C(C)=O] | 431 | 8.67 | D | >10 | 434.1 |
| 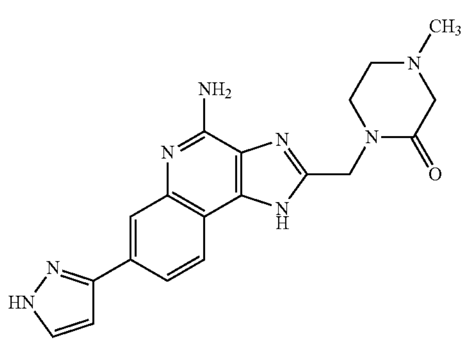 [SMILES: CN1CCN(Cc2nc3c(N)nc4cc(-c5cc[nH]n5)ccc4c3[nH]2)C(=O)C1] | 432 | ~10 | | | 377.2 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 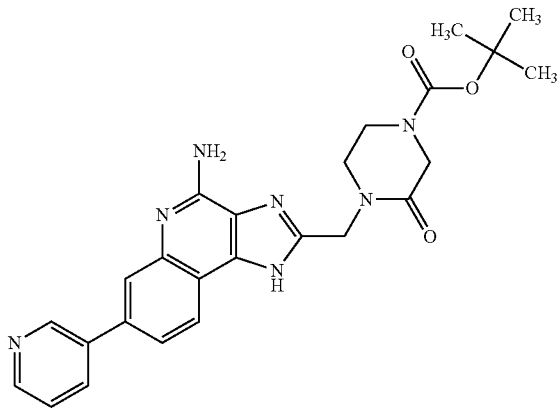 [SMILES: CC(C)(C)OC(=O)N1CCN(Cc2nc3c(N)nc4cc(-c5cccnc5)ccc4c3[nH]2)C(=O)C1] | 433 | 11.5 | | | 474.3 |
| 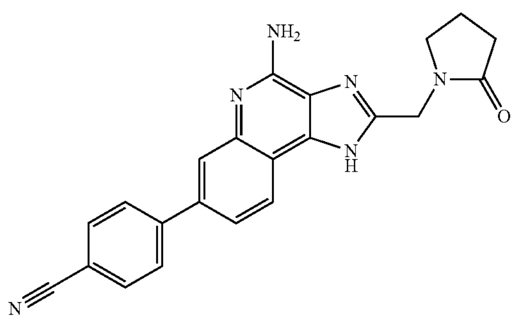 [SMILES: N#Cc1ccc(-c2ccc3c(c2)nc(N)c2nc(CN4CCCC4=O)[nH]c23)cc1] | 434 | 15.5 | >30 | >30 | |
| 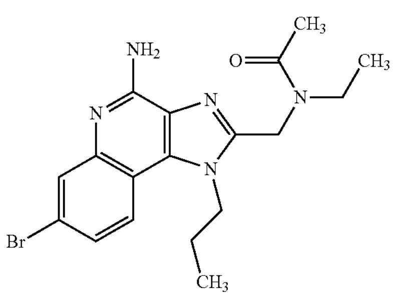 [SMILES: CCCn1c(CN(CC)C(C)=O)nc2c(N)nc3cc(Br)ccc3c21] | 435 | 19.3 | D | | 404.2 |
| 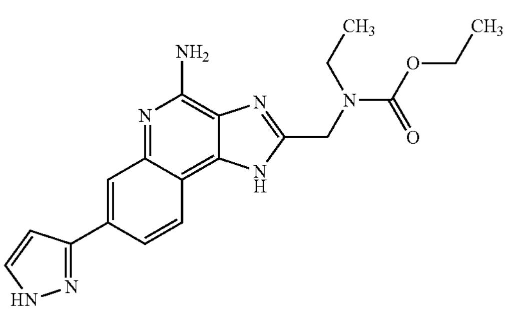 [SMILES: CCOC(=O)N(CC)Cc1nc2c(N)nc3cc(-c4cc[nH]n4)ccc3c2[nH]1] | 436 | 1.3 | >50 | >50 | 390.0 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 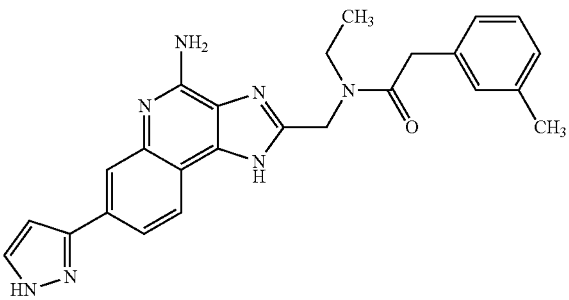 [SMILES: CCN(Cc1nc2c(N)nc3cc(-c4cc[nH]n4)ccc3c2[nH]1)C(=O)Cc1cccc(C)c1] | 437 | 1.1 | D | D | 440.4 |
| 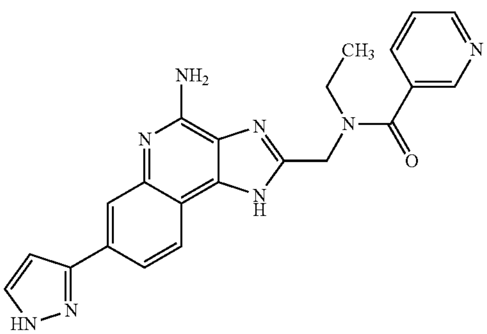 [SMILES: CCN(Cc1nc2c(N)nc3cc(-c4cc[nH]n4)ccc3c2[nH]1)C(=O)c1cccnc1] | 438 | 4.2 | D | D | 413.0 |
| 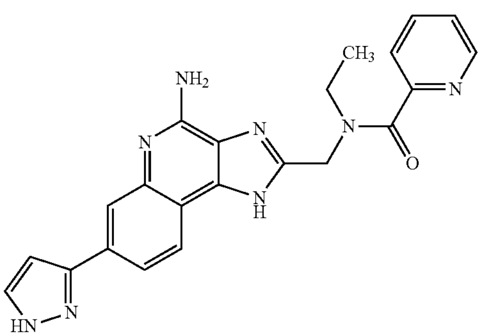 [SMILES: CCN(Cc1nc2c(N)nc3cc(-c4cc[nH]n4)ccc3c2[nH]1)C(=O)c1ccccn1] | 439 | 5.7 | D | D | 413.2 |
| 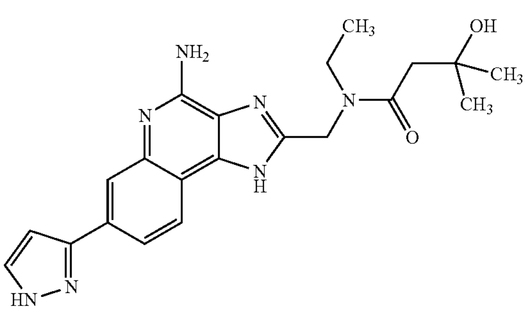 [SMILES: CCN(Cc1nc2c(N)nc3cc(-c4cc[nH]n4)ccc3c2[nH]1)C(=O)CC(C)(C)O] | 440 | 18.4 | D | D | 408.4 |

TABLE 1-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 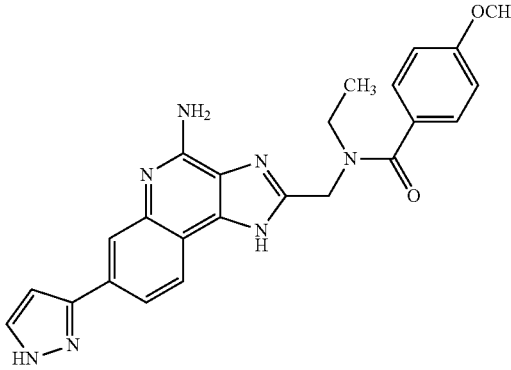 [SMILES: CCN(Cc1nc2c(N)nc3cc(-c4cc[nH]n4)ccc3c2[nH]1)C(=O)c1ccc(OC)cc1] | 441 | 0.69 | D | >62 | 442.0 |
| 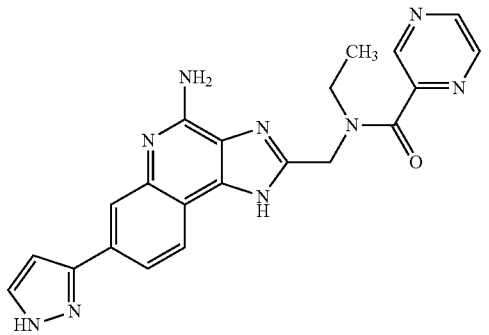 [SMILES: CCN(Cc1nc2c(N)nc3cc(-c4cc[nH]n4)ccc3c2[nH]1)C(=O)c1cnccn1] | 442 | 2.6 | D | D | 414.0 |
| 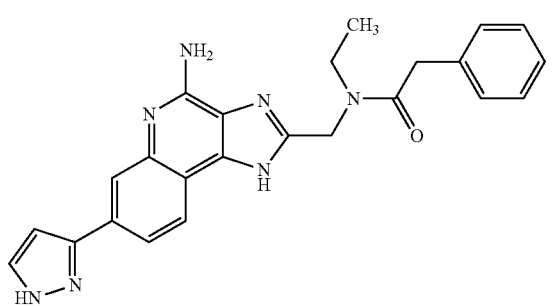 [SMILES: CCN(Cc1nc2c(N)nc3cc(-c4cc[nH]n4)ccc3c2[nH]1)C(=O)Cc1ccccc1] | 443 | 0.86 | D | >62 | 426.0 |
| 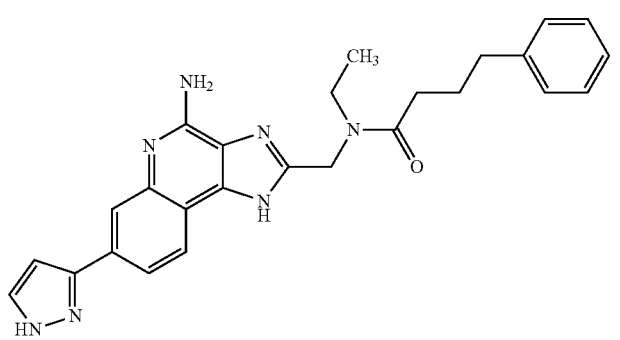 [SMILES: CCN(Cc1nc2c(N)nc3cc(-c4cc[nH]n4)ccc3c2[nH]1)C(=O)CCCc1ccccc1] | 444 | 0.93 | D | B | 454.1 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 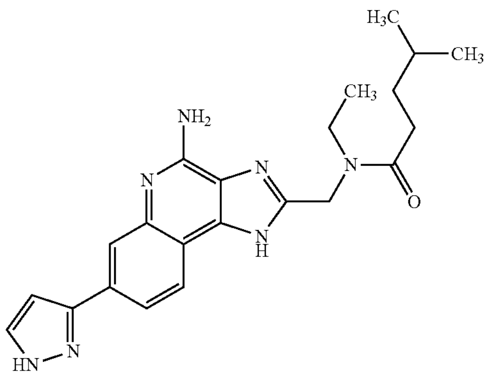 [SMILES: CCN(Cc1nc2c(N)nc3cc(-c4cc[nH]n4)ccc3c2[nH]1)C(=O)CCC(C)C] | 445 | 0.74 | D | >62 | 406.1 |
| 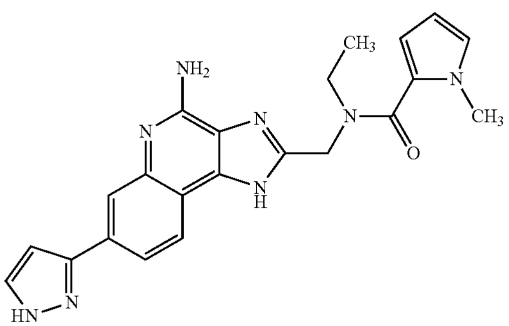 [SMILES: CCN(Cc1nc2c(N)nc3cc(-c4cc[nH]n4)ccc3c2[nH]1)C(=O)c1cccn1C] | 446 | 0.67 | D | D | 415.2 |
| 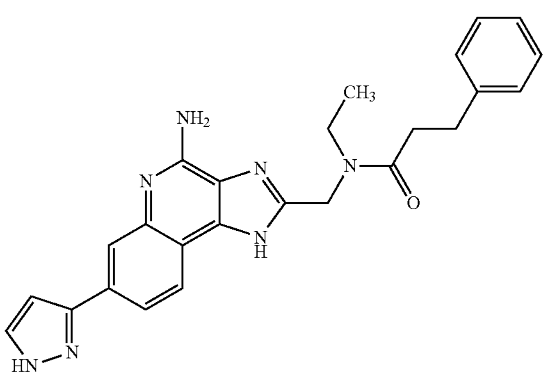 [SMILES: CCN(Cc1nc2c(N)nc3cc(-c4cc[nH]n4)ccc3c2[nH]1)C(=O)CCc1ccccc1] | 447 | 1.5 | D | B | 440.2 |
| 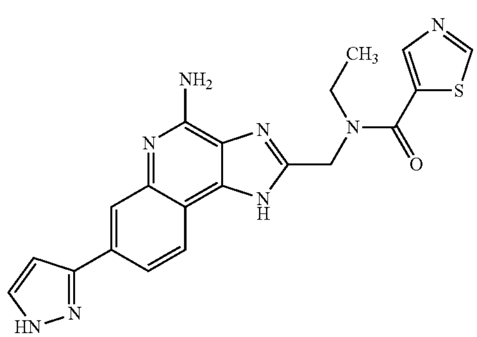 [SMILES: CCN(Cc1nc2c(N)nc3cc(-c4cc[nH]n4)ccc3c2[nH]1)C(=O)c1cncs1] | 448 | 2.0 | D | D | 419.3 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 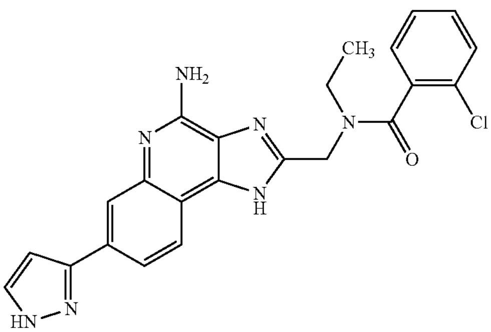 [SMILES: CCN(Cc1nc2c(N)nc3cc(-c4cc[nH]n4)ccc3c2[nH]1)C(=O)c1ccccc1Cl] | 449 | 0.90 | D | C | 446.0 |
| 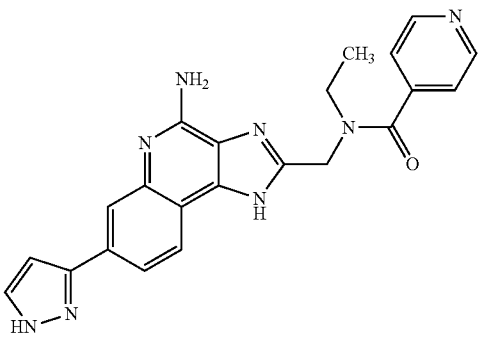 [SMILES: CCN(Cc1nc2c(N)nc3cc(-c4cc[nH]n4)ccc3c2[nH]1)C(=O)c1ccncc1] | 450 | 4.5 | D | D | 413.0 |
| 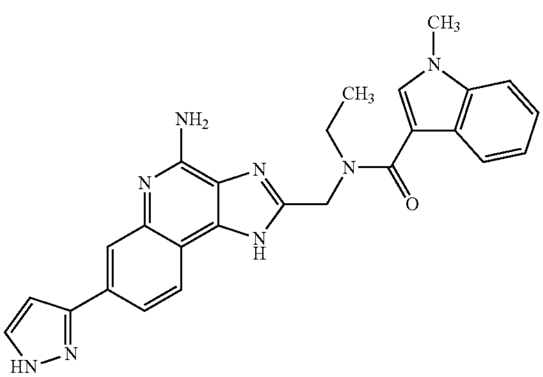 [SMILES: CCN(Cc1nc2c(N)nc3cc(-c4cc[nH]n4)ccc3c2[nH]1)C(=O)c1cn(C)c2ccccc12] | 451 | 1.3 | D | C | 465.2 |
| 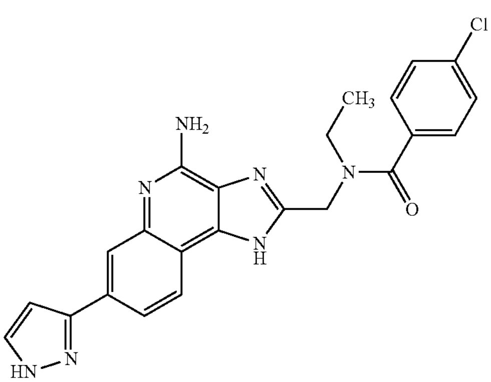 [SMILES: CCN(Cc1nc2c(N)nc3cc(-c4cc[nH]n4)ccc3c2[nH]1)C(=O)c1ccc(Cl)cc1] | 452 | 1.2 | D | >62 | 446.0 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 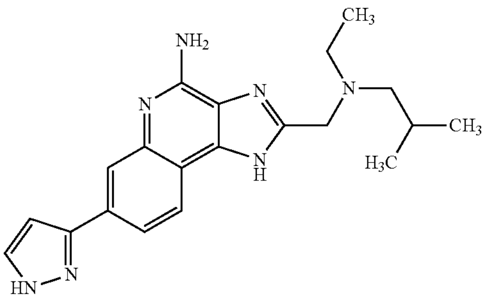 [SMILES: CCN(Cc1nc2c(N)nc3cc(-c4cc[nH]n4)ccc3c2[nH]1)CC(C)C] | 453 | 0.71 | D | D | 364.1 |
| 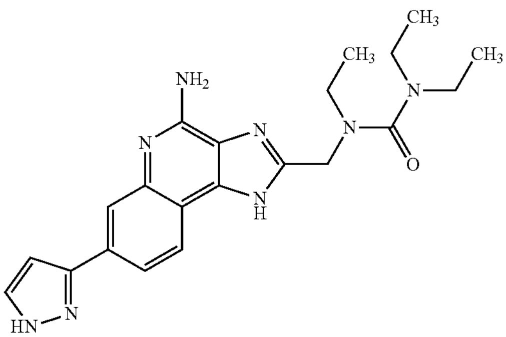 [SMILES: CCN(CC)C(=O)N(CC)Cc1nc2c(N)nc3cc(-c4cc[nH]n4)ccc3c2[nH]1] | 454 | 0.74 | D | D | 407.1 |
| 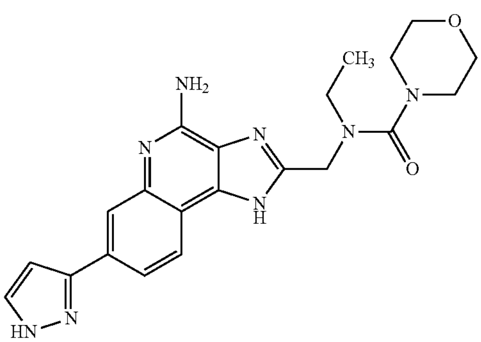 [SMILES: CCN(Cc1nc2c(N)nc3cc(-c4cc[nH]n4)ccc3c2[nH]1)C(=O)N1CCOCC1] | 455 | 2.0 | D | D | 421.4 |
| 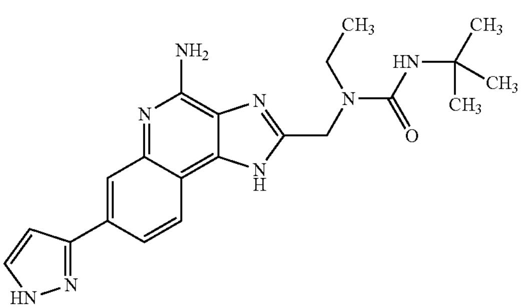 [SMILES: CCN(Cc1nc2c(N)nc3cc(-c4cc[nH]n4)ccc3c2[nH]1)C(=O)NC(C)(C)C] | 456 | 2.2 | D | D | 407.1 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 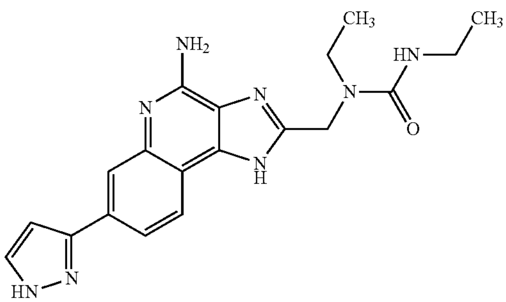 [SMILES: CCNC(=O)N(CC)Cc1nc2c(N)nc3cc(-c4cc[nH]n4)ccc3c2[nH]1] | 457 | 6.6 | D | D | 379.3 |
| 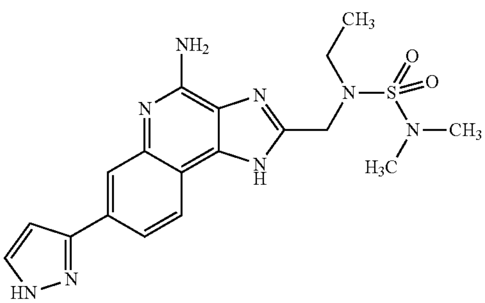 [SMILES: CCN(Cc1nc2c(N)nc3cc(-c4cc[nH]n4)ccc3c2[nH]1)S(=O)(=O)N(C)C] | 458 | 2.1 | D | D | 415.0 |
| 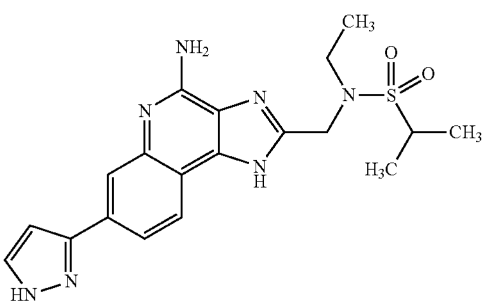 [SMILES: CCN(Cc1nc2c(N)nc3cc(-c4cc[nH]n4)ccc3c2[nH]1)S(=O)(=O)C(C)C] | 459 | 6.7 | D | D | 413.9 |
| 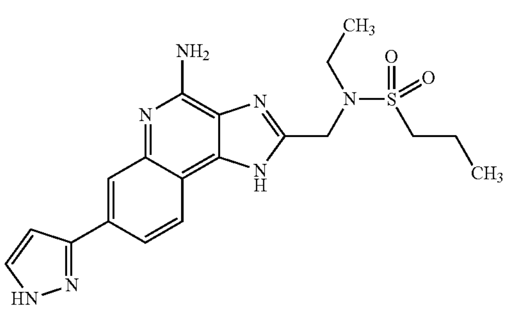 [SMILES: CCCS(=O)(=O)N(CC)Cc1nc2c(N)nc3cc(-c4cc[nH]n4)ccc3c2[nH]1] | 460 | 1.5 | D | >62 | 414.0 |
| 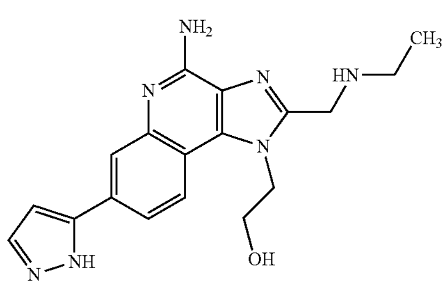 [SMILES: CCNCc1nc2c(N)nc3cc(-c4ccn[nH]4)ccc3c2n1CCO] | 562 | 5.5 | D | D | 352.3 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| (structure) | 463 | 0.22 | D | D | 392.2 |
| (structure) | 464 | 0.24 | D | D | 336.3 |
| (structure) | 465 | 1.0 | D | D | 376.2 |
| (structure) | 466 | 1.1 | D | D | 376.2 |
| (structure) | 467 | 1.2 | D | D | 336.3 |

TABLE 1-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 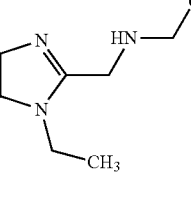 | 468 | 2.1 | D | D | 352.1 |
| 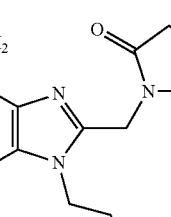 | 469 | 0.67 | D | D | 408.0 |
| 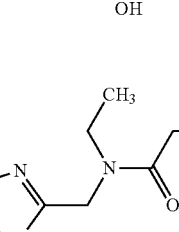 | 470 | 0.69 | D | D | 424.1 |
| 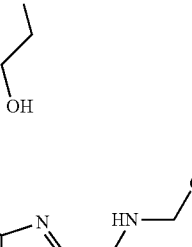 | 471 | 1.2 | D | D | 368.1 |
| 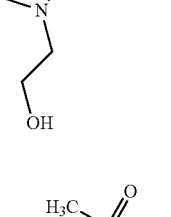 | 472 | 0.43 | D | D | 393.9 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 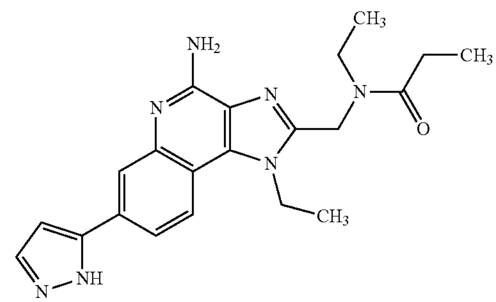 [SMILES: CCC(=O)N(CC)Cc1nc2c(N)nc3cc(-c4ccn[nH]4)ccc3c2n1CC] | 473 | 0.22 | D | D | 392.3 |
| 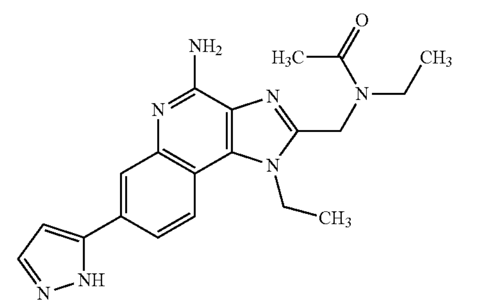 [SMILES: CCN(Cc1nc2c(N)nc3cc(-c4ccn[nH]4)ccc3c2n1CC)C(C)=O] | 474 | 1.2 | D | D | 378.3 |
| 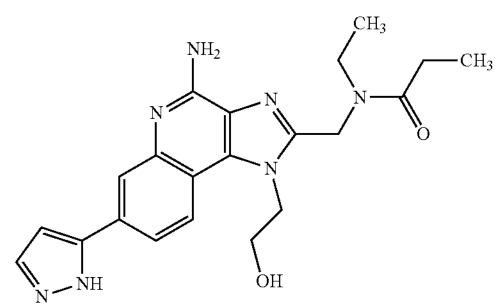 [SMILES: CCC(=O)N(CC)Cc1nc2c(N)nc3cc(-c4ccn[nH]4)ccc3c2n1CCO] | 475 | 23 | D | D | 408.1 |
| 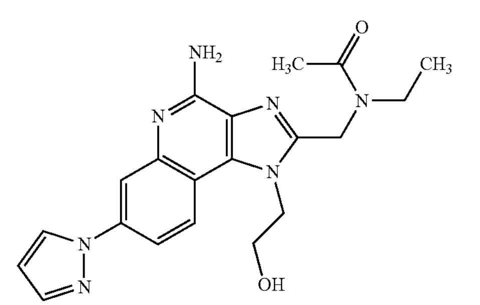 [SMILES: CCN(Cc1nc2c(N)nc3cc(-n4cccn4)ccc3c2n1CCO)C(C)=O] | 476 | 6.1 | D | D | 394.1 |
| 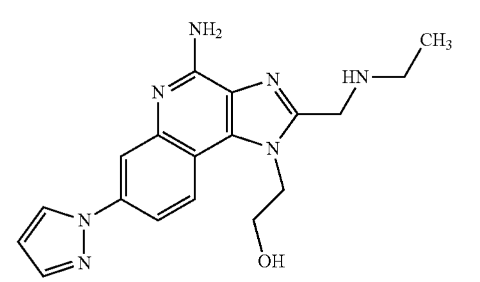 [SMILES: CCNCc1nc2c(N)nc3cc(-n4cccn4)ccc3c2n1CCO] | 477 | 6.3 | D | D | 352.1 |

TABLE 1-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 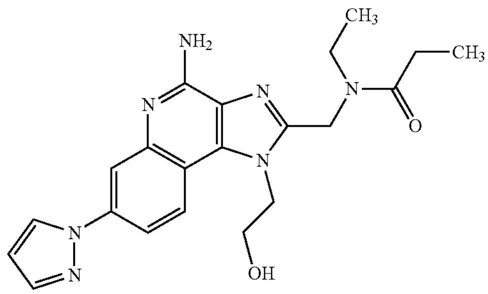 [SMILES: CCC(=O)N(CC)Cc1nc2c(N)nc3cc(-n4cccn4)ccc3c2n1CCO] | 478 | 3.7 | D | D | 408.1 |
| 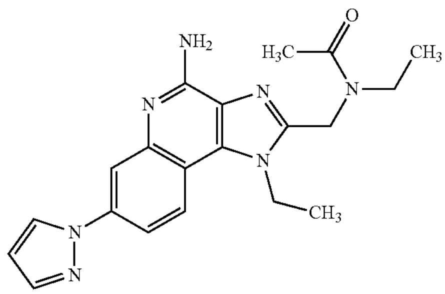 [SMILES: CCN(Cc1nc2c(N)nc3cc(-n4cccn4)ccc3c2n1CC)C(C)=O] | 479 | 0.67 | D | D | 378.0 |
| 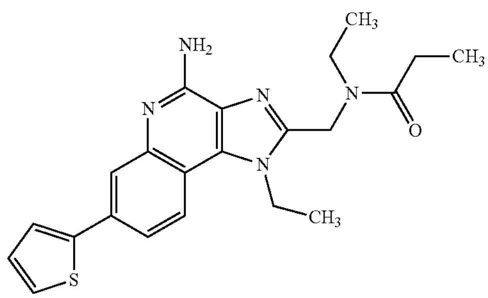 [SMILES: CCC(=O)N(CC)Cc1nc2c(N)nc3cc(-c4cccs4)ccc3c2n1CC] | 480 | 1.9 | D | D | 408.0 |
| 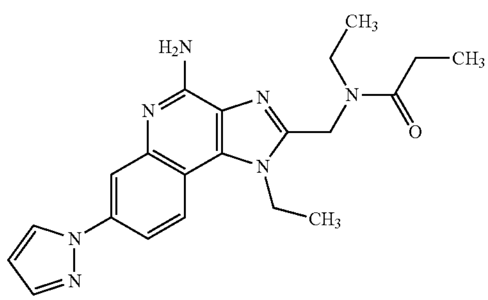 [SMILES: CCC(=O)N(CC)Cc1nc2c(N)nc3cc(-n4cccn4)ccc3c2n1CC] | 481 | 0.63 | D | D | 392.2 |
| | 482 | 0.43 | D | D | 410.1 | and pharmaceutically acceptable salts thereof.

Pharmaceutical Compositions and Administration

General

In some embodiments, a chemical entity (e.g., a compound that modulates (e.g., agonizes or partially agonizes) NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, a pharmaceutical composition comprising a compound of the present invention or a salt thereof, and one or more pharmaceutically acceptable excipients. In certain embodiments, a pharmaceutical composition comprising a compound of the present invention or a pharmaceutically acceptable salt thereof, and one or more pharmaceutically acceptable excipients. In certain embodiments, a pharmaceutical composition comprising a therapeutically effective amount of a compound of the present invention or a pharmaceutically acceptable salt thereof, and one or more pharmaceutically acceptable excipients.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, U K. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral). In certain embodiments, a preferred route of administration is systemic.

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 10:788-795 (2006).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

Indications

In any of the methods described herein, the subject can have a cancer. In some examples of any of the methods described herein, the mammal has been identified as having a cancer, or has been diagnosed as having a cancer.

Non-limiting examples of cancer include: acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In certain embodiments, non-limiting examples of cancer include: breast cancer, colon cancer, rectal cancer, colorectal cancer, pancreatic cancer, and prostate cancer.

Methods for diagnosing a subject as having a cancer or identifying a mammal as having a cancer are well known in the art. For example, a medical professional (e.g., a physician, a physician's assistant, or a technician) can diagnose cancer in a mammal by observing one or more symptoms of cancer in a mammal. Non-limiting examples of symptoms of cancer include: fatigue, lump or area of thickening felt under the skin, weight change, jaundice, darkening or redness of the skin, sores that won't heal, changes to existing moles, changes in bowel or bladder habits, persistent cough or trouble breathing, difficulty swallowing, hoarseness, persistent indigestion or discomfort after eating, persistent, unexplained muscle or joint pain, persistent, unexplained fevers or night sweats, and unexplained bleeding or bruising. Methods of diagnosing a subject as having a cancer or identifying a subject as having a cancer can further include performing one or more diagnostic tests (e.g., performing one or more diagnostic tests on a biopsy or a blood sample).

In some examples of any of the methods described herein, a subject can be a subject having a cancer, a subject diagnosed as having a cancer, or a subject identified as having a cancer that has been unresponsive to a previously administered treatment for cancer. Diagnostic tests for diagnosing a subject as having a cancer or identifying a mammal as having a cancer are known in the art.

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

In some embodiments, the present invention provides a method of treating cancer, wherein the cancer can be any cancer that does not elicit an optimal innate immune system response.

Innate immune system refers to a part of the immune system consisting of cells that react to threats for the organism like infections or cancer in an antigen-non-specific way and stimulate the adaptive, antigen-specific immune system. In general, complete removal of the threat and long-lasting protection (=immunity) requires activity of the adaptive, antigen-specific immune system that in turn depends on stimulation by the innate immune system.

In some embodiments, the present invention provides a method of treating case, the cancer is selected based on resistance to T-cell checkpoint inhibition, either independent of cancer type and based on failure to respond to previous T-cell checkpoint inhibitor therapy or based on cancer type that is generally resistant to T-cell checkpoint inhibitor therapy such as hormone receptor positive breast cancer, microsatellite stable colon or rectal cancer, pancreatic cancer and prostate cancer.

In certain other embodiments, the present invention provides a method of treating cancer comprising an NLPR3 agonist of the present invention to treat non-inflamed tumors with low CD8+ T-cell infiltration to enhance tumor immunogenicity and promote inflammatory responses. For example, the combination may be used to treat a solid tumor based on results of a biopsy that demonstrated low CD8+ T-cell infiltration or low expression of genes produced by CD8+ T-cells.

Resistance to T-cell checkpoint inhibition refers to cancer progression on therapy or lack of response within 6 months of therapy according to consensus response criteria for the respective cancer, such as RECIST1.1 for most solid tumors.

T-cell infiltration refers to percent of T-cells of all nucleated cells by immunohistochemistry of tumor biopsy specimens.

CD8+ T-cell infiltration refers to percent of CD8+ cells of all nucleated cells by immunohistochemistry of tumor biopsy specimens.

In addition to immunohistochemistry for quantifying CD8+ T-cells in biopsy specimens, expression of genes produced by CD8+ T-cells like interferon-γ can be measured by quantifying mRNA using for example next generation sequencing and inform about CD8+ T-cell infiltration. Thresholds for low and high CD8+ T-cell infiltration by immunohistochemistry of mRNA quantifying techniques are being developed by various groups and take the spectrum of CD8+ T-cell infiltration across cancers as well as for specific cancers into account.

In any of the methods described herein, the subject can have an infectious disease. In some examples of any of the methods described herein, the subject has been identified as having an infectious disease, or has been diagnosed as having an infectious disease. For example, an infectious disease can be caused by a bacterium, virus, fungus, parasite, or a *mycobacterium*.

Non-limiting examples of infectious disease include: *Acinobacter* infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, *Burkholderi* infection, Buruli ulcer, *Calicivirus* infection, camptobacteriosis, candidiasis, cat-scratch disease, cellulitis, Chagas disease, chancroid, chickenpox, chikungunya, chlamydia, *Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, *Desmodesmus* infection, deintamoebiasis, diphtheria, diphyllobothriasis, dracunculiasis, ebola hemorrhagic fever, echinococcosis, ehrlichiosis, enterobiasis, *Enterococcus* infection, *Enterovirus* infection, epidemic typhus, erythema infection, exanthema subitum, fasciolopsiasis, fasciolosis, fatal familial insomnia, filariasis, food poisoning by *Clostridium myonecrosis*, free-living amebic infection, *Fusobacterium* infection, gas gangrene, geotrichosis, Gerstmann-Sträussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human ewingii ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, *Kingella kingae* infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, staphylococcal infection, strongyloidiasis, subacute sclerosing panencephalitis, syphilis, taeniasis, tetanus, tinea barbae, tinea capitis, tinea corporis, tinea cruris, tinea manum, tinea nigra, tinea pedis, tinea unguium, tinea *versicolor*, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

Methods for diagnosing a subject as having an infectious disease, or identifying a subject as having an infectious disease are well known in the art. For example, a medical professional (e.g., a physician, a physician's assistant, or a technician) can diagnose infectious disease in a subject by observing one or more symptoms of infectious disease in a subject. Non-limiting examples of symptoms of infectious disease include: fever, diarrhea, fatigue, and muscle aches. Methods of diagnosing a mammal as having an infectious disease or identifying a subject as having an infectious disease can further include performing one or more diagnostic tests (e.g., performing one or more diagnostic tests on a biopsy or a blood sample). Diagnostic tests for diagnosing a subject as having an infectious disease or identifying a subject as having an infectious disease are known in the art.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies is chemotherapy, which can include administering one or more additional chemotherapeutic agents.

In certain embodiments, the additional cancer therapy comprises (chemotherapeutic agent) an immunomodulatory moiety, e.g., an immune checkpoint inhibitor. In certain of these embodiments, the immune checkpoint inhibitor targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9—TIM3, Phosphatidylserine—TIM3, lymphocyte activation gene 3 protein (LAG3), MHC class II—LAG3, 4-1BB-4-1BB ligand, OX40-OX40 ligand, GITR, GITR ligand—GITR, CD27, CD70-CD27, TNFRSF25, TNFRSF25-TL1A, CD40L, CD40-CD40 ligand, HVEM-LIGHT-LTA, HVEM, HVEM—BTLA, HVEM—CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine—TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12. See, e.g., Postow, M. *J. Clin. Oncol.* 33, 1 (2015).

In certain embodiments, the immune checkpoint inhibitor targets an immune checkpoint receptor selected from CTLA-4, PD-1, PD-L1, PD-1-PD-L1, and PD-1-PD-L2.

In certain embodiments, the immune checkpoint inhibitor is selected from: nivolumab (also known as "OPDIVO"; formerly designated 5C4, BMS-936558, MDX-1106, or ONO-4538), pembrolizumab (also known as "KEYTRUDA", lambrolizumab, and MK-3475. See WO 2008/156712), PDR001 (Novartis; see WO 2015/112900), MEDI-0680 (AstraZeneca; AMP-514; see WO 2012/145493), cemiplimab (REGN-2810) (Regeneron; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (SHR-1210; Jiangsu Hengrui Medicine; see WO 2015/085847; Si-Yang Liu et al., *J Hematol. Oncol.* 10:136 (2017)), TSR-042 (ANB011; Tesaro Biopharmaceutical; see WO2014/179664), GLS-010 (WBP3055; Wuxi/Harbin Gloria Pharmaceuticals; see Si-Yang Liu et al., *J Hematol. Oncol.* 10:136 (2017)), AM-0001 (Armo), STI-1110 (Sorrento Therapeutics; see WO 2014/194302), AGEN2034 (Agenus; see WO 2017/040790), MGD013 (Macrogenics); IBI308 (Innovent; see WO 2017/024465, WO 2017/025016, WO 2017/132825, WO2017/133540); BMS-936559 (formerly 12A4 or MDX-1105; see, e.g., U.S. Pat. No. 7,943,743 and WO 2013/173223), MPDL3280A (also known as RG7446, atezolizumab, and TECENTRIQ; U.S. Pat. No. 8,217,149; see, also, Herbst et al. (2013) J Clin Oncol 31(suppl):3000), durvalumab (IMFINZI; MEDI-4736; AstraZeneca; see WO 2011/066389), avelumab (Pfizer; MSB-0010718C; BAVENCIO; see WO 2013/079174), STI-1014 (Sorrento; see WO2013/181634), CX-072 (Cytomx; see WO2016/149201), KN035 (3D Med/Alphamab; see Zhang et al., *Cell Discov.* 7:3 (March 2017), LY3300054 (Eli Lilly Co.; see, e.g, WO 2017/034916), CK-301 (Checkpoint Therapeutics; see Gorelik et al., AACR:Abstract 4606 (April 2016)); urelumab, PF-05082566, MEDI6469, TRX518, varlilumab, CP-870893, BMS-986016, MGA271, lirilumab, IPH2201, emactuzumab, INCB024360, galunisertib, ulocuplumab, BKT140, Bavituximab, CC-90002, bevacizumab, MNRP1685A, ipilimumab (YERVOY; U.S. Pat. No. 6,984,720), MK-1308 (Merck), AGEN-1884 (Agenus Inc.; WO 2016/196237), and tremelimumab (formerly ticilimumab, CP-675,206; AstraZeneca; see, e.g., WO 2000/037504 and Ribas, *Update Cancer Ther.* 2(3): 133-39 (2007)).

In certain embodiments, the immune checkpoint inhibitor is selected from: nivolumab, pembrolizumab, JS001, BGB-A317, INCSHR1210, TSR-042, GLS-010, STI-1110, MGD013, IBI308, BMS-936559, atezolizumab, durvalumab, avelumab, STI-1014, CX-072, KN035, LY3300054, CK-301, urelumab, PF-05082566, MEDI6469, TRX518, varlilumab, BMS-986016, ipilimumab, AGEN-1884, and tremelimumab.

In certain of these embodiments, the immune checkpoint inhibitor is selected from: Urelumab, PF-05082566, MEDI6469, TRX518, Varlilumab, CP-870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS-986016, MGA271, Lirilumab, IPH2201, Emactuzumab, INCB024360, Galunisertib, Ulocuplumab, BKT140, Bavituximab, CC-90002, bevacizumab, and MNRP1685A.

In certain embodiments, the immune checkpoint inhibitor is selected from: nivolumab, ipilimumab, pembrolizumab, atezolizumab, durvalumab and avelumab.

In certain embodiments, the immune checkpoint inhibitor is selected from: nivolumab and ipilimumab.

In certain embodiments, the additional anti-cancer agent (chemotherapeutic agent) is a STING agonist. For example, the STING agonist can include cyclic di-nucleotides, such as cAMP, cGMP, and cGAMP as well as modified cyclic di-nucleotides that include one or more of the following modification features (2'-O/3'-O linkage, phosphorothioate linkage, adenine and/or guanine analogue, 2'-OH modification (e.g., —OCH$_3$ or replacement, e.g., —F or N$_3$). See, e.g., WO 2014/189805.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semisynthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an antimetabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a *vinca* alkaloid, a podophyllotoxin and/or a taxane. Vinca alkaloids, in general, bind to specific sites on tubulin, inhibiting the assembly of tubulin into microtubules, generally during the M phase of the cell cycle. In an embodiment, a *vinca* alkaloid is derived, without limitation, from the Madagascar periwinkle, Catharanthus *roseus* (formerly known as *Vinca rosea*). In an embodiment, a vinca alkaloid includes, without limitation, Vincristine, Vinblastine, Vinorelbine and/or Vindesine. In an embodiment, a taxane includes, but is not limited to, Taxol, Paclitaxel and/or Docetaxel. In a further embodiment a plant alkaloid or terpenoid is a synthetic, semisynthetic or derivative. In a further embodiment, a podophyllotoxin is, without limitation, an etoposide and/or teniposide. In an embodiment, a taxane is, without limitation, docetaxel and/or ortataxel. In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613.

In yet another embodiment, the methods can further include administering one or both of: (i) one or more anti-fungal agents (e.g., selected from the group of bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and balsam of peru) and (ii) one or more antibiotics (e.g., selected from the group of amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, amoxicillin, calvulanate, ampicillin, subbactam, piperacillin, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanilimide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycline, tinidazole, trimethoprim, and teixobactin).

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the NLRP3 protein can serve as a biomarker for certain types of cancer.

In some embodiments, the chemical entities, methods, and compositions described herein can be administered to certain treatment-resistant patient populations (e.g., patients resistant to checkpoint inhibitors).

In some embodiments, the compounds of the present invention may be used in therapy. In certain embodiments, the present invention provides a combined preparation of a compound of the present invention, or a pharmaceutically acceptable salt thereof, and additional therapeutic agent(s) for simultaneous, separate or sequential use in therapy.

In some embodiments, a compound of the present invention, or a pharmaceutically acceptable salt thereof, or a pharmaceutical composition containing the same, may be used as a medicament. In certain embodiments, the compounds of the invention may be used for the manufacture of a medicament for the treatment of cancer.

EXAMPLES

As can be appreciated by the skilled artisan, methods of synthesizing the compounds of the formulae herein will be evident to those of ordinary skill in the art. For example, the compounds described herein can be synthesized, e.g., using one or more of the methods described herein and/or using methods described in, e.g., US 2015/0056224.

Synthetic chemistry transformations and protecting group methodologies (protection and deprotection) useful in synthesizing the compounds described herein are known in the art and include, for example, those such as described in R.

Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The starting materials used in preparing the compounds of the invention are known, made by known methods, or are commercially available. The skilled artisan will also recognize that conditions and reagents described herein that can be interchanged with alternative art-recognized equivalents. For example, in many reactions, triethylamine can be interchanged with other bases, such as non-nucleophilic bases (e.g. diisopropylamine, 1,8-diazabicycloundec-7-ene, 2,6-di-tert-butylpyridine, or tetrabutylphosphazene).

The skilled artisan will recognize a variety of analytical methods that can be used to characterize the compounds described herein, including, for example, $^1$H NMR, heteronuclear NMR, mass spectrometry, liquid chromatography, and infrared spectroscopy. The foregoing list is a subset of characterization methods available to a skilled artisan and is not intended to be limiting.

To further illustrate the foregoing, the following non-limiting, exemplary synthetic schemes are included. Variations of these examples within the scope of the claims are within the purview of one skilled in the art and are considered to fall within the scope of the invention as described, and claimed herein. The reader will recognize that the skilled artisan, provided with the present disclosure, and skill in the art is able to prepare and use the invention without exhaustive examples.

The following abbreviations have the indicated meanings:
ACN=acetonitrile
$CH_2Cl_2$=dichloromethane
$CH_3ReO_3$=methyltrioxorhenium
$Cs_2CO_3$=cesium carbonate
d=doublet
DCM=dichloromethane
DIEA=N,N-diethylisopropylamine
DMF=N,N-dimethylformamide
DMSO=dimethylsulfoxide
ES=electrospray ionization
EA, EtOAc=ethyl acetate
EtOH=ethanol
equiv=equivalents
g=grams
h=hours
HCl=hydrogen chloride (usually as a solution)
$H_2O$=water
$H_2O_2$=hydrogen peroxide
HATU=1-[Bis(dimethylamino)methylene]-1H-1,2,3-triazolo[4,5-b]pyridinium 3-oxide hexafluorophosphate
HPLC=high-performance liquid chromatography
$K_2CO_3$=potassium carbonate
LC/MS=liquid chromatography mass spectrometer
$LiBH_4$=lithium borohydride
m=multiplet
M=molar
m-CPBA=meta-chloroperoxybenzoic acid
mg=milligram(s)
MeOH=methanol
MHz=megahertz
mL=milliliter(s)
mmol=millimole(s)
$NaHCO_3$=sodium hydrogen carbonate
$Na_2CO_3$=sodium carbonate
NaOH=sodium hydroxide
$Na_2SO_4$=sodium sulfate
$NEt_3$=trimethylamine
$NH_3$=ammonia
$NH_4OH$ or $NH_3H_2O$=ammonium hydroxide
$NH_4HCO_3$=ammonium hydrogen carbonate
nm=nanometer
$PdCl_2(PPh_3)_2$=bis(triphenylphosphine)palladium (II) dichloride
$Pd(dppf)Cl_2$=[1,1'-Bis(diphenylphosphino)ferrocene]dichloropalladium (II)
PE=petroleum ether
PMB=para-methoxybenzyl
$POCl_3$=phosphorous oxychloride
ppm=parts per million
Py=pyridine
s=singlet
t=triplet
$T_3P$=2,4,6-Tripropyl-1,3,5,2,4,6-trioxatriphosphorinane-2,4,6-trioxide
TFA=trifluoroacetic acid
TLC=thin layer chromatography TsCl=para-toluenesulfonyl chloride
° C.=degrees Celsius
µmol=micromolar Generic Procedure for the Synthesis of Compounds of Formula I The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification. The synthesis of the compounds of Formula (I) can be made using the methods summarized in Scheme 1.

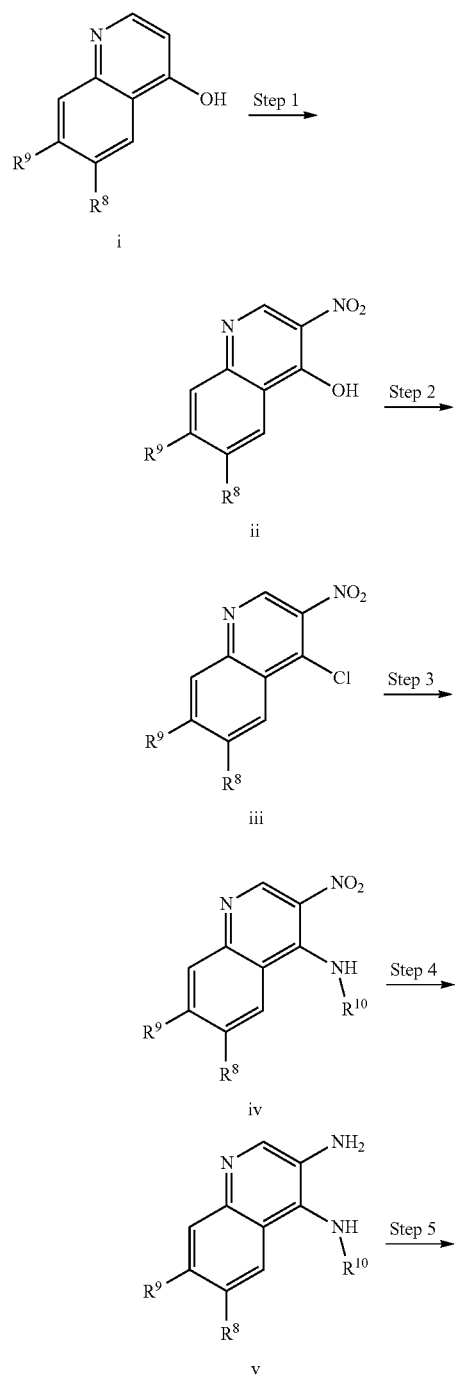

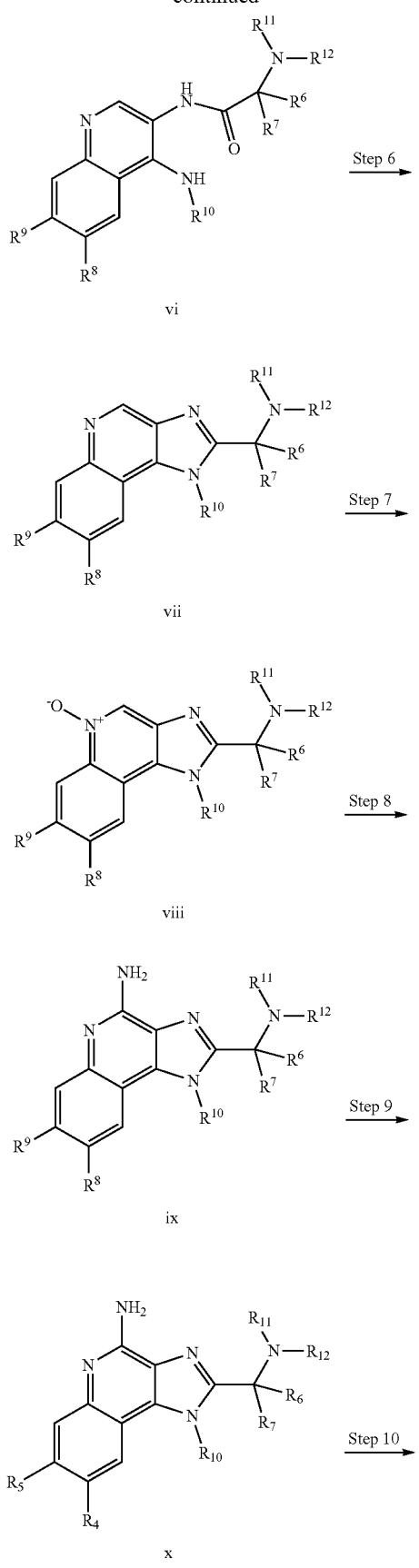

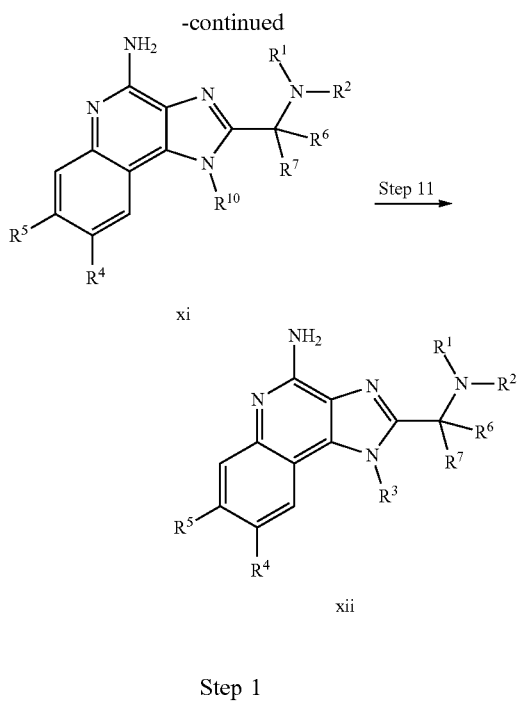

Step 1

The first step of Scheme 11 begins with a suitably functionalized quinolinol (i). If desired, the groups $R^8$ and $R^9$ may be the groups $R^4$ and $R^5$ found in the final product (xii). Alternatively, one or both of $R^8$ and $R^9$ may be groups that can be modified at a later stage of the synthesis, such as bromo. The first step of Scheme 1 may be accomplished by treating compound (i) with a suitable nitrating agent, such as nitric acid, in a suitable solvent, such as propionic acid, at an appropriate temperature, such as 130° C., to give compound (ii).

Step 2

The second step of Scheme 1 may be accomplished by treating compound (ii) with a suitable chlorinating agent, such as phosphorous oxychloride, at an appropriate temperature, such as 120° C., to give compound (iii).

Step 3

In the third step of Scheme 1, the group $R^{10}$ installed may be the desired group $R^3$ found in the final product (xii). Alternatively, a protecting group such as p-methoxybenzyl may be installed and removed at a later stage of the synthesis. Step 3 may be accomplished by treating compound (iii) with a suitable amine, such as p-methoxybenzylamine, and base, such as triethylamine, in a solvent such as dichloromethane at a suitable temperature, such as room temperature, to give compound (iv).

Step 4

The fourth step of Scheme 1 may be accomplished by treating compound (iv) with a suitable reducing agent, such as tin(II) chloride, in a solvent such as ethanol, at an appropriate temperature, such as 65° C., to give compound (v).

Step 5

In the fifth step of Scheme 1, the groups $R^{11}$ and $R^{12}$ installed may be the groups $R^1$ and $R^2$ desired in the final product (xii). Alternatively, they may be groups that allow the installation of $R^1$ and/or $R^2$ in a later step, such as a Boc protecting group. Step 5 may be accomplished by treating compound (v) with a suitably functionalized carboxylic acid, such as N-Boc-N-ethyl glycine, a suitable coupling agent, such as HATU, and a suitable amine, such as triethylamine, in a solvent such as dichloromethane at an appropriate temperature, such as room temperature, to give compound (vi).

Step 6

The sixth step of Scheme 1 may be accomplished by treating compound (vi) with a suitable base, such as triethylamine, in a solvent such as ethanol at an appropriate temperature, such as 70° C., to give compound (vii).

Step 7

The seventh step of Scheme 1 may be accomplished by treating compound (vii) with a suitable oxidant, such as m-CPBA, in a solvent such as dichloromethane to give compound (viii).

Step 8

The eighth step of Scheme 1 may be accomplished by treating compound (viii) with a reagent, such as tosyl chloride, and an amine, such as ammonia, in a solvent such as dichloromethane to give compound (ix).

Steps 9, 10, and 11 of Scheme 1 may optionally be conducted to transform one or more of the groups $R^8$, $R^9$, $R^{10}$, $R^{11}$, and $R^{12}$ into the groups $R^1$, $R^2$, $R^3$, $R^4$, and $R^5$ desired in the final product (xii). An individual skilled in the art will recognize that one or more of these steps may not be necessary, depending on the reagents selected earlier in the synthesis and final product desired. Furthermore, an individual skilled in the art will recognize that these steps may be conducted in an alternative order, depending on the final product desired.

Step 9

The ninth step of Scheme 1 may optionally be conducted to transform one or both of the groups $R^8$ and $R^9$ into the groups $R^4$ and $R^5$ desired in the final product. For example, if $R^9$ is bromo, and the desired $R^5$ is 3-pyrazoyl, this transformation may be accomplished by treating compound (ix) with a suitable boronic ester, such as 3-(tetramethyl-1,3,2-dioxaborolan-2-yl)-1H-pyrazole, in the presence of a catalyst such as Pd(dppf)Cl$_2$ dichloromethane complex, and a base such as cesium carbonate in a solvent mixture such as dioxane/water at a suitable temperature, such as 100° C., to give compound (x). Alternatively, if $R^9$ is bromo, and the desired $R^5$ is 1-pyrazolyl, this step may be accomplished by treating compound (ix) with pyrazole in the presence of a catalyst, such as copper(I) iodide, a ligand, such as N,N'-dimethylethylenediamine, and a base, such as sodium carbonate, in a solvent such as dimethylsulfoxide at an appropriate temperature, such as 120° C., to give compound (x).

Step 10

The tenth step of Scheme 1 may optionally be conducted to transform one or both of the groups $R^{11}$ and $R^{12}$ into the groups $R^1$ and $R^2$ desired in the final product. If one or both of the groups $R^{11}$ and $R^{12}$ is a protecting group such as Boc, this group may be removed under suitable conditions, such as by treating compound (x) with HCl in dioxane. If $R^{11}$ and/or $R^{12}$ is H, and the desired $R^1$ and/or $R^2$ is an amide, this step may be accomplished by treating compound (x) with a suitable anhydride and base, such as acetic anhydride and triethylamine, in a solvent such as dichloromethane, or by treating compound (x) with a suitable acid, coupling agent, and base, such as 3-hydroxy-3-methylbutanoic acid, 2,4,6-tripropyl-1,3,5,2,4,6-trioxatriphosphinane 2,4,6-trioxide, and Hunig's base in a solvent such as DMF, to give compound (xi). Alternatively, If $R^{11}$ and/or $R^{12}$ is H, and the desired $R^1$ and/or $R^2$ is an amine, this step may be accomplished by treating compound (x) with an appropriate aldehyde or ketone, such as isobutyraldehyde, and reducing agent, such as sodium triacetoxyborohydride, in a solvent such as methanol to give compound (xi). Alternatively, if $R^{11}$ and/or $R^{12}$ is H, and the desired $R^1$ and/or $R^2$ is a carbamate, this step may be accomplished by treating compound (x) with an appropriate chloroformate, such as ethyl chloroformate, and appropriate base, such as triethylamine, in a solvent such as dichloromethane, followed by treatment with an appropriate base, such as triethylamine, in an alcohol solvent, such as methanol, to give compound (xi). Alternatively, if $R_{11}$ and/or $R_{12}$ is H, and the desired $R_1$ and/or $R_2$ is a urea, this step may be accomplished by treating compound (x) with an appropriate carbamoyl chloride, such as morpholine-4-carbonyl chloride, or an appropriate isocyante, such as ethyl isocyante, in the presence of a base such as Hunig's base in a solvent such as DMF. Alternatively, if $R^{11}$ and/or $R^{12}$ is H, and the desired $R^1$ and/or $R^2$ is a sulfonylurea, this step may be accomplished by treating compound (x) with an appropriate sulfamoyl chloride, such as dimethylsulfamoyl chloride, and base, such as Hunig's base, in a solvent such as DMF to give compound (xi). Alternatively, if $R^{11}$ and/or $R^{12}$ is H, and the desired $R^1$ and/or $R^2$ is a sulfonamide, this step may be accomplished by treating compound (x) with an appropriate sulfonyl chloride and base, such as 2-propylsulfonyl chloride and Hunig's base, in a solvent such as DMF.

Step 11

The eleventh step of Scheme 1 may optionally be conducted to transform the group $R^{10}$ into the group $R^3$ desired in the final product (xii). For example, if $R^{10}$ is a protecting group such as p-methoxybenzyl, it may be removed under appropriate conditions, such as treating with trifluoroacetic acid at suitable temperature, such as 70° C., to give compound (xii).

Example 1: Procedure for Synthesis of 7-Bromo-$N^4$-(4-methoxybenzyl)quinoline-3,4-diamine Scheme 2

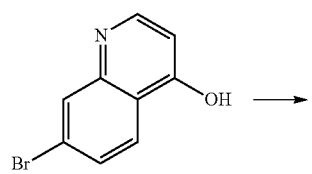

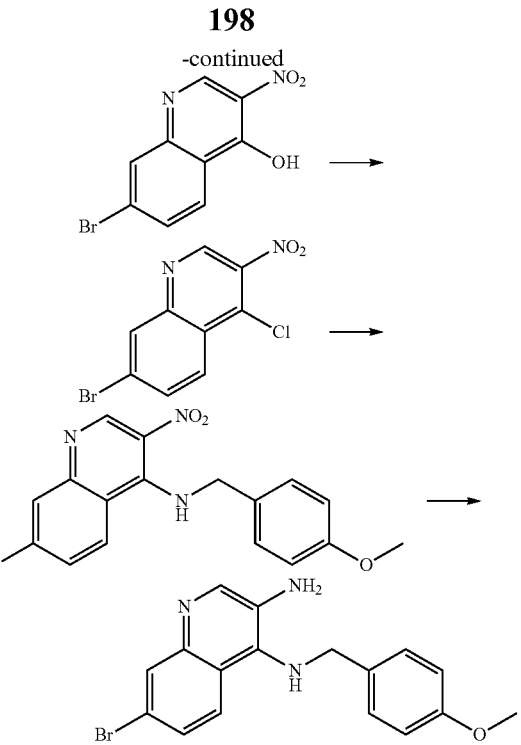

Step 1. Preparation of 7-bromo-3-nitroquinolin-4-ol

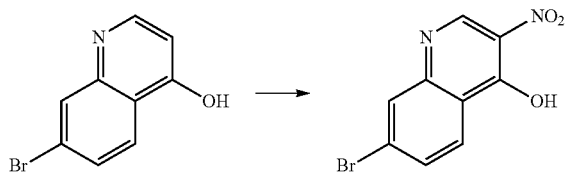 [SMILES: Oc1ccnc2cc(Br)ccc12 ; O=[N+]([O-])c1cnc2cc(Br)ccc2c1O]

7-bromoquinolin-4-ol (4.5 g, 20.0 mol) was dissolved in propionic acid (34 mL). The mixture was heated to 130° C., and nitric acid (1.7 mL, 70%) was added. The reaction was heated at 130° C. (bath temperature) for 4 hours at which time it was cooled to room temperature and filtered. The resulting solid was washed with water (3×20 mL), 2-propanol (20 mL), and hexanes (20 mL). The product was then dried under high vacuum to provide 3.8 g (70.6%) of 7-bromo-3-nitroquinolin-4-ol as a tan powder, which was used in the next step without further purification. (ES, m/z): [M+H]+=269.2/271.3.

Step 2. Preparation of 7-bromo-4-chloro-3-nitroquinoline

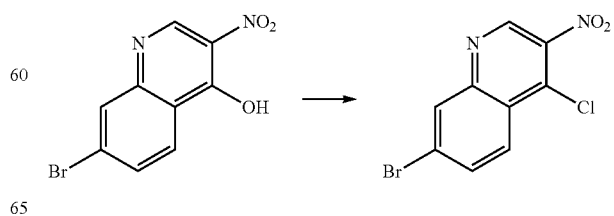

7-Bromo-3-nitroquinolin-4-ol (3.8 g, 14.12 mmol) was suspended in POCl$_3$ (20 mL). Anhydrous DMF (1 mL) was added. The mixture was then heated to 120° C. under an atmosphere of nitrogen for 3 hours at which time the reaction was cooled to room temperature. The precipitate was collected by filtration, washed with water, and then partitioned between $CH_2Cl_2$ (60 mL) and a saturated aqueous solution of $Na_2CO_3$. The organic layer was separated, washed with brine, dried over $Na_2SO_4$, filtered, and concentrated to afford 3.3 g (11.5 mmol, 81%) of 7-bromo-4-chloro-3-nitroquinoline as a beige-colored solid. (ES, m/z): [M+H]+=287.1/288.9.

Note: It was discovered that if higher temperatures and longer reaction times are used, a significant amount of Cl—Br exchange occurs which affords an intermediate that does not undergo subsequent cross-coupling reactions.

Step 3. Preparation of 7-bromo-N-(4-methoxybenzyl)-3-nitroquinolin-4-amine

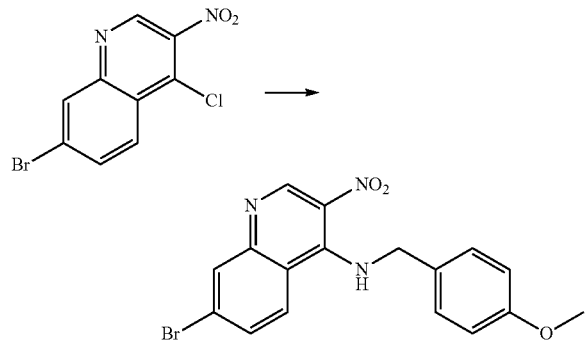

7-bromo-4-chloro-3-nitroquinoline (1.9 g, 6.62 mmol) was dissolved in $CH_2Cl_2$ (20 mL). 4-methoxy benzylamine (0.85 mL, 6.7 mmol) was added, followed by $NEt_3$ (0.95 mL, 6.7 mmol). The mixture was stirred at room temperature for 4 h at which time it was diluted with $CH_2Cl_2$ (30 mL), washed with water, washed with brine, dried over $Na_2SO_4$, and filtered. The resulting solution was evaporated to dryness to afford (7-bromo-3-nitro-quinolin-4-yl)-(4-methoxy-benzyl)-amine as a yellow foam (2.5 g, 6.44 mmol, 97%). This material was used in the next step without further purification. (ES, m/z): [M+H]+=388.3/390.1.

Step 4. Preparation of 7-bromo-N4-(4-methoxybenzyl)quinoline-3,4-diamine

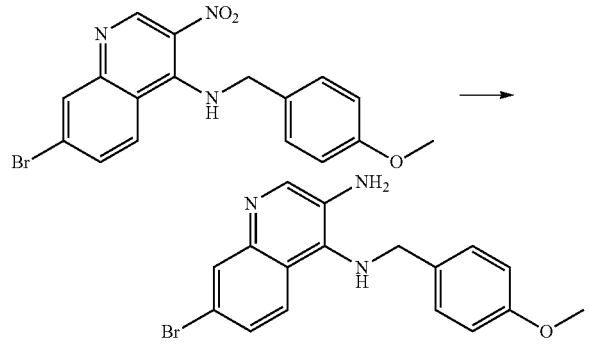

(7-Bromo-3-nitro-quinolin-4-yl)-(4-methoxy-benzyl)-amine (2.5 g, 6.44 mmol) was dissolved in ethanol (60 mL) at room temperature. Tin (II) chloride hydrate (4.8 g, 21.2 mmol) was added in one portion. The mixture was stirred at 65° C. for 3 h at which time water (50 mL) was added, followed by a saturated aqueous solution of $NaHCO_3$ to pH ~9. The mixture was extracted with EtOAc (3×60 mL), and the combined organic layers were dried over $Na_2SO_4$, filtered, and concentrated to afford 7-bromo-N4-(4-methoxybenzyl)-quinoline-3,4-diamine (1.5 g, 4.2 mmol, 65%). This material was used in the next step without further purification. (ES, m/z): [M+H]+=357.9/360.1.

Example 2: Preparation Method of Analogs Wherein $R^1/R^2$=Alkyl, Acetyl and $R^5$=Aryl, Heteroaryl, Heterocyclyl, or Amino Scheme 3

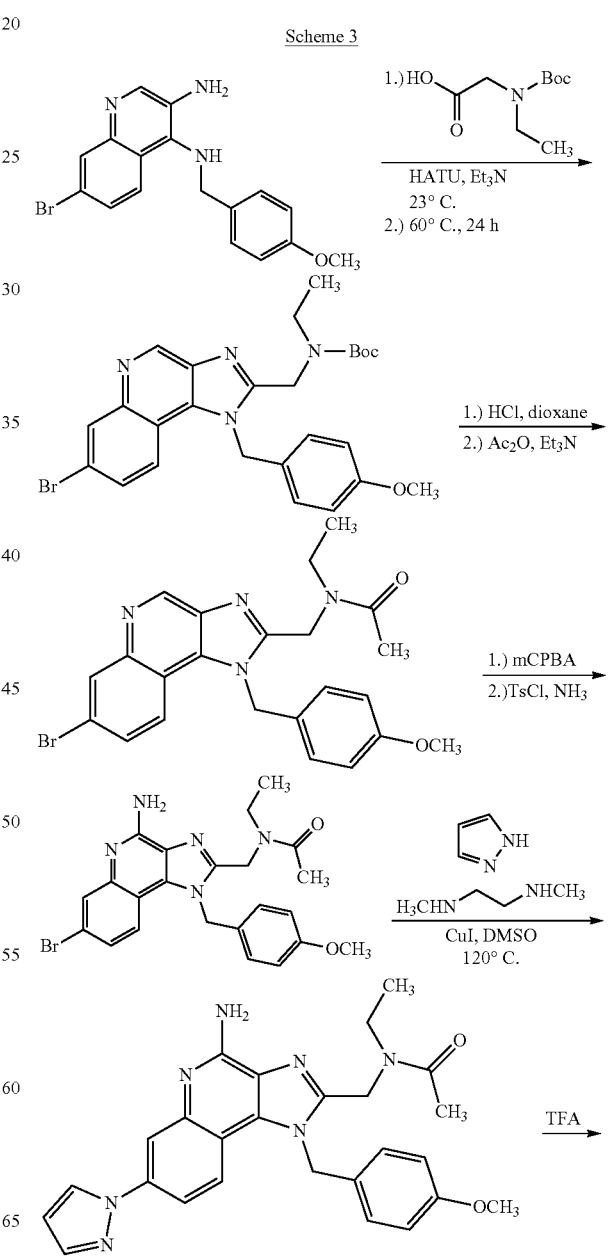

-continued

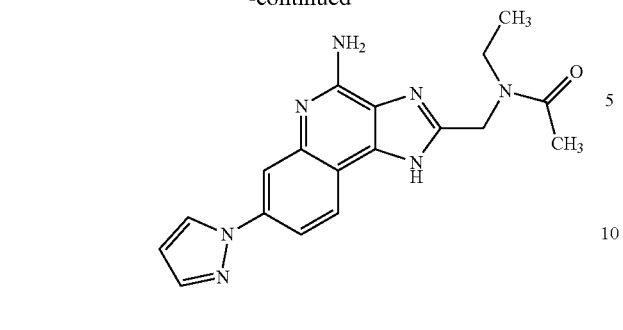

Step 1. Preparation of tert-butyl ((7-bromo-1-(4-methoxybenzyl)-1H-imidazo[4,5-c]quinolin-2-yl)methyl)(ethyl)carbamate

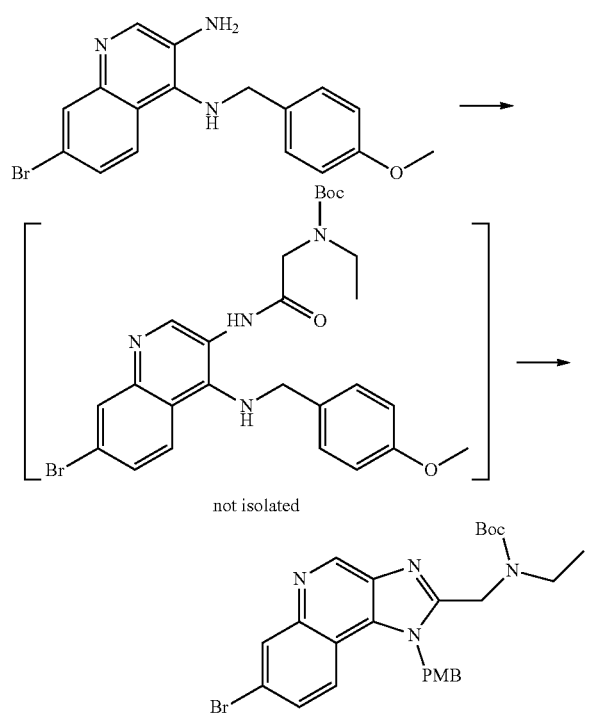

To a solution of 7-bromo-$N^4$-(4-methoxy-benzyl)-quinoline-3,4-diamine (0.950 g, 2.65 mmol, Example 1) and (tert-butoxycarbonyl-ethyl-amino)-acetic acid (0.600 g, 2.92 mmol)) in $CH_2Cl_2$ (20 mL) was added HATU (1.1 g, 2.65 mmol) and $NEt_3$ (0.4 mL, 2.87 mmol). The mixture was stirred at room temperature for 12 hours at which time it was then concentrated to remove all volatiles. EtOH (10 mL) was added, followed by $NEt_3$ (4 mL). The mixture was stirred in a 70° C. oil bath for 15 hours and then cooled to room temperature. Most of the volatiles were evaporated in vacuo, and the resulting residue was partitioned between $CH_2Cl_2$ (30 mL) and water (30 mL). The organic layer was further washed with water (30 mL), brine, dried over $Na_2SO_4$, filtered, and concentrated. The crude tert-butyl ((7-bromo-1-(4-methoxybenzyl)-1H-imidazo[4,5-c]quinolin-2-yl)methyl)(ethyl)carbamate (0.972 g, 1.85 mmol, 70% yield) was used in the next step without further purification. (ES, m/z): $[M+H]^+$=525.1/527.4.

Step 2. Preparation of N-((7-bromo-1-(4-methoxybenzyl)-1H-imidazo[4,5-c]quinolin-2-yl)methyl)-N-ethylacetamide

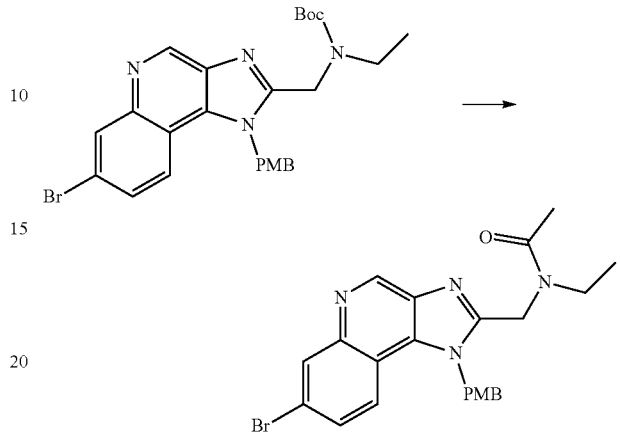

To a solution of tert-butyl ((7-bromo-1-(4-methoxybenzyl)-1H-imidazo[4,5-c]quinolin-2-yl)methyl)(ethyl)carbamate (0.972 g, 1.85 mmol) in dioxane (10 mL) was added HCl (10 mL, 4 N in dioxane). The mixture was stirred at room temperature for 4 hours at which time it was concentrated to remove all volatiles, then taken up in $CH_2Cl_2$ (20 mL). The mixture was stirred in an ice water bath for 5 min, then $NEt_3$ (0.4 mL, 2.88 mmol) and $Ac_2O$ (0.25 mL, 2.64 mmol) were added sequentially. The mixture was further stirred at room temperature for 30 min and then diluted with water (20 mL). The layers were separated and the organic layer was washed with water (20 mL), brine, dried over $Na_2SO_4$, filtered, and concentrated. The crude N-((7-bromo-1-(4-methoxybenzyl)-1H-imidazo[4,5-c]quinolin-2-yl)methyl)-N-ethylacetamide (0.800 g, 1.71 mmol, 92% yield) was used in the next step without further purification. (ES, m/z): $[M+H]^+$=467.2/469.4

Step 3. Preparation of 7-bromo-2-((N-ethylacetamido)methyl)-1-(4-methoxybenzyl)-1H-imidazo[4,5-c]quinoline 5-oxide

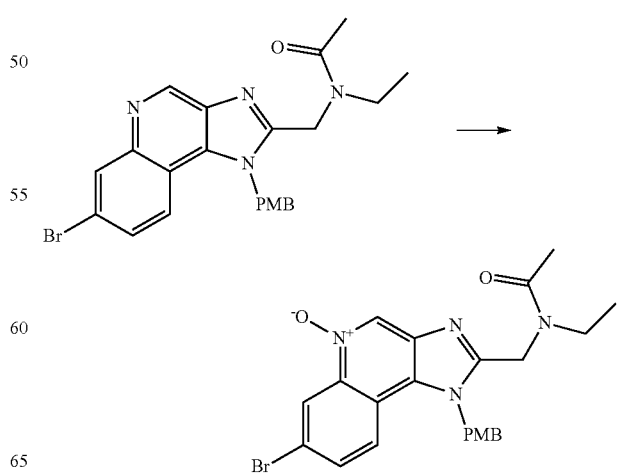

To a solution of N-((7-bromo-1-(4-methoxybenzyl)-1H-imidazo[4,5-c]quinolin-2-yl)methyl)-N-ethylacetamide (0.800 g, 1.71 mmol) in $CH_2Cl_2$ (20 mL) were added $H_2O_2$ (10 mL) and m-chloroperoxybenzoic acid (70% grade, 0.500 g, 0.2 mmol). The mixture was stirred for 15 hours at room temperature at which time it was diluted with a saturated aqueous solution of $NaHCO_3$ and extracted with $CH_2Cl_2$ (3×20 mL). The combined organic layers were washed with brine, dried over $Na_2SO_4$, filtered, and concentrated to afford crude 7-bromo-2-((N-ethylacetamido)methyl)-1-(4-methoxybenzyl)-1H-imidazo[4,5-c]quinoline 5-oxide (0.800 g, 1.65 mmol, 96% yield) as a brownish foam. (ES, m/z): $[M+H]^+$=483.2/485.5.

Step 4. Preparation of N-((4-amino-7-bromo-1-(4-methoxybenzyl)-1H-imidazo[4,5-c]quinolin-2-yl)methyl)-N-ethylacetamide

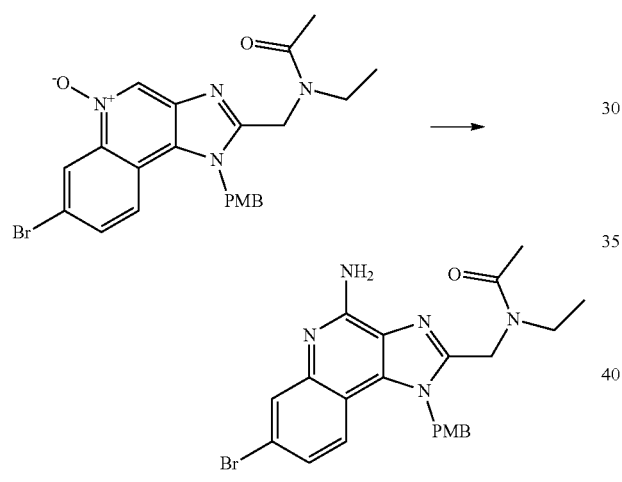

To a solution of 7-bromo-2-((N-ethylacetamido)methyl)-1-(4-methoxybenzyl)-1H-imidazo[4,5-c]quinoline 5-oxide (0.800 g, 1.65 mmol) and $NH_4OH$ (10 mL) in dichloromethane (20 mL) cooled in an ice water bath, was added p-toluenesulfonyl chloride (0.439 g, 2.3 mmol) in $CH_2Cl_2$ (10 mL) dropwise. The resulting solution was stirred another 30 min after addition was complete. Water (20 mL) was added and the layers were separated. The aqueous layer was extracted with $CH_2Cl_2$ (30 mL). The combined organic layers were filtered through a pad of $Na_2SO_4$ and the filtrate was concentrated in vacuo. The residue was triturated with EtOAc/hexanes (1/3) and dried under high vacuum to afford N-((4-amino-7-bromo-1-(4-methoxybenzyl)-1H-imidazo[4,5-c]quinolin-2-yl)methyl)-N-ethylacetamide as a yellow solid (677 mg, 1.4 mmol, 85% yield). (ES, m/z): $[M+H]^+$= 482.3/484.2.

Step 5. Coupling with Aryl Bromide

5a. Preparation of N-((4-amino-1-(4-methoxybenzyl)-7-(1H-pyrazol-1-yl)-1H-imidazo[4,5-c]quinolin-2-yl)methyl)-N-ethylacetamide (General Procedure for Ullman Coupling of N-heterocycles)

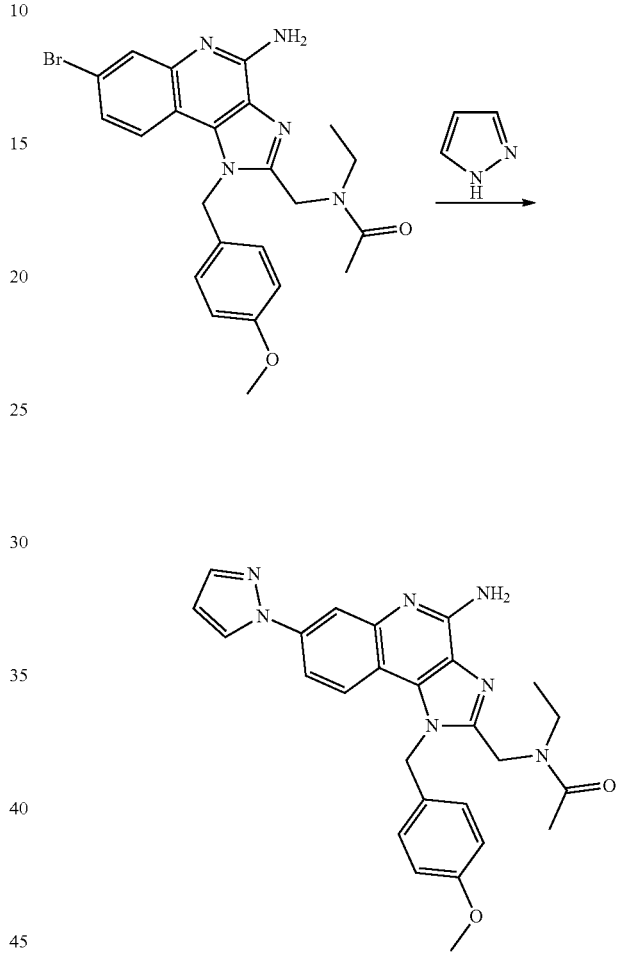

To a solution of N-((4-amino-7-bromo-1-(4-methoxybenzyl)-1H-imidazo[4,5-c]quinolin-2-yl)methyl)-N-ethylacetamide (25 mg, 52 μmol) in dry DMSO (2 mL) was added the N-heterocycle (2 equiv; pyrazole in the example above) followed by CuI (25 mg, 2 equiv) and $Na_2CO_3$ (30 mg, 4 equiv). The mixture was degassed, N,N'-dimethylethylenediamine (20 mg, 3 equiv) was added, and the mixture was stirred at 120° C. for 2 h. The cooled mixture was diluted with EtOAc, filtered, and the solvent evaporated. The resulting crude N-((4-amino-1-(4-methoxybenzyl)-7-(1H-pyrazol-1-yl)-1H-imidazo[4,5-c]quinolin-2-yl)methyl)-N-ethylacetamide was used in the deprotection step without further purification.

or

5b. Alternative Preparation to Install Aryl Groups Instead of N-Heterocycles: General Procedure for Suzuki Coupling of Arylboronic Acids and Esters

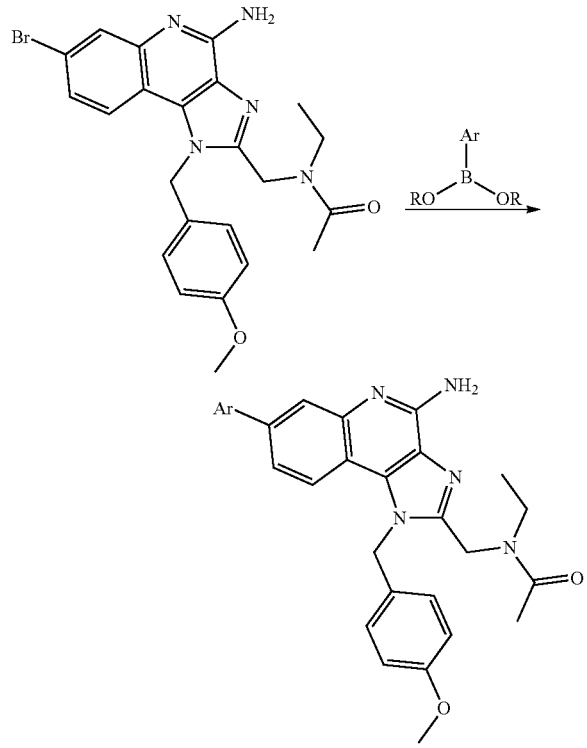

To a solution of N-((4-amino-7-bromo-1-(4-methoxybenzyl)-1H-imidazo[4,5-c]quinolin-2-yl)methyl)-N-ethylacetamide (25 mg, 52 µmol) was added the aryl(heteroaryl) boronic acid (or aryl boronate ester) (2 equiv), followed by Pd(dppf)Cl$_2$·CH$_2$Cl$_2$ (5 mg) and an aqueous solution of K$_2$CO$_3$ (1 mL, 2M aqueous). The mixture was heated in a Biotage Initiator microwave reactor at 120° C. for 10 min. The organic layer was diluted with EtOAc and separated, and the aqueous layer was washed with EtOAc. The combined organic phases were filtered, evaporated and the product residue used in the next step without further purification.

Step 6. General Deprotection Procedure—Preparation of N-((4-amino-7-aryl(heteroaryl)-1H-imidazo[4,5-c]quinolin-2-yl)methyl)-N-ethylacetamide

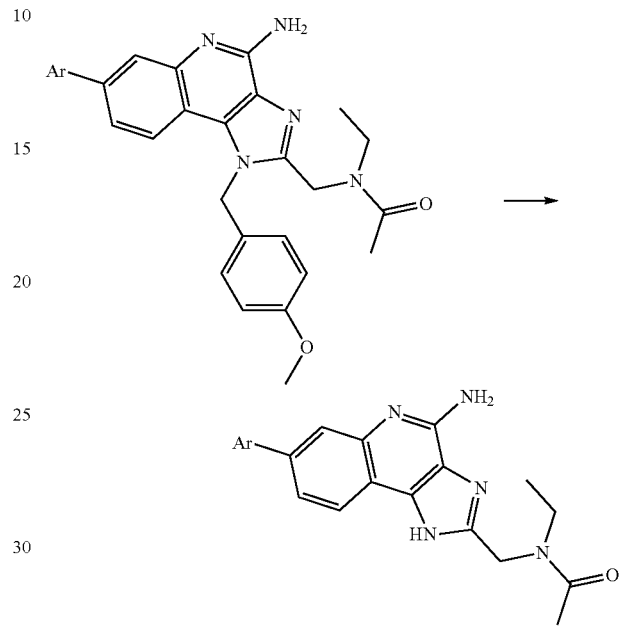

The crude product from the previous step was dissolved in TFA (2 mL) and stirred at 70° C. for 1 h while monitoring the reaction progress by LC/MS. Once the PMB protecting group was completely cleaved as indicated by LC/MS, the solvent was evaporated and the residue purified by HPLC to afford N-((4-amino-7-aryl(heteroaryl)-1H-imidazo[4,5-c]quinolin-2-yl)methyl)-N-ethylacetamide as the trifluoroacetate salt.

The compounds depicted in Table 2 were made according to the above synthetic procedures.

TABLE 2

| Compound | NAME | [M + H]+ |
|---|---|---|
| 165 | N-[(4-amino-7-phenyl-1H-imidazo[4,5-c]quinolin-2-yl)methyl]-N-ethylacetamide | 360.2 |
| 166 | N-[(4-amino-7-pyridin-3-yl-1H-imidazo[4,5-c]quinolin-2-yl)methyl]-N-ethylacetamide | 361.2 |
| 167 | N-[(4-amino-7-pyridin-4-yl-1H-imidazo[4,5-c]quinolin-2-yl)methyl]-N-ethylacetamide | 361.2 |
| 168 | N-[[4-amino-7-(2,5-dimethylpyrazol-3-yl)-1H-imidazo[4,5-c]quinolin-2-yl]methyl]-N-ethylacetamide | 378.2 |
| 169 | N-[[4-amino-7-(1-propylpyrazol-4-yl)-1H-imidazo[4,5-c]quinolin-2-yl]methyl]-N-ethylacetamide | 392.2 |
| 170 | N-[(4-amino-7-propan-2-yl-1H-imidazo[4,5-c]quinolin-2-yl)methyl]-N-ethylacetamide | 326.2 |
| 171 | N-[(4-amino-7-ethyl-1H-imidazo[4,5-c]quinolin-2-yl)methyl]-N-ethylacetamide | 312.2 |
| 172 | N-[(4-amino-7-propyl-1H-imidazo[4,5-c]quinolin-2-yl)methyl]-N-ethylacetamide | 326.2 |
| 173 | N-[(4-amino-7-cyclopentyl-1H-imidazo[4,5-c]quinolin-2-yl)methyl]-N-ethylacetamide | 352.2 |

TABLE 2-continued

| Compound | NAME | [M + H]+ |
|---|---|---|
| 175 | N-[[4-amino-7-(2-fluoropyridin-3-yl)-1H-imidazo[4,5-c]quinolin-2-yl]methyl]-N-ethylacetamide | 379.2 |
| 177 | N-[(4-amino-7-bromo-1H-imidazo[4,5-c]quinolin-2-yl)methyl]-N-ethylacetamide | 362.1 |
| 179 | N-[(4-amino-7-chloro-1H-imidazo[4,5-c]quinolin-2-yl)methyl]-N-ethylacetamide | 318.1 |
| 180 | N-[(4-amino-7-pyrazol-1-yl-1H-imidazo[4,5-c]quinolin-2-yl)methyl]-N-ethylacetamide | 350.2 |
| 182 | N-[1-(4-amino-7-bromo-1H-imidazo[4,5-c]quinolin-2-yl)ethyl]-N-ethylacetamide | 376.1 |

Example 3: Example Preparation Method of Analogs Wherein $R^1$=H, $R^2$=Alkyl, and $R^5$=Aryl, Heteroaryl, Heterocyclyl, or Amino The following synthetic schemes was used to prepare compound 101 and related analogs, compounds 463, 465 and 468. Additional analogs of these compounds may be prepared by, for example, substituting the hydrogen of the secondary amino group of compound 101 with a range of additional substituents, by means of, for example, acylation and sulfonylation using transformations known to those of skill in the art, as described in Example 4. The additional analogs made in this manner include, for example, compounds 105, 109, 110, 112 (described in Example 4a), 114, 118, 121, 123, 124, 125, 126, 133, 379, 383, 395, 406, 410, and 411.

Example 3a. Preparation of 2-[(Ethylamino)methyl]-7-(1H-pyrazol-3-yl)-1H-imidazo[4,5-c]quinolin-4-amine hydrochloride (Compound 101)

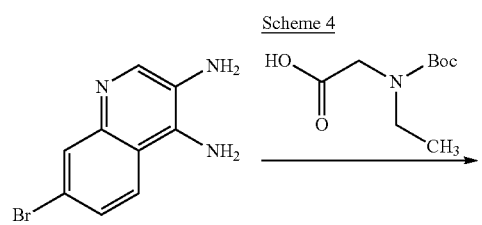

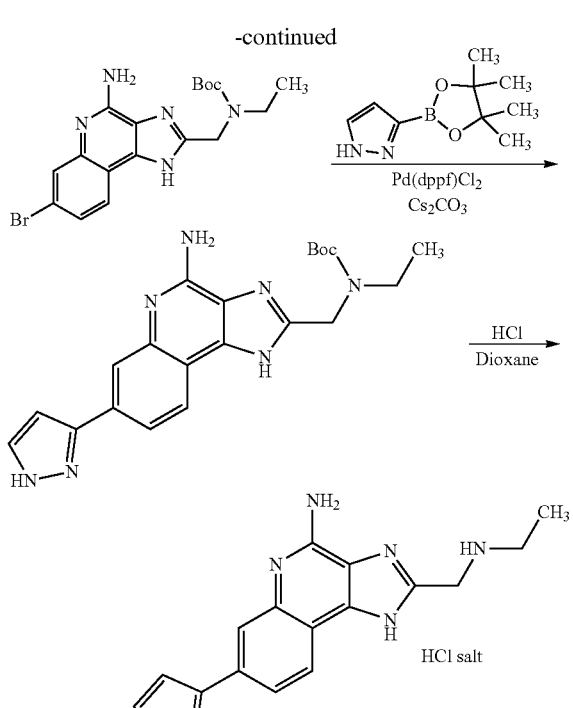

Step 1. tert-Butyl N-[[(4-amino-7-bromoquinolin-3-yl)carbamoyl]methyl]-N-ethylcarbamate

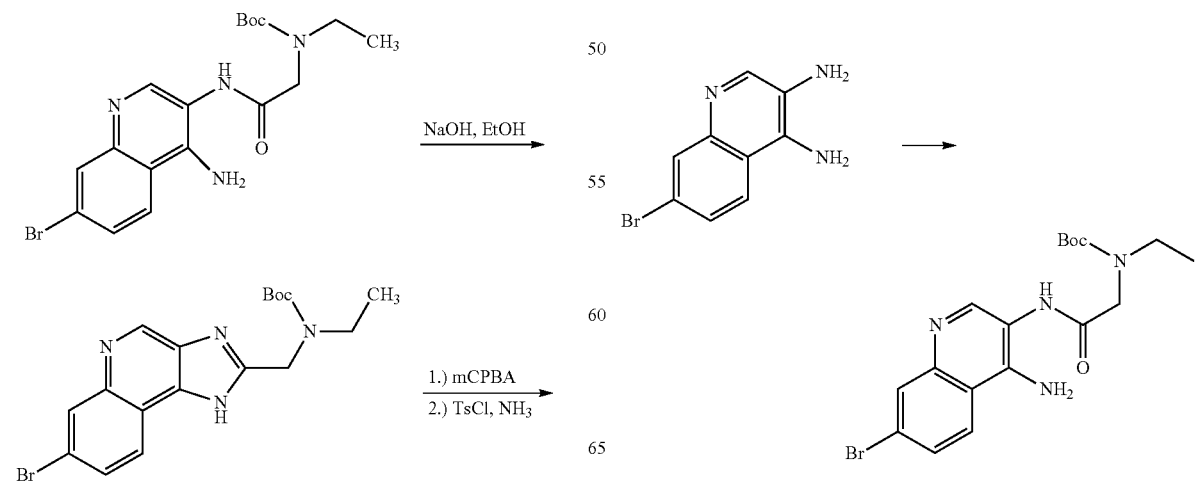

Into a 10-L 3-necked round-bottom flask purged and maintained with an inert atmosphere of nitrogen, was placed a solution of 7-bromoquinoline-3,4-diamine (375 g, 1.58 mol, 1.00 equiv; *Bioorg. Med. Chem. Lett,* 2012, 22, 285) in ethyl acetate (6 L). To the solution were added pyridine (623 g, 7.88 mol, 5.00 equiv), 2-[(tert-butoxy)carbonyl](ethyl) aminoacetic acid (480 g, 2.36 mol, 1.50 equiv) and T$_3$P (2004 g, 3.15 mol, 2 equiv). The resulting solution was stirred for 16 h at room temperature. The resulting mixture was washed with sodium hydroxide aqueous (3×10 L) and brine (2×10 L). The resulting mixture was concentrated under vacuum. This resulted in 592 g (89%) of tert-butyl N-[[(4-amino-7-bromoquinolin-3-yl)carbamoyl]methyl]-N-ethylcarbamate as a yellow solid.

Step 2. tert-Butyl N-([7-bromo-1H-imidazo[4,5-c]quinolin-2-yl]methyl)-N-ethylcarbamate

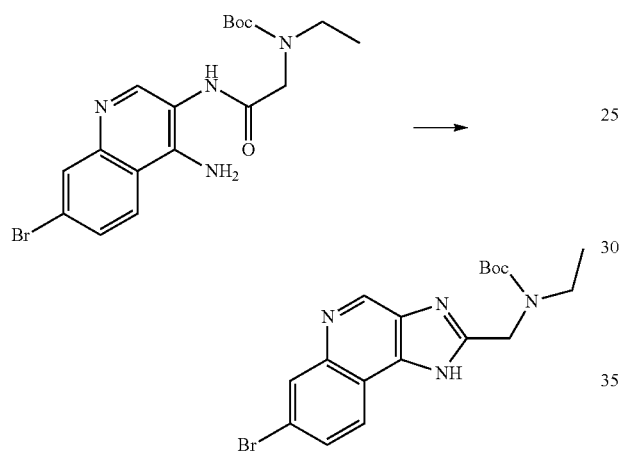

Into a 10-L round-bottom flask, was placed a solution of tert-butyl N-[[(4-amino-7-bromoquinolin-3-yl)carbamoyl]methyl]-N-ethylcarbamate (592 g, 1.40 mol, 1.00 equiv) in ethanol (6 L). To the solution, sodium hydroxide (558 g, 13.95 mol, 10.00 equiv) was added. The resulting solution was stirred for 1 h at 80° C. in an oil bath. The resulting mixture was concentrated under vacuum and diluted with 5 L of DCM. The resulting mixture was washed with brine (5×10 L), dried over anhydrous sodium sulfate and concentrated under vacuum. This resulted in 400 g (71%) of tert-butyl N-([7-bromo-1H-imidazo[4,5-c]quinolin-2-yl]methyl)-N-ethylcarbamate as a yellow solid.

Step 3. 7-Bromo-2-([[(tert-butoxy)carbonyl](ethyl)amino]methyl)-1H-imidazo[4,5-c]quinolin-5-ium-5-olate

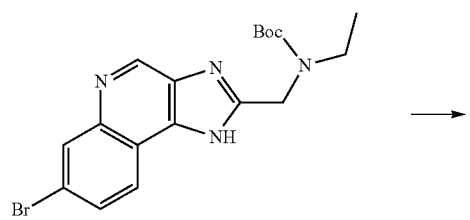

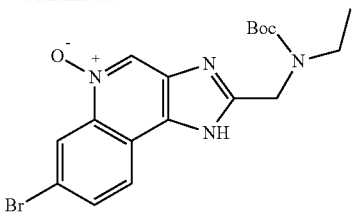

Into a 10-L 3-necked round-bottom flask purged and maintained with an inert atmosphere of nitrogen, was placed a solution of tert-butyl N-([7-bromo-1H-imidazo[4,5-c]quinolin-2-yl]methyl)-N-ethylcarbamate (400 g, 986.95 mmol, 1.00 equiv) in dichloromethane (6 L). To the solution, mCPBA (342 g, 1.98 mol, 2.00 equiv) was added. The resulting solution was stirred for 16 h at room temperature. The resulting mixture was washed with sodium carbonate aqueous (3×10 L), dried over anhydrous sodium sulfate and concentrated under vacuum. The residue was washed with 5 L of ethyl acetate. The solids were collected by filtration. This resulted in 218.6 g (pure) and 341 g (crude) of 7-bromo-2-([[(tert-butoxy)carbonyl](ethyl)amino]methyl)-1H-imidazo[4,5-c]quinolin-5-ium-5-olate as a light yellow solid.

Step 4. tert-butyl N-([4-amino-7-bromo-1H-imidazo[4,5-c]quinolin-2-yl]methyl)-N-ethylcarbamate

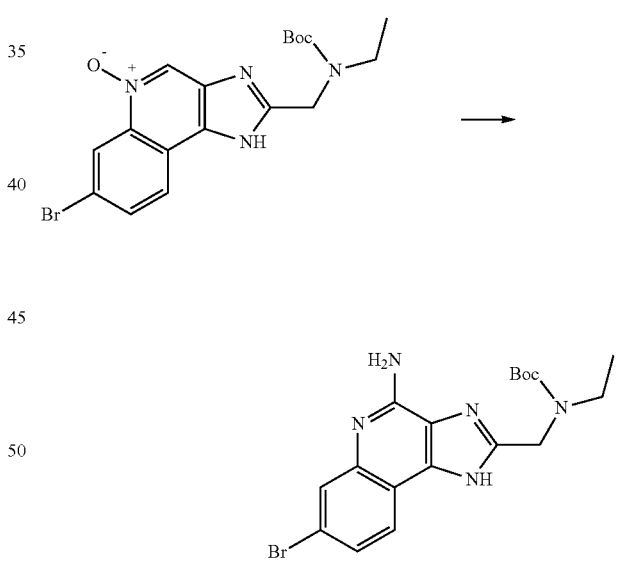

Into a 5-L 3-necked round-bottom flask, was placed a solution of 7-bromo-2-([[(tert-butoxy)carbonyl](ethyl)amino]methyl)-H-imidazo[4,5-c]quinolin-5-ium-5-olate (214 g, 518.31 mmol, 1.00 equiv) in dichloromethane (3 L) and NH$_3$—H$_2$O (1 L). To the solution, 4-methylbenzene-1-sulfonyl chloride (194 g, 1.037 mol, 2.00 equiv) was then added. The resulting solution was stirred for 6 h at room temperature. The solids were collected by filtration, washed with DCM (3×2 L) and dried. This resulted in 188 g (86%) of tert-butyl N-([4-amino-7-bromo-1H-imidazo[4,5-c]quinolin-2-yl]methyl)-N-ethylcarbamate as a light yellow solid.

211

Step 5. tert-butyl N-[[4-amino-7-(1H-pyrazol-3-yl)-1H-imidazo[4,5-c]quinolin-2-yl]methyl]-N-ethylcarbamate

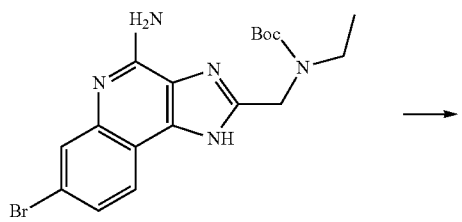

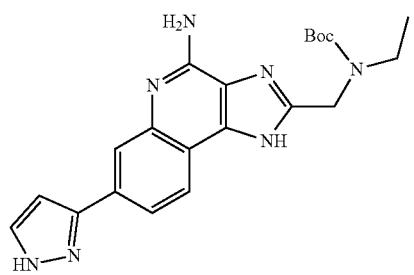

Into a 5-L round-bottom flask purged and maintained with an inert atmosphere of nitrogen, was placed a solution of tert-butyl N-([4-amino-7-bromo-1H-imidazo[4,5-c]quinolin-2-yl]methyl)-N-ethylcarbamate (156 g, 371.16 mmol, 1.00 equiv) in 1,4-dioxane/H$_2$O (3/0.3 L). To the solution were added Cs$_2$CO$_3$ (363 g, 1.11 mol, 3.00 equiv), 3-(tetramethyl-1,3,2-dioxaborolan-2-yl)-1H-pyrazole (144 g, 742.12 mmol, 2.00 equiv) and Pd(dppf)Cl$_2$ dichloromethane complex (30 g, 36.72 mmol, 0.10 equiv). The resulting solution was stirred for 24 h at 100° C. in an oil bath. The resulting solution was cooled to room temperature and diluted with 3 L of H$_2$O. The solids were collected by filtration and applied onto a silica gel column with dichloromethane/methanol (20/1). This resulted in 76.3 g (50%) of tert-butyl N-[[4-amino-7-(1H-pyrazol-3-yl)-1H-imidazo[4,5-c]quinolin-2-yl]methyl]-N-ethylcarbamate as a yellow solid.

Step 6. Compound 101

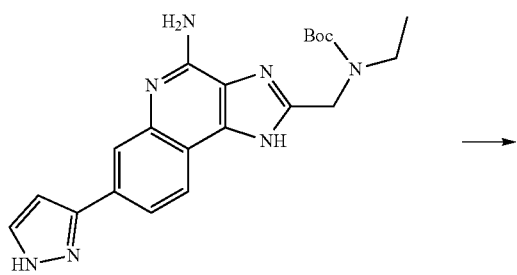

212

-continued

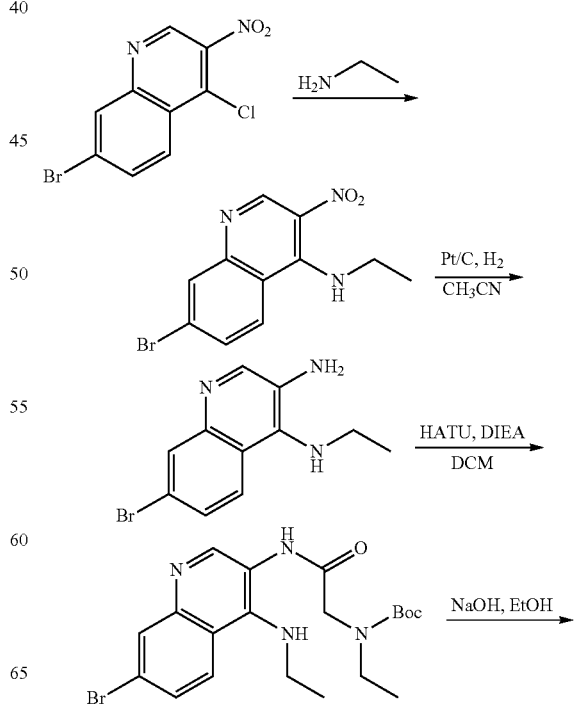

Into a 5-L round-bottom flask, was placed a solution of tert-butyl N-[[4-amino-7-(1H-pyrazol-3-yl)-1H-imidazo[4,5-c]quinolin-2-yl]methyl]-N-ethylcarbamate (75.6 g, 185.54 mmol, 1.00 equiv) in 1,4-dioxane/HCl (2 L, 4M). The resulting solution was stirred for 16 h at room temperature. The resulting mixture was concentrated under vacuum. The residue was made a slurry in 2 L of DCM and the solid was collected by filtration. This procedure was repeated three times. Then the collected solid was dried and this resulted in 75.7 g (crude) of 2-[(ethylamino)methyl]-7-(1H-pyrazol-3-yl)-1H-imidazo[4,5-c]quinolin-4-amine hydrochloride as a yellow solid. LC/MS [M$^+$+H] 308.3. LC/MS Method conditions: Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min; LC RT=0.46 min. $^1$H NMR (400 MHz, METHANOL-d$_4$) δ 8.11 (d, J=8.3 Hz, 1H), 8.04 (s, 1H), 7.84-7.77 (m, 1H), 7.72 (s, 1H), 6.79 (d, J=2.1 Hz, 1H), 4.13 (s, 2H), 2.80 (q, J=7.2 Hz, 2H), 1.22 (t, J=7.2 Hz, 3H).

Example 3b. Preparation of 1-ethyl-2-[(ethylamino)methyl]-7-(1H-pyrazol-5-yl)-1H-imidazo[4,5-c]quinolin-4-amine (Compound 464)

Scheme 5

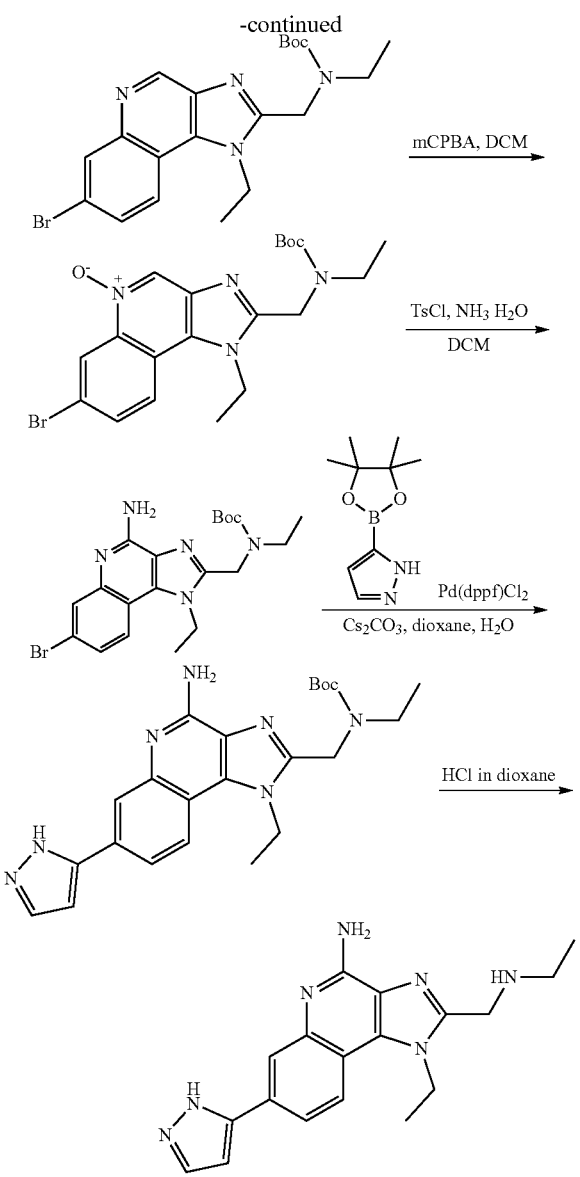

Step 1. 7-bromo-N-ethyl-3-nitroquinolin-4-amine

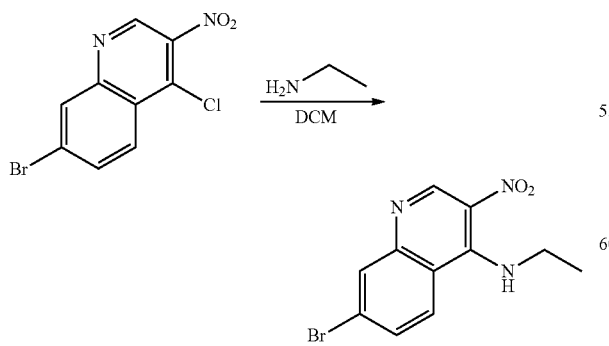

Into a 500-mL round-bottom flask was placed a solution of 7-bromo-4-chloro-3-nitroquinoline (20 g, 62.61 mmol, 1 equiv, 90%) in dichloromethane (300 mL). Then ethanamine (4.23 g, 93.91 mmol, 1.5 equiv) and triethylamine (19.01 g, 187.83 mmol, 3 equiv) were added. The resulting solution was stirred for 1 hour at room temperature. The reaction was then quenched by the addition of water. The resulting solution was extracted with 3×100 ml of dichloromethane and the organic layers were combined. The solution was dried over anhydrous sodium sulfate and concentrated. This resulted in 20 g of 7-bromo-N-ethyl-3-nitroquinolin-4-amine as a yellow crude solid.

Step 2. 7-bromo-$N^4$-ethylquinoline-3,4-diamine

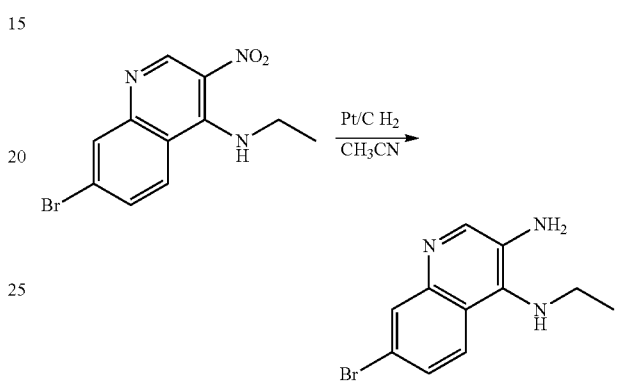

Into a 1000-mL round-bottom flask, was placed a solution of 7-bromo-N-ethyl-3-nitroquinolin-4-amine (20 g, 67.54 mmol, 1 equiv) in $CH_3CN$ (500 mL). To the solution was added Pt/C (3 g, 15.38 mmol, 0.23 equiv). The resulting solution was degassed and back filled with H2. The resulting solution was stirred for 24 hour at room temperature. The solids were filtered. The filtrate was concentrated to provide 19.7 g of 7-bromo-$N^4$-ethylquinoline-3,4-diamine as yellow crude oil. LC-MS: (ES, m/z): $[M+H]^+$=226.1

Step 3. tert-butyl (2-((7-bromo-4-(ethylamino)quinolin-3-yl)amino)-2-oxoethyl)(ethyl)carbamate

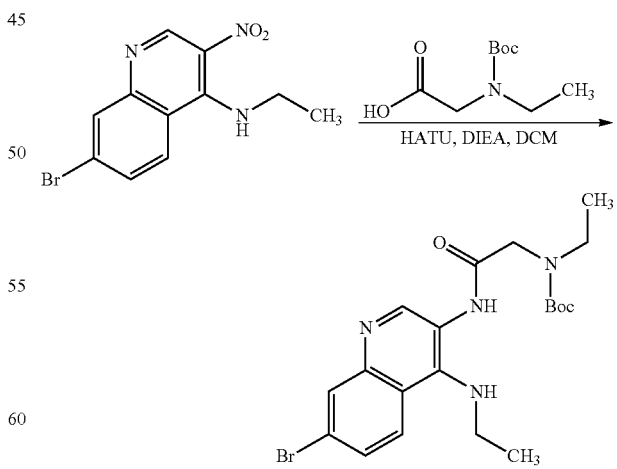

Into a 1000-mL round-bottom flask was placed a solution of 7-bromo-$N^4$-ethylquinoline-3,4-diamine (10 g, 35.70 mmol, 1 equiv, 95%) and 2-[[(tert-butoxy)carbonyl](ethyl)amino]acetic acid (10.88 g, 53.54 mmol, 1.5 equiv) in dichloromethane (500 mL). This was followed by the addition of HATU (16.29 g, 42.83 mmol, 1.2 equiv) and DIEA (15.34 g, 107.09 mmol, 3 equiv). The resulting solution was stirred for 3 hour at room temperature. The reaction was then quenched by the addition of water. The resulting solution was extracted with 3×100 ml of dichloromethane and the organic layers were combined. The solution was dried over anhydrous sodium sulfate and concentrated. This resulted in 40 g (crude) of tert-butyl N-([[7-bromo-4-(ethylamino)quinolin-3-yl]carbamoyl]methyl)-N-ethylcarbamate as yellow oil.

Step 4. tert-butyl N-([7-bromo-1-ethyl-1H-imidazo[4,5-c]quinolin-2-yl]methyl)-N-ethylcarbamate

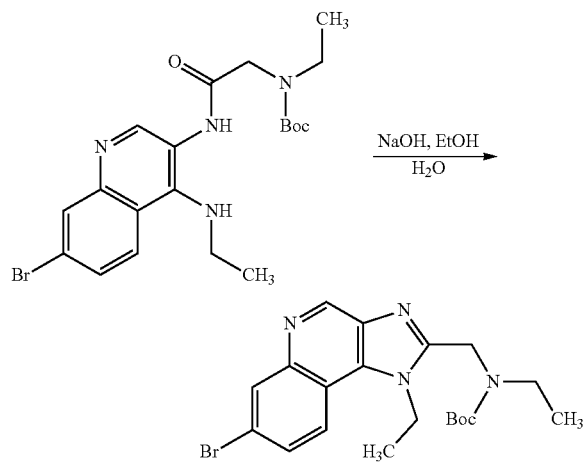

Into a 1000-mL round-bottom flask, was placed a solution of tert-butyl N-[[(3-amino-7-bromoquinolin-4-yl)(ethyl)carbamoyl]methyl]-N-ethylcarbamate (40 g, 88.62 mmol, 1 equiv) in ethanol (500 mL) and water (20 mL). To the solution was added sodium hydroxide (35.45 g, 886.20 mmol, 10 equiv). The resulting solution was stirred for 2 hours at 100° C. The resulting mixture was concentrated. The residue was diluted with water. The resulting solution was then extracted with ethyl acetate and the organic layers were combined. The solution was dried over anhydrous sodium sulfate and concentrated. This resulted in 34.8 g (crude) of tert-butyl N-([7-bromo-1-ethyl-1H-imidazo[4,5-c]quinolin-2-yl]methyl)-N-ethylcarbamate as yellow oil. LC-MS: (ES, m/z): [M+H]$^+$=433.3

Step 5. 7-bromo-2-([[(tert-butoxy)carbonyl](ethyl)amino]methyl)-1-ethyl-1H-imidazo[4,5-c]quinolin-5-ium-5-olate

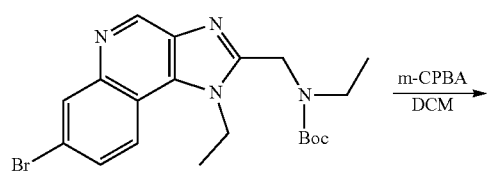

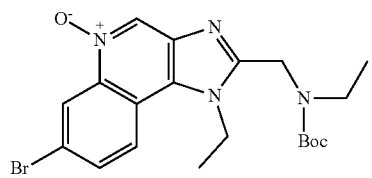

Into a 1000-mL round-bottom flask, was placed tert-butyl N-([7-bromo-1-ethyl-1H-imidazo[4,5-c]quinolin-2-yl]methyl)-N-ethylcarbamate (6 g, 13.85 mmol, 1 equiv) in dichloromethane (300 mL). This was followed by the addition of m-CPBA (3.58 g, 20.77 mmol, 1.5 equiv) in portions. The resulting solution was stirred for 2 hour at room temperature. The reaction was then quenched by the addition of 150 ml H$_2$O. The resulting solution was extracted with DCM and the organic layers were combined. The solution was dried over anhydrous sodium sulfate and concentrated. This resulted in 7.5 g of 7-bromo-2-([[(tert-butoxy)carbonyl](ethyl)amino]methyl)-1-ethyl-1H-imidazo[4,5-c]quinolin-5-ium-5-olate as a yellow crude solid.

Step 6. tert-butyl N-([4-amino-7-bromo-1-ethyl-1H-imidazo[4,5-c]quinolin-2-yl]methyl)-N-ethylcarbamate

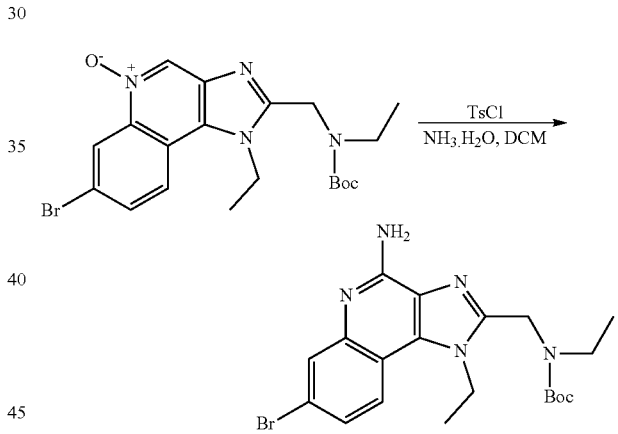

Into a 500-mL round-bottom flask, was placed 7-bromo-2-([[(tert-butoxy)carbonyl](ethyl)amino]methyl)-1-ethyl-1H-imidazo[4,5-c]quinolin-5-ium-5-olate (6 g, 13.35 mmol, 1 equiv, crude) in dichloromethane (250 mL) and NH$_3$H$_2$O (5 mL, 20 mmol). This was followed by the addition of a solution of 4-methylbenzene-1-sulfonyl chloride (5.09 g, 26.71 mmol, 2 equiv) in dichloromethane (10 mL) dropwise with stirring. The resulting solution was stirred for 2 hour at room temperature. The reaction was then quenched by the addition of water. The resulting solution was extracted with dichloromethane and the organic layers were combined. The solution was dried over anhydrous sodium sulfate and concentrated. This resulted in 2 g of tert-butyl N-([4-amino-7-bromo-1-ethyl-1H-imidazo[4,5-c]quinolin-2-yl]methyl)-N-ethylcarbamate as a white solid. LC-MS: (ES, m/z): [M+H]$^+$=448.1. $^1$H-NMR: (400 MHz, CD$_3$OD) δ 8.04-8.02 (m, 1H), 7.85-7.84 (m, 1H), 7.47-7.45 (m, 1H), 4.84-4.82 (m, 2H), 4.67 (s, 2H), 3.35 (m, 2H), 1.5-1.29 (m, 12H), 1.09-0.89 (m, 3H).

Step 7. tert-butyl N-[[4-amino-1-ethyl-7-(1H-pyrazol-5-yl)-1H-imidazo[4,5-c]quinolin-2-yl]methyl]-N-ethylcarbamate

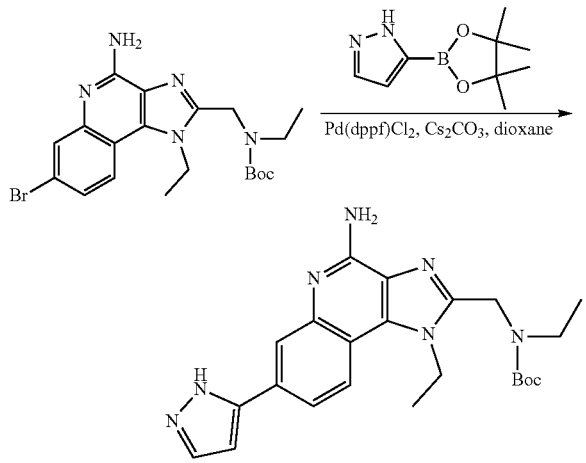

Into a 100-mL round-bottom flask purged and maintained with an inert atmosphere of nitrogen, was placed a solution of tert-butyl N-([4-amino-7-bromo-1-ethyl-1H-imidazo[4,5-c]quinolin-2-yl]methyl)-N-ethylcarbamate (150 mg, 0.30 mmol, 1 equiv, 90%), 5-(4,4,5,5-tetramethyl-1,3,2-dioxaborolan-2-yl)-1H-pyrazole (116.8 mg, 0.60 mmol, 2 equiv) in dioxane (25 mL) under $N_2$. To the solution were added $Cs_2CO_3$ (294.3 mg, 0.90 mmol, 3 equiv), and Pd(dppf)Cl$_2$ (11.0 mg, 0.02 mmol, 0.05 equiv). The resulting solution was stirred for 24 hour at 100° C. The reaction was then quenched by the addition of water. The resulting solution was extracted with ethyl acetate. The organic layers were combined and dried over anhydrous sodium sulfate. The resulting mixture was concentrated. The residue was applied onto a silica gel column and eluted with dichloromethane/methanol (10:1). This resulted in 100 mg (76%) of tert-butyl N-[[4-amino-1-ethyl-7-(1H-pyrazol-5-yl)-1H-imidazo[4,5-c]quinolin-2-yl]methyl]-N-ethylcarbamate as a yellow solid.

Step 8. Synthesis of Compound 465

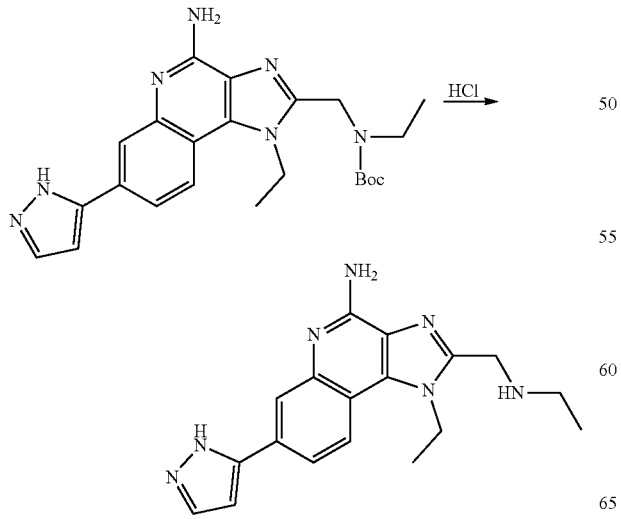

Into a 250-mL round-bottom flask, was placed tert-butyl N-[[4-amino-1-ethyl-7-(1H-pyrazol-5-yl)-1H-imidazo[4,5-c]quinolin-2-yl]methyl]-N-ethylcarbamate (100 mg, 0.23 mmol, 1 equiv) in dichloromethane (20 mL). This was followed by the addition of HCl in dioxane (1.5 mL) dropwise with stirring. The resulting solution was stirred for 1 hour at room temperature. The resulting mixture was concentrated. The crude product was purified by Prep-HPLC with the following conditions Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 5% B to 30% B in 8 min; 254/210 nm; Rt: 7.03 min. This resulted in 18 mg (13.77%) of 1-ethyl-2-[(ethylamino)methyl]-7-(1H-pyrazol-5-yl)-1H-imidazo[4,5-c]quinolin-4-amine; bis(trifluoroacetic acid) as a white solid. LC Methods: Column: Express C18 2.1 mm×50 mm, 2.7 μm particles; Mobile Phase A: water with 0.05% TFA; Mobile Phase B: acetonitrile with 0.05% TFA; Temperature: 40° C.; Gradient: 5% B to 100% B over 2 min, then a 0.75 min hold at 100% B; Flow: 0.8 mL/min. LC retention time: 0.81 min. LC-MS: (ES, m/z): [M+H]$^+$=336.3. $^1$H-NMR: (300 MHz, CD$_3$OD, ppm) δ 8.38-8.35 (d, J=8.7 Hz, 1H), 8.22 (m, 1H), 8.12-8.09 (m, 1H), 7.80-7.79 (d, J=2.8 Hz, 1H), 6.89-6.86 (m, 1H), 4.76-4.69 (m, 4H), 3.45-3.38 (m, 2H), 1.63 (t, J=7.2 Hz, 3H), 1.48 (t, J=7.2 Hz, 3H).

Example 3c. Preparation of 1-ethyl-2-((ethylamino)methyl)-7-(1H-pyrazol-1-yl)-1H-imidazo[4,5-c]quinolin-4-amine (Compound 467)

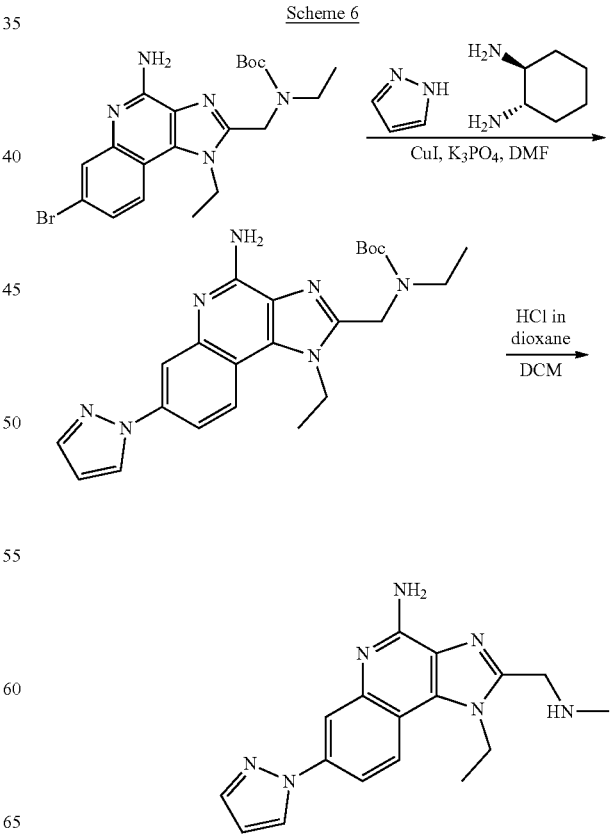

Step 1. Synthesis of 1-ethyl-2-[(ethylamino)methyl]-7-(1H-pyrazol-1-yl)-1H-imidazo[4,5-c]quinolin-4-amine

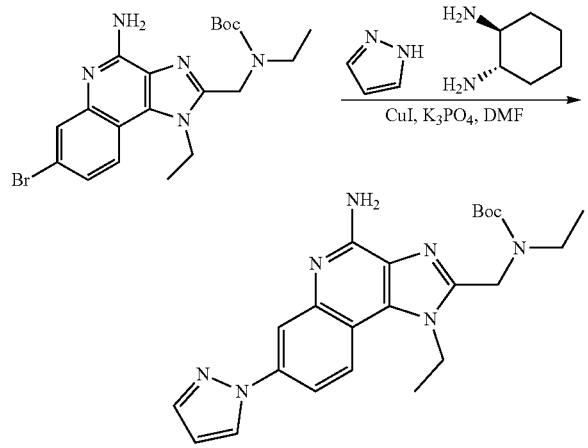

Into a 50-mL round-bottom flask purged and maintained with an inert atmosphere of nitrogen, was placed tert-butyl N-([4-amino-7-bromo-1-ethyl-1H-imidazo[4,5-c]quinolin-2-yl]methyl)-N-ethylcarbamate (150 mg, 0.33 mmol, 1 equiv), 1H-pyrazole (45.6 mg, 0.67 mmol, 2 equiv) and K$_3$PO$_4$ (213.0 mg, 1.00 mmol, 3 equiv) in DMF (5 mL). Then (1S,2S)-cyclohexane-1,2-diamine (15.3 mg, 0.13 mmol, 0.4 equiv) and CuI (25.5 mg, 0.13 mmol, 0.4 equiv) were added. The resulting solution was stirred for 24 hr at 100° C. under N$_2$ atmosphere. The reaction was then diluted with water. The resulting solution was extracted with 3×50 ml of ethyl acetate and the organic layers were combined. The solution was dried over anhydrous sodium sulfate and concentrated. The residue was applied onto a silica gel column with dichloromethane/methanol (10:1). This resulted in 100 mg (80.20%) of 1-ethyl-2-[(ethylamino)methyl]-7-(1H-pyrazol-1-yl)-1H-imidazo[4,5-c]quinolin-4-amine as a white solid. LC-MS: (ES, m/z): [M+H]$^+$=436.2.

Step 2. Synthesis of Compound 468

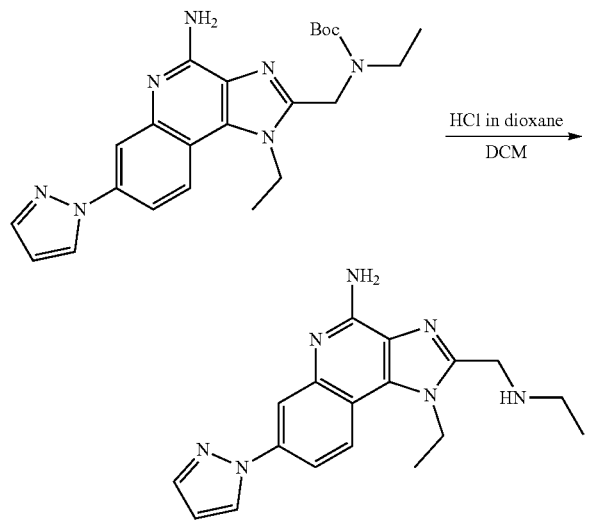

Into a 50-mL round-bottom flask, was placed a solution of tert-butyl N-[[4-amino-1-ethyl-7-(1H-pyrazol-1-yl)-1H-imidazo[4,5-c]quinolin-2-yl]methyl]-N-ethylcarbamate (100 mg, 0.23 mmol, 1 equiv) in DCM (10 mL). This was followed by the addition of HCl in dioxane (1.5 mL) dropwise with stirring. The resulting solution was stirred for 1 hr at room temperature. The resulting mixture was concentrated. The crude product was purified by Prep-HPLC with the following conditions Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 5% B to 30% B in 10 min; 254/210 nm; Rt: 9.20 min. This resulted in 33.5 mg (25.64%) of 1-ethyl-2-((ethylamino)methyl)-7-(1H-pyrazol-1-yl)-1H-imidazo[4,5-c]quinolin-4-amine as a white solid. LC-MS condition: Column: Kinetex EVO, 3.0 mm×50 mm, 2.6 μm particles; Mobile Phase A: water with 5 mM ammonium bicarbonate; Mobile Phase B: acetonitrile; Temperature: 40° C.; Gradient: 10% B to 95% B over 2 min, then a 0.79 min hold at 95% B; Flow: 1 mL/min. LC retention time: 1.01 min. LC-MS: (ES, m/z): [M+H]+=336.3; 1H-NMR: 1H NMR (300 MHz, CD$_3$OD) δ 8.46-8.40 (m, 2H), 8.25-8.24 (m, 1H), 8.10-8.06 (m, 1H), 7.84-7.83 (m, 1H), 6.64-6.63 (m, 1H), 4.72 (s, 2H), 4.70-4.63 (m, 2H), 3.54-3.08 (m, 2H), 1.62 (t, J=6.0 Hz, 3H), 1.48 (t, J=9.0 Hz, 3H).

Example 3d. Preparation of 2-[4-Amino-2-[(ethylamino)methyl]-7-(1H-pyrazol-5-yl)-1H-imidazo[4,5-c]quinolin-1-yl]ethan-1-ol (Compound 462)

Scheme 7

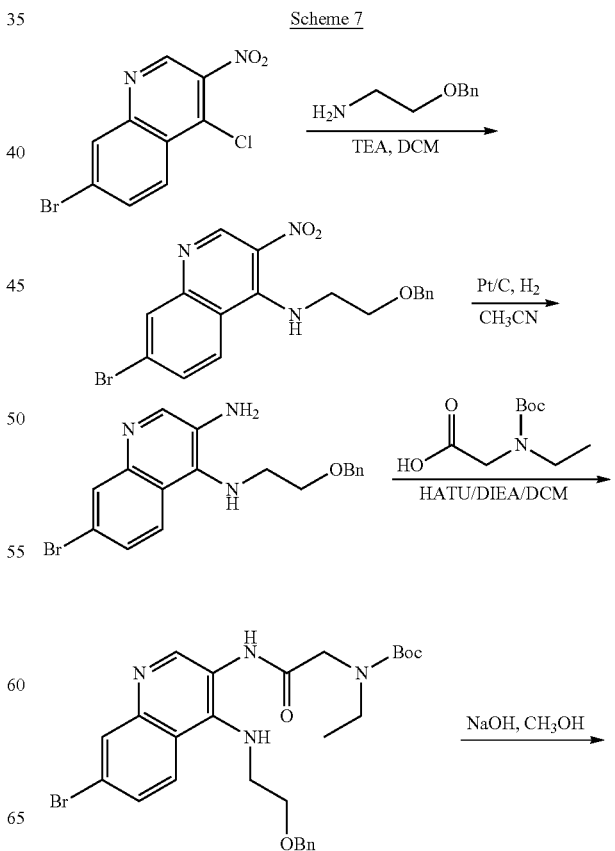

221

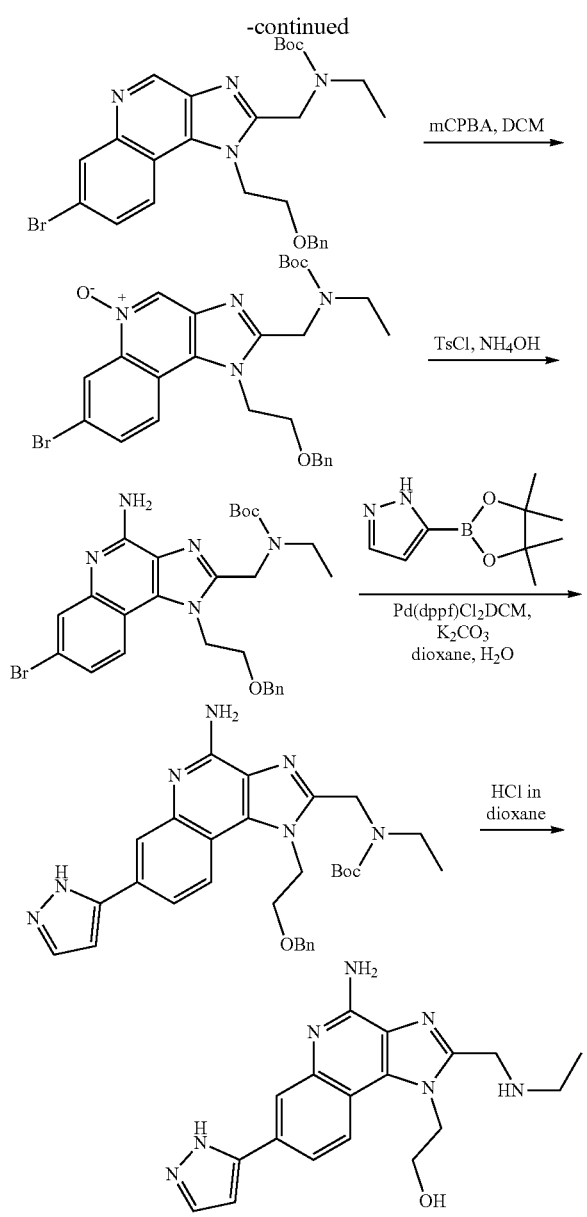

Step 1. N-[2-(benzyloxy)ethyl]-7-bromo-3-nitroquinolin-4-amine

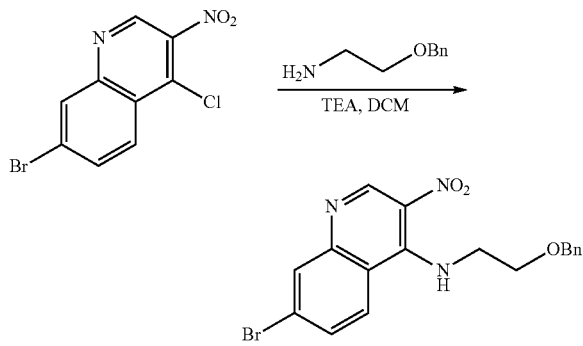

222

To a stirred mixture of 7-bromo-4-chloro-3-nitroquinoline (20 g, 69.57 mmol, 1 equiv) and 2-(benzyloxy)ethan-1-amine (12.0 g, 79.30 mmol, 1.14 equiv) in DCM (400 mL) was added TEA (10.6 g, 104.35 mmol, 1.50 equiv) at room temperature under nitrogen atmosphere. The resulting mixture was stirred for 16 h at room temperature under nitrogen atmosphere. The resulting mixture was concentrated under vacuum. This resulted in N-[2-(benzyloxy)ethyl]-7-bromo-3-nitroquinolin-4-amine (30 g) as a yellow crude solid. LC-MS: (ES, m/z): [M+H]$^+$=402.2/404.2.

Step 2. N$^4$-[2-(benzyloxy)ethyl]-7-bromoquinoline-3,4-diamine

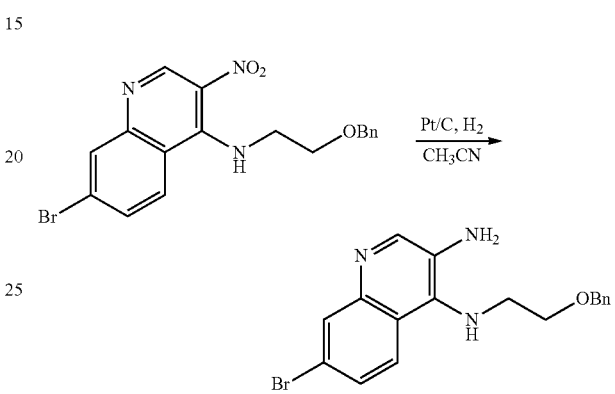

To a solution of N-[2-(benzyloxy)ethyl]-7-bromo-3-nitroquinolin-4-amine (30 g, 74.58 mmol, 1 equiv) in CH$_3$CN (400 mL) was added Pt/C (2.9 g, 14.87 mmol, 0.20 equiv) under nitrogen atmosphere in a 1000 mL round-bottom flask. The mixture was hydrogenated at room temperature for 16 h under hydrogen atmosphere using a hydrogen balloon, filtered through a Celite pad and concentrated under reduced pressure. The residue was purified by silica gel column chromatography, eluted with CH$_2$Cl$_2$/MeOH (20:1) to afford N4-[2-(benzyloxy)ethyl]-7-bromoquinoline-3,4-diamine (23.4 g, 84.28%) as a yellow solid. LC-MS: (ES, m/z): [M+H]$^+$=372.3/374.2.

Step 3. tert-butyl N-[[(4-[[2-(benzyloxy)ethyl]amino]-7-bromoquinolin-3-yl)carbamoyl]methyl]-N-ethylcarbamate

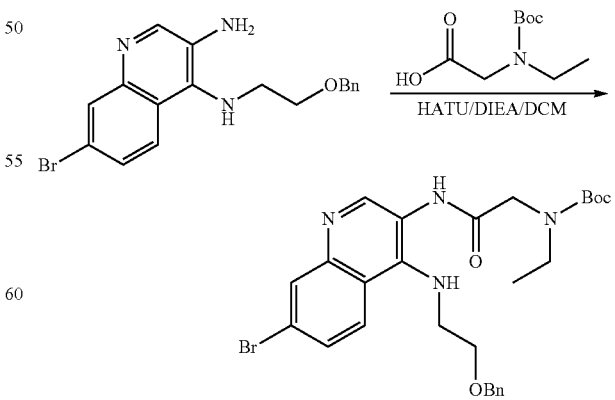

To a stirred mixture of N4-[2-(benzyloxy)ethyl]-7-bromoquinoline-3,4-diamine (14.9 g, 40.03 mmol, 1 equiv) and 2-[[(tert-butoxy)carbonyl](ethyl)amino]acetic acid (8.9 g, 44.03 mmol, 1.1 equiv) in DCM (500 mL) were added HATU (18.3 g, 48.03 mmol, 1.2 equiv) and DIEA (10.3 g, 79.69 mmol, 1.99 equiv) at room temperature. The resulting mixture was stirred for 16 h at room temperature under nitrogen atmosphere. The resulting mixture was concentrated under vacuum. This resulted in tert-butyl N-[[(4-[[2-(benzyloxy)ethyl]amino]-7-bromoquinolin-3-yl)carbamoyl]methyl]-N-ethylcarbamate (24 g, 107.56%) as a red crude oil. The crude product was used in the next step directly without further purification. LC-MS: (ES, m/z): [M+H]⁺= 557.2/559.2

Step 4. tert-butyl N-([1-[2-(benzyloxy)ethyl]-7-bromo-1H-imidazo[4,5-c]quinolin-2-yl]methyl)-N-ethylcarbamate

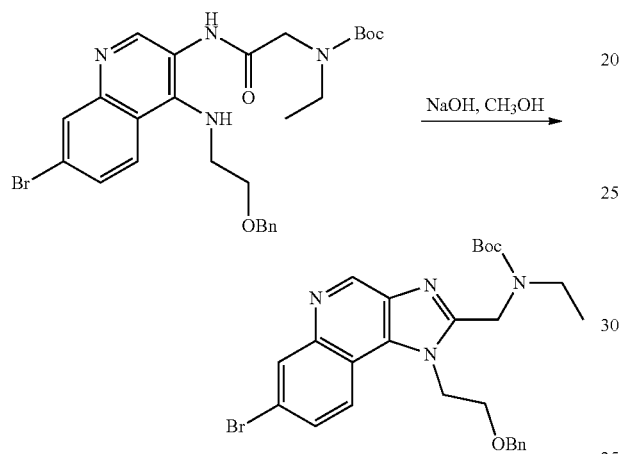

A mixture of tert-butyl N-[[(4-[[2-(benzyloxy)ethyl]amino]-7-bromoquinolin-3-yl)carbamoyl]methyl]-N-ethylcarbamate (23 g, 41.26 mmol, 1 equiv) and NaOH (3.3 g, 82.51 mmol, 2 equiv) in MeOH (250 mL) was stirred for 16 h at 65° C. The resulting mixture was concentrated under vacuum. The residue was purified by silica gel column chromatography, eluted with PE/EtOAc (1.5:1) to afford tert-butyl N-([1-[2-(benzyloxy)ethyl]-7-bromo-1H-imidazo[4,5-c]quinolin-2-yl]methyl)-N-ethylcarbamate (17.4 g, 78.18%) as a light yellow solid. LC-MS-: (ES, m/z): [M+H]⁺=539.2/541.2 H-NMR: ¹H NMR (400 MHz, DMSO-d₆) δ 9.23 (s, 1H), 8.42-8.31 (m, 2H), 7.75 (dd, J=8.9, 2.2 Hz, 1H), 7.14 (dd, J=5.0, 2.0 Hz, 3H), 7.00 (dd, J=6.7, 2.9 Hz, 2H), 4.95 (s, 2H), 4.83 (s, 2H), 4.39 (s, 2H), 3.86 (d, J=6.0 Hz, 2H), 2.51 (p, J=1.8 Hz, 2H), 1.38 (d, J=42.6 Hz, 9H), 0.99 (t, J=7.0 Hz, 3H).

Step 5. tert-butyl N-([1-[2-(benzyloxy)ethyl]-7-bromo-1H-imidazo[4,5-c]quinolin-2-yl]methyl)-N-ethylcarbamate

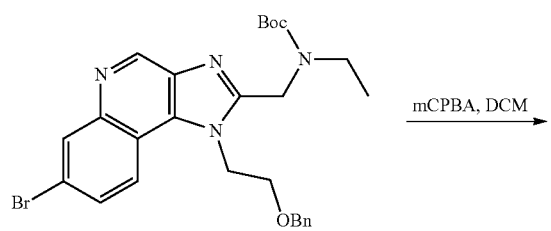

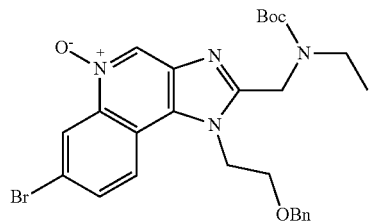

A mixture of 1-[2-(benzyloxy)ethyl]-7-bromo-2-([[(tert-butoxy)carbonyl](ethyl) amino]methyl)-1H-imidazo[4,5-c]quinolin-5-ium-5-olate (2.1 g, 3.78 mmol, 1 equiv) and mCPBA (1.0 g, 5.67 mol, 1.5 equiv) in DCM (35 mL) was stirred for 4 h at room temperature under nitrogen atmosphere. The resulting mixture was concentrated under vacuum. The residue was purified by silica gel column chromatography, eluted with CH₂Cl₂/MeOH (20:1) to afford tert-butyl N-([1-[2-(benzyloxy)ethyl]-7-bromo-1H-imidazo[4,5-c]quinolin-2-yl]methyl)-N-ethylcarbamate (1.15 g, 56.39%) as an off-white solid. LC-MS: (ES, m/z): [M+H]⁺= 555.2/557.2.

Step 6. tert-butyl N-([4-amino-1-[2-(benzyloxy)ethyl]-7-bromo-1H-imidazo[4,5-c]quinolin-2-yl]methyl)-N-ethylcarbamate

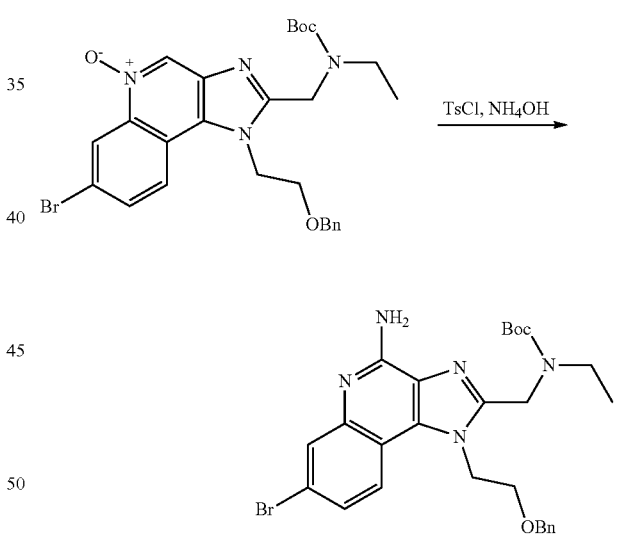

To a stirred mixture of 1-[2-(benzyloxy)ethyl]-7-bromo-2-([[(tert-butoxy)carbonyl](ethyl)amino]methyl)-1H-imidazo[4,5-c]quinolin-5-ium-5-olate (1.15 g, 2.07 mmol, 1 equiv) and NH₄OH (5 mL) in DCM (20 mL) were added TsCl (0.8 g, 4.20 mol, 2.03 equiv) at room temperature. The resulting mixture was stirred for 1 h at room temperature. The resulting mixture was concentrated under vacuum. The residue was purified by silica gel column chromatography, eluted with CH₂Cl₂/MeOH (30:1) to afford tert-butyl N-([4-amino-1-[2-(benzyloxy)ethyl]-7-bromo-1H-imidazo[4,5-c]quinolin-2-yl]methyl)-N-ethylcarbamate (775 mg, 67.51%) as an off-white solid. LC-MS: (ES, m/z): [M+H]⁺=554.2/556.2.

Step 7. tert-butyl N-([4-amino-1-[2-(benzyloxy)ethyl]-7-(1H-pyrazol-5-yl)-1H-imidazo[4,5-c]quinolin-2-yl]methyl)-N-ethylcarbamate Step 8. Compound 463

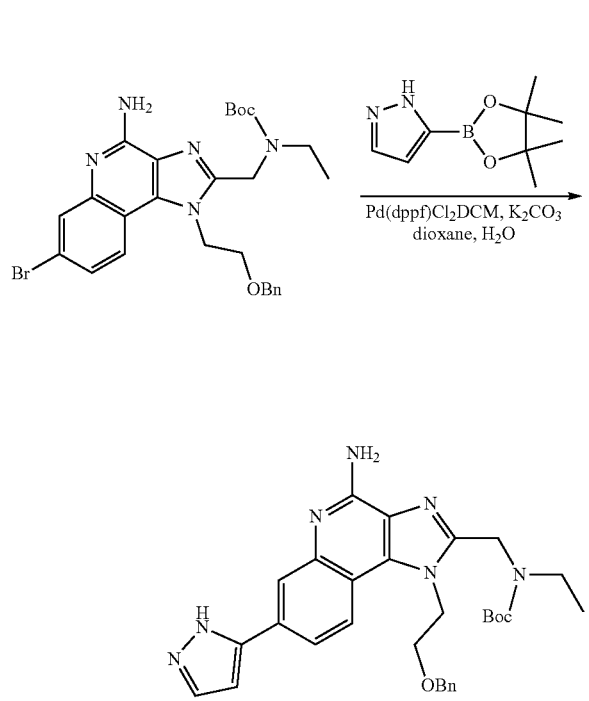

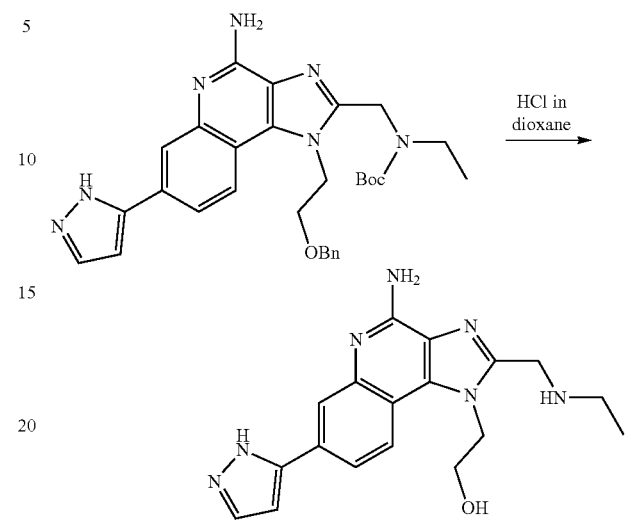

To a solution of tert-butyl N-([4-amino-1-[2-(benzyloxy)ethyl]-7-bromo-1H-imidazo[4,5-c]quinolin-2-yl]methyl)-N-ethylcarbamate (350 mg, 0.63 mmol, 1 equiv) and 5-(4,4,5,5-tetramethyl-1,3,2-dioxaborolan-2-yl)-1H-pyrazole (245.0 mg, 1.26 mmol, 2.00 equiv) in dioxane (8 mL) and H$_2$O (0.8 mL) were added K$_2$CO$_3$ (261.7 mg, 1.89 mmol, 3 equiv) and Pd(dppf)Cl$_2$CH$_2$Cl$_2$ (103.1 mg, 0.13 mmol, 0.2 equiv) under a nitrogen atmosphere. After stirring for 20 h at 90 degrees C. under a nitrogen atmosphere, the resulting mixture was concentrated under reduced pressure. The residue was purified by silica gel column chromatography, eluted with CH$_2$Cl$_2$/MeOH (20:1) to afford tert-butyl N-([4-amino-1-[2-(benzyloxy)ethyl]-7-(1H-pyrazol-5-yl)-1H-imidazo[4,5-c]quinolin-2-yl]methyl)-N-ethylcarbamate (250 mg, 73.12%) as a brown solid. LC-MS: (ES, m/z): [M+H]$^+$= 542.2.

A mixture of tert-butyl N-([4-amino-1-[2-(benzyloxy)ethyl]-7-(1H-pyrazol-5-yl)-1H-imidazo[4,5-c]quinolin-2-yl]methyl)-N-ethylcarbamate (210 mg, 390 mmol, 1 equiv) in HCl in dioxane (10 mL, 4 mol/L) was stirred for 24 h at 60° C. The resulting mixture was concentrated under vacuum. The crude product was purified by Prep-HPLC with the following conditions (Column: XBridge Prep C18 OBD Column, 5 um, 19*150 mm; Mobile Phase A:Water (10 MMOL/L NH$_4$HCO$_3$), Mobile Phase B: ACN; Flow rate: 25 mL/min; Gradient: 12% B to 26% B in 10 min; 254/210 nm; Rt: 8.63 min) to afford 2-[4-amino-2-[(ethylamino)methyl]-7-(1H-pyrazol-5-yl)-1H-imidazo[4,5-c]quinolin-1-yl]ethan-1-ol (8.1 mg, 5.95%) as a white solid. LC Methods: Column: Shim-pack XR-ODS 3.0 mm×50 mm, 2.2 μm particles; Mobile Phase A: water with 0.05% TFA; Mobile Phase B: acetonitrile with 0.05% TFA; Temperature: 40° C.; Gradient: 0% B to 95% B over 2 min, then a 0.7 min hold at 95% B; Flow: 1.5 mL/min. LC retention time: 0.76 min. LC-MS: (ES, m/z): [M+H]$^+$=352.3 H-NMR: 1H NMR (300 MHz, DMSO-d$_6$) δ 13.15 (m, 1H), 8.16-7.95 (m, 2H), 7.89-7.48 (m, 2H), 6.80 (s, 1H), 6.54 (s, 2H), 5.57 (s, 1H), 4.75 (d, J=6.3 Hz, 2H), 4.05 (s, 2H), 3.91 (t, J=5.3 Hz, 2H), 2.61 (q, J=7.1 Hz, 2H), 1.04 (t, J=7.0 Hz, 3H).

The compounds in Table 3 were prepared procedures found above.

TABLE 3

| Cmpd | Name | LC/MS [M$^+$ + H] | LC RT | LC Method |
|---|---|---|---|---|
| 468 | 1-ethyl-2-[(ethylamino)methyl]-7-(thiophen-2-yl)-1H-imidazo[4,5-c]quinolin-4-amine | 352.1 | 1.29 min | A |
| 471 | 2-{4-amino-2-[(ethylamino)methyl]-7-(thiophen-2-yl)-1H-imidazo[4,5-c]quinolin-1-yl}ethan-1-ol | 368.1 | 1.12 min | B |
| 477 | 2-[4-amino-2-[(ethylamino)methyl]-7-(1H-pyrazol-1-yl)-1H-imidazo[4,5-c]quinolin-1-yl]ethan-1-ol | 352.0 | 0.92 min | B |

LC Methods:
A: Column: Kinetex EVO, 3.0 mm × 50 mm, 2.6 μm particles; Mobile Phase A: water with 5 mM ammonium bicarbonate; Mobile Phase B: acetonitrile; Temperature: 40° C.; Gradient: 10% B to 95% B over 2 min, then a 0.79 min hold at 95% B; Flow: 1 mL/min.
B: Column: Kinetex EVO, 3.0 mm × 50 mm, 2.6 μm particles; Mobile Phase A: water with 0.03% NH3H2O; Mobile Phase B: acetonitrile; Temperature: 40° C.; Gradient: 10% B to 95% B over 2 min, then a 0.60 min hold at 95% B; Flow: 1.2 mL/min

Example 4: Example Preparation Method of Analogs Wherein R¹/R²=H, Alkyl, Acetyl, Sulfonyl, Carbonyl, Amido, Carboxy and R⁵=Aryl, Heteroaryl, Heterocyclyl, or Amino

Example 4a. Example Procedure for Acetamide Formation

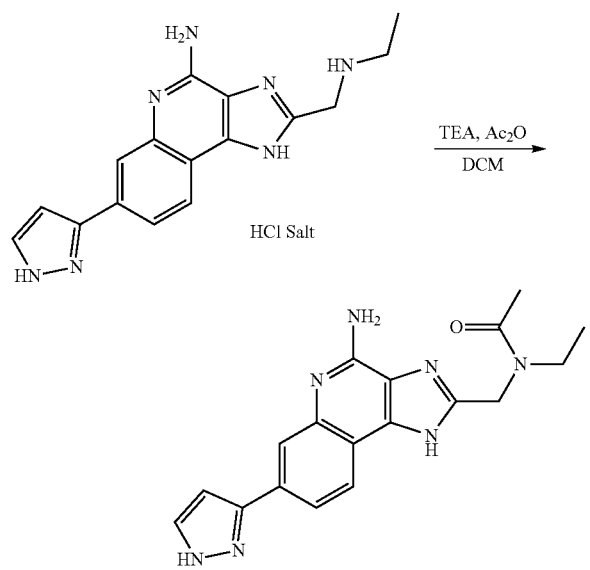

Preparation of N-[[4-amino-7-(1H-pyrazol-3-yl)-1H-imidazo[4,5-c]quinolin-2-yl]methyl]-N-ethylacetamide (Compound 112)

Into a 5-L round-bottom flask, was placed a solution of 2-[(ethylamino)methyl]-7-(1H-pyrazol-3-yl)-1H-imidazo[4,5-c]quinolin-4-amine (75.7 g, 245.97 mmol, 1.00 equiv, Example 3a) in dichloromethane (2 L). To the solution, TEA (124 g, 1.23 mol, 5.00 equiv) and acetic anhydride (50 g, 490.20 mmol, 2.00 equiv) were added. The resulting solution was stirred for 6 h at room temperature. Then the resulting mixture was concentrated under vacuum. The residue was dissolved in 3 L of MeOH and allowed to react with stirring for an additional 16 h while the temperature was maintained at 80° C. in an oil bath. The reaction mixture was cooled to room temperature, and evaporated to get the crude product. The crude material was stirred with 2 L of DCM and the solid was collected by filtration. This procedure was repeated three times. The resulting solid was stirred with 3 L of water and the pH was adjusted to 10 by the addition of aqueous NH₃. The precipitated solid was collected by filtration. The mother liquor was evaporated and the resulting precipitate was collected by filtration (3×). The combined solid was dissolved in methanol and stirred with ~10% Si-thiol at reflux for 4-6 hours and filtered. The filtrate was evaporated to get the crude product. This procedure was repeated until the Pd content in the resulting product was <50 ppm. The crude product was washed with 3×250 mL of water, collected by filtration and dried. This resulted in 20.28 g (24%) of Compound 112 as a light yellow solid.

¹HNMR (400 MHz, MeOD, ppm) δ: 8.15-8.07 (m, 1H), 7.98 (s, 1H), 7.80-7.67 (m, 2H), 6.80-6.70 (m, 1H), 4.88-4.85 (m, 2H), 3.60-3.48 (m, 2H), 2.30-2.20 (m, 3H), 1.23 (t, J=7.2 Hz, 2H), 1.11 (t, J=7.2 Hz, 1H); LC/MS [M++H] 350.1. LC/MS Method conditions: Column: Shim-pack XR-ODS 3.0×50 mm, 2.2 m particles; Mobile Phase A: water with 0.05% TFA; Mobile Phase B: acetonitrile with 0.05% TFA; Temperature: 40° C.; Gradient: 5-100% B over 3.8 min; Flow: 1.2 mL/min; 5 min run time. LC RT 1.349 min.

Preparation of N-[[4-amino-7-(1H-pyrazol-3-yl)-1H-imidazo[4,5-c]quinolin-2-yl]methyl]-N-ethylacetamide (Compound 112, alternate procedure)

2-[(Ethylamino)methyl]-7-(1H-pyrazol-3-yl)-1H-imidazo[4,5-c]quinolin-4-amine hydrochloride (107 g, 311 mmol) and CH₂Cl₂ (1.6 L) was stirred at room temperature. Et₃N (130 mL, 3 equiv) was added over 15 to 30 minutes, maintaining the temperature between 15-25° C. Acetic anhydride (41 mL, 1.4 eq) was added over 15 to 30 min, and the reaction mixture was stirred for 90 min. CH₃OH (54 mL) was added, and the reaction was stirred for 20 minutes before concentrating under reduced pressure. The crude material was treated with MeOH (2.2 L) and stirred at 60-70° C. for 2 h. After cooling to rt, the crude product was collected by filtration and washed with CH₃OH (220 mL). The resulting solid was dried under vacuum and then stirred into n-butanol (5.4 L) and H₂O (1.3 L). The mixture was heated to 60° C. and the pH was adjusted to 8 with 20% aqueous Na₂CO₃ solution (~60 mL). The organic layer was separated and the aqueous layer was extracted with an additional portion of n-butanol (540 mL) at 60° C. The combined organic layers were washed with brine (540 mL) at 50° C. for 15 minutes (2×) and concentrated under reduced pressure. The crude product was treated with CH₃OH (7.6 L) and H₂O (540 mL) and heated to 70° C. SiliaMetS-Thiol (22 g) was added and the mixture was stirred for 2 h, then filtered at 60° C. The filter cake was washed with CH₃OH (220 mL). The filtrate was concentrated under reduced pressure to ca. 800 mL, and stirred at rt for 2 h. The precipitate was filtered and washed with MeOH (220 mL), and H₂O (2×220 mL). The resulting solid was dried under vacuum and N₂, then transferred to a 100° C. vacuum oven to complete the drying process. This afforded 83.5 g (77%) of Compound 112.

Example 4b. Example Procedure for Amide Formation

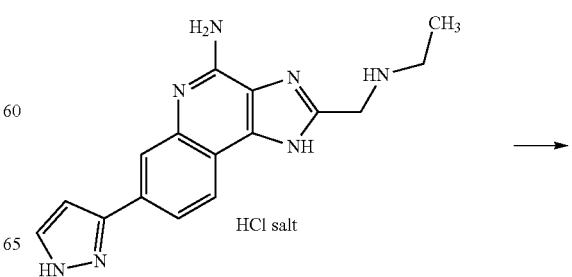

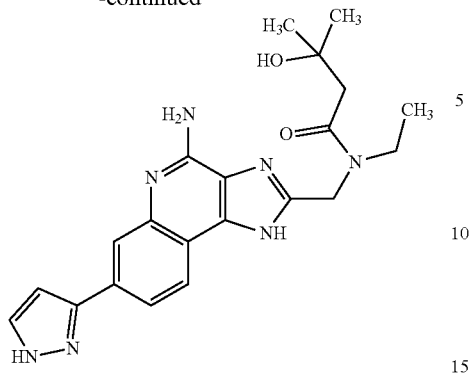

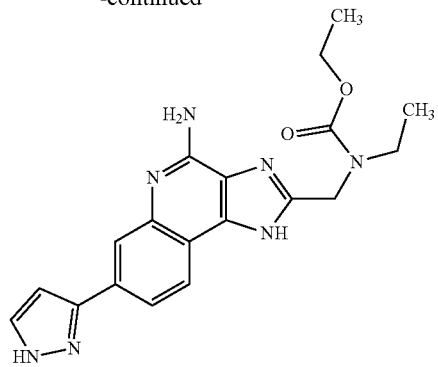

Preparation of N-{[4-amino-7-(1H-pyrazol-3-yl)-1H-imidazo[4,5-c]quinolin-2-yl]methyl}-N-ethyl-3-hydroxy-3-methylbutanamide (Compound 440)

To a suspension of 3-hydroxy-3-methylbutanoic acid (10.31 mg, 0.087 mmol) and 2-((ethylamino)methyl)-7-(1H-pyrazol-3-yl)-1H-imidazo[4,5-c]quinolin-4-amine, HCl (20 mg, 0.058 mmol) in DMF (582 μl) was added Hunig's Base (25.4 μl, 0.145 mmol) and 2,4,6-tripropyl-1,3,5,2,4,6-trioxatriphosphinane 2,4,6-trioxide (50% in DMF) (37.2 μl, 0.064 mmol). The reaction was stirred at rt overnight, then diluted with MeOH and purified by preparative HPLC with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 13% B, 13-38% B over 25 minutes, then a 2-minute hold at 100% B; Flow Rate: 20 mL/min; Column Temperature: 25° C. Fractions containing the desired product were combined and dried via centrifugal evaporation to give N-{[4-amino-7-(1H-pyrazol-3-yl)-1H-imidazo[4,5-c]quinolin-2-yl]methyl}-N-ethyl-3-hydroxy-3-methylbutanamide as the bis trifluoroacetate salt (8.4 mg, 22%). $^1$H NMR (500 MHz, DMSO-$d_6$) δ 8.78 (br d, J=14.6 Hz, 1H), 8.38-8.12 (m, 2H), 8.00 (br s, 1H), 7.81 (s, 1H), 6.82 (br s, 1H), 5.03-4.73 (m, 2H), 3.65-3.41 (m, 2H), 2.64-2.54 (m, 2H), 1.31-0.84 (m, 9H). LC/MS Conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50 OC; Gradient: 0-100% B over 3 minutes, then a 0.75-minute hold at 100% B; Flow: 1.0 mL/min. LC RT: 0.933 min. M/Z=408.3.

Preparation of Ethyl N-{[4-amino-7-(1H-pyrazol-3-yl)-1H-imidazo[4,5-c]quinolin-2-yl]methyl}-N-ethylcarbamate (Compound 436)

2-((Ethylamino)methyl)-7-(1H-pyrazol-3-yl)-1H-imidazo[4,5-c]quinolin-4-amine (15 mg, 0.049 mmol) was suspended in CH$_2$Cl$_2$ (488 μl) at rt. Pyridine (15.79 μl, 0.195 mmol) was added, followed by ethyl chloroformate (9.37 μl, 0.098 mmol). After 2 days, the reaction was concentrated and redissolved in MeOH. TEA (13.60 μl, 0.098 mmol) was added, and the reaction was stirred at rt overnight. The reaction was diluted with MeOH and purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 4% B, 4-44% B over 20 minutes, then a 4-minute hold at 100% B; Flow Rate: 20 mL/min; Column Temperature: 25° C. Fractions containing the desired product were combined and dried via centrifugal evaporation to give ethyl N-{[4-amino-7-(1H-pyrazol-3-yl)-1H-imidazo[4,5-c]quinolin-2-yl]methyl}-N-ethylcarbamate (7.4 mg, 39%). $^1$H NMR (500 MHz, DMSO-$d_6$) δ 8.12 (br d, J=8.2 Hz, 1H), 7.98 (s, 1H), 7.70 (br d, J=8.5 Hz, 2H), 6.77 (s, 1H), 4.72 (s, 2H), 4.11 (br s, 2H), 3.52-3.32 (m, 2H), 1.29-1.11 (m, 3H), 1.08 (br t, J=6.9 Hz, 3H). LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50 OC; Gradient: 0% B to 100% B over 3 min, then a 0.75 min hold at 100% B; Flow: 1 mL/min. LC RT: 1.29 min. M/Z=390.0.

Example 4c. Example Procedure for Carbamate Formation

Example 4d. Example Procedure for Sulfonamide Formation

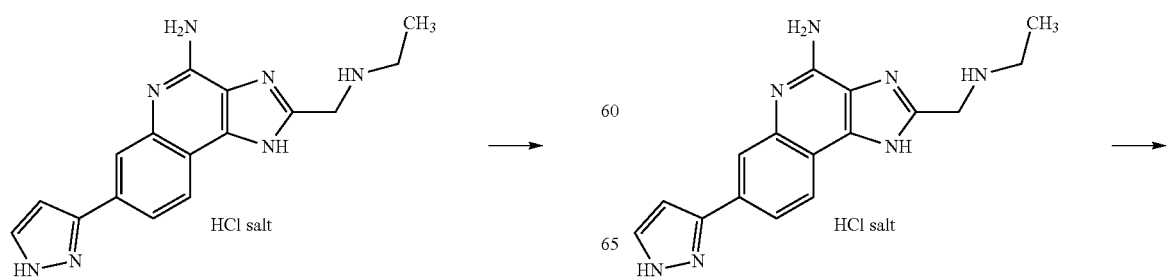

231

-continued

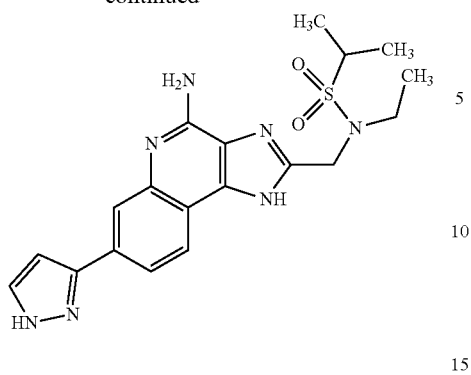

Preparation of N-{[4-amino-7-(1H-pyrazol-3-yl)-1H-imidazo[4,5-c]quinolin-2-yl]methyl}-N-ethyl-propane-2-sulfonamide (Compound 459)

To a solution of propane-2-sulfonyl chloride (10.37 mg, 0.073 mmol) in DMF (582 μl) was added 2-((ethylamino)methyl)-7-(1H-pyrazol-3-yl)-1H-imidazo[4,5-c]quinolin-4-amine, HCl (20 mg, 0.058 mmol) and Hunig's Base (25.4 μl, 0.145 mmol). The reaction was stirred at rt overnight, then diluted with DMF and purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 3% B, 3-43% B over 30 minutes, then a 4-minute hold at 100% B; Flow Rate: 20 mL/min; Column Temperature: 25° C. Fractions containing the desired product were combined and dried via centrifugal evaporation to give N-{[4-amino-7-(1H-pyrazol-3-yl)-1H-imidazo[4,5-c]quinolin-2-yl]methyl}-N-ethylpropane-2-sulfonamide (1.4 mg, 4.6%). $^1$H NMR (500 MHz, DMSO-$d_6$) δ 8.28 (br s, 1H), 8.20 (br s, 1H), 8.02-7.95 (m, 1H), 7.89-7.82 (m, 1H), 6.83 (br s, 1H), 4.73 (br s, 2H), 3.53-3.40 (m, 2H), 3.31 (br s, 1H), 1.24 (br d, J=6.4 Hz, 6H), 1.13 (br t, J=6.9 Hz, 3H). LC/MS Conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50 OC; Gradient: 0% B to 100% B over 3 min, then a 0.75 min hold at 100% B; Flow: 1 mL/min. LC RT: 1.24 min. M/Z=413.9.

Example 4e. Example Procedure for Urea Formation with Carbamoyl Chlorides

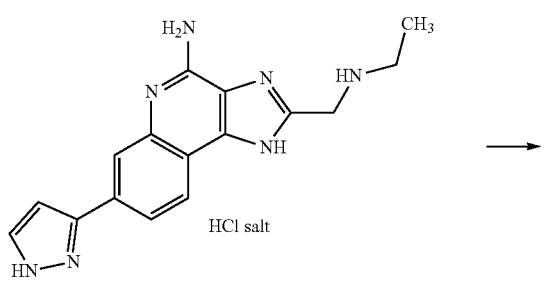

HCl salt

232

-continued

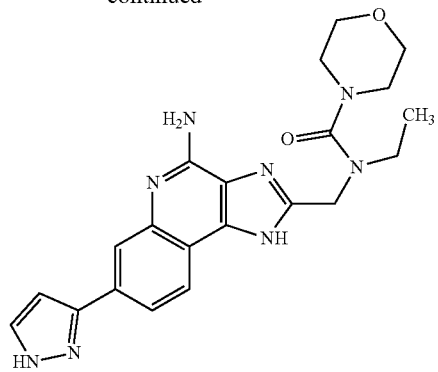

Preparation of N-{[4-amino-7-(1H-pyrazol-3-yl)-1H-imidazo[4,5-c]quinolin-2-yl]methyl}-N-ethyl-morpholine-4-carboxamide (Compound 455)

To a suspension of 2-((ethylamino)methyl)-7-(1H-pyrazol-3-yl)-1H-imidazo[4,5-c]quinolin-4-amine, HCl (20 mg, 0.058 mmol) in DMF (582 μl) was added Hunig's Base (25.4 μl, 0.145 mmol) and morpholine-4-carbonyl chloride (10.18 μl, 0.087 mmol). After ca. 1.5 hours, the reaction was quenched with MeOH, filtered through a syringe filter, and purified by preparative HPLC with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 0% B, 0-40% B over 20 minutes, then a 4-minute hold at 100% B; Flow Rate: 20 mL/min; Column Temperature: 25° C. Fractions containing the desired product were combined and dried via centrifugal evaporation to give N-{[4-amino-7-(1H-pyrazol-3-yl)-1H-imidazo[4,5-c]quinolin-2-yl]methyl}-N-ethylmorpholine-4-carboxamide (14.9 mg, 60%). $^1$H NMR (500 MHz, DMSO-$d_6$) δ 8.09 (br d, J=7.9 Hz, 1H), 8.01-7.90 (m, 1H), 7.74-7.63 (m, 2H), 6.76 (s, 1H), 4.59 (s, 2H), 3.60 (br s, 2H), 3.27-3.18 (m, 4H), 1.90 (s, 4H), 1.10 (br t, J=6.7 Hz, 3H). LC/MS Conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0-100% B over 3 minutes, then a 0.75-minute hold at 100% B; Flow: 1.0 mL/min. LC RT: 0.914 min, M/Z=421.4.

Example 4f. Example Procedure for Urea Formation with Isocyanates

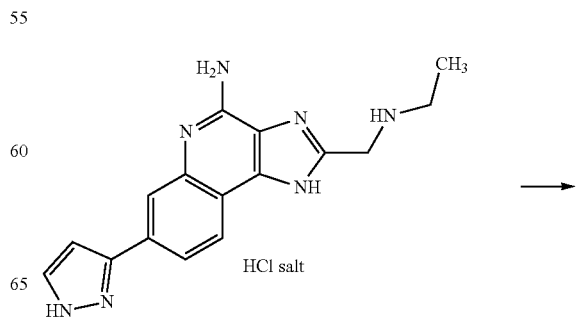

HCl salt

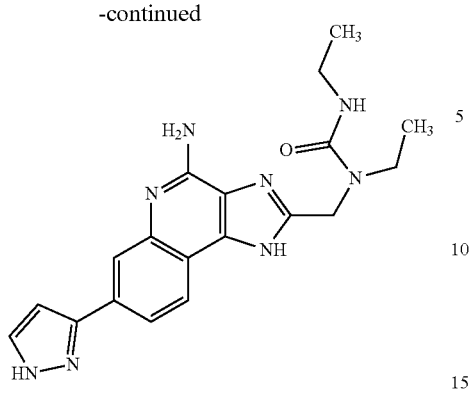

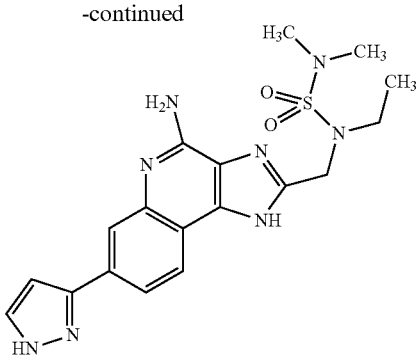

Preparation of 1-{[4-amino-7-(1H-pyrazol-3-yl)-1H-imidazo[4,5-c]quinolin-2-yl]methyl}-1,3-diethylurea (Compound 457)

To a suspension of 2-((ethylamino)methyl)-7-(1H-pyrazol-3-yl)-1H-imidazo[4,5-c]quinolin-4-amine, HCl (20 mg, 0.058 mmol) in DMF (582 µl) was added Hunig's Base (25.4 µl, 0.145 mmol) and isocyanatoethane (5.76 µl, 0.073 mmol). After 1.5 hours, the reaction was quenched with MeOH, filtered through a syringe filter, and purified by preparative HPLC with the following conditions: Column: XBridge C18, 200 mm×19 mm, 5-µm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 0% B, 0-40% B over 20 minutes, then a 4-minute hold at 100% B; Flow Rate: 20 mL/min; Column Temperature: 25° C. Fractions containing the desired product were combined and dried via centrifugal evaporation to give 1-{[4-amino-7-(1H-pyrazol-3-yl)-1H-imidazo[4,5-c]quinolin-2-yl]methyl}-1,3-diethylurea (4.8 mg, 21%). $^1$H NMR (500 MHz, DMSO-$d_6$) δ 8.13 (br d, J=8.2 Hz, 1H), 7.97 (s, 1H), 7.73-7.63 (m, 2H), 6.81-6.73 (m, 1H), 6.58 (br s, 1H), 4.68 (s, 2H), 3.36-3.26 (m, 2H), 3.17-3.07 (m, 2H), 1.09-0.96 (m, 6H). LC/MS Conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min. LC RT: 0.82 min. M/Z=379.3.

Example 4g. Example Procedure for Sulfonylurea Formation

Preparation of 2-{[(dimethylsulfamoyl)(ethyl)amino]methyl}-7-(1H-pyrazol-3-yl)-1H-imidazo[4,5-c]quinolin-4-amine (Compound 458)

To a suspension of 2-((ethylamino)methyl)-7-(1H-pyrazol-3-yl)-1H-imidazo[4,5-c]quinolin-4-amine, HCl (20 mg, 0.058 mmol) in DMF (582 µl) was added Hunig's Base (25.4 µl, 0.145 mmol) and dimethylsulfamoyl chloride (10.44 mg, 0.073 mmol). The reaction was stirred at rt overnight, then quenched with MeOH, filtered through a syringe filter, and purified via preparative LC/MS with the following conditions: Column: XBridge C18, 200 mm×19 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 16% B, 16-40% B over 25 minutes, then a 2-minute hold at 100% B; Flow Rate: 20 mL/min; Column Temperature: 25° C. Fractions containing the desired product were combined and dried via centrifugal evaporation to give 2-{[(dimethylsulfamoyl)(ethyl)amino]methyl}-7-(1H-pyrazol-3-yl)-1H-imidazo[4,5-c]quinolin-4-amine as the bis-triflouroacetate salt (13.5 mg, 35%). $^1$H NMR (500 MHz, DMSO-$d_6$) δ 8.32 (br d, J=8.3 Hz, 1H), 8.22 (br s, 1H), 8.00 (br d, J=7.8 Hz, 1H), 7.82 (br s, 1H), 6.82 (d, J=1.9 Hz, 1H), 4.68 (s, 2H), 3.43 (q, J=7.0 Hz, 2H), 2.75 (s, 6H), 1.17 (t, J=7.1 Hz, 3H). LC/MS conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min. LC RT: 1.17 min. M/Z=415.04.

Example 4h. Example Procedure for Amine Formation

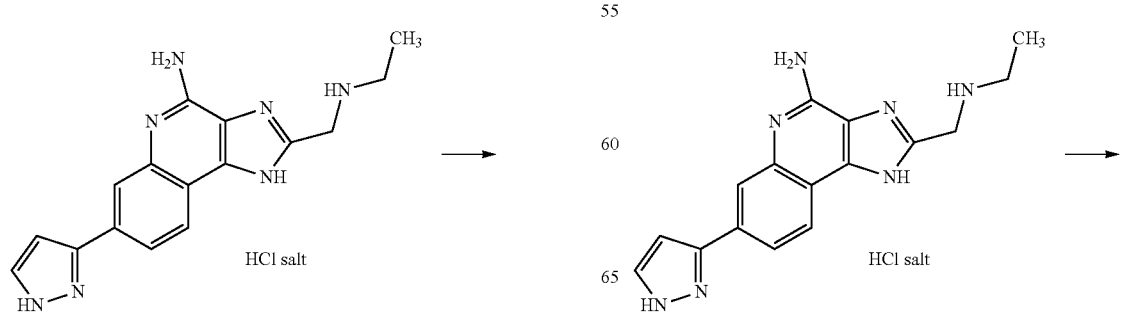

-continued

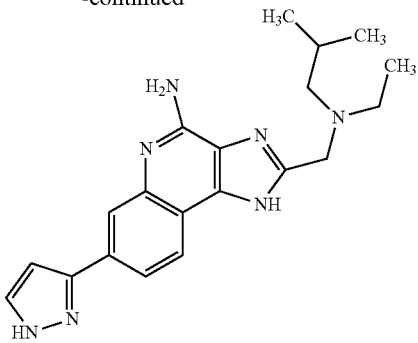

Preparation of 2-{[ethyl(2-methylpropyl)amino]
methyl}-7-(1H-pyrazol-3-yl)-1H-imidazo[4,5-c]
quinolin-4-amine (Compound 453)

To a suspension of isobutyraldehyde (20.97 mg, 0.291 mmol) and 2-((ethylamino)methyl)-7-(1H-pyrazol-3-yl)-1H-imidazo[4,5-c]quinolin-4-amine, HCl (20 mg, 0.058 mmol) in MeOH (582 μl) was added sodium triacetoxyborohydride (37.0 mg, 0.175 mmol). After 4.5 hours, isobutyraldehyde (20.97 mg, 0.291 mmol) and sodium triacetoxyborohydride (37.0 mg, 0.175 mmol) were added. After 2.75 hours, the reaction was partially concentrated, diluted with water and extracted three times with EtOAC. The organic layers were concentrated. The residue was dissolved in DMF, filtered through a syringe filter, and purified by preparative HPLC with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 20% B, 20-44% B over 25 minutes, then a 2-minute hold at 100% B; Flow Rate: 20 mL/min; Column Temperature: 25° C. Fractions containing the desired product were combined and dried via centrifugal evaporation to give 2-{[ethyl(2-methylpropyl)amino]methyl}-7-(1H-pyrazol-3-yl)-1H-imidazo[4,5-c]quinolin-4-amine (1.1 mg, 5.2%). $^1$H NMR (500 MHz, DMSO-$d_6$) δ 8.15 (d, J=8.2 Hz, 1H), 7.98 (s, 1H), 7.72-7.64 (m, 2H), 6.73 (d, J=1.9 Hz, 1H), 3.86 (s, 2H), 2.61 (q, J=7.0 Hz, 2H), 2.27 (d, J=7.1 Hz, 2H), 1.78-1.69 (m, 1H), 1.06 (t, J=7.0 Hz, 3H), 0.86 (d, J=6.6 Hz, 6H). LC/MS Conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50 OC; Gradient: 0% B to 100% B over 3 min, then a 0.75 min hold at 100% B; Flow: 1 mL/min; LC RT: 1.36 min; M/Z=364.1.

The compounds of Table 4 were prepared using the procedures outlined above. LC/MS Method conditions: Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min.

TABLE 4

| Cmpd | Name | LC/MS [M$^+$ + H] | LC RT | NMR Data |
|---|---|---|---|---|
| 102 | N-((4-Amino-7-(1H-pyrazol-1-yl)-1H-imidazo[4,5-c]quinolin-2-yl)methyl)-N-methylacetamide | 336.3 | 0.54 min | $^1$H NMR (400 MHz, METHANOL-$d_4$) δ 8.36-8.31 (m, 1H), 8.26-8.16 (m, 1H), 8.02-7.96 (m, 1H), 7.81-7.75 (m, 2H), 6.61-6.58 (m, 1H), 4.95-4.92 (m, 2H), 3.23 (s, 2H), 3.07 (s, 1H), 2.32 (s, 1H), 2.26 (s, 2H) |
| 106 | 2-((Ethylamino)methyl)-1-methyl-7-(1H-pyrazol-3-yl)-1H-imidazo[4,5-c]quinolin-4-amine | 322.1 | 0.48 min | $^1$H NMR (400 MHz, METHANOL-$d_4$) δ 8.30 (br d, J = 8.6 Hz, 1H), 8.15-7.98 (m, 1H), 7.89-7.64 (m, 2H), 6.79 (s, 1H), 4.24 (s, 3H), 4.12 (s, 2H), 2.80 (q, J = 7.2 Hz, 2H), 1.21 (t, J = 7.2 Hz, 3H) |
| 108 | N-((4-Amino-7-(1H-pyrazol-1-yl)-1H-imidazo[4,5-c]quinolin-2-yl)methyl)-N-ethylmethanesulfonamide | 386.3 | 0.59 min | $^1$H NMR (400 MHz, METHANOL-$d_4$) δ 8.34 (d, J = 2.4 Hz, 1H), 8.30-8.20 (m, 1H), 7.99 (d, J = 2.1 Hz, 1H), 7.82-7.75 (m, 2H), 6.59 (t, J = 2.1 Hz, 1H), 4.77 (s, 2H), 3.46 (q, J = 7.1 Hz, 2H), 3.04 (s, 3H), 1.22 (t, J = 7.1 Hz, 3H) |
| 109 | tert-Butyl ((4-amino-7-(1H-pyrazol-3-yl)-1H-imidazo[4,5-c]quinolin-2-yl)methyl)(ethyl)carbamate | 408.3 | 0.69 min | $^1$H NMR (400 MHz, METHANOL-$d_4$) δ 8.22-8.09 (m, 1H), 8.07-7.98 (m, 1H), 7.91-7.51 (m, 2H), 6.79 (br s, 1H), 4.77 (s, 2H), 3.63-3.42 (m, 2H), 1.64-1.32 (m, 9H), 1.19 (br s, 3H) |
| 110 | 1-((4-Amino-7-(1H-pyrazol-3-yl)-1H-imidazo[4,5-c]quinolin-2-yl)methyl)-1-ethyl-3,3-dimethylurea | 379.3 | 0.58 min | $^1$H NMR (400 MHz, METHANOL-$d_4$) δ 8.25-8.10 (m, 1H), 8.09-7.99 (m, 1H), 7.91-7.65 (m, 2H), 6.79 (br s, 1H), 4.67 (s, 2H), 3.39-3.34 (m, 2H), 2.97 (s, 6H), 1.23 (t, J = 7.1 Hz, 3H) |
| 113 | N-((4-Amino-7-(1H-pyrazol-3-yl)-1H-imidazo[4,5-c]quinolin-2-yl)methyl)acetamide | 322.3 | 0.49 min | $^1$H NMR (400 MHz, METHANOL-$d_4$) δ 8.13 (br d, J = 8.3 Hz, 1H), 8.03 (br s, 1H), 7.88-7.65 (m, 2H), 6.78 (s, 1H), 4.71 (s, 2H), 2.11 (s, 3H) |
| 158 | N-((4-Amino-7-methoxy-1H-imidazo[4,5-c]quinolin-2-yl)methyl)- | 314.3 | 0.55 min | $^1$H NMR (400 MHz, METHANOL-$d_4$) δ 8.07-7.95 (m, 1H), 7.13 (d, J = 2.2 Hz, 1H), 7.07-6.97 (m, 1H), |

TABLE 4-continued

| Cmpd | Name | LC/MS [M+ + H] | LC RT | NMR Data |
|---|---|---|---|---|
| | N-ethylacetamide | | | 3.92 (s, 1H), 3.91 (s, 2H), 3.61-3.50 (m, 2H), 2.29 (s, 1H), 2.26 (s, 2H), 1.26 (t, J = 7.1 Hz, 2H), 1.13 (t, J = 7.1 Hz, 1H) |
| 419 | N-((4-Amino-7-(thiophen-3-yl)-1H-imidazo[4,5-c]quinolin-2-yl)methyl)-N-ethylacetamide | 366.3 | 0.65 min | $^1$H NMR (400 MHz, METHANOL-$d_4$) δ 8.20-8.10 (m, 1H), 7.94-7.90 (m, 1H), 7.80-7.75 (m, 1H), 7.75-7.67 (m, 1H), 7.62-7.53 (m, 2H), 4.91 (s, 2H), 3.66-3.52 (m, 2H), 2.31 (s, 1H), 2.27 (s, 2H), 1.27 (t, J = 7.2 Hz, 2H), 1.15 (t, J = 7.1 Hz, 1H) |

The compounds of Table 5 were prepared using the procedures outlined above.

TABLE 5

| Cmpd | Name | LC/MS [M+ + H] | LC RT | LC Method |
|---|---|---|---|---|
| 436 | ethyl N-{[4-amino-7-(1H-pyrazol-3-yl)-1H-imidazo[4,5-c]quinolin-2-yl]methyl}-N-ethylcarbamate | 390.0 | 1.29 min | A |
| 437 | N-{[4-amino-7-(1H-pyrazol-3-yl)-1H-imidazo[4,5-c]quinolin-2-yl]methyl}-N-ethyl-2-(3-methylphenyl)acetamide | 440.4 | 1.30 min | A |
| 438 | N-{[4-amino-7-(1H-pyrazol-3-yl)-1H-imidazo[4,5-c]quinolin-2-yl]methyl}-N-ethylpyridine-3-carboxamide | 413.0 | 1.13 min | B |
| 439 | N-{[4-amino-7-(1H-pyrazol-3-yl)-1H-imidazo[4,5-c]quinolin-2-yl]methyl}-N-ethylpyridine-2-carboxamide | 413.2 | 1.19 min | B |
| 440 | N-{[4-amino-7-(1H-pyrazol-3-yl)-1H-imidazo[4,5-c]quinolin-2-yl]methyl}-N-ethyl-3-hydroxy-3-methylbutanamide | 408.4 | 0.97 min | B |
| 441 | N-{[4-amino-7-(1H-pyrazol-3-yl)-1H-imidazo[4,5-c]quinolin-2-yl]methyl}-N-ethyl-4-methoxybenzamide | 442.01 | 1.21 min | A |
| 442 | N-{[4-amino-7-(1H-pyrazol-3-yl)-1H-imidazo[4,5-c]quinolin-2-yl]methyl}-N-ethylpyrazine-2-carboxamide | 414.0 | 0.88 min | A |
| 443 | N-{[4-amino-7-(1H-pyrazol-3-yl)-1H-imidazo[4,5-c]quinolin-2-yl]methyl}-N-ethyl-2-phenylacetamide | 426.0 | 1.26 min | B |
| 444 | N-{[4-amino-7-(1H-pyrazol-3-yl)-1H-imidazo[4,5-c]quinolin-2-yl]methyl}-N-ethyl-4-phenylbutanamide | 454.1 | 1.48 min | A |
| 445 | N-{[4-amino-7-(1H-pyrazol-3-yl)-1H-imidazo[4,5-c]quinolin-2-yl]methyl}-N-ethyl-4-methylpentanamide | 406.1 | 1.41 min | A |
| 446 | N-{[4-amino-7-(1H-pyrazol-3-yl)-1H-imidazo[4,5-c]quinolin-2-yl]methyl}-N-ethyl-1-methyl-1H-pyrrole-2-carboxamide | 415.2 | 1.17 min | A |
| 447 | N-{[4-amino-7-(1H-pyrazol-3-yl)-1H-imidazo[4,5-c]quinolin-2-yl]methyl}-N-ethyl-3-phenylpropanamide | 440.2 | 1.37 min | A |
| 448 | N-{[4-amino-7-(1H-pyrazol-3-yl)-1H-imidazo[4,5-c]quinolin-2-yl]methyl}-N-ethyl-1,3-thiazole-4-carboxamide | 419.3 | 1.12 min | A |
| 449 | N-{[4-amino-7-(1H-pyrazol-3-yl)-1H-imidazo[4,5-c]quinolin-2-yl]methyl}-2-chloro-N-ethylbenzamide | 446.0 | 1.28 min | A |
| 450 | N-{[4-amino-7-(1H-pyrazol-3-yl)-1H-imidazo[4,5-c]quinolin-2-yl]methyl}-N-ethylpyridine-4-carboxamide | 413.0 | 0.92 min | A |
| 451 | N-{[4-amino-7-(1H-pyrazol-3-yl)-1H-imidazo[4,5-c]quinolin-2-yl]methyl}-N-ethyl-1-methyl-1H-indole-3-carboxamide | 465.2 | 1.31 min | B |
| 452 | N-{[4-amino-7-(1H-pyrazol-3-yl)-1H-imidazo[4,5-c]quinolin-2-yl]methyl}-4-chloro-N-ethylbenzamide | 446.0 | 1.36 min | A |

TABLE 5-continued

| Cmpd | Name | LC/MS [M+ + H] | LC RT | LC Method |
|---|---|---|---|---|
| 453 | 2-{[ethyl(2-methylpropyl)amino]methyl}-7-(1H-pyrazol-3-yl)-1H-imidazo[4,5-c]quinolin-4-amine | 364.1 | 1.36 min | A |
| 454 | 1-{[4-amino-7-(1H-pyrazol-3-yl)-1H-imidazo[4,5-c]quinolin-2-yl]methyl}-1,3,3-triethylurea | 407.1 | 1.31 min | A |
| 455 | N-{[4-amino-7-(1H-pyrazol-3-yl)-1H-imidazo[4,5-c]quinolin-2-yl]methyl}-N-ethylmorpholine-4-carboxamide | 421.4 | 0.91 min | B |
| 456 | 1-{[4-amino-7-(1H-pyrazol-3-yl)-1H-imidazo[4,5-c]quinolin-2-yl]methyl}-3-tert-butyl-1-ethylurea | 407.1 | 1.29 min | A |
| 457 | 1-{[4-amino-7-(1H-pyrazol-3-yl)-1H-imidazo[4,5-c]quinolin-2-yl]methyl}-1,3-diethylurea | 379.3 | 0.82 min | A |
| 458 | 2-{[(dimethylsulfamoyl)(ethyl)amino]methyl}-7-(1H-pyrazol-3-yl)-1H-imidazo[4,5-c]quinolin-4-amine | 415.0 | 1.17 min | A |
| 459 | N-{[4-amino-7-(1H-pyrazol-3-yl)-1H-imidazo[4,5-c]quinolin-2-yl]methyl}-N-ethylpropane-2-sulfonamide | 413.9 | 1.24 min | A |
| 460 | N-{[4-amino-7-(1H-pyrazol-3-yl)-1H-imidazo[4,5-c]quinolin-2-yl]methyl}-N-ethylpropane-1-sulfonamide | 414.0 | 1.16 min | A |
| 470 | N-{[4-amino-1-(2-hydroxyethyl)-7-(thiophen-2-yl)-1H-imidazo[4,5-c]quinolin-2-yl]methyl}-N-ethylpropanamide | 424.1 | 1.24 min | D |
| 472 | N-{[4-amino-1-ethyl-7-(thiophen-2-yl)-1H-imidazo[4,5-c]quinolin-2-yl]methyl}-N-ethylacetamide | 393.9 | 2.27 min | E |
| 473 | N-{[4-amino-1-ethyl-7-(1H-pyrazol-5-yl)-1H-imidazo[4,5-c]quinolin-2-yl]methyl}-N-ethylpropanamide | 392.3 | 1.75 min | E |
| 474 | N-{[4-amino-1-ethyl-7-(1H-pyrazol-5-yl)-1H-imidazo[4,5-c]quinolin-2-yl]methyl}-N-ethylacetamide | 378.3 | 1.95 min | C |
| 475 | N-{[4-amino-1-(2-hydroxyethyl)-7-(1H-pyrazol-5-yl)-1H-imidazo[4,5-c]quinolin-2-yl]methyl}-N-ethylpropanamide | 408.1 | 0.92 min | D |
| 476 | N-{[4-amino-1-(2-hydroxyethyl)-7-(1H-pyrazol-1-yl)-1H-imidazo[4,5-c]quinolin-2-yl]methyl}-N-ethylacetamide | 394.1 | 0.93 min | D |
| 478 | N-{[4-amino-1-(2-hydroxyethyl)-7-(1H-pyrazol-1-yl)-1H-imidazo[4,5-c]quinolin-2-yl]methyl}-N-ethylpropanamide | 408.1 | 1.00 min | D |
| 479 | N-{[4-amino-1-ethyl-7-(1H-pyrazol-1-yl)-1H-imidazo[4,5-c]quinolin-2-yl]methyl}-N-ethylacetamide | 378.0 | 1.12 min | E |
| 480 | N-{[4-amino-1-ethyl-7-(thiophen-2-yl)-1H-imidazo[4,5-c]quinolin-2-yl]methyl}-N-ethylpropanamide | 408.0 | 1.50 min | E |
| 481 | N-{[4-amino-1-ethyl-7-(1H-pyrazol-1-yl)-1H-imidazo[4,5-c]quinolin-2-yl]methyl}-N-ethylpropanamide | 392.2 | 1.33 min | C |
| 482 | N-{[4-amino-1-(2-hydroxyethyl)-7-(thiophen-2-yl)-1H-imidazo[4,5-c]quinolin-2-yl]methyl}-N-ethylacetamide | 410.1 | 1.79 min | D |

LC Methods for Table 4:

A: Column: Waters XBridge C18, 2.1 mm × 50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min.
B: Column: Waters Acquity UPLC BEH C18, 2.1 × 50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min.
C: Column: Shim-pack XR-ODS 3.0 mm × 50 mm, 2.2 μm particles; Mobile Phase A: water with 0.05% TFA; Mobile Phase B: acetonitrile with 0.05% TFA; Temperature: 40° C.; Gradient: 0% B to 95% B over 2 min, then a 0.7 min hold at 95% B; Flow: 1.5 mL/min.
D: Column: Kinetex EVO, 3.0 mm × 50 mm, 2.6 μm particles; Mobile Phase A: water with 0.03% NH3H2O; Mobile Phase B: acetonitrile; Temperature: 40° C.; Gradient: 10% B to 95% B over 2 min, then a 0.60 min hold at 95% B; Flow: 1.2 mL/min.
E: Column: XBridge BEH Shield RP18, 2.1 mm × 50 mm, 2.5 μm particles; Mobile Phase A: water with 6.5 mM ammonium bicarbonate; Mobile Phase B: acetonitrile; Temperature: 40° C.; Gradient: 10% B to 50% B over 2.2 min, then to 95% B over 0.60 min, then 0.70 min hold at 95% B; Flow: 1 mL/min

241

Example 5: Example Preparation Method of Analogs Wherein R¹/R²=Lactam and R⁵=Aryl

242

Step 1. Preparation of 1-((7-bromo-1-(4-methoxybenzyl)-1H-imidazo[4,5-c]quinolin-2-yl)methyl)pyrrolidin-2-one

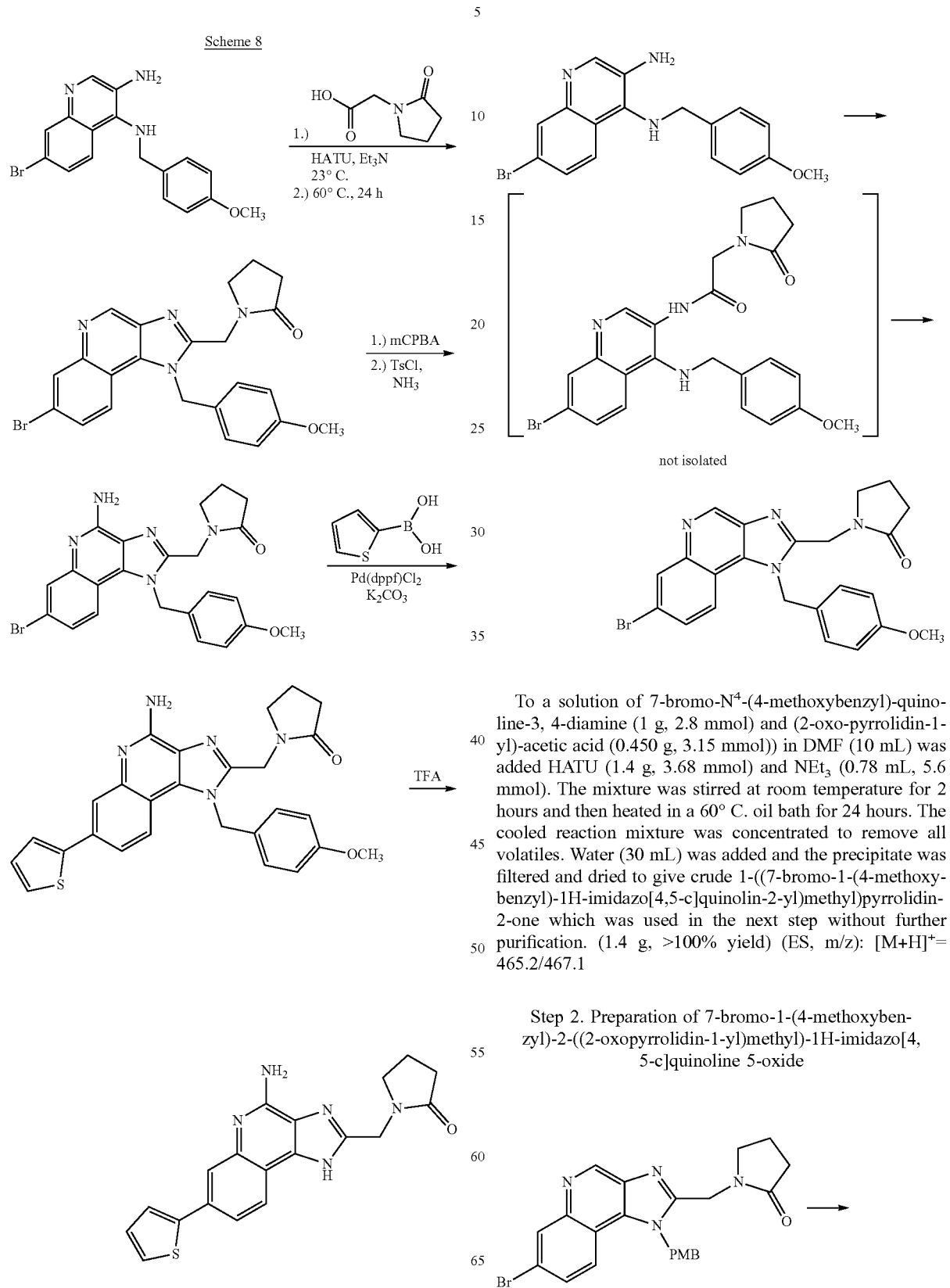

To a solution of 7-bromo-$N^4$-(4-methoxybenzyl)-quinoline-3, 4-diamine (1 g, 2.8 mmol) and (2-oxo-pyrrolidin-1-yl)-acetic acid (0.450 g, 3.15 mmol)) in DMF (10 mL) was added HATU (1.4 g, 3.68 mmol) and $NEt_3$ (0.78 mL, 5.6 mmol). The mixture was stirred at room temperature for 2 hours and then heated in a 60° C. oil bath for 24 hours. The cooled reaction mixture was concentrated to remove all volatiles. Water (30 mL) was added and the precipitate was filtered and dried to give crude 1-((7-bromo-1-(4-methoxybenzyl)-1H-imidazo[4,5-c]quinolin-2-yl)methyl)pyrrolidin-2-one which was used in the next step without further purification. (1.4 g, >100% yield) (ES, m/z): $[M+H]^+$= 465.2/467.1

Step 2. Preparation of 7-bromo-1-(4-methoxybenzyl)-2-((2-oxopyrrolidin-1-yl)methyl)-1H-imidazo[4,5-c]quinoline 5-oxide

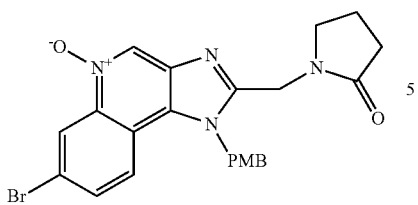

To a solution of 1-((7-bromo-1-(4-methoxybenzyl)-1H-imidazo[4,5-c]quinolin-2-yl)methyl)pyrrolidin-2-one (370 mg, 1.01 mmol) in CHCl$_3$ (10 mL) was added m-chloroperoxybenzoic acid (70% grade, 263 mg, 1.5 mmol). The mixture was stirred for 60 OC for 3 hours at which time the cooled mixture was diluted with a saturated aqueous solution of NaHCO$_3$ and extracted with CH$_2$Cl$_2$ (2×20 mL). The combined organic layers were washed with brine, dried over Na$_2$SO$_4$, filtered, and concentrated to give the crude N-oxide (400 mg, 1.05 mmol, 99%) as a brownish foam. (ES, m/z): [M+H]$^+$=481.2/483.1

Step 3. Preparation of 1-((4-amino-7-bromo-1-(4-methoxybenzyl)-1H-imidazo[4,5-c]quinolin-2-yl)methyl)pyrrolidin-2-one

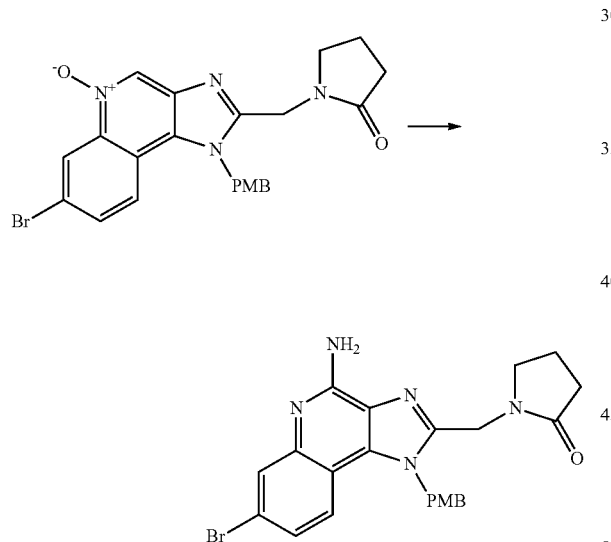

To a solution of 7-bromo-1-(4-methoxybenzyl)-2-((2-oxopyrrolidin-1-yl)methyl)-1H-imidazo[4,5-c]quinoline 5-oxide (400 mg, 1.05 mmol) and NH$_4$OH (10 mL) in dichloromethane (20 mL) cooled in an ice water bath, was added p-toluenesulfonyl chloride (300 mg, 1.57 mmol) in CH$_2$Cl$_2$ (10 mL) dropwise. The resulting solution was stirred another 30 min after complete addition. Water (20 mL) was added and the layers were separated. The aqueous layer was extracted one more time with CH$_2$Cl$_2$ (30 mL). The solution was filtered through a pad of Na$_2$SO$_4$ and the filtrate was concentrated in vacuo. The residue was triturated with EtOAc/hexanes (1/3) and dried under high vacuum to afford 1-((4-amino-7-bromo-1-(4-methoxybenzyl)-1H-imidazo[4,5-c]quinolin-2-yl)methyl)pyrrolidin-2-one as a yellow solid (317 mg, 0.66 mmol, 66%). (ES, m/z): [M+H]$^+$=480.3/482.2

Step 4. Preparation of 1-((4-amino-1-(4-methoxybenzyl)-7-aryl (heteroaryl)-1H-imidazo[4,5-c]quinolin-2-yl)methyl)pyrrolidin-2-one

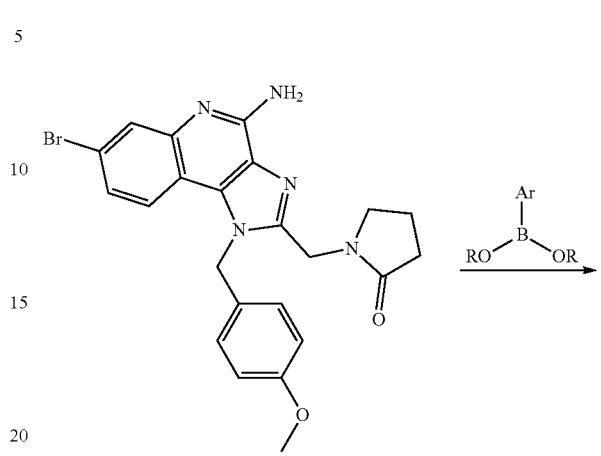

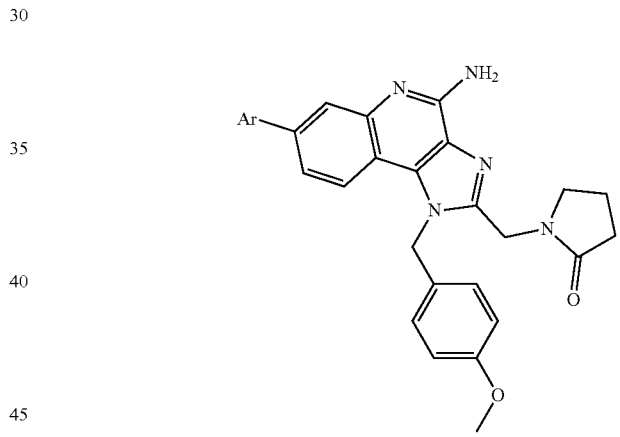

To a dioxane solution of 1-((4-amino-7-bromo-1-(4-methoxybenzyl)-1H-imidazo[4,5-c]quinolin-2-yl)methyl)pyrrolidin-2-one (400 mg, 833 µmol) was added an aryl (heteroaryl) boronic acid (or arylboronate ester) (1.5 equiv), Pd(dppf)Cl$_2$.CH$_2$Cl$_2$ (50 mg), and an aqueous solution of K$_2$CO$_3$ (10 mL, 2M) sequentially. The mixture was irradiated in a Biotage Initiator microwave apparatus at 120° C. for 10 min. The organic layer was diluted with EtOAc and separated, and the aqueous layer was washed with EtOAc. The combined organic layers were filtered, evaporated and flash chromatographed on silica gel eluting with chloroform/methanol to afford pure 1-((4-amino-1-(4-methoxybenzyl)-7-aryl (heteroaryl)-1H-imidazo[4,5-c]quinolin-2-yl)methyl) pyrrolidin-2-one.

Step 5. General Procedure for Deprotection

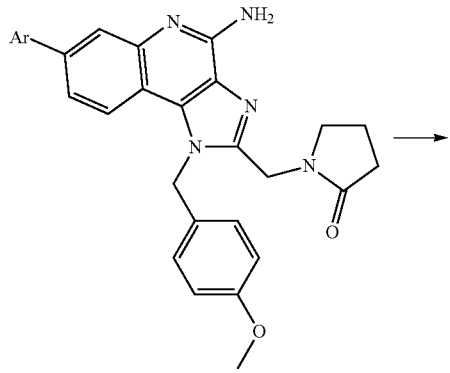

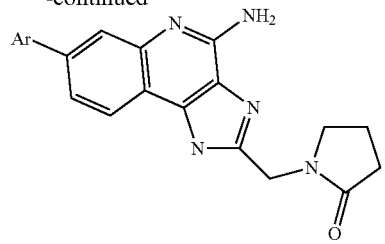

The product from the previous step was dissolved in TFA (20 mL) and stirred at 70° C. for 1 hour, at which time LCMS analysis indicated that the PMB protecting group was completely cleaved. The mixture was evaporated and flash chromatographed on silica gel eluting with chloroform/methanol to furnish the product as a free base. The material was dissolved in a methanolic solution of hydrogen chloride (1 N), the solvent evaporated, and the resulting solid washed with diethyl ether and dried to afford 1-((4-amino-7-aryl (heteroaryl)-1H-imidazo[4,5-c]quinolin-2-yl)methyl)pyrrolidin-2-one as the hydrochloride salt.

The compounds depicted in Table 6 were made according to the above synthetic procedures.

TABLE 6

| Compound | NAME | [M + H]+ |
|---|---|---|
| 279 | 1-[(4-amino-7-pyridin-3-yl-1H-imidazo[4,5-c]quinolin-2-yl)methyl]pyrrolidin-2-one | 359.1 |
| 280 | 1-[(4-amino-7-phenyl-1H-imidazo[4,5-c]quinolin-2-yl)methyl]pyrrolidin-2-one | 358.2 |
| 281 | 1-[[4-amino-7-(2-chlorophenyl)-1H-imidazo[4,5-c]quinolin-2-yl]methyl]pyrrolidin-2-one | 392.1 |
| 282 | 1-[[4-amino-7-(2-methylphenyl)-1H-imidazo[4,5-c]quinolin-2-yl]methyl]pyrrolidin-2-one | 372.2 |
| 283 | 1-[[4-amino-7-(2-methoxyphenyl)-1H-imidazo[4,5-c]quinolin-2-yl]methyl]pyrrolidin-2-one | 388.2 |
| 284 | 1-[[4-amino-7-(2-fluorophenyl)-1H-imidazo[4,5-c]quinolin-2-yl]methyl]pyrrolidin-2-one | 376.1 |
| 285 | 1-[[4-amino-7-(3-chlorophenyl)-1H-imidazo[4,5-c]quinolin-2-yl]methyl]pyrrolidin-2-one | 392.1 |
| 286 | 1-[[4-amino-7-(3-methylphenyl)-1H-imidazo[4,5-c]quinolin-2-yl]methyl]pyrrolidin-2-one | 372.2 |
| 287 | 1-[[4-amino-7-(3-methoxyphenyl)-1H-imidazo[4,5-c]quinolin-2-yl]methyl]pyrrolidin-2-one | 388.2 |
| 288 | 3-[4-amino-2-[(2-oxopyrrolidin-1-yl)methyl]-1H-imidazo[4,5-c]quinolin-7-yl]benzonitrile | 383.1 |
| 289 | 1-[[4-amino-7-(3-fluorophenyl)-1H-imidazo[4,5-c]quinolin-2-yl]methyl]pyrrolidin-2-one | 376.1 |
| 291 | 1-[[4-amino-7-(4-methylphenyl)-1H-imidazo[4,5-c]quinolin-2-yl]methyl]pyrrolidin-2-one | 372.2 |
| 292 | 1-[[4-amino-7-(4-methoxyphenyl)-1H-imidazo[4,5-c]quinolin-2-yl]methyl]pyrrolidin-2-one | 388.2 |
| 294 | 1-[(4-amino-7-bromo-1H-imidazo[4,5-c]quinolin-2-yl)methyl]pyrrolidin-2-one | 360.0 |
| 295 | 1-[(4-amino-7-pyrazol-1-yl-1H-imidazo[4,5-c]quinolin-2-yl)methyl]pyrrolidin-2-one | 348.1 |
| 296 | 1-[[4-amino-7-(4-methylpyrazol-1-yl)-1H-imidazo[4,5-c]quinolin-2-yl]methyl]pyrrolidin-2-one | 362.2 |
| 298 | 1-[[4-amino-7-(oxan-4-yl)-1H-imidazo[4,5-c]quinolin-2-yl]methyl]pyrrolidin-2-one | 366.2 |
| 301 | 1-[[4-amino-7-(3-methylpyrazol-1-yl)-1H-imidazo[4,5-c]quinolin-2-yl]methyl]pyrrolidin-2-one | 362.2 |
| 302 | 1-[(4-amino-7-cyclohexyl-1H-imidazo[4,5-c]quinolin-2-yl)methyl]pyrrolidin-2-one | 364.2 |
| 303 | 1-[1-(4-amino-7-bromo-1H-imidazo[4,5-c]quinolin-2-yl)ethyl]pyrrolidin-2-one | 374.1 |
| 304 | 1-[[4-amino-7-(6-methoxypyridin-3-yl)-1H-imidazo[4,5-c]quinolin-2-yl]methyl]pyrrolidin-2-one | 389.2 |
| 307 | 1-[[4-amino-7-(2-fluoropyridin-3-yl)-1H-imidazo[4,5-c]quinolin-2-yl]methyl]pyrrolidin-2-one | 377.1 |
| 308 | 1-1[(4-amino-7-thiophen-3-yl-1H-imidazo[4,5-c]quinolin-2-yl)methyl]pyrrolidin-2-one | 364.1 |

TABLE 6-continued

| Compound | NAME | [M + H]+ |
|---|---|---|
| 309 | 1-[(4-amino-7-thiophen-2-yl-1H-imidazo[4,5-c]quinolin-2-yl)methyl]pyrrolidin-2-one | 364.1 |
| 315 | 2-[4-amino-2-[(2-oxopyrrolidin-1-yl)methyl]-1H-imidazo[4,5-c]quinolin-7-yl]benzonitrile | 383.2 |
| 316 | 1-[(4-amino-7-bromo-1H-imidazo[4,5-c]quinolin-2-yl)methyl]-4-phenylpyrrolidin-2-one | 436.1 |
| 319 | 1-[[4-amino-7-(2-methoxypyridin-3-yl)-1H-imidazo[4,5-c]quinolin-2-yl]methyl]pyrrolidin-2-one | 389.2 |
| 320 | 1-[[4-amino-7-(2-chloropyridin-3-yl)-1H-imidazo[4,5-c]quinolin-2-yl]methyl]pyrrolidin-2-one | 393.1 |
| 321 | 1-[[4-amino-7-(4-chloropyridin-3-yl)-1H-imidazo[4,5-c]quinolin-2-yl]methyl]pyrrolidin-2-one | 393.1 |
| 324 | 1-[[4-amino-7-[6-(trifluoromethyl)pyridin-3-yl]-1H-imidazo[4,5-c]quinolin-2-yl]methyl]pyrrolidin-2-one | 427.1 |
| 326 | 5-[4-amino-2-[(2-oxopyrrolidin-1-yl)methyl]-1H-imidazo[4,5-c]quinolin-7-yl]pyridine-3-carbonitrile | 384.1 |
| 327 | 5-[4-amino-2-[(2-oxopyrrolidin-1-yl)methyl]-1H-imidazo[4,5-c]quinolin-7-yl]pyridine-2-carbonitrile | 384.1 |
| 328 | 1-[[4-amino-7-(5-chloropyridin-3-yl)-1H-imidazo[4,5-c]quinolin-2-yl]methyl]pyrrolidin-2-one | 393.1 |
| 330 | 1-[[4-amino-7-(6-fluoropyridin-3-yl)-1H-imidazo[4,5-c]quinolin-2-yl]methyl]pyrrolidin-2-one | 377.1 |
| 331 | 1-[[4-amino-7-(5-fluoropyridin-3-yl)-1H-imidazo[4,5-c]quinolin-2-yl]methyl]pyrrolidin-2-one | 377.1 |
| 332 | 1-[(4-amino-7-cycloheptyl-1H-imidazo[4,5-c]quinolin-2-yl)methyl]pyrrolidin-2-one | 378.2 |
| 333 | 1-[(4-amino-7-pyridin-3-yl-1H-imidazo[4,5-c]quinolin-2-yl)methyl]-4-phenylpyrrolidin-2-one | 435.2 |

The compounds depicted in Table 7 were made according to the above synthetic procedures.

TABLE 7

| Compound | Name | LC/MS [M+ + H] | LC RT | LC Method |
|---|---|---|---|---|
| 463 | 1-{[4-amino-1-ethyl-7-(thiophen-2-yl)-1H-imidazo[4,5-c]quinolin-2-yl]methyl}pyrrolidin-2-one | 392.2 | 1.16 min | C |
| 465 | 1-{[4-amino-1-ethyl-7-(1H-pyrazol-1-yl)-1H-imidazo[4,5-c]quinolin-2-yl]methyl}pyrrolidin-2-one | 376.2 | 0.98 min | C |
| 466 | 1-{[4-amino-1-ethyl-7-(1H-pyrazol-5-yl)-1H-imidazo[4,5-c]quinolin-2-yl]methyl}pyrrolidin-2-one | 376.2 | 0.95 min | C |
| 469 | 1-{[4-amino-1-(2-hydroxyethyl)-7-(thiophen-2-yl)-1H-imidazo[4,5-c]quinolin-2-yl]methyl}pyrrolidin-2-one | 408.0 | 1.16 min | A |

LC Methods:
A: Column: Kinetex EVO, 3.0 mm × 50 mm, 2.6 μm particles; Mobile Phase A: water with 5 mM ammonium bicarbonate; Mobile Phase B: acetonitrile; Temperature: 40° C.; Gradient: 10% B to 95% B over 2 min, then a 0.79 min hold at 95% B; Flow: 1 mL/min;
B: Column: Kinetex EVO, 3.0 mm × 50 mm, 2.6 μm particles; Mobile Phase A: water with 0.03% NH3H2O; Mobile Phase B: acetonitrile; Temperature: 40° C.; Gradient: 10% B to 95% B over 2 min, then a 0.60 min hold at 95% B; Flow: 1.2 mL/min;
C: Column: Express C18 2.1 mm × 50 mm, 2.7 μm particles; Mobile Phase A: water with 0.05% TFA; Mobile Phase B: acetonitrile with 0.05% TFA; Temperature: 40° C.; Gradient: 5% B to 100% B over 2 min, then a 0.75 min hold at 100% B; Flow: 0.8 mL/min Example 6: Biological Assays Measurement of IL-1β production in PMA-differentiated THP-1 cells THP-1 cells were purchased from the American Type Culture Collection and sub-cultured according to instructions from the supplier. Prior to experiments, cells were cultured in RPMI 1640 containing 10% heat inactivated FBS, penicillin (100 units/ml) and streptomycin (100 μg/ml), and maintained in log phase prior to experimental setup. Prior to the experiment THP-1 were treated with PMA (Phorbol 12-myristate 13-acetate) (10 μg/ml) for 24 hours. The day of the experiment the media was removed and attaching cells were treated with trypsin for 2 minutes, cells were then collected, washed with PBS (phosphate buffer saline), spin down, resuspended in 2% heat inactivated FBS with RPMI at a concentration of 1×10⁶ cells/ml, and 100 μl was plated in a 96 well plate. Compounds were dissolved in dimethyl sulfoxide (DMSO) and added to the culture medium to achieve desired concentration (e.g. 100, 30, 10, 3, 1, 0.3 or 0.1 μM). Cells were incubated with compounds for 4 hours. Cell free supernatant was collected and the production of IL-1β was evaluated by ELISA. A vehicle only control was run concurrently with each experiment. Final DMSO concentration was 1%. Compounds exhibit a dose-related increase of IL-1β production in PMA-differentiated THP-1 cells.

Measurement of IL-1β production in PMA-differentiated THP-1 cells (Alternative Procedure)

THP-1 cells were purchased from the American Type Culture Collection and sub-cultured according to instructions from the supplier. Prior to experiments, cells were cultured in RPMI 1640 containing 10% heat inactivated FBS, penicillin (100 units/ml), streptomycin (100 μg/ml), HEPES (10 mM) and sodium pyruvate (1 mM) and maintained in log phase prior to experimental setup. Prior to the experiment, THP-1 cells were treated with PMA (Phorbol 12-myristate 13-acetate) (20 μg/ml) overnight. The day of the experiment, the media was removed and attached cells were treated with trypsin for 2 minutes, cells were then collected, washed with PBS (phosphate buffer saline), pelleted by centrifugation and resuspended in 2% heat inactivated FBS with RPMI at a concentration of 50,000 cells/well in a 384 well plate. Cell free supernatant was collected and the production of IL-1β was evaluated by ELISA. Compounds were dissolved in dimethyl sulfoxide (DMSO) and added to the culture medium to achieve desired concentration (e.g. 100, 30, 10, 3, 1, 0.3 or 0.1 μM). Cells were incubated with compounds for 2 hours. A vehicle only control was run concurrently with each experiment. Final DMSO concentration was 1%. Compounds exhibit a dose-related increase of IL-1β production in PMA-differentiated THP-1 cells.

Measurement of IL-1β Production—hTRF Protocol (Second Alternative Procedure)

Serial dilutions of compounds in DMSO were added to low volume 384 well plates at 100 nl/well using an ECHO 550 acoustic dispenser (Labcyte) to achieve final starting concentration of 10 μM in assay.

THP-1 cells in RPMI (Gibco, 11875) media with 10% FBS at a density of $1 \times 10^6$ cell/ml in a T175 flask were treated with a final concentration of phorbol 12-myristate 13-acetate (PMA) (Sigma, P1585) of 50 ng/ml overnight at 37° C. at 5% $CO_2$ for differentiation. Cells were harvested the next day after rinsing well with dPBS using 0.5% trypsin. A cell solution was prepared of $1 \times 10^6$ cells/ml for 50,000 cells in 50 μl/well in RPMI media with 2% FBS. Cells were plated using a multichannel pipette onto the compound dilutions in Greiner, 384 well, black clear bottom tissue culture treated plates (781090). The plates were incubated in 37° C. incubator at 5% $CO_2$ for 2 hours.

After the 2 hour incubation, the cell plates were spun in the centrifuge for 5 minutes at 1200 rpm. Using the Felix (CyBio), 8 μl of the supernatant was transferred to 384 well, low volume, white proxy plates. (Perkin Elmer, 6008230). A human IL1beta hTRF kit was used to analyze the supernatant (CISBIO, 62HIL1BPEG). The kit instructions were followed for preparing the IL1Beta standard curve and then the antibodies from the kit were diluted 1:40 rather than 1:20 as kit instructed. Once combined, the antibodies were added across the plates, 5 μl/well. The plates were sealed and incubated at 4° C. overnight. The plates were then read on the Perkin Elmer EnVision at 665/615 nm using the hTRF laser. Compounds exhibited a dose-related increase of IL-1β production.

Measurement of IL-1β Production—Human Whole Blood Assay

Serial dilutions of compounds in DMSO were added to low volume 384 well plates at 100 nl/well using an ECHO 550 acoustic dispenser (Labcyte) to achieve final starting concentration of 10 uM in assay.

Human venous whole blood obtained from healthy donors was pre-treated with LPS (Invivogen, Cat# tlrl-eblps) at 1 ng/ml for four hours at 37° C. in a humidified 95% air/5% CO2 incubator. Primed blood was added to the compound plate and incubated for additional 4 hours at 37° C. IL-1beta in the supernatants was measured using AlphLISA kit (Cat#AL220) according to manufacturer's instructions. Compounds exhibited a dose-related increase of IL-1β production. EC50 was determined using primed but untreated blood as baseline.

Measurement of IL-1β Production—Mouse hTRF Protocol

Immortalized mouse macrophages derived from C57BL/6 mice were obtained from Ericke Latz, University of Bonn/University of Massachusetts Worchester, Mass. The cells were harvested using 0.05% Trypsin and washed with PBS. Cell were plated at 30,000 cells per well in 25 ul in DMEM (Gibco, 11965) supplemented with 2% FBS and incubated for 10 minutes at 37° C. at 5% $CO_2$. LPS-EB (Invivogen, tlr-eblps) was added to a final concentration of 200 ng/ml at 5 ul/well and cells were incubated for 2 hours at 37° C. at 5% CO2.

Serial dilutions of compounds in DMSO were added to cells in low volume 384 well plates at 60 nl/well using an ECHO 550 acoustic dispenser (Labcyte) to achieve final starting concentration of 50 uM in assay and incubated with compounds for additional 2 hours at 37° C. at 5% CO2.

After the 2 hour incubation, the cell plates were spun in the centrifuge for 5 minutes at 1200 rpm. Using the Felix (CyBio), 8 ul of the supernatant was transferred to 384 well, low volume, white proxy plates. (Perkin Elmer, 6008230). A human IL1beta hTRF kit was used to analyze the supernatant (CISBIO, 62MIL1BPEH). The kit instructions were followed for preparing the IL1Beta standard curve (the antibodies from the kit were diluted 1:40 rather than 1:20 as kit instructed). Once combined, the antibodies were added across the plates at 5 ul/well. The plates were sealed and incubated at 4° C. overnight. The plates were read on the Perkin Elmer EnVision at 665/615 nm using the hTRF laser. Data was then converted to pg/ml of Il1Beta. Compounds exhibited a dose-related increase of IL-1β production.

In Vitro Human TLR7 and TLR8 Binding Reporter Assays

Logarithmically-growing human HEK-Blue cells co-expressing a TLR7 or TLR8 gene and a NF-kB/AP1-inducible SEAP (secreted embryonic alkaline phosphatase; Invivogen, San Diego, Calif.) reporter gene are added to individual wells of a 384-well plate (15,000 cells per 20 μL per well) and maintained for 24 h at 37° C., 5% $CO_2$. Test compounds or DMSO are distributed to separate wells the next day using acoustic liquid handling technology (100 nL per well) and cells are subsequently incubated for 18 h at 37° C., 5% $CO_2$. Cellular SEAP production is measured using an Envision plate reader instrument thirty minutes after adding freshly-made Quanti-Blue reagent (prepared by following manufacturer instructions; Invivogen, San Diego, Calif.) to the HEK-Blue TLR Nf-kB-SEAP cell reactions. All $EC_{50}$ values (half-maximal effective concentration) are determined using proprietary data analysis software. Normalized $EC_{50}$ value=absolute value determined by setting 100% Ymax using a reference standard RLU (relative light unit) values from cells treated with 50 μM of the reference standard.

In Vivo Pharmacology

Compounds are assessed for in vivo efficacy in preclinical syngeneic tumor models such as MC38, CT26 and 4T1 respectively. The tumor lines are implanted subcutaneously in syngeneic, immunocompetent mice. For intra-tumoral (IT) route of compound administration abscopal tumor models are utilized. In the abscopal model mice are subcutaneously injected with 0.1 mL cells ($1 \times 10^7$ cells/ml) into the right and left flank respectively, using a 1 mL tuberculin syringe with a 25 g needle. Tumored animals are sorted and randomized when tumors on each side reach approximately 100 mm3. The compounds are administered with an IT injection in the right flank at appropriate doses and dosing frequency either alone or in combination with checkpoint blockers such as anti-PD-1 and/or anti-CTLA4. For combination studies the checkpoint blockers are administered intraperitoneally (IP) at optimal doses and dosing frequency. Efficacy is determined by monitoring the tumor volumes of the injected and abscopal tumor respectively.

Additional studies are carried out in the abscopal tumor models to determine the PK/PD relationship as well as to assess the profile of tumor-infiltrating lymphocytes (TILs). Other routes of administration, such as intravenous or intramuscular, are explored along with various dosing regimens to determine the dosing routes and regimen that provide optimal efficacy.

Table 1 depicted above includes biological data of compounds that were assayed using one or more of the above procedures.

A number of embodiments of the invention have been described. Nevertheless, it will be understood that various modifications may be made without departing from the spirit and scope of the invention. Accordingly, other embodiments are within the scope of the following claims.

What is claimed is:
1. A compound having Formula (II):

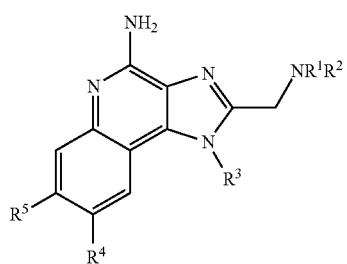

(II)

or a pharmaceutically acceptable salt thereof, wherein:
$R^1$ is independently unsubstituted $C_{1-6}$ alkyl or C(=O)$R^a$;
$R^2$ is independently H or unsubstituted $C_{1-6}$ alkyl;
$R^3$ is:
(i) H;
(ii) unsubstituted $C_{1-2}$ alkyl; or
(iii) X—$R^8$, wherein X is an unbranched $C_{1-6}$ alkylene, and $R^8$ is —OH, $C_{1-4}$ alkoxy, $C_{1-4}$ haloalkoxy, CO$_2R^a$, or —CONR$^cR^d$;
$R^4$ is independently H or halo;
$R^5$ is independently selected from:
(i) $C_{3-6}$ cycloalkyl substituted with 0 to 2 $R^f$;
(ii) phenyl substituted with 0 to 3 $R^g$;
(iii) heteroaryl including from 5 to 6 ring atoms, wherein from 1 to 3 ring atoms are each independently selected from: N, NH, O, and S, wherein the heteroaryl is substituted with 0 to 3 $R^g$;
(iv) $C_{1-6}$ alkyl substituted with 0 to 2 $R^h$; and
(v) $C_{5-6}$ cycloalkenyl substituted with 0 to 2 $R^f$;
$R^a$ is:
(i) $C_{1-6}$ alkyl substituted with 0 to 2 $R^h$;
(ii) —($C_{0-3}$ alkylene)-$C_{3-6}$ cycloalkyl, wherein the cycloalkyl is substituted with 0 to 2 $R^f$;
(iii) —($C_{1-3}$ alkylene)-heterocyclyl including from 5 to 6 ring atoms, wherein 1 to 3 ring atoms are each independently selected from N($R^e$), O, and S, wherein the heterocyclyl is substituted with 0 to 4 independently selected $R^f$;
(iv) —($C_{0-3}$ alkylene)-phenyl substituted with 0 to 4 independently selected $R^g$; or
(v) —($C_{0-3}$ alkylene)-heteroaryl including from 5 to 10 ring atoms, wherein from 1 to 4 ring atoms are each independently selected from N, N($R^e$), O, and S, wherein the heteroaryl is substituted with 0 to 3 independently selected $R^g$;
each occurrence of $R^c$ and $R^d$ is independently H or $C_{1-4}$ alkyl;
each occurrence of $R^e$ is independently H or $C_{1-4}$ alkyl;
each occurrence of $R^f$ is independently $C_{1-6}$ alkyl, $C_{1-4}$ haloalkyl, —OH, F, Cl, $C_{1-4}$ alkoxy, $C_{1-4}$ haloalkoxy, or cyano;
each occurrence of $R^g$ is independently halo, cyano, $C_{1-6}$ alkyl, $C_{1-4}$ haloalkyl, $C_{1-4}$ alkoxy, or $C_{1-4}$ haloalkoxy; and
each occurrence of $R^h$ is independently —OH, F, $C_{1-4}$ alkoxy, $C_{1-4}$ haloalkoxy, or cyano.

2. The compound of claim 1, wherein:
$R^2$ is independently H or unsubstituted $C_{1-3}$ alkyl; and
$R^3$ is H, unsubstituted $C_{1-2}$ alkyl, or X—$R^8$, wherein X is an unbranched $C_{2-4}$ alkylene, and $R^8$ is CO$_2R^a$, or —CONR$^cR^d$; and
$R^a$ is H, $C_{1-4}$ alkyl substituted with 0 to 1 OH, $C_{3-6}$ cycloalkyl, phenyl, or heteroaryl including from 5 to 6 ring atoms, wherein from 1 to 4 ring atoms are each independently selected from N, N($R^e$), O, and S.

3. The compound of claim 2, wherein:
$R^2$ is independently H, CH$_3$ or CH$_2$CH$_3$;
$R^3$ is H, CH$_3$, or —(CH$_2$)$_3$C(=O)OCH$_3$;
$R^5$ is independently CH$_3$, cyclopentyl, cyclopentenyl, phenyl, pyrazol-1-yl, or pyrazol-3-yl; and
$R^a$ is H, CH$_3$, CH$_2$CH$_3$, CH(CH$_3$)$_2$, C(CH$_3$)$_3$, cyclopropyl, or thiazolyl.

4. The compound of claim 3, wherein:
$R^2$ is independently H, CH$_3$ or CH$_2$CH$_3$;
$R^3$ is H or CH$_3$;
$R^5$ is independently CH$_3$, cyclopentyl, cyclopentenyl, phenyl, pyrazol-1-yl, or pyrazol-3-yl; and
$R^a$ is CH$_3$, CH$_2$CH$_3$, CH(CH$_3$)$_2$, C(CH$_3$)$_3$, or cyclopropyl.

5. The compound of claim 4, wherein:
$R^1$ is independently CH$_3$, CH$_2$CH$_3$, CH(CH$_3$)$_2$, C(CH$_3$)$_3$, or C(=O)$R^a$;
$R^2$ is independently H, CH$_3$ or CH$_2$CH$_3$;
$R^3$ is H;
$R^5$ is independently cyclopentyl, cyclopentenyl, phenyl, pyrazol-1-yl, or pyrazol-3-yl; and
$R^a$ is CH$_3$, CH$_2$CH$_3$, CH(CH$_3$)$_2$, C(CH$_3$)$_3$, or cyclopropyl.

6. The compound of claim 1, wherein:
$R^1$ is C(=O)$R^a$;
$R^2$ is independently H, CH$_3$ or CH$_2$CH$_3$;
$R^3$ is independently H, CH$_3$, CH$_2$CH$_3$ or CH$_2$CH$_2$OH;
$R^4$ is H;
$R^5$ is independently cyclopentyl, cyclopentenyl, thienyl, pyrazol-1-yl, pyrazol-3-yl, pyrazol-5-yl or (phenyl substituted with 0-1 $C_{1-4}$ alkyl); and
$R^a$ is CH$_3$, CH$_2$CH$_3$, CH(CH$_3$)$_2$, C(CH$_3$)$_3$, —(CH)$_2$CH(CH$_3$)$_2$, cyclopropyl, 1-methyl-1H-pyrrol-2-yl, or (phenyl substituted with $C_{1-4}$ alkoxy or Cl).

7. The compound of claim 1, wherein:
$R^1$ is independently CH$_3$, CH$_2$CH$_3$, CH(CH$_3$)$_2$, or C(CH$_3$)$_3$;
$R^2$ is independently H, CH$_3$ or CH$_2$CH$_3$;
$R^3$ is independently H, CH$_3$ or CH$_2$CH$_3$;
$R^4$ is H; and
$R^5$ is independently pyrazol-1-yl, pyrazol-3-yl or pyrazol-5-yl.

8. A compound selected from:

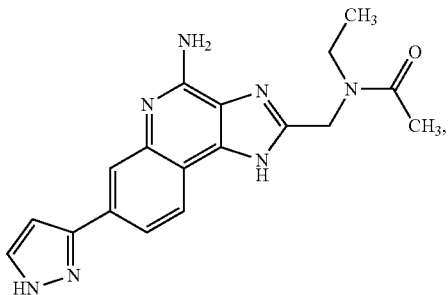

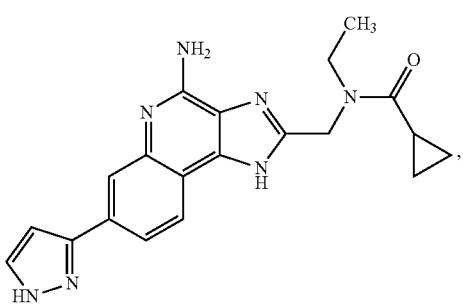

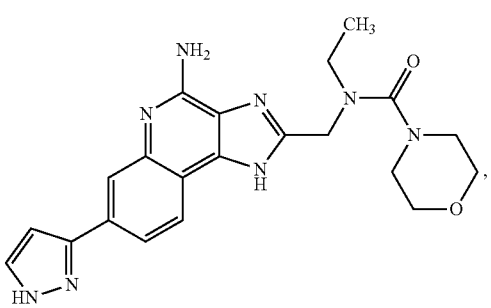

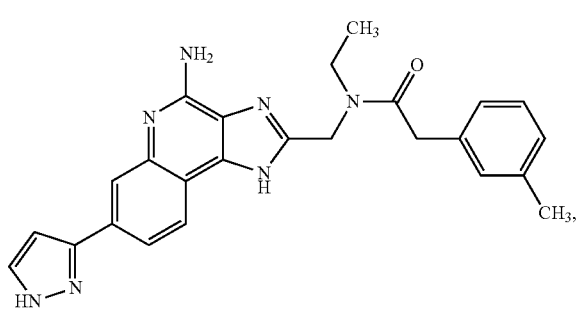

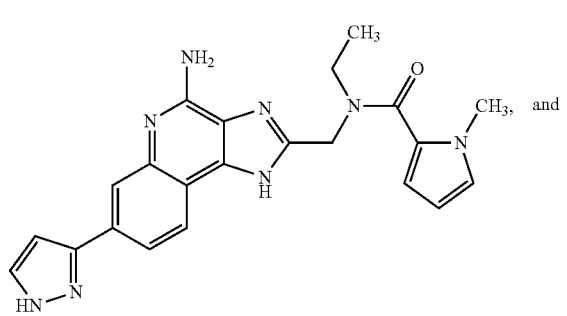

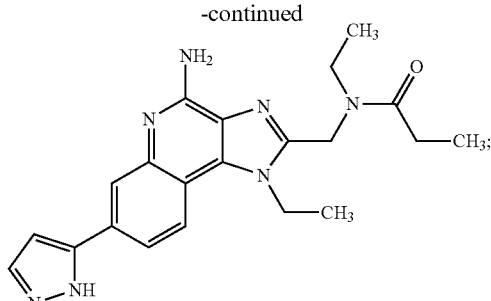

or a pharmaceutically acceptable salt thereof.

9. A pharmaceutical composition comprising a compound or a pharmaceutically acceptable salt thereof as claimed in claim 1 and one or more pharmaceutically acceptable excipients.

10. A compound of the formula:

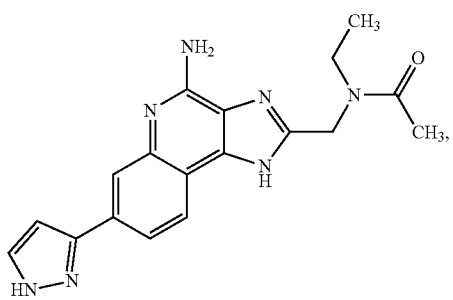 [SMILES: CCN(Cc1nc2c(N)nc3cc(-c4cc[nH]n4)ccc3c2[nH]1)C(C)=O]

or a pharmaceutically acceptable salt thereof.

11. A compound of the formula:

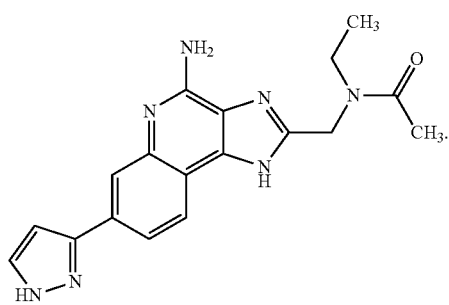 [SMILES: CCN(Cc1nc2c(N)nc3cc(-c4cc[nH]n4)ccc3c2[nH]1)C(C)=O]

12. A compound of the formula:

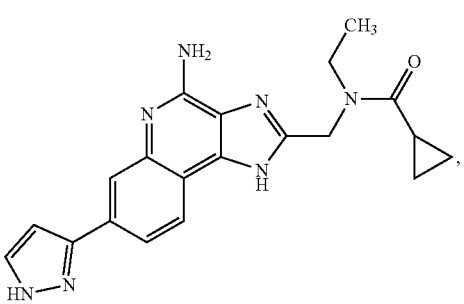 [SMILES: CCN(Cc1nc2c(N)nc3cc(-c4cc[nH]n4)ccc3c2[nH]1)C(=O)C1CC1]

or a pharmaceutically acceptable salt thereof.

13. A compound of the formula:

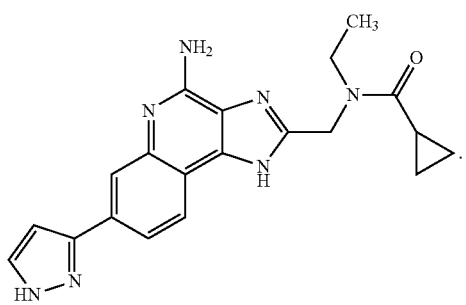 [SMILES: CCN(Cc1nc2c(N)nc3cc(-c4cc[nH]n4)ccc3c2[nH]1)C(=O)C1CC1]

14. A compound of the formula:

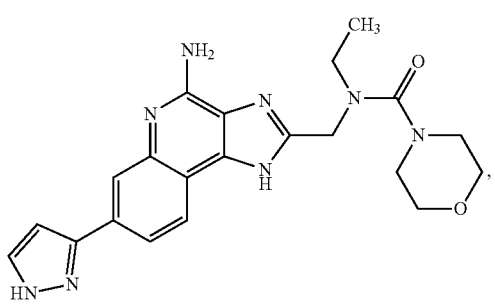 [SMILES: CCN(Cc1nc2c(N)nc3cc(-c4cc[nH]n4)ccc3c2[nH]1)C(=O)N1CCOCC1]

or a pharmaceutically acceptable salt thereof.

15. A compound of the formula:

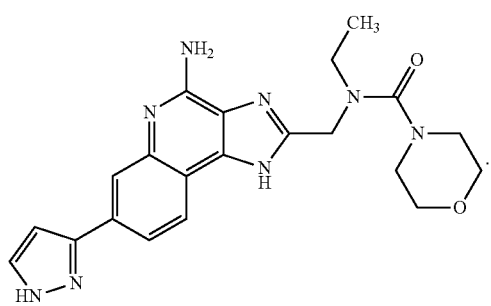 [SMILES: CCN(Cc1nc2c(N)nc3cc(-c4cc[nH]n4)ccc3c2[nH]1)C(=O)N1CCOCC1]

16. A compound of the formula:

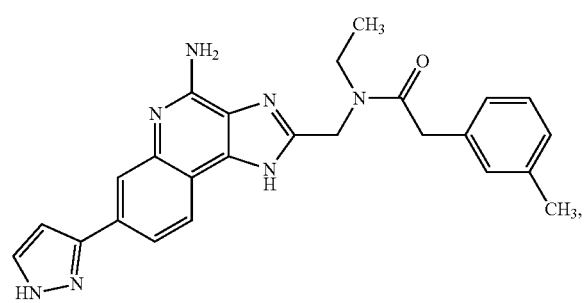 [SMILES: CCN(Cc1nc2c(N)nc3cc(-c4cc[nH]n4)ccc3c2[nH]1)C(=O)Cc1cccc(C)c1]

or a pharmaceutically acceptable salt thereof.

17. A compound of the formula:

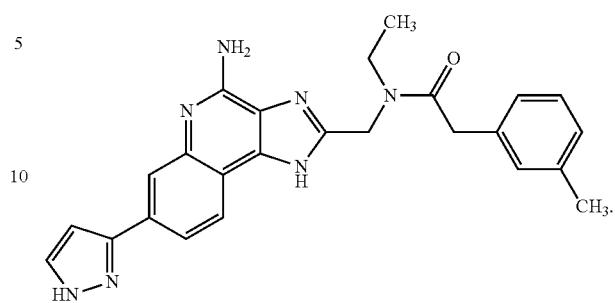

18. A compound of the formula:

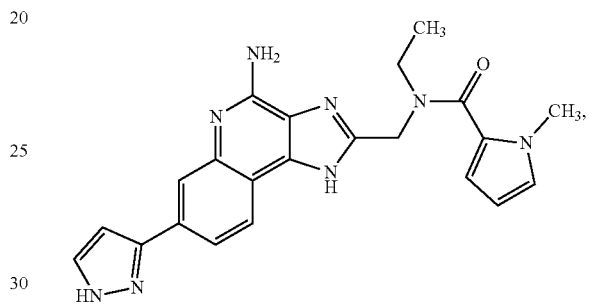

or a pharmaceutically acceptable salt thereof.

19. A compound of the formula:

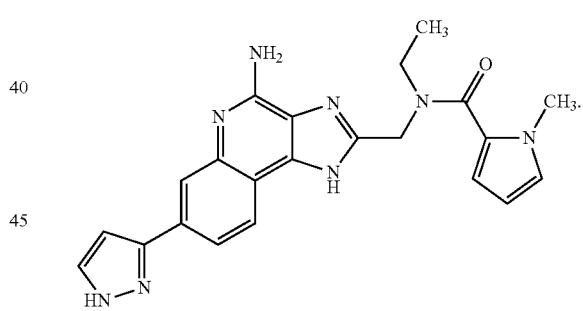

20. A compound of the formula:

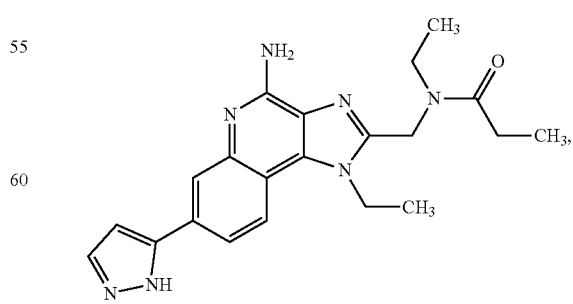

or a pharmaceutically acceptable salt thereof.

21. A compound of the formula:

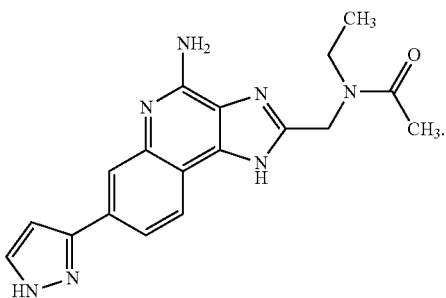 [SMILES: CCN(Cc1nc2c(N)nc3cc(-c4cc[nH]n4)ccc3c2[nH]1)C(C)=O]

22. A pharmaceutical composition comprising a compound or a pharmaceutically acceptable salt thereof as claimed in claim 8 and one or more pharmaceutically acceptable excipients.

23. A pharmaceutical composition comprising the compound or a pharmaceutically acceptable salt thereof as claimed in claim 10 and one or more pharmaceutically acceptable excipients.

24. A pharmaceutical composition comprising the compound as claimed in claim 11 and one or more pharmaceutically acceptable excipients.

25. A pharmaceutical composition comprising the compound or a pharmaceutically acceptable salt thereof as claimed in claim 12 and one or more pharmaceutically acceptable excipients.

26. A pharmaceutical composition comprising the compound as claimed in claim 13 and one or more pharmaceutically acceptable excipients.

27. A pharmaceutical composition comprising the compound or a pharmaceutically acceptable salt thereof as claimed in claim 14 and one or more pharmaceutically acceptable excipients.

28. A pharmaceutical composition comprising the compound as claimed in claim 15 and one or more pharmaceutically acceptable excipients.

29. A pharmaceutical composition comprising the compound or a pharmaceutically acceptable salt thereof as claimed in claim 16 and one or more pharmaceutically acceptable excipients.

30. A pharmaceutical composition comprising the compound as claimed in claim 17 and one or more pharmaceutically acceptable excipients.

31. A pharmaceutical composition comprising the compound or a pharmaceutically acceptable salt thereof as claimed in claim 18 and one or more pharmaceutically acceptable excipients.

32. A pharmaceutical composition comprising the compound as claimed in claim 19 and one or more pharmaceutically acceptable excipients.

33. A pharmaceutical composition comprising the compound or a pharmaceutically acceptable salt thereof as claimed in claim 20 and one or more pharmaceutically acceptable excipients.

34. A pharmaceutical composition comprising the compound as claimed in claim 21 and one or more pharmaceutically acceptable excipients.

35. A pharmaceutical composition comprising the compound or a pharmaceutically acceptable salt thereof as claimed in claim 1 and one or more pharmaceutically acceptable excipients.

36. A pharmaceutical composition comprising the compound as claimed in claim 2 and one or more pharmaceutically acceptable excipients.

37. A pharmaceutical composition comprising the compound or a pharmaceutically acceptable salt thereof as claimed in claim 3 and one or more pharmaceutically acceptable excipients.

38. A pharmaceutical composition comprising the compound as claimed in claim 4 and one or more pharmaceutically acceptable excipients.

39. A pharmaceutical composition comprising the compound or a pharmaceutically acceptable salt thereof as claimed in claim 5 and one or more pharmaceutically acceptable excipients.

40. A pharmaceutical composition comprising the compound as claimed in claim 6 and one or more pharmaceutically acceptable excipients.

41. A pharmaceutical composition comprising the compound as claimed in claim 7 and one or more pharmaceutically acceptable excipients.

* * * * *

UNITED STATES PATENT AND TRADEMARK OFFICE
CERTIFICATE OF CORRECTION

PATENT NO. : 10,533,005 B2
APPLICATION NO. : 15/898258
DATED : January 14, 2020
INVENTOR(S) : Gary D Glick et al.

Page 1 of 1

It is certified that error appears in the above-identified patent and that said Letters Patent is hereby corrected as shown below:

In the Claims

Column 257

Line 2 Claim 21, " 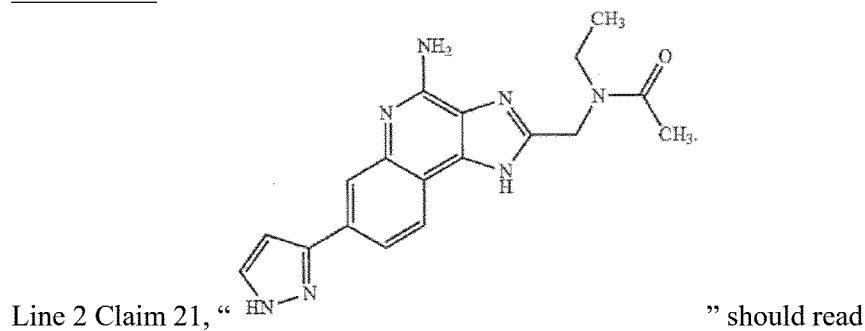 " should read

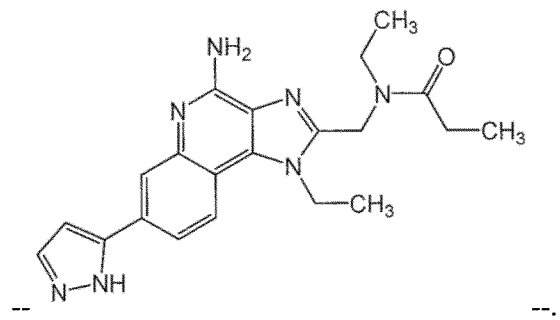

--      --.

Signed and Sealed this
Third Day of March, 2020

Andrei Iancu
*Director of the United States Patent and Trademark Office*